US010533227B2

(12) United States Patent
Veiby et al.

(10) Patent No.: US 10,533,227 B2
(45) Date of Patent: Jan. 14, 2020

(54) COMPOSITIONS, KITS, AND METHODS FOR IDENTIFICATION, ASSESSMENT, PREVENTION AND THERAPY OF BREAST AND OVARIAN CANCER

(71) Applicants: Millennium Pharmaceuticals, Inc., Cambridge, MA (US); Board of Regents, University of Texas System, Cambridge, MA (US)

(72) Inventors: Ole Petter Veiby, Westborough, MA (US); Robert C. Bast, Houston, TX (US); Gordon B. Mills, Houston, TX (US); Gabriel N. Hortobagyi, Bellaire, TX (US)

(73) Assignees: Millennium Pharmaceuticals, Inc., Cambridge, MA (US); Board of Regents, University of Texas System, Cambridge, MA (US)

( * ) Notice: Subject to any disclaimer, the term of this patent is extended or adjusted under 35 U.S.C. 154(b) by 0 days.

(21) Appl. No.: 14/930,985

(22) Filed: Nov. 3, 2015

(65) Prior Publication Data
US 2016/0326591 A1 Nov. 10, 2016

Related U.S. Application Data

(63) Continuation of application No. 13/629,973, filed on Sep. 28, 2012, now abandoned, which is a continuation of application No. 12/317,003, filed on Dec. 17, 2008, now Pat. No. 8,323,906, which is a continuation of application No. 11/080,991, filed on Mar. 11, 2005, now Pat. No. 7,494,775, which is a continuation of application No. 10/176,847, filed on Jun. 21, 2002, now abandoned.

(60) Provisional application No. 60/301,351, filed on Jun. 27, 2001, provisional application No. 60/300,159, filed on Jun. 21, 2001.

(51) Int. Cl.
C12Q 1/6886 (2018.01)
G01N 33/574 (2006.01)
G01N 33/68 (2006.01)
C07K 16/28 (2006.01)

(52) U.S. Cl.
CPC ............ *C12Q 1/6886* (2013.01); *C07K 16/28* (2013.01); *G01N 33/57415* (2013.01); *G01N 33/6893* (2013.01); *C12Q 2600/136* (2013.01); *C12Q 2600/158* (2013.01); *G01N 2333/47* (2013.01); *G01N 2500/20* (2013.01)

(58) Field of Classification Search
None
See application file for complete search history.

(56) References Cited

U.S. PATENT DOCUMENTS

2004/0053248 A1* 3/2004 Tang ...................... C07H 21/04
435/6.11

FOREIGN PATENT DOCUMENTS

| CA | 2374341 | * | 11/2000 |
|----|---------|---|---------|
| WO | WO 00/06698 | * | 2/2000 |
| WO | WO 00/71581 | * | 11/2000 |
| WO | WO 02/059377 | * | 8/2002 |
| WO | WO 02/071928 | * | 9/2002 |

OTHER PUBLICATIONS

McNicol et al (Journal of Pathology, 1997, 182:250-261).*
Shoji et al (American Journal of Pathology, 1998, 152:399-411).*

* cited by examiner

*Primary Examiner* — Laura B Goddard
(74) *Attorney, Agent, or Firm* — McCarter & English, LLP; Maria Laccotripe Zacharakis; Deborah L. Nagle

(57) ABSTRACT

The invention relates to newly discovered nucleic acid molecules and proteins associated with breast or ovarian cancer. Compositions, kits, and methods for detecting, characterizing, preventing, and treating human breast or ovarian cancers are provided.

24 Claims, No Drawings
Specification includes a Sequence Listing.

SEQUENCE LISTING

<160> NUMBER OF SEQ ID NOS: 112

<210> SEQ ID NO 1
<211> LENGTH: 4275
<212> TYPE: DNA
<213> ORGANISM: Homo sapiens
<220> FEATURE:
<221> NAME/KEY: modified_base
<222> LOCATION: (4241)..(4241)
<223> OTHER INFORMATION: a, c, t or g
<220> FEATURE:
<221> NAME/KEY: modified_base
<222> LOCATION: (4243)..(4244)
<223> OTHER INFORMATION: a, c, t or g
<220> FEATURE:
<221> NAME/KEY: modified_base
<222> LOCATION: (4246)..(4247)
<223> OTHER INFORMATION: a, c, t or g
<220> FEATURE:
<221> NAME/KEY: modified_base
<222> LOCATION: (4250)..(4250)
<223> OTHER INFORMATION: a, c, t or g
<220> FEATURE:
<221> NAME/KEY: modified_base
<222> LOCATION: (4253)..(4255)
<223> OTHER INFORMATION: a, c, t or g
<220> FEATURE:
<221> NAME/KEY: modified_base
<222> LOCATION: (4259)..(4263)
<223> OTHER INFORMATION: a, c, t or g
<220> FEATURE:
<221> NAME/KEY: modified_base
<222> LOCATION: (4266)..(4266)
<223> OTHER INFORMATION: a, c, t or g
<220> FEATURE:
<221> NAME/KEY: modified_base
<222> LOCATION: (4270)..(4273)
<223> OTHER INFORMATION: a, c, t or g

<400> SEQUENCE: 1

```
ccgggccagg cgcggagctg gcggcagtga caggaggcgc gaacccgcag cgcttaccgc      60
gcggcgccgc accatggagc ccgccgtgtc gctggccgtg tgcgcgctgc tcttcctgct     120
gtgggtgcgc ctgaaggggc tggagttcgt gctcatccac cagcgctggg tgttcgtgtg     180
cctcttcctc ctgccgctct cgcttatctt cgatatctac tactacgtgc gcgcctgggt     240
ggtgttcaag ctcagcagcg ctccgcgcct gcacgagcag cgcgtgcggg acatccagaa     300
gcaggtgcgg gaatggaagg agcagggtag caagaccttc atgtgcacgg ggcgccctgg     360
ctggctcact gtctcactac gtgtcgggaa gtacaagaag acacacaaaa acatcatgat     420
caacctgatg acattctgg aagtggacac caagaaacag attgtccgtg tggagccctt     480
ggtgaccatg ggccaggtga ctgccctgct gacctccatt ggctggactc tccccgtgtt     540
gcctgagctt gatgacctca cagtgggggg cttgatcatg ggcacaggca tcgagtcatc     600
```

-continued

```
atcccacaag tacggcctgt tccaacacat ctgcactgct tacgagctgg tcctggctga      660
tggcagcttt gtgcgatgca ctccgtccga aaactcagac ctgttctatg ccgtaccctg      720
gtcctgtggg acgctgggtt tcctggtggc cgctgagatc cgcatcatcc ctgccaagaa      780
gtacgtcaag ctgcgtttcg agccagtgcg gggcctggag ctatctgtg ccaagttcac       840 ccacgagtcc cagcggcagg agaaccactt cgtggaaggg ctgctctact ccctggatga      900
ggctgtcatt atgacagggg tcatgacaga tgaggcagag cccagcaagc tgaatagcat      960
tggcaattac tacaagccgt ggttctttaa gcatgtggag aactatctga agacaaaccg      1020
agagggcctg gagtacattc ccttgagaca ctactaccac cgccacacgc gcagcatctt      1080
ttgggagctc caggacatca tcccctttgg caacaacccc atcttccgct acctctttgg      1140
ctggatggtg cctcccaaga tctccctcct gaagctgacc cagggtgaga ccctgcgcaa      1200
gctgtacgag cagcaccacg tggtgcagga catgctggtg cccatgaagt gcctgcagca      1260
ggccctgcac accttccaaa acgacatcca cgtctacccc atctggctgt gtccgttcat      1320
cctgcccagc cagccaggcc tagtgcaccc caaaggaaat gaggcagagc tctacatcga      1380
cattggagca tatggggagc gcgtgtgaa acactttgaa gccaggtcct gcatgaggca       1440
gctggagaag tttgtccgca gcgtgcatgg cttccagatg ctgtatgccg actgctacat      1500
gaaccgggag gagttctggg agatgtttga tggctccttg taccacaagc tgcgagagaa      1560
gctgggttgc caggacgcct tccccgaggt gtacagacaag atctgcaagg ccgccaggca     1620
ctgagctgga gcccgcctgg agagacagac acgtgtgagt ggtcaggcat cttcccttca     1680
ctcaagcttg gctgctttcc tagatccaca ctttcaaaga gaaaccctc cagaactccc      1740 accctgacag cccaacacca ccttcctcct ggcttccagg gggcagccca gtggaatgga      1800
aagaatgtgg gatttggagt cagacaagcc tgagtccagt tccccgttta gaactcatta     1860
gctgtgtgac tctgggtgag tcccttaacc cctctgagcc cgggtctctt cattagttga     1920
aagggatagt aataccctact tgcaggttgt tgtcatctga gttgagcact ggtcacattg     1980
aaggtgctgg gtaagtggta gctcttgttg cttcccgttc agcgtcacat ctgcagtgga     2040
gcctgaaaag gctccacatt aggtcacctg tgcacagcca tggctggaat gatgaagggg      2100
atacgctgga gttgccctgc catcgcctcc atcagccaga cgaggtcctc acaggagaag     2160
gacagctctt ccccaccctg ggatctcagg agggcagcca cggagtgggg aggcccaga      2220 tgcgctgtgc caaagccagg tccgaggcca aagttctccc tgccatcctt ggtgccgtcc      2280 tgcccttcc tccttcatgc ctgggcctgc aggcccaccc cagccaccac tgagtccact      2340
cggagtgccc tgtgttcctg gagaaggcat tccagggttg aatcttgtcc cagcctcagc     2400
ctgggacacc taggtggaga gagtggtctc cgctctgaat tggatccagg ggacctgggc     2460
tcattcttct tggctcacca accctgcagg cctcatcttt cccaaaaccc actttgtctt      2520
ggtgggagtg ggtccgcgct gctctgcagc aggggctggg gagtggacag catcaggtgg      2580
gaaagtggag tccacccctca tgtttctgta ggattctcac cgtggggctg gaagaaaaga     2640
gcatcgactt gatttctcca accactcatc cctcttttc tttcttccac cactccccac      2700
cccagctgta gttaatttca gtgccttaca aatcctaagc tcagagaaag ttccattcc       2760 gttccagagg gaagggaacc tccctaggtc cttccctggc ttgttataac gcaaagcttg      2820 gttgttatg caactctatc ttaagaactg cccagcctca gctgaaaacc cgaatctgag      2880
aaggaattgc gtcatgtaag ggaagctgga attaagggag ctgagccagt catggttgtg      2940
gcgtgtgagt caggagacct aggtttcagc ccctctctac tgtcagcgag ctgtgcaacg      3000
```

```
tgggcaagtc attgtcctct gagctgcagt ttcctcatct gtcacatcgc tacagacaag    3060
acctccctgg aacccttctg attgtcttag acactgtggt tgcaaaaccc acggaaagcc    3120
tcatttgtgt ggaaagtcag aggaaaaatg atccagtgga cacttgggga ttatctgtca    3180
ttcaagatcc ttccttcaac cccaaggtca gctcccatct catttccaga aaggctcata    3240
cctggcttgc agggaagcat ctgtcttgtc attccaggtg ccagaatcct ctcagagtca    3300
ttgaagggtg ttcacccatc ccacccaagg cttggcacac tgccagtgtc ttagcagggt    3360
cttgtgaggg ctgggggcat ccaggcactc agaaggcaaa ggaaccaccc tacccatttg    3420
gcctctggag ggggcagaag aaagaaagaa acctcatcct atattttaca aagcatgtga    3480
attctggcat tagctctcat aggagaccca tgtgcttcct tgctcagtgc aaaactgatg    3540
attctacttg ctgtagatga atggttaaca cgagctagtt aaacagtgcc attgttttgc    3600
cagtgaagcc tccaacccta agccactggg acggtggcca gagatgccag cagcctctgt    3660 cgccctagt catataacca aaatccagac cttatccaca acccggggct tggaaaggaa    3720
ggtattttgg aatcacaccc tccggttatg ttgctccagt aaaatcttgc ctggaaagag    3780
gcagtcttct tagcatggtg agctgagttc atggcttttt tttgtagcca gtcctgtccc    3840
tggccatcca tgtgatggtt ttggatggag ttaaacttga tgccagtggg cagtgcatgt    3900
ggaaagtatc agagtaagcc tctcccctcc agagccctga gtttcttggc tgcatgaagg    3960
ttttctttag aatcagaatt gtagccagtt tctttggcca gaaggatgaa tacttggata    4020
ttactgaaag ggagggtgg agatgggtgt ggcagtgtat ggtgtgtgat ttttatttc    4080 ttctttggtc atgggggcca aggagaaagg catgaatctt ccctgtcagg ctcttacagc    4140
cacaggcact gtgtctactg tctgaagac atgtccccgt ggctgtgggg ccgctgcttc    4200
tgtttaaata aaagtggcct ggaaaaaaaa aaaaaaaaa ngnnannstn yknnnctknn    4260
nnngtnhgsn nnnts                                                    4275
```

<210> SEQ ID NO 2
<211> LENGTH: 516
<212> TYPE: PRT
<213> ORGANISM: Homo sapiens

<400> SEQUENCE: 2

Met Glu Pro Ala Val Ser Leu Ala Val Cys Ala Leu Leu Phe Leu Leu
1               5                   10                  15

Trp Val Arg Leu Lys Gly Leu Glu Phe Val Leu Ile His Gln Arg Trp
            20                  25                  30

Val Phe Val Cys Leu Phe Leu Leu Pro Leu Ser Leu Ile Phe Asp Ile
        35                  40                  45

Tyr Tyr Tyr Val Arg Ala Trp Val Val Phe Lys Leu Ser Ser Ala Pro
    50                  55                  60

Arg Leu His Glu Gln Arg Val Arg Asp Ile Gln Lys Gln Val Arg Glu
65                  70                  75                  80

Trp Lys Glu Gln Gly Ser Lys Thr Phe Met Cys Thr Gly Arg Pro Gly
                85                  90                  95

Trp Leu Thr Val Ser Leu Arg Val Gly Lys Tyr Lys Lys Thr His Lys
            100                 105                 110

Asn Ile Met Ile Asn Leu Met Asp Ile Leu Glu Val Asp Thr Lys Lys
        115                 120                 125

Gln Ile Val Arg Val Glu Pro Leu Val Thr Met Gly Gln Val Thr Ala
    130                 135                 140

Leu Leu Thr Ser Ile Gly Trp Thr Leu Pro Val Leu Pro Glu Leu Asp
145                 150                 155                 160

Asp Leu Thr Val Gly Gly Leu Ile Met Thr Gly Ile Glu Ser Ser
            165                 170                 175

Ser His Lys Tyr Gly Leu Phe Gln His Ile Cys Thr Ala Tyr Glu Leu
            180                 185                 190

Val Leu Ala Asp Gly Ser Phe Val Arg Cys Thr Pro Ser Glu Asn Ser
            195                 200                 205

Asp Leu Phe Tyr Ala Val Pro Trp Ser Cys Gly Thr Leu Gly Phe Leu
    210                 215                 220

Val Ala Ala Glu Ile Arg Ile Pro Ala Lys Lys Tyr Val Lys Leu
225                 230                 235                 240

Arg Phe Glu Pro Val Arg Gly Leu Glu Ala Ile Cys Ala Lys Phe Thr
                245                 250                 255

His Glu Ser Gln Arg Gln Glu Asn His Phe Val Glu Gly Leu Leu Tyr
            260                 265                 270

Ser Leu Asp Glu Ala Val Ile Met Thr Gly Val Met Thr Asp Glu Ala
    275                 280                 285

Glu Pro Ser Lys Leu Asn Ser Ile Gly Asn Tyr Tyr Lys Pro Trp Phe
290                 295                 300

Phe Lys His Val Glu Asn Tyr Leu Lys Thr Asn Arg Glu Gly Leu Glu
305                 310                 315                 320

Tyr Ile Pro Leu Arg His Tyr His Arg His Thr Arg Ser Ile Phe
                325                 330                 335

Trp Glu Leu Gln Asp Ile Ile Pro Phe Gly Asn Asn Pro Ile Phe Arg
                340                 345                 350

Tyr Leu Phe Gly Trp Met Val Pro Pro Lys Ile Ser Leu Leu Lys Leu
                355                 360                 365

Thr Gln Gly Glu Thr Leu Arg Lys Leu Tyr Glu Gln His Val Val
370                 375                 380

Gln Asp Met Leu Val Pro Met Lys Cys Leu Gln Gln Ala Leu His Thr
385                 390                 395                 400

Phe Gln Asn Asp Ile His Val Tyr Pro Ile Trp Leu Cys Pro Phe Ile
                405                 410                 415

Leu Pro Ser Gln Pro Gly Leu Val His Pro Lys Gly Asn Glu Ala Glu
                420                 425                 430

Leu Tyr Ile Asp Ile Gly Ala Tyr Gly Glu Pro Arg Val Lys His Phe
            435                 440                 445

Glu Ala Arg Ser Cys Met Arg Gln Leu Glu Lys Phe Val Arg Ser Val
            450                 455                 460

His Gly Phe Gln Met Leu Tyr Ala Asp Cys Tyr Met Asn Arg Glu Glu
465                 470                 475                 480

Phe Trp Glu Met Phe Asp Gly Ser Leu Tyr His Lys Leu Arg Glu Lys
                485                 490                 495

Leu Gly Cys Gln Asp Ala Phe Pro Glu Val Tyr Asp Lys Ile Cys Lys
            500                 505                 510

Ala Ala Arg His
        515

<210> SEQ ID NO 3
<211> LENGTH: 2342
<212> TYPE: DNA
<213> ORGANISM: Homo sapiens

<400> SEQUENCE: 3

```
gtcgacccac gcgtccggca gggccaacag tcacagcagc cctgaccaga gcattcctgg    60
agctcaagct cctctacaaa gaggtggaca gagaagacag cagagaccat gggaccccc    120
tcagcccctc cctgcagatt gcatgtcccc tggaaggagg tcctgctcac agcctcactt   180
ctaaccttct ggaacccacc caccactgcc aagctcacta ttgaatccac gccgttcaat   240
gtcgcagagg ggaaggaggt tcttctactc gcccacaacc tgccccagaa tcgtattggt   300
tacagctggt acaaaggcga aagagtggat ggcaacagtc taattgtagg atatgtaata   360
ggaactcaac aagctacccc agggcccgca tacagtggtc gagagacaat ataccccaat   420
gcatccctgc tgatccagaa cgtcacccag aatgacacag gattctatac cctacaagtc   480
ataaagtcag atcttgtgaa tgaagaagca accggacagt tccatgtata cccggagctg   540
cccaagccct ccatctccag caacaactcc aaccccgtgg aggacaagga tgctgtggcc   600
ttcacctgtg aacctgaggt tcagaacaca acctacctgt ggtgggtaaa tggtcagagc   660
ctcccggtca gtcccaggct gcagctgtcc aatggcaaca tgaccctcac tctactcagc   720
gtcaaaagga acgatgcagg atcctatgaa tgtgaaatac agaacccagc gagtgccaac   780
cgcagtgacc cagtcaccct gaatgtcctc tatggcccag atggcccac catttccccc   840
tcaaaggcca attaccgtcc aggggaaaat ctgaacctct cctgccacgc agcctctaac   900
ccacctgcac agtactcttg gtttatcaat gggacgttcc agcaatccac acaagagctc   960
tttatcccca acatcactgt gaataatagc ggatcctata tgtgccaagc ccataactca   1020
gccactggcc tcaataggac cacagtcacg atgatcacag tctctggaag tgctcctgtc   1080
ctctcagctg tggccaccgt cggcatcacg attggagtgc tggccagggt ggctctgata   1140
tagcagccct ggtgtatttt cgatatttca ggaagactgg cagattggac cagaccctga   1200
attcttctag ctcctccaat cccatttat cccatggaac cactaaaaac aaggtctgct   1260
ctgctcctga agccctatat gctggagatg acaactcaa tgaaaattta aagggaaaac   1320
cctcaggcct gaggtgtgtg ccactcagag acttcaccta actagagaca ggcaaactgc   1380
aaaccatggt gagaaattga cgacttcaca ctatggacag cttttcccaa gatgtcaaaa   1440
caagactcct catcatgata aggctcttac ccccttttaa tttgtccttg cttatgcctg   1500
cctctttcgc ttggcaggat gatgctgtca ttagtatttc acaagaagta gcttcagagg   1560
gtaacttaac agagtatcag atctatcttg tcaatcccaa cgttttacat aaaataagag   1620
atcctttagt gcacccagtg actgacatta gcagcatctt taacacagcc gtgtgttcaa   1680
atgtacagtg gtccttttca gagttggact tctagactca cctgttctca ctccctgttt   1740
taattcaacc cagccatgca atgccaaata atagaattgc tccctaccag ctgaacaggg   1800
aggagtctgt gcagtttctg acacttgttg ttgaacatgg ctaaatacaa tgggtatcgc   1860
tgagactaag ttgtagaaat taacaaatgt gctgcttggt taaatggct acactcatct   1920
gactcattct ttattctatt ttagttggtt tgtatcttgc ctaaggtgcg tagtccaact   1980
cttggtatta ccctcctaat agtcatacta gtagtcatac tccctggtgt agtgtattct   2040
ctaaaagctt taaatgtctg catgcagcca gccatcaaat agtgaatggt ctctctttgg   2100
ctggaattac aaaactcaga gaaatgtgtc atcaggagaa catcataacc catgaaggat   2160
aaaagcccca aatggtggta actgataata gcactaatgc tttaagattt ggtcacactc   2220
tcacctaggt gagcgcattg agccagtggt gctaaatgct acatactcca actgaaatgt   2280
taaggaagaa gatagatcca attaaaaaaa aaaaaaaaa aaaaaaaaa aagggcggcc   2340
``` gc 2342

<210> SEQ ID NO 4
<211> LENGTH: 344
<212> TYPE: PRT
<213> ORGANISM: Homo sapiens

<400> SEQUENCE: 4

```
Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Ala His Asn Leu Pro Gln Asn Arg Ile Gly
    50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Met Thr Leu Thr Leu Leu Ser Val Lys Arg Asn
        195                 200                 205

Asp Ala Gly Ser Tyr Glu Cys Glu Ile Gln Asn Pro Ala Ser Ala Asn
    210                 215                 220

Arg Ser Asp Pro Val Thr Leu Asn Val Leu Tyr Gly Pro Asp Gly Pro
225                 230                 235                 240

Thr Ile Ser Pro Ser Lys Ala Asn Tyr Arg Pro Gly Glu Asn Leu Asn
                245                 250                 255

Leu Ser Cys His Ala Ala Ser Asn Pro Pro Ala Gln Tyr Ser Trp Phe
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
    290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
            340
```

<210> SEQ ID NO 5

```
<211> LENGTH: 2557
<212> TYPE: DNA
<213> ORGANISM: Homo sapiens
<220> FEATURE:
<221> NAME/KEY: modified_base
<222> LOCATION: (47)..(47)
<223> OTHER INFORMATION: a, c, t or g
<220> FEATURE:
<221> NAME/KEY: modified_base
<222> LOCATION: (2120)..(2120)
<223> OTHER INFORMATION: a, c, t or g
<220> FEATURE:
<221> NAME/KEY: modified_base
<222> LOCATION: (2127)..(2127)
<223> OTHER INFORMATION: a, c, t or g
<220> FEATURE:
<221> NAME/KEY: modified_base
<222> LOCATION: (2131)..(2131)
<223> OTHER INFORMATION: a, c, t or g
<220> FEATURE:
<221> NAME/KEY: modified_base
<222> LOCATION: (2135)..(2135)
<223> OTHER INFORMATION: a, c, t or g
<220> FEATURE:
<221> NAME/KEY: modified_base
<222> LOCATION: (2143)..(2144)
<223> OTHER INFORMATION: a, c, t or g
<220> FEATURE:
<221> NAME/KEY: modified_base
<222> LOCATION: (2162)..(2162)
<223> OTHER INFORMATION: a, c, t or g
<220> FEATURE:
<221> NAME/KEY: modified_base
<222> LOCATION: (2166)..(2166)
<223> OTHER INFORMATION: a, c, t or g
<220> FEATURE:
<221> NAME/KEY: modified_base
<222> LOCATION: (2172)..(2172)
<223> OTHER INFORMATION: a, c, t or g
<220> FEATURE:
<221> NAME/KEY: modified_base
<222> LOCATION: (2186)..(2186)
<223> OTHER INFORMATION: a, c, t or g
<220> FEATURE:
<221> NAME/KEY: modified_base
<222> LOCATION: (2192)..(2192)
<223> OTHER INFORMATION: a, c, t or g
<220> FEATURE:
<221> NAME/KEY: modified_base
<222> LOCATION: (2200)..(2200)
<223> OTHER INFORMATION: a, c, t or g
<220> FEATURE:
<221> NAME/KEY: modified_base
<222> LOCATION: (2219)..(2219)
<223> OTHER INFORMATION: a, c, t or g
<220> FEATURE:
<221> NAME/KEY: modified_base
<222> LOCATION: (2246)..(2246)
<223> OTHER INFORMATION: a, c, t or g
<220> FEATURE:
<221> NAME/KEY: modified_base
<222> LOCATION: (2265)..(2265)
<223> OTHER INFORMATION: a, c, t or g
<220> FEATURE:
<221> NAME/KEY: modified_base
<222> LOCATION: (2375)..(2377)
<223> OTHER INFORMATION: a, c, t or g
<220> FEATURE:
<221> NAME/KEY: modified_base
<222> LOCATION: (2411)..(2411)
<223> OTHER INFORMATION: a, c, t or g
<220> FEATURE:
<221> NAME/KEY: modified_base
<222> LOCATION: (2439)..(2439)
<223> OTHER INFORMATION: a, c, t or g
<220> FEATURE:
<221> NAME/KEY: modified_base
<222> LOCATION: (2456)..(2458)
<223> OTHER INFORMATION: a, c, t or g
```

<220> FEATURE:
<221> NAME/KEY: modified_base
<222> LOCATION: (2461)..(2462)
<223> OTHER INFORMATION: a, c, t or g
<220> FEATURE:
<221> NAME/KEY: modified_base
<222> LOCATION: (2552)..(2557)
<223> OTHER INFORMATION: a, c, t or g

<400> SEQUENCE: 5

```
gggcgaaggg gcagccgcag cgcagaggcc cgccccgccc tccccctnccg tcacagccca      60
gccttccggc ccttgggctg ctcgcggcct ttttttcccg gctgggctcg ggctcagctc     120
gactgggctc ggcgggcggc ggcggcgcg ccggcggctg gcggaggagg gagggcgagg      180
gcgggcgcgg gccggcggc gggcggaaga gggaggagag gcgcggggag ccaggcctcg      240
gggcctcgga gcaaccaccc gagcagacgg agtacacgga gcagcggccc cggccccgcc     300
aacgctgccg ccgggatgct ccagaccttg tatgattact tctggtggga acgtctgtgg     360
ctgcctgtga acttgacctg ggccgatcta gaagaccgag atggacgtgt ctacgccaaa     420
gcctcagatc tctatatcac gctgccctg gccttgctct tcctcatcgt tcgatacttc      480
tttgagctgt acgtggctac accactggct gccctcttga acataaagga gaaaactcgg     540
ctgcgggcac ctcccaacgc caccttggaa catttctacc tgaccagtgg caagcagccc     600
aagcaggtgg aagtagagct tttgtcccgg cagagcgggc tctctggccg ccaggtagag     660
cgttggttcc gtcgccgccg caaccaggac cggcccagtc tcctcaagaa gttccgagaa     720
gccagctgga gattcacatt ttacctgatt gccttcattg ccggcatggc cgtcattgtg     780
gataaaccct ggttctatga catgaagaaa gtttgggagg gatatcccat acagagcact     840
atcccttccc agtattggta ctacatgatt gaactttcct tctactggtc cctgctcttc     900
agcattgcct ctgatgtcaa gcgaaaggat ttcaaggaac agatcatcca ccatgtggcc     960
accatcattc tcatcagctt ttcctggttt gccaattaca tccgagctgg gactctaatc    1020
atggctctgc atgactcttc cgattacctg ctggagtcag ccaagatgtt taactacgcg    1080
ggatggaaga acacctgcaa caacatcttc atcgtcttcg ccattgtttt tatcatcacc    1140
cgactggtca tcctgccctt ctggatcctg cattgcaccc tggtgtaccc actggagctc    1200
tatcctgcct tctttggcta ttacttcttc aattccatga tgggagttct acagctgctg    1260
catatcttct gggcctacct catttgcgc atggcccaca agttcataac tggaaagctg    1320
gtagaagatg aacgcagtga ccgggaagaa acagagagct cagaggggga ggaggctgca    1380
gctgggggag gagcaaagag ccggccccta gccaatggcc accccatcct caataacaac    1440
catcgtaaga atgactgaac cattattcca gctgcctccc agattaatgc ataaagccaa    1500
ggaactaccc cgctccctgc gctatagggt cactttaagc tctggggaaa aaggagaaag    1560
tgagaggaga gttctctgca tcctccctcc ttgcttgtca cccagttgcc tttaaaccaa    1620
attctaaccca gcctatcccc aggtaggggg acgttggtta tattctgtta gaggggacg    1680
gtcgtatttt cctccctacc cgccaagtca tcctttctac tgcttttgag gccctccctc    1740
agctctctgt gggtaggggt tacaattcac attccttatt ctgagaattt ggccccagct    1800
gtttgccttt gactccctga cctccagagc cagggttgtg ccttattgtc ccatctgtgg    1860
gcctcattct gccaaagctg gaccaaggct aacctttcta agctccctaa cttgggccag    1920
aaaccaaagc tgagctttta actttctccc tctatgacac aaatgaattg agggtaggag    1980
gagggtgcac ataacccctta ccctacctct gccaaaaagt gggggctgta ctgggactg     2040
```

-continued

```
ctcggatgat ctttcttagt gctacttctt tcagctgtcc ctgtagcgac aggtctaaga   2100
tctgactgcc tcctcctctn ctctggncct ncttncccccc ttnnccctct tctcttcagc   2160
tnaggnctag cntggtttgg agtagnaatg gncaactaan ttctaattttt tatttattna   2220 aatatttggg gttttggttt taaagnccag aattacggct agcancctag catttcagca   2280
gagggaccat tttagaccaa aatgtactgt taatgggttt ttttttaaaa ttaaaagatt   2340
aaataaaaaa tattaaataa aaaaaaaaaa taagnnncag actattagga attgagaagg   2400
gggatcaact naaataaacg aagagagtct ttcttatgnm tgccttavma aaaaannncc   2460
nnacaaaaaa acgggggggg ggccttacaa attttaaaaa aaaaaccccc cccccccccc   2520
cccggaaccg aaaaaaaaaa aaaagcccca annnnnn                            2557
```

<210> SEQ ID NO 6
<211> LENGTH: 380
<212> TYPE: PRT
<213> ORGANISM: Homo sapiens

<400> SEQUENCE: 6

```
Met Leu Gln Thr Leu Tyr Asp Tyr Phe Trp Trp Glu Arg Leu Trp Leu
1               5                   10                  15

Pro Val Asn Leu Thr Trp Ala Asp Leu Glu Asp Arg Asp Gly Arg Val
            20                  25                  30

Tyr Ala Lys Ala Ser Asp Leu Tyr Ile Thr Leu Pro Leu Ala Leu Leu
        35                  40                  45

Phe Leu Ile Val Arg Tyr Phe Phe Glu Leu Tyr Val Ala Thr Pro Leu
    50                  55                  60

Ala Ala Leu Leu Asn Ile Lys Glu Lys Thr Arg Leu Arg Ala Pro Pro
65                  70                  75                  80

Asn Ala Thr Leu Glu His Phe Tyr Leu Thr Ser Gly Lys Gln Pro Lys
                85                  90                  95

Gln Val Glu Val Glu Leu Leu Ser Arg Gln Ser Gly Leu Ser Gly Arg
            100                 105                 110

Gln Val Glu Arg Trp Phe Arg Arg Arg Asn Gln Asp Arg Pro Ser
        115                 120                 125

Leu Leu Lys Lys Phe Arg Glu Ala Ser Trp Arg Phe Thr Phe Tyr Leu
130                 135                 140

Ile Ala Phe Ile Ala Gly Met Ala Val Ile Val Asp Lys Pro Trp Phe
145                 150                 155                 160

Tyr Asp Met Lys Lys Val Trp Glu Gly Tyr Pro Ile Gln Ser Thr Ile
                165                 170                 175

Pro Ser Gln Tyr Trp Tyr Tyr Met Ile Glu Leu Ser Phe Tyr Trp Ser
            180                 185                 190

Leu Leu Phe Ser Ile Ala Ser Asp Val Lys Arg Lys Asp Phe Lys Glu
        195                 200                 205

Gln Ile Ile His His Val Ala Thr Ile Leu Ile Ser Phe Ser Trp
    210                 215                 220

Phe Ala Asn Tyr Ile Arg Ala Gly Thr Leu Ile Met Ala Leu His Asp
225                 230                 235                 240

Ser Ser Asp Tyr Leu Leu Glu Ser Ala Lys Met Phe Asn Tyr Ala Gly
                245                 250                 255

Trp Lys Asn Thr Cys Asn Asn Ile Phe Ile Val Phe Ala Ile Val Phe
            260                 265                 270

Ile Ile Thr Arg Leu Val Ile Leu Pro Phe Trp Ile Leu His Cys Thr
        275                 280                 285
```

```
Leu Val Tyr Pro Leu Glu Leu Tyr Pro Ala Phe Phe Gly Tyr Tyr Phe
    290                 295                 300

Phe Asn Ser Met Met Gly Val Leu Gln Leu Leu His Ile Phe Trp Ala
305                 310                 315                 320

Tyr Leu Ile Leu Arg Met Ala His Lys Phe Ile Thr Gly Lys Leu Val
                325                 330                 335

Glu Asp Glu Arg Ser Asp Arg Glu Glu Thr Glu Ser Ser Glu Gly Glu
            340                 345                 350

Glu Ala Ala Ala Gly Gly Gly Ala Lys Ser Arg Pro Leu Ala Asn Gly
        355                 360                 365

His Pro Ile Leu Asn Asn Asn His Arg Lys Asn Asp
    370                 375                 380

<210> SEQ ID NO 7
<211> LENGTH: 1861
<212> TYPE: DNA
<213> ORGANISM: Homo sapiens
<220> FEATURE:
<221> NAME/KEY: modified_base
<222> LOCATION: (1249)..(1249)
<223> OTHER INFORMATION: a, c, t or g

<400> SEQUENCE: 7
aagcgggcvc gagccgccgc gcgcgcgccg cgcactgcag ccccaggccc cggccccca      60 cccacgtctg cgttgctgcc ccgcctgggc cgggcccaa aggcaaggac aaagcagctg    120
tcagggaacc tccgccggag tcgaatttac gtgcagctgc cggcaaccac aggttccaag   180
atggtttgcg ggggcttcgc gtgttccaag aactgcctgt gcgccctcaa cctgctttac   240
accttggtta gtctgctgct aattggaatt gctgcgtggg gcattggctt cgggctgatt   300
tccagtctcc gagtggtcgg cgtggtcatt gcagtgggca tcttcttgtt cctgattgct   360
ttagtgggtc tgattggagc tgtaaaacat catcaggtgt tgctattttt ttatatgatt   420
attctgttac ttgtatttat tgttcagttt tctgtatctt gcgcttgttt agccctgaac   480
caggagcaac agggtcagct tctggaggtt ggttggaaca atacggcaag tgctcgaaat   540
gacatccaga gaaatctaaa ctgctgtggg ttccgaagtg ttaacccaaa tgacacctgt   600
ctggctagct gtgttaaaag tgaccactcg tgctcgccat gtgctccaat cataggagaa   660
tatgctggaa aggttttgag atttgttggt ggcattggcc tgttcttcag ttttacagag   720
atcctgggtg tttggctgac ctacagatac aggaaccaga agacccccg cgcgaatcct   780 agtgcattcc tttgatgaga aaacaaggaa gatttccttt cgtattatga tcttgttcac   840
tttctgtaat tttctgttaa gctccatttg ccagtttaag gaaggaaaca ctatctggaa   900 aagtaccttta tgatagtgg aattatatat ttttactcta tgtttctcta catgtttttt   960
tctttccgtt gctgaaaaat atttgaaact tgtggtctct gaagctcggt ggcacctgga  1020
atttactgta tcattgtcg ggcactgtcc actgtggcct tcttagcat ttttacctgc   1080 agaaaaactt tgtatggtac cactgtgttg gttatatggt gaatctgaac gtacatctca  1140
ctggtataat tatatgtagc actgtgctgt gtagatagtt cctactggaa aaagagtgga  1200
aatttattaa aatcagaaag tatgagatcc tgttatgtta agggaaatnc caaattccca  1260 atttttttg gtcttttag gaaagatgtg ttgtggtaaa agtgttagt ataaaaatga   1320 taatttactt gtagtcttttt atgattacac caatgtattc tagaaatagt tatgtcttag   1380
gaaattgtgg tttaatttttt gacttttaca ggtaagtgca aaggaaaagt ggtttcatga  1440
```

```
aatgttctaa tgtataataa catttacctt cagcctccat ccagaatgga acggagtttt    1500
gagtaatcca gggaagtata tctatatgat cttgatattg ttttataata atttgaagtc    1560
taaaagactg cattttaaa caagttagta ttaatgcgtt ggcccacgta gcaaaaagat     1620
atttgattat cttaaaaatt gttaaatacc gttttcatga aakttctcag tattgtaaca    1680
gcaacttgtc aaacctaagc gatatttgaa tatgatctcc cataatttga aattgaaatc    1740
gtattgtgtg gctctgtata ttctgttaaa aaattaaagg acagaaacct ttctttgtgt    1800
atgcatgttt gaattaaaag aaagtaatgg aagaattgww mrawraaaaa aaaaaaaaaa    1860
a                                                                   1861
```

```
<210> SEQ ID NO 8
<211> LENGTH: 204
<212> TYPE: PRT
<213> ORGANISM: Homo sapiens

<400> SEQUENCE: 8
```

| Met | Val | Cys | Gly | Gly | Phe | Ala | Cys | Ser | Lys | Asn | Cys | Leu | Cys | Ala | Leu |
|---|---|---|---|---|---|---|---|---|---|---|---|---|---|---|---|
| 1 | | | | 5 | | | | | 10 | | | | | 15 | |

Asn Leu Leu Tyr Thr Leu Val Ser Leu Leu Ile Gly Ile Ala Ala
            20                  25                  30

Trp Gly Ile Gly Phe Gly Leu Ile Ser Ser Leu Arg Val Gly Val
        35                  40                  45

Val Ile Ala Val Gly Ile Phe Leu Phe Leu Ile Ala Leu Val Gly Leu
    50                  55                  60

Ile Gly Ala Val Lys His His Gln Val Leu Leu Phe Phe Tyr Met Ile
65                  70                  75                  80

Ile Leu Leu Leu Val Phe Ile Val Gln Phe Ser Val Ser Cys Ala Cys
                85                  90                  95

Leu Ala Leu Asn Gln Glu Gln Gln Gly Gln Leu Leu Glu Val Gly Trp
            100                 105                 110

Asn Asn Thr Ala Ser Ala Arg Asn Asp Ile Gln Arg Asn Leu Asn Cys
        115                 120                 125

Cys Gly Phe Arg Ser Val Asn Pro Asn Asp Thr Cys Leu Ala Ser Cys
    130                 135                 140

Val Lys Ser Asp His Ser Cys Ser Pro Cys Ala Pro Ile Ile Gly Glu
145                 150                 155                 160

Tyr Ala Gly Glu Val Leu Arg Phe Val Gly Gly Ile Gly Leu Phe Phe
                165                 170                 175

Ser Phe Thr Glu Ile Leu Gly Val Trp Leu Thr Tyr Tyr Arg Asn
            180                 185                 190

Gln Lys Asp Pro Arg Ala Asn Pro Ser Ala Phe Leu
        195                 200

```
<210> SEQ ID NO 9
<211> LENGTH: 3579
<212> TYPE: DNA
<213> ORGANISM: Homo sapiens
<220> FEATURE:
<221> NAME/KEY: modified_base
<222> LOCATION: (3350)..(3350)
<223> OTHER INFORMATION: a, c, t or g
<220> FEATURE:
<221> NAME/KEY: modified_base
<222> LOCATION: (3546)..(3546)
<223> OTHER INFORMATION: a, c, t or g

<400> SEQUENCE: 9
```

```
ccgaaaaaat cttagtgtct gcaaaacagg tgggtttaag atttattgat attagggaaa      60
gtgaaattaa tgagctactc aagtttctgt ctttggtcat cactgagagt ctatttccat     120
aggaagaagt ctttgcagag gaaattgaat gctgtctgat gctacaattc atatggatcc     180
tttcctggat tgaagcctga cttttaaaaa aggtttcaat aaattgctta tacctatgaa     240
gagatgcaaa agaaccttca aaataaagca aaggacttga agaaagagaa ggaagacatg     300
aagaaggagga tgtcatttag gtgaagggcc atgctggata aggagctggc tgcctctgtg     360
aacatcctac tcaaggcatc ttcactgctg tacatccttt tgaaatccca gagatcttca     420
gtctccctgt ggattaagga gatgtgcagt atttaaagtg gcttcaggaa ggcatggaag     480
aggactgagt ggggaaagct ttttgtgcat gctgctggct acctccagcg ctgcctcca      540
gcctccatca gctgcactct ggggaagagg aggctgcctt ctacctccca gcatctctgg     600
atttcatgtt cctgtcagca cagaggagct aaatggcctg tagaggctga aggtctgagg     660
ctcctaaagc tggaagaaaa ggctgggcca gtcaggccaa gcaagaacac wrwrywwsty     720
gcctgaagtg ccttccatgg ttaaagggggg cctaaagcag gccacaaagg gccatgaagg    780
aatggttaat atgtaacaga ctgaagggga gaaagccag tgaagatgaa gacttgccca      840
tcttccttga agtcagtaag gcctgcctca ggtgcctagg atgtaattgc tctgctgctt     900
ctcatgggga ggagtggccc tcatgacctt gtttacctgg aagagtgtgg gatgaatgcc     960
tcctcctatg gggactcgca agtgctttag caaaaggata aattgctaat tgtggcattt    1020
cgtggatcag caggattatt tctccttgct aaagaggatt tgttggtcc tgaattctga     1080
ggaggtggga ctaggaatgg gctccatgag cctgtgtatg actcagggaa tattaggact    1140
ttggcacagc ctcatgggtt gggagtaagt cttggctctt ccctagcctg aatgacagac    1200
atcagatcat tctggtgctt tgtccatgaa gatgtagatt ctgagcccac ccaactaatc    1260
ttttcacttg agcacagaaa cagccccggg aatcggacag accgtgtctt ttcaggtttg    1320
cttcacagag ccccaggggt tgacaatagg tgccttggag actgcctgca tgggattttt    1380
taaaaagctt tctttgttaa aggtttgtaa accactcctc tgagcctgtt ttcatttttat   1440
agattattca gggaactgaa ctgcacagag atccagaaag tgggtagtgc aggctgtagt    1500
gctgataact actgtactac ttggatcttt gtgctcccaa ataccaaatg gaagaggatc    1560
tctgagagtc ctttgcaaag atcttgtagg gactttaggc tggggccttc ggaaaattcc    1620
agaggattcc aatggagatt tgagggact gactcagaag aacaaagaga atgataatgg      1680
tgatgtccct gctttttaca acagatcatg ttctgatata tatgcaaatc tgtgtaaagt    1740
aaaccctacc taaaatgtac tggggaccca agatggactg cctgtattgc ttccaggata    1800
aagtccaatt tctagctctg gttttttataa ccttgcttca gctcacctttt tccgtcatca   1860
tccctccat ctcctctccc acgctgggaa atggatggct gcactatact gtgtgatgtt     1920
attgctatgt tcatgccatc ccctctgcct ggaatgccct tctgcatgaa tgcctgtgaa    1980
atgttgttgc tcctttgtat ggcctggctt ccgtggttgg caggaatctc ttctttcgtg    2040
gtattcctgt catctttgtg catcacagtc agctttgtat tcctagcttg taagctactt    2100
gaggataggg gcatgtctga atctatttaa tctcttgcac ctgtttggca aattgatgtt    2160
ttaagtattt aaataactaa agctctctct acagtacata ctcactttg atttatgaat     2220
tgcaaaatt caactttttt ccttgaatat tcttaaagtg agatgaattc caaaggagag     2280
tgttctgtgt gtggccttca ttgagtggtt ttctgttacc agaaagctct tggtggcctt    2340
cctcttccct ggtgtcaagg ttgactgtta taggaaatgg gaggggagag ggccgtttct    2400
```

```
gccacgcatt gtcctaggtt cttaacatta tttaatcctt ataatgcaat gttatcctca    2460
ttttacagat gaaacctgag accaaagaac atgtaacaca taaagtacat tgcagagtta    2520
ggatgtgaac ccaactctga ttctaaacct aatgctctca ctctttcatt cagaggttca    2580
gtcagttctt tgtaggctgt agatccagag aagctgccgt agccaacaat aaagttgtta    2640 gttttttaaaa catctatgtg gtaagttggt ctggcactta aaaatgtatt gtttcccagg    2700
cacggtggtt cacacctgta atcccagcat tttgggaggc cgaggcaggc ggatcattag    2760
gtcaaaagat tgagaccatc ctgaccaaca tggtgaaacc ccgtctctac taaaagttac    2820
aaaaattagc tgggtgtggt ggcgcatgcc tctagtccca gctacctggg aggctgaggc    2880
aggagaattg cttgaaccca ggaggcagag gttgcagtga gccaagatca tgctactgca    2940
ctacagcctg gcaacaaagc gagactctgt ctaaaatata tatatatata tatatatata    3000
tatatattgt ttactactca ccacagatct gcaggagttc actgatctct aggatctgcc    3060
ttaactccaa cttacatgtt ttggtcacta ttacaaactg tcatcccaga atgatgctgc    3120
agaggctagg gctaggacac agaccagtgt ttcccatgtg ggaattccct cccagtattt    3180
cttaggaaat gtatgttttt tgaatccata atccctagaa aaatcagttg aggaaatgag    3240
aagtattgta attattctgt gaatagtaac acttaccatt atggagacat cactagtttg    3300
aaagaatcca acttcatcaa atattaacgt accgagttga aggctacaan gaactgagac    3360
aggagcatag cagagagaaa cggtcaccat ctcattagcc ctattttggg ttgttgtgat    3420
gccattacat ctgtatatct ggccatatca gctgctaatg gtgagttctt gcaaacaaaa    3480
tgatttgata aacaacctac catactttat acaaatctta tggtgttccg agaaataaac    3540
tttggnaagc aaaataaaaa aaaaaamaaa aaaaaaaag                           3579
```

```
<210> SEQ ID NO 10
<211> LENGTH: 79
<212> TYPE: PRT
<213> ORGANISM: Homo sapiens

<400> SEQUENCE: 10
```

Met Asp Gly Cys Thr Ile Leu Cys Asp Val Ile Ala Met Phe Met Pro
1               5                   10                  15

Ser Pro Leu Pro Gly Met Pro Phe Cys Met Asn Ala Cys Glu Met Leu
                20                  25                  30

Leu Leu Leu Cys Met Ala Trp Leu Pro Trp Leu Ala Gly Ile Ser Ser
            35                  40                  45

Phe Val Val Phe Leu Ser Ser Leu Cys Ile Thr Val Ser Phe Val Phe
        50                  55                  60

Leu Ala Cys Lys Leu Leu Glu Asp Arg Gly Met Ser Glu Ser Ile
65                  70                  75

```
<210> SEQ ID NO 11
<211> LENGTH: 1076
<212> TYPE: DNA
<213> ORGANISM: Homo sapiens
<220> FEATURE:
<221> NAME/KEY: modified_base
<222> LOCATION: (708)..(708)
<223> OTHER INFORMATION: a, c, t or g
<220> FEATURE:
<221> NAME/KEY: modified_base
<222> LOCATION: (977)..(977)
<223> OTHER INFORMATION: a, c, t or g
<220> FEATURE:
<221> NAME/KEY: modified_base
```

```
<222> LOCATION: (1003)..(1003)
<223> OTHER INFORMATION: a, c, t or g
<220> FEATURE:
<221> NAME/KEY: modified_base
<222> LOCATION: (1028)..(1028)
<223> OTHER INFORMATION: a, c, t or g
<220> FEATURE:
<221> NAME/KEY: modified_base
<222> LOCATION: (1036)..(1036)
<223> OTHER INFORMATION: a, c, t or g

<400> SEQUENCE: 11
tcgaccacgc gtccggtgcc catctatcag caggctccgg gctgaagatt gcttctcttc      60
tctcctccaa ggtctagtga cggagcccgc gcgcggcgcc accatgcggc agaaggcggt     120
atcgcttttc ttgtgctacc tgctgctctt cacttgcagt ggggtggagg caggtgagaa     180
tgcgggtaag gatgcaggta agaaaaagtg ctccggagagc tcgacagcg gctccgggtt     240
ctggaaggcc ctgaccttca tggccgtcgg aggaggactc gcagtcgccg gctgcccgc     300
gctgggcttc accggcgccg gcatcgcggc caactcggtg gctgcctcgc tgatgagctg     360
gtctgcgatc ctgaatgggg gcggcgtgcc cgccgggggg ctagtggcca cgctgcagag     420
cctcggggct ggtggcagca gcgtcgtcat aggtaatatt ggtgccctga tgggctacgc     480
cacccacaag tatctcgata gtgaggagga tgaggagtag ccagcagctc ccagaacctc     540
ttcttccttc ttggcctaac tcttccagtt aggatctaga actttgcctt tttttttttt     600
tttttttttt ttgagatggg ttctcactat attgtccagg ctagagtgca gtggctattc     660
acagatgcga acatagtaca ctgcagcctc caactcctag cctcaggnga tcctcctgtc     720
tcaacctccc aagtaggatt acaagcatgc gccgacgatg cccagaatcc agaactttgt     780
ctatcactct ccccaacaac ctagatgtga aaacagaata aacttcaccc agaaaacaaa     840
aaaaaaaaaa aagggcggcc gctagactag tctagagaaa aaacctccca cacctccccc     900
tgaacctgaa acataaaatg aatgcaattg ttgttgttaa cttgtttatt gcagcttata     960
atggttacaa ataaagncaa ttagcatcac aaatttcaca aanaaaggca tttttttcac    1020
tgcattcnta gttggngggt ttggtccaaa actcatcaaa tggtatcttt atcatg        1076

<210> SEQ ID NO 12
<211> LENGTH: 138
<212> TYPE: PRT
<213> ORGANISM: Homo sapiens

<400> SEQUENCE: 12

Met Arg Gln Lys Ala Val Ser Leu Phe Leu Cys Tyr Leu Leu Leu Phe
1               5                   10                  15

Thr Cys Ser Gly Val Glu Ala Gly Glu Asn Ala Gly Lys Asp Ala Gly
            20                  25                  30

Lys Lys Lys Cys Ser Glu Ser Ser Asp Ser Gly Ser Gly Phe Trp Lys
        35                  40                  45

Ala Leu Thr Phe Met Ala Val Gly Gly Gly Leu Ala Val Ala Gly Leu
    50                  55                  60

Pro Ala Leu Gly Phe Thr Gly Ala Gly Ile Ala Ala Asn Ser Val Ala
65                  70                  75                  80

Ala Ser Leu Met Ser Trp Ser Ala Ile Leu Asn Gly Gly Gly Val Pro
                85                  90                  95

Ala Gly Gly Leu Val Ala Thr Leu Gln Ser Leu Gly Ala Gly Gly Ser
            100                 105                 110

Ser Val Val Ile Gly Asn Ile Gly Ala Leu Met Gly Tyr Ala Thr His
```

```
                   115                 120                 125
Lys Tyr Leu Asp Ser Glu Glu Asp Glu Glu
    130                 135

<210> SEQ ID NO 13
<211> LENGTH: 1352
<212> TYPE: DNA
<213> ORGANISM: Homo sapiens
<220> FEATURE:
<221> NAME/KEY: modified_base
<222> LOCATION: (1139)..(1140)
<223> OTHER INFORMATION: a, c, t or g
<220> FEATURE:
<221> NAME/KEY: modified_base
<222> LOCATION: (1150)..(1150)
<223> OTHER INFORMATION: a, c, t or g
<220> FEATURE:
<221> NAME/KEY: modified_base
<222> LOCATION: (1155)..(1155)
<223> OTHER INFORMATION: a, c, t or g
<220> FEATURE:
<221> NAME/KEY: modified_base
<222> LOCATION: (1166)..(1166)
<223> OTHER INFORMATION: a, c, t or g
<220> FEATURE:
<221> NAME/KEY: modified_base
<222> LOCATION: (1171)..(1171)
<223> OTHER INFORMATION: a, c, t or g
<220> FEATURE:
<221> NAME/KEY: modified_base
<222> LOCATION: (1181)..(1181)
<223> OTHER INFORMATION: a, c, t or g
<220> FEATURE:
<221> NAME/KEY: modified_base
<222> LOCATION: (1186)..(1186)
<223> OTHER INFORMATION: a, c, t or g
<220> FEATURE:
<221> NAME/KEY: modified_base
<222> LOCATION: (1189)..(1189)
<223> OTHER INFORMATION: a, c, t or g
<220> FEATURE:
<221> NAME/KEY: modified_base
<222> LOCATION: (1212)..(1212)
<223> OTHER INFORMATION: a, c, t or g
<220> FEATURE:
<221> NAME/KEY: modified_base
<222> LOCATION: (1214)..(1214)
<223> OTHER INFORMATION: a, c, t or g
<220> FEATURE:
<221> NAME/KEY: modified_base
<222> LOCATION: (1252)..(1252)
<223> OTHER INFORMATION: a, c, t or g
<220> FEATURE:
<221> NAME/KEY: modified_base
<222> LOCATION: (1311)..(1311)
<223> OTHER INFORMATION: a, c, t or g

<400> SEQUENCE: 13
tcaccacgcg tccggaagct ccgggtgtcg cggggcggg  aggaattaag ggagggagag      60
aggcgcgcgg gtgaaaggcg cattgatgca gcctgcggcg gcctcggagc gcggcggagc    120
cagacgctga ccacgttcct ctcctcggtc tcctccgcct ccagctccgc gctgcccggc    180
agccgggagc catgcgaccc cagggccccg ccgcctcccc gcagcggctc cgcggcctcc    240
tgctgctcct gctgctgcag ctgcccgcgc cgtcgagcgc ctctgagatc cccaagggga    300
agcaaaaggc gcagctccgg cagagggagg tggtggacct gtataatgga atgtgcttac    360
aagggccagc aggagtgcct ggtcgagacg ggagccctgg ggccaatggc attccgggta    420
cacctgggat cccaggtcgg gatggattca aaggagaaaa gggggaatgt ctgagggaaa    480
gctttgagga gtcctggaca cccaactaca agcagtgttc atggagttca ttgaattatg    540
```

```
gcataaatct tgggaaaatt gcggagtgta catttacaaa gatgcgttca aatagtgctc    600
taagagtttt gttcagtggc tcacttcggc taaaatgcag aaatgcatgc tgtcagcgtt    660
ggtatttcac attcaatgga gctgaatgtt caggacctct tcccattgaa gctataattt    720
atttggacca aggaagccct gaaatgaatt caacaattaa tattcatcgc acttcttctg    780
tggaaggact tgtgaagga attggtgctg gattagtgga tgttgctatc tgggttggca    840
cttgttcaga ttacccaaaa ggagatgctt ctactggatg gaattcagtt tctcgcatca    900
ttattgaaga actaccaaaa taaatgcttt aattttcatt tgctacctct tttttatta    960 tgccttggaa tggttcactt aaatgacatt ttaaataagt ttatgtatac atctgaatga   1020
aaagcaaagc taaatatgtt tacagaccaa agtgtgattt cccctgtttt ttaaatctag   1080
cattattcat tttgcttcaa tcaaaagtgg tttcaatatt ttttttagtt ggttagaann   1140
ctttcttcan agtcncattc tctcanccta naatttggaa nattgntgng gtcttttgtt   1200
ttttctctta gnanagcatt tttaaaaaaa tataaaagct accaatcttt gnacaatttg   1260
taaatgttaa gaattttttt tatatctgtt aaataaaaat tatttccacc naaaaaaaaa   1320
aaaaaaaaaa aaaaaaaaa gggcggccgc ta                                  1352
```

<210> SEQ ID NO 14
<211> LENGTH: 243
<212> TYPE: PRT
<213> ORGANISM: Homo sapiens

<400> SEQUENCE: 14

```
Met Arg Pro Gln Gly Pro Ala Ala Ser Pro Gln Arg Leu Arg Gly Leu
1               5                   10                  15

Leu Leu Leu Leu Leu Leu Gln Leu Pro Ala Pro Ser Ser Ala Ser Glu
            20                  25                  30

Ile Pro Lys Gly Lys Gln Lys Ala Gln Leu Arg Gln Arg Glu Val Val
        35                  40                  45

Asp Leu Tyr Asn Gly Met Cys Leu Gln Gly Pro Ala Gly Val Pro Gly
    50                  55                  60

Arg Asp Gly Ser Pro Gly Ala Asn Gly Ile Pro Gly Thr Pro Gly Ile
65                  70                  75                  80

Pro Gly Arg Asp Gly Phe Lys Gly Glu Lys Gly Glu Cys Leu Arg Glu
                85                  90                  95

Ser Phe Glu Glu Ser Trp Thr Pro Asn Tyr Lys Gln Cys Ser Trp Ser
            100                 105                 110

Ser Leu Asn Tyr Gly Ile Asn Leu Gly Lys Ile Ala Glu Cys Thr Phe
        115                 120                 125

Thr Lys Met Arg Ser Asn Ser Ala Leu Arg Val Leu Phe Ser Gly Ser
    130                 135                 140

Leu Arg Leu Lys Cys Arg Asn Ala Cys Cys Gln Arg Trp Tyr Phe Thr
145                 150                 155                 160

Phe Asn Gly Ala Glu Cys Ser Gly Pro Leu Pro Ile Glu Ala Ile Ile
                165                 170                 175

Tyr Leu Asp Gln Gly Ser Pro Glu Met Asn Ser Thr Ile Asn Ile His
            180                 185                 190

Arg Thr Ser Ser Val Glu Gly Leu Cys Glu Gly Ile Gly Ala Gly Leu
        195                 200                 205

Val Asp Val Ala Ile Trp Val Gly Thr Cys Ser Asp Tyr Pro Lys Gly
    210                 215                 220

Asp Ala Ser Thr Gly Trp Asn Ser Val Ser Arg Ile Ile Ile Glu Glu
```

Leu Pro Lys

<210> SEQ ID NO 15
<211> LENGTH: 2142
<212> TYPE: DNA
<213> ORGANISM: Homo sapiens

<400> SEQUENCE: 15

```
ggagtcgacc cacgcgtccg ccccggggga cccgccgccc agctcccgag ggtgcggcag      60
cctctggcca ctcagccggg gccgagaggg agctgccggg cggggaggcg ccgcaggcac     120
ccggcgggca gggcggggca gggcaagacg gccgcctccg caagtgccac ccggcccacc     180
cgggcctctc ccttctgccy srgrcgtcag cggacsgggc gctcgcgggc cggggctgta     240
tggggctccc gcgcgggtcg ttcttctggc tgctgctcct gctcacggct gcctgctcgg     300
ggctcctctt tgccctgtac ttctcggcg tgcagcggta cccggggcca gcggccggag      360
ccagggacac cacatcattt gaagcattct ttcaatccaa ggcatcgaat tcttggacag     420
gaaagggcca ggcctgccga cacctgcttc acctggccat tcagcggcac ccccacttcc     480
gtggcctgtt caatctctcc attccagtgc tgctgtgggg ggacctcttc accccagcgc     540
tctgggaccg cctgagccaa cacaaagccc cgtatggctg gcggggctc tctcaccaag     600 tcatcgcctc caccctgagc cttctgaacg gctcagagag tgccaagctg tttgccccgc     660
ccagggacac ccctccaaag tgtatccggt gtgccgtggt gggcaacgga ggcattctga     720
atgggtcccg ccagggtccc aacatcgatg cccatgacta tgtattcaga ctcaatggag     780
ctgtgatcaa aggcttcgag cgcgatgtgg gcaccaagac ttccttctat ggtttcactg     840
tgaacacgat gaagaactcc ctcgtctcct actggaatct gggcttcacc tccgtgccac     900
aaggacagga cctgcagtat atcttcatcc cctcagacat ccgcgactat gtgatgctga     960
gatcggccat tctgggcgtg cctgtccctg agggcctaga taagggggac aggccgcacg    1020 cctatttttgg accagaagcc tctgccagta aattcaagct gctacatccg gacttcatca    1080
gctacctgac agaaaggttc ttgaaatcaa agttgattaa cacacatttt ggagaccctat    1140 atatgcctag taccggggct ctcatgctgc tgacagcttt gcatacctgt gaccaggtca    1200
gtgcctatgg attcatcaca agcaactact ggaaattttc cgaccactat ttcgaacgaa    1260
aaatgaagcc attgatattt tatgcaaacc acgatctgtc cctggaagct gccctgtgga    1320
gggacctgca caaggccggc atccttcagc tgtaccagcg ctgaccccaa tgcactgagc    1380
cctttgcttc ttcaagagtt gcggcctgat cctctcaagt ggccaaaagc ttttttaact    1440
tttcaatctt caccttccct tgccaacaga gggcactggg gtgaattcaa gattttcatc    1500
gaggtctgtt caatatagga cacccagct tgtccttggc tcatccaaga actcttctgt      1560
atctaaaaca atacatctca atcttggcca agggaaaacg gactgctttg ctggattggc    1620
actgagcaac tttaggaaat gtcggtggag tgttcagcaa gatcagacag cagtccaggt    1680
caaaggcaaa cacacacgct ccagcccaaa tcctcctggt ggcacatcct accccagatg    1740
ctaaagtgat tcaaggactc caggacacct cttaagagcc tttctaagaa catgataggc    1800
ttacttctgc tccataataa agtgggagaa aaaagccaga atataaaact taaractaga    1860
taactgcgya satgatggac catttttttt ttttggctgg gtagagaaat catataaaac    1920
gcaggctgtt tagcatggag atgactctca gaacactggr agggtctggc acttgatggg    1980
ggttagttgc ttggcagcct gcctgaagtc ccattagaga tgtatcaccc ccttgtcacc    2040
```
aacaggatga tgtccccagg taataaacct tcatcctcat aaaaaaaaaa aaaaaaaaaa    2100
aaaaaaaaaa aaaaaaaaaa aagggcggcc gctagactag tc                       2142

<210> SEQ ID NO 16
<211> LENGTH: 374
<212> TYPE: PRT
<213> ORGANISM: Homo sapiens

<400> SEQUENCE: 16

```
Met Gly Leu Pro Arg Gly Ser Phe Phe Trp Leu Leu Leu Leu Thr
 1               5                  10                  15

Ala Ala Cys Ser Gly Leu Leu Phe Ala Leu Tyr Phe Ser Ala Val Gln
             20                  25                  30

Arg Tyr Pro Gly Pro Ala Ala Gly Ala Arg Asp Thr Thr Ser Phe Glu
         35                  40                  45

Ala Phe Phe Gln Ser Lys Ala Ser Asn Ser Trp Thr Gly Lys Gly Gln
     50                  55                  60

Ala Cys Arg His Leu Leu His Leu Ala Ile Gln Arg His Pro His Phe
 65                  70                  75                  80

Arg Gly Leu Phe Asn Leu Ser Ile Pro Val Leu Leu Trp Gly Asp Leu
                 85                  90                  95

Phe Thr Pro Ala Leu Trp Asp Arg Leu Ser Gln His Lys Ala Pro Tyr
            100                 105                 110

Gly Trp Arg Gly Leu Ser His Gln Val Ile Ala Ser Thr Leu Ser Leu
        115                 120                 125

Leu Asn Gly Ser Glu Ser Ala Lys Leu Phe Ala Pro Pro Arg Asp Thr
    130                 135                 140

Pro Pro Lys Cys Ile Arg Cys Ala Val Val Gly Asn Gly Gly Ile Leu
145                 150                 155                 160

Asn Gly Ser Arg Gln Gly Pro Asn Ile Asp Ala His Asp Tyr Val Phe
                165                 170                 175

Arg Leu Asn Gly Ala Val Ile Lys Gly Phe Glu Arg Asp Val Gly Thr
            180                 185                 190

Lys Thr Ser Phe Tyr Gly Phe Thr Val Asn Thr Met Lys Asn Ser Leu
        195                 200                 205

Val Ser Tyr Trp Asn Leu Gly Phe Thr Ser Val Pro Gln Gly Gln Asp
    210                 215                 220

Leu Gln Tyr Ile Phe Ile Pro Ser Asp Ile Arg Asp Tyr Val Met Leu
225                 230                 235                 240

Arg Ser Ala Ile Leu Gly Val Pro Val Pro Glu Gly Leu Asp Lys Gly
                245                 250                 255

Asp Arg Pro His Ala Tyr Phe Gly Pro Glu Ala Ser Ala Ser Lys Phe
            260                 265                 270

Lys Leu Leu His Pro Asp Phe Ile Ser Tyr Leu Thr Glu Arg Phe Leu
        275                 280                 285

Lys Ser Lys Leu Ile Asn Thr His Phe Gly Asp Leu Tyr Met Pro Ser
    290                 295                 300

Thr Gly Ala Leu Met Leu Leu Thr Ala Leu His Thr Cys Asp Gln Val
305                 310                 315                 320

Ser Ala Tyr Gly Phe Ile Thr Ser Asn Tyr Trp Lys Phe Ser Asp His
                325                 330                 335

Tyr Phe Glu Arg Lys Met Lys Pro Leu Ile Phe Tyr Ala Asn His Asp
            340                 345                 350
```

Leu Ser Leu Glu Ala Ala Leu Trp Arg Asp Leu His Lys Ala Gly Ile
        355                 360                 365

Leu Gln Leu Tyr Gln Arg
    370

<210> SEQ ID NO 17
<211> LENGTH: 1707
<212> TYPE: DNA
<213> ORGANISM: Homo sapiens

<400> SEQUENCE: 17

| | | | | | |
|---|---|---|---|---|---|
| tacttaggga | gtcgaccacg | cgtccgacta | gttctagatc | gcgggcaaag | atggcggcgg | 60 |
| ccaggtgttg | gaggcctttg | ctacgcggtc | cgaggctttc | attgcacacc | gcggctaatg | 120 |
| ccgccgccac | ggctacagaa | acgacctgcc | aagacgtcgc | ggcgaccccc | gtcgcgcggt | 180 |
| acccgccgat | tgtggcctcc | atgacagccg | acagcaaagc | tgcacggctg | cggcggatcg | 240 |
| agcgctggca | ggcgacggtg | cacgctgcgg | agtcggtaga | cgagaagctg | cgaatcctca | 300 |
| ccaagatgca | gtttatgaag | tacatggttt | acccgcagac | cttcgcgctg | aatgccgacc | 360 |
| gctggtacca | gtacttcacc | aagaccgtgt | tcctgtcggg | tctgccgccg | ccccagcgg | 420 |
| agcccgagcc | cgagcccgaa | cccgaacctg | aacctgcgct | ggacctcgcg | gcgctgcgtg | 480 |
| cggtcgcctg | cgactgcctg | ctgcaggagc | acttctacct | gcggcgcagg | cggcgcgtgc | 540 |
| accgttacga | ggagagcgag | gtcatatctt | tgcccttcct | ggatcagctg | gtgtcaaccc | 600 |
| tcgtgggcct | cctcagccca | cacaacccgg | ccctggccgc | tgccgcccctc | gattatagat | 660 |
| gcccagttca | ttttttactgg | gtgcgtggtg | aagaaattat | tcctcgtggt | catcgaagag | 720 |
| gtcgaattga | tgacttgcga | taccagatag | atgataaacc | aaacaaccag | attcgaatat | 780 |
| ccaagcaact | cgcagagttt | gtgccattgg | attattctgt | tcctatagaa | atccccacta | 840 |
| taaaatgtaa | accagacaaa | cttccattat | tcaaacggca | gtatgaaaac | cacatatttg | 900 |
| ttggctcaaa | aactgcagat | ccttgctgtt | acggtcacac | ccagtttcat | ctgttacctg | 960 |
| acaaattaag | aagggaaagg | cttttgagac | aaaactgtgc | tgatcagata | gaagttgttt | 1020 |
| ttagagctaa | tgctattgca | agcctttttg | cttggactgg | agcacaagct | atgtatcaag | 1080 |
| gattctggag | tgaagcagat | gttactcgac | cttttgtctc | ccaggctgtg | atcacagatg | 1140 |
| gaaaatactt | ttcctttttc | tgctaccagc | taaatacttt | ggcactgact | acacaagctg | 1200 |
| atcaaaataa | ccctcgtaaa | aatatatgtt | ggggtacaca | aagtaagcct | ctttatgaaa | 1260 |
| caattgagga | taatgatgtg | aaaggtttta | atgatgatgt | tctacttcag | atagttcact | 1320 |
| ttctactgaa | tagaccaaaa | gaagaaaaat | cacagctgtt | ggaaaactga | aaaagcatat | 1380 |
| ttgattgaga | actgtgggaa | tatttaaatt | ttactgaagg | aacaataatg | atgagatttg | 1440 |
| taactgtcaa | ctattaaata | cattgatttt | tgagacaaat | aaaaaaatg | tcaacctgtt | 1500 |
| attagatctc | ttactctgct | caaattcatc | actgaaagat | ttaattttag | ttaccttttg | 1560 |
| ttgatttaaa | aataattgca | tttgtatatt | gctaactgat | aagacaaatt | gagttattga | 1620 |
| gctattaaat | gcacatttta | atataaatgc | agaaatccca | aataaaatgc | taacatactg | 1680 |
| aattcagtaa | ttaaaagaac | ccactgc | | | | 1707 |

<210> SEQ ID NO 18
<211> LENGTH: 439
<212> TYPE: PRT
<213> ORGANISM: Homo sapiens

<400> SEQUENCE: 18

-continued

```
Met Ala Ala Ala Arg Cys Trp Arg Pro Leu Leu Arg Gly Pro Arg Leu
1               5                   10                  15

Ser Leu His Thr Ala Ala Asn Ala Ala Ala Thr Ala Thr Glu Thr Thr
            20                  25                  30

Cys Gln Asp Val Ala Ala Thr Pro Val Ala Arg Tyr Pro Pro Ile Val
        35                  40                  45

Ala Ser Met Thr Ala Asp Ser Lys Ala Ala Arg Leu Arg Arg Ile Glu
    50                  55                  60

Arg Trp Gln Ala Thr Val His Ala Ala Glu Ser Val Asp Glu Lys Leu
65              70                  75                  80

Arg Ile Leu Thr Lys Met Gln Phe Met Lys Tyr Met Val Tyr Pro Gln
                85                  90                  95

Thr Phe Ala Leu Asn Ala Asp Arg Trp Tyr Gln Tyr Phe Thr Lys Thr
            100                 105                 110

Val Phe Leu Ser Gly Leu Pro Pro Pro Ala Glu Pro Glu Pro Glu
        115                 120                 125

Pro Glu Pro Glu Pro Glu Pro Ala Leu Asp Leu Ala Ala Leu Arg Ala
    130                 135                 140

Val Ala Cys Asp Cys Leu Leu Gln Glu His Phe Tyr Leu Arg Arg Arg
145                 150                 155                 160

Arg Arg Val His Arg Tyr Glu Glu Ser Glu Val Ile Ser Leu Pro Phe
                165                 170                 175

Leu Asp Gln Leu Val Ser Thr Leu Val Gly Leu Leu Ser Pro His Asn
            180                 185                 190

Pro Ala Leu Ala Ala Ala Ala Leu Asp Tyr Arg Cys Pro Val His Phe
        195                 200                 205

Tyr Trp Val Arg Gly Glu Glu Ile Ile Pro Arg Gly His Arg Arg Gly
    210                 215                 220

Arg Ile Asp Asp Leu Arg Tyr Gln Ile Asp Asp Lys Pro Asn Asn Gln
225                 230                 235                 240

Ile Arg Ile Ser Lys Gln Leu Ala Glu Phe Val Pro Leu Asp Tyr Ser
                245                 250                 255

Val Pro Ile Glu Ile Pro Thr Ile Lys Cys Lys Pro Asp Lys Leu Pro
            260                 265                 270

Leu Phe Lys Arg Gln Tyr Glu Asn His Ile Phe Val Gly Ser Lys Thr
        275                 280                 285

Ala Asp Pro Cys Cys Tyr Gly His Thr Gln Phe His Leu Leu Pro Asp
    290                 295                 300

Lys Leu Arg Arg Glu Arg Leu Leu Arg Gln Asn Cys Ala Asp Gln Ile
305                 310                 315                 320

Glu Val Val Phe Arg Ala Asn Ala Ile Ala Ser Leu Phe Ala Trp Thr
                325                 330                 335

Gly Ala Gln Ala Met Tyr Gln Gly Phe Trp Ser Glu Ala Asp Val Thr
            340                 345                 350

Arg Pro Phe Val Ser Gln Ala Val Ile Thr Asp Gly Lys Tyr Phe Ser
        355                 360                 365

Phe Phe Cys Tyr Gln Leu Asn Thr Leu Ala Leu Thr Thr Gln Ala Asp
    370                 375                 380

Gln Asn Asn Pro Arg Lys Asn Ile Cys Trp Gly Thr Gln Ser Lys Pro
385                 390                 395                 400

Leu Tyr Glu Thr Ile Glu Asp Asn Asp Val Lys Gly Phe Asn Asp Asp
                405                 410                 415
```

Val Leu Leu Gln Ile Val His Phe Leu Leu Asn Arg Pro Lys Glu Glu
        420                 425                 430

Lys Ser Gln Leu Leu Glu Asn
        435

<210> SEQ ID NO 19
<211> LENGTH: 2844
<212> TYPE: DNA
<213> ORGANISM: Homo sapiens
<220> FEATURE:
<221> NAME/KEY: modified_base
<222> LOCATION: (767)..(767)
<223> OTHER INFORMATION: a, c, t or g
<220> FEATURE:
<221> NAME/KEY: modified_base
<222> LOCATION: (2839)..(2839)
<223> OTHER INFORMATION: a, c, t or g
<220> FEATURE:
<221> NAME/KEY: modified_base
<222> LOCATION: (2842)..(2842)
<223> OTHER INFORMATION: a, c, t or g

<400> SEQUENCE: 19

```
cgacccacgc cgtccgggcg gcggcgtccg caggagcccg ggaggcggag gcgggaggcg      60
gcggcggcgc gcggagacgc agcagcggca gcggcagcat gtcggccggc ggagcgtcag     120
tcccgccgcc cccgaacccc gccgtgtcct tcccgccgcc ccgggtcacc ctgcccgccg     180
gccccgacat cctgcggacc tactcgggcg ccttcgtctg cctggagatt ctgttcgggg     240
gtcttgtctg gattttggtt gcctcctcca atgttcctct acctctacta caaggatggg     300
tcatgttttgt gtccgtgaca gcgttttttct tttcgctcct ctttctgggc atgttcctct     360
ctggcatggt ggctcaaatt gatgctaact ggaacttcct ggattttgcc taccatttta     420
cagtatttgt cttctatttt ggagcctttt tattggaagc agcagccaca tccctgcatg     480
atttgcattg caatacaacc ataaccgggc agccactcct gagtgataac cagtataaca     540
taaacgtagc agcctcaatt tttgccttta tgacgacagc ttgttatggt tgcagtttgg     600
gtctggcttt acgaagatgg cgaccgtaac actccttaga aactggcagt cgtatgttag     660
tttcacttgt ctactttata tgtctgatca atttggatac catttttgtcc agatgcaaaa     720
acattccaaa agtaatgtgt ttagtagaga gagactctaa gctcaangtt ctggtttatt     780
tcatggatgg aatgttaatt ttattatgat attaaagaaa tggcctttta ttttacatct     840
ctcccctttt tcccttttccc cctttatttt cctcctttttc tttctgaaag tttccttttta     900
tgtccataaa atacaaatat attgttcata aaaaattagt atcccttttg tttggttgct     960
gagtcacctg aaccttaatt ttaattggta attacagccc ctaaaaaaaa cacatttcaa    1020
ataggcttcc cactaaactc tatattttag tgtaaaccag gaattggcac acttttttta    1080
gaatgggcca gatggtaaat atttatgctt cacggtccat acagtctctg tcacaactat    1140
tcagttctgc tagtatagcg tgaaagcagc tatacacaat acagaaatga atgagtgtgg    1200
ttatgttcta ataaaactta tttataaaaa caaggggagg ctgggtttag cctgtgggcc    1260
atagtttgtc aaccactggt gtaaaacctt agttatatat gatctgcatt ttcttgaact    1320
gatcattgaa aacttataaa cctaacagaa aagccacata atatttagtg tcattatgca    1380
ataatcacat tgcctttgtg ttaatagtca aatacttacc tttggagaat acttaccttt    1440
ggaggaatgt ataaaatttc tcaggcagag tcctggatat aggaaaaagt aatttatgaa    1500
gtaaacttca gttgcttaat caaactaatg atagtctaac aactgagcaa gatcctcatc    1560
tgagagtgct taaaatggga tccccagaga ccattaacca atactggaac tggtatctag    1620
```

-continued

```
ctactgatgt cttactttga gtttatttat gcttcagaat acagttgttt gccctgtgca    1680
taatataccc atatttgtgt gtggatatgt gaagcttttc caaatagagc tctcagaaga    1740
attaagtttt tacttctaat tatttttgcat tactttgagt taaatttgaa tagagtatta   1800
aatataaagt tgtagattct tatgtgtttt tgtattagcc cagacatctg taatgttttt    1860
gcactggtga cagacaaaat ctgttttaaa atcatatcca gcacaaaaac tatttctggc    1920
tgaatagcac agaaaagtat tttaacctac ctgtagagat cctcgtcatg gaaaggtgcc    1980
aaactgtttt gaatggaagg acaagtaaga gtgaggccac agttcccacc acacgagggc    2040
ttttgtattg ttctactttt tcagcccttt actttctggc tgaagcatcc ccttggagtg    2100
ccatgtataa gttgggctat tagagttcat ggaacataga acaaccatga atgagtggca    2160
tgatccgtgc ttaatgatca agtgttactt atctaataat cctctagaaa gaaccctgtt    2220
agatcttggt ttgtgataaa aatataaaga cagaagacat gaggaaaaac aaaaggtttg    2280
aggaaatcag gcatatgact ttatacttaa catcagatct tttctataat atcctactac    2340
tttggttttc ctagctccat accacacacc taaacctgta ttatgaatta catattacaa    2400
agtcataaat gtgccatatg gatatacagt acattctagt tggaatcgtt tactctgcta    2460
gaatttaggt gtgagatttt ttgtttccca ggtatagcag gcttatgttt ggtggcatta    2520
aattggtttc tttaaaaatgc tttggtggca cttttgtaaa cagattgctt ctagattgtt    2580
acaaaccaag cctaagacac atctgtgaat acttagattt gtagcttaat cacattctag    2640
acttgtgagt tgaatgacaa agcagttgaa caaaaattat ggcatttaag aatttaacat    2700
gtcttagctg taaaaatgag aaagtgttgg ttggttttaa aatctggtaa ctccatgatg    2760
aaaagaaatt tatttatac gtgttatgtc tctaataaag tattcatttg ataaaaaaaa    2820
aaaaaaaaaa aaaaaaaang tnhg                                           2844
```

<210> SEQ ID NO 20
<211> LENGTH: 176
<212> TYPE: PRT
<213> ORGANISM: Homo sapiens

<400> SEQUENCE: 20

```
Met Ser Ala Gly Gly Ala Ser Val Pro Pro Pro Asn Pro Ala Val
1               5                   10                  15

Ser Phe Pro Pro Pro Arg Val Thr Leu Pro Ala Gly Pro Asp Ile Leu
                20                  25                  30

Arg Thr Tyr Ser Gly Ala Phe Val Cys Leu Glu Ile Leu Phe Gly Gly
            35                  40                  45

Leu Val Trp Ile Leu Val Ala Ser Ser Asn Val Pro Leu Pro Leu Leu
        50                  55                  60

Gln Gly Trp Val Met Phe Val Ser Val Thr Ala Phe Phe Phe Ser Leu
65                  70                  75                  80

Leu Phe Leu Gly Met Phe Leu Ser Gly Met Val Ala Gln Ile Asp Ala
                85                  90                  95

Asn Trp Asn Phe Leu Asp Phe Ala Tyr His Phe Thr Val Phe Val Phe
            100                 105                 110

Tyr Phe Gly Ala Phe Leu Leu Glu Ala Ala Thr Ser Leu His Asp
        115                 120                 125

Leu His Cys Asn Thr Thr Ile Thr Gly Gln Pro Leu Leu Ser Asp Asn
    130                 135                 140

Gln Tyr Asn Ile Asn Val Ala Ala Ser Ile Phe Ala Phe Met Thr Thr
```

```
                145                 150                 155                 160
Ala Cys Tyr Gly Cys Ser Leu Gly Leu Ala Leu Arg Arg Trp Arg Pro
                    165                 170                 175

<210> SEQ ID NO 21
<211> LENGTH: 12642
<212> TYPE: DNA
<213> ORGANISM: Homo sapiens
<220> FEATURE:
<221> NAME/KEY: modified_base
<222> LOCATION: (7145)..(7145)
<223> OTHER INFORMATION: a, c, t or g
<220> FEATURE:
<221> NAME/KEY: modified_base
<222> LOCATION: (7158)..(7158)
<223> OTHER INFORMATION: a, c, t or g
<220> FEATURE:
<221> NAME/KEY: modified_base
<222> LOCATION: (7460)..(7463)
<223> OTHER INFORMATION: a, c, t or g
<220> FEATURE:
<221> NAME/KEY: modified_base
<222> LOCATION: (7467)..(7467)
<223> OTHER INFORMATION: a, c, t or g
<220> FEATURE:
<221> NAME/KEY: modified_base
<222> LOCATION: (7717)..(7717)
<223> OTHER INFORMATION: a, c, t or g
<220> FEATURE:
<221> NAME/KEY: modified_base
<222> LOCATION: (7756)..(7756)
<223> OTHER INFORMATION: a, c, t or g
<220> FEATURE:
<221> NAME/KEY: modified_base
<222> LOCATION: (7795)..(7795)
<223> OTHER INFORMATION: a, c, t or g
<220> FEATURE:
<221> NAME/KEY: modified_base
<222> LOCATION: (7799)..(7799)
<223> OTHER INFORMATION: a, c, t or g
<220> FEATURE:
<221> NAME/KEY: modified_base
<222> LOCATION: (7803)..(7803)
<223> OTHER INFORMATION: a, c, t or g
<220> FEATURE:
<221> NAME/KEY: modified_base
<222> LOCATION: (7818)..(7818)
<223> OTHER INFORMATION: a, c, t or g
<220> FEATURE:
<221> NAME/KEY: modified_base
<222> LOCATION: (7822)..(7822)
<223> OTHER INFORMATION: a, c, t or g
<220> FEATURE:
<221> NAME/KEY: modified_base
<222> LOCATION: (7833)..(7833)
<223> OTHER INFORMATION: a, c, t or g
<220> FEATURE:
<221> NAME/KEY: modified_base
<222> LOCATION: (7842)..(7843)
<223> OTHER INFORMATION: a, c, t or g
<220> FEATURE:
<221> NAME/KEY: modified_base
<222> LOCATION: (7852)..(7852)
<223> OTHER INFORMATION: a, c, t or g
<220> FEATURE:
<221> NAME/KEY: modified_base
<222> LOCATION: (7860)..(7860)
<223> OTHER INFORMATION: a, c, t or g
<220> FEATURE:
<221> NAME/KEY: modified_base
<222> LOCATION: (7864)..(7864)
<223> OTHER INFORMATION: a, c, t or g
<220> FEATURE:
<221> NAME/KEY: modified_base
<222> LOCATION: (7871)..(7871)
<223> OTHER INFORMATION: a, c, t or g
<220> FEATURE:
```

```
<221> NAME/KEY: modified_base
<222> LOCATION: (7876)..(7876)
<223> OTHER INFORMATION: a, c, t or g
<220> FEATURE:
<221> NAME/KEY: modified_base
<222> LOCATION: (8141)..(8141)
<223> OTHER INFORMATION: a, c, t or g
<220> FEATURE:
<221> NAME/KEY: modified_base
<222> LOCATION: (11251)..(11251)
<223> OTHER INFORMATION: a, c, t or g
<220> FEATURE:
<221> NAME/KEY: modified_base
<222> LOCATION: (11283)..(11283)
<223> OTHER INFORMATION: a, c, t or g
<220> FEATURE:
<221> NAME/KEY: modified_base
<222> LOCATION: (11294)..(11294)
<223> OTHER INFORMATION: a, c, t or g
<220> FEATURE:
<221> NAME/KEY: modified_base
<222> LOCATION: (11301)..(11301)
<223> OTHER INFORMATION: a, c, t or g
<220> FEATURE:
<221> NAME/KEY: modified_base
<222> LOCATION: (11309)..(11309)
<223> OTHER INFORMATION: a, c, t or g
<220> FEATURE:
<221> NAME/KEY: modified_base
<222> LOCATION: (11336)..(11336)
<223> OTHER INFORMATION: a, c, t or g
<220> FEATURE:
<221> NAME/KEY: modified_base
<222> LOCATION: (11341)..(11341)
<223> OTHER INFORMATION: a, c, t or g
<220> FEATURE:
<221> NAME/KEY: modified_base
<222> LOCATION: (11345)..(11345)
<223> OTHER INFORMATION: a, c, t or g
<220> FEATURE:
<221> NAME/KEY: modified_base
<222> LOCATION: (11352)..(11352)
<223> OTHER INFORMATION: a, c, t or g
<220> FEATURE:
<221> NAME/KEY: modified_base
<222> LOCATION: (11357)..(11357)
<223> OTHER INFORMATION: a, c, t or g
<220> FEATURE:
<221> NAME/KEY: modified_base
<222> LOCATION: (11363)..(11363)
<223> OTHER INFORMATION: a, c, t or g
<220> FEATURE:
<221> NAME/KEY: modified_base
<222> LOCATION: (11373)..(11373)
<223> OTHER INFORMATION: a, c, t or g
<220> FEATURE:
<221> NAME/KEY: modified_base
<222> LOCATION: (11380)..(11380)
<223> OTHER INFORMATION: a, c, t or g
<220> FEATURE:
<221> NAME/KEY: modified_base
<222> LOCATION: (11391)..(11391)
<223> OTHER INFORMATION: a, c, t or g
<220> FEATURE:
<221> NAME/KEY: modified_base
<222> LOCATION: (11399)..(11399)
<223> OTHER INFORMATION: a, c, t or g
<220> FEATURE:
<221> NAME/KEY: modified_base
<222> LOCATION: (11402)..(11402)
<223> OTHER INFORMATION: a, c, t or g
<220> FEATURE:
<221> NAME/KEY: modified_base
<222> LOCATION: (11412)..(11412)
<223> OTHER INFORMATION: a, c, t or g
<220> FEATURE:
<221> NAME/KEY: modified_base
<222> LOCATION: (11424)..(11424)
<223> OTHER INFORMATION: a, c, t or g
```

-continued

```
<220> FEATURE:
<221> NAME/KEY: modified_base
<222> LOCATION: (11427)..(11428)
<223> OTHER INFORMATION: a, c, t or g
<220> FEATURE:
<221> NAME/KEY: modified_base
<222> LOCATION: (11435)..(11435)
<223> OTHER INFORMATION: a, c, t or g
<220> FEATURE:
<221> NAME/KEY: modified_base
<222> LOCATION: (11445)..(11445)
<223> OTHER INFORMATION: a, c, t or g
<220> FEATURE:
<221> NAME/KEY: modified_base
<222> LOCATION: (11461)..(11461)
<223> OTHER INFORMATION: a, c, t or g
<220> FEATURE:
<221> NAME/KEY: modified_base
<222> LOCATION: (11472)..(11472)
<223> OTHER INFORMATION: a, c, t or g
<220> FEATURE:
<221> NAME/KEY: modified_base
<222> LOCATION: (11478)..(11478)
<223> OTHER INFORMATION: a, c, t or g
<220> FEATURE:
<221> NAME/KEY: modified_base
<222> LOCATION: (11488)..(11488)
<223> OTHER INFORMATION: a, c, t or g
<220> FEATURE:
<221> NAME/KEY: modified_base
<222> LOCATION: (11490)..(11490)
<223> OTHER INFORMATION: a, c, t or g
<220> FEATURE:
<221> NAME/KEY: modified_base
<222> LOCATION: (11497)..(11497)
<223> OTHER INFORMATION: a, c, t or g
<220> FEATURE:
<221> NAME/KEY: modified_base
<222> LOCATION: (11519)..(11519)
<223> OTHER INFORMATION: a, c, t or g
<220> FEATURE:
<221> NAME/KEY: modified_base
<222> LOCATION: (11527)..(11527)
<223> OTHER INFORMATION: a, c, t or g
<220> FEATURE:
<221> NAME/KEY: modified_base
<222> LOCATION: (11548)..(11548)
<223> OTHER INFORMATION: a, c, t or g
<220> FEATURE:
<221> NAME/KEY: modified_base
<222> LOCATION: (11551)..(11551)
<223> OTHER INFORMATION: a, c, t or g
<220> FEATURE:
<221> NAME/KEY: modified_base
<222> LOCATION: (12281)..(12281)
<223> OTHER INFORMATION: a, c, t or g
<220> FEATURE:
<221> NAME/KEY: modified_base
<222> LOCATION: (12298)..(12298)
<223> OTHER INFORMATION: a, c, t or g
<220> FEATURE:
<221> NAME/KEY: modified_base
<222> LOCATION: (12394)..(12394)
<223> OTHER INFORMATION: a, c, t or g
<220> FEATURE:
<221> NAME/KEY: modified_base
<222> LOCATION: (12615)..(12615)
<223> OTHER INFORMATION: a, c, t or g
<220> FEATURE:
<221> NAME/KEY: modified_base
<222> LOCATION: (12617)..(12618)
<223> OTHER INFORMATION: a, c, t or g
<220> FEATURE:
<221> NAME/KEY: modified_base
<222> LOCATION: (12620)..(12621)
<223> OTHER INFORMATION: a, c, t or g
<220> FEATURE:
<221> NAME/KEY: modified_base
<222> LOCATION: (12624)..(12624)
```

```
<223> OTHER INFORMATION: a, c, t or g
<220> FEATURE:
<221> NAME/KEY: modified_base
<222> LOCATION: (12627)..(12629)
<223> OTHER INFORMATION: a, c, t or g
<220> FEATURE:
<221> NAME/KEY: modified_base
<222> LOCATION: (12633)..(12637)
<223> OTHER INFORMATION: a, c, t or g
<220> FEATURE:
<221> NAME/KEY: modified_base
<222> LOCATION: (12640)..(12640)
<223> OTHER INFORMATION: a, c, t or g

<400> SEQUENCE: 21
atggcgagcc tcgccgcgct cgccctcagc ctgctcctga ggctgcagct gccgccactg      60
cccggcgccc gggctcagag cgccccaggt ggctgttcct ttgatgagca ctacagcaac     120
tgtggttata gtgtggctct agggaccaat gggttcacct gggagcagat taacacaacg     180
gagaaaccaa tgctggacca ggcagtgccc acaggatctt tcatgatggt aacagctct      240 gggagagcct ctggccagaa ggcccacctt ctcctgccaa ccctgaagga aatgacacc      300 cactgcatcg acttccatta ctacttctcc agccgtgaca ggtccagccc aggggccttg     360
aacgtctacg tgaaggtgaa tggtggcccc aagggaacc ctgtgtggaa tgtgtccggg      420
gtcgtcactg agggctgggt gaaggcagag ctcgccatca gcactttctg ccacatttc      480 tatcaggtga tatttgaatc cgtctcattg aagggtcatc ctggctacat cgccgtggac     540
gaggtccggg tccttgctca tccatgcaga aaagcacctc attttctgcg actccaaaac     600
gtggaggtga atgtggggca gaatgccaca tttcagtgca ttgctggtgg aagtggtct      660 cagcatgaca agctttggct ccagcaatgg aatggcaggg acacggccct gatggtcacc     720
cgtgtggtca accacaggcg cttctcagcc acagtcagtg tggcagacac tgcccagcgg     780
agcgtcagca gtaccgctg tgtgatccgc tctgatggtg ggtctggtgt gtccaactac     840
gcggagctga tcgtgaaaga gcctcccacg cccattgctc cccagagct gctggctgtg      900 ggggccacat acctgtggat caagccaaat gccaactcca tcatcgggga tggccccatc     960
atcctgaagg aagtggaata tcgcaccacc acaggcacgt gggcagagac ccacatagtc    1020
gactctccca actataagct gtggcatctg accccgatg ttgagtatga tccgagtg      1080 ctcctcacac gaccaggtga ggggggtacg ggaccgccag gggctcccct caccaccagg    1140
accaagtgtg cagatccggt acatggccca cagaacgtgg aaatcgtaga catcagagcc    1200
cggcagctga ccctgcagtg ggagcccttc ggctacgcgg tgaccccgctg ccatagctac    1260 aacctcaccg tgcagtacca gtatgtgttc aaccagcagc agtacgaggc cgaggaggtc    1320
atccagacct cctcccacta caccctgcga ggcctgcgcc ccttcatgac catccggctg    1380
cgactcttgc tgtctaaccc cgagggccga atggagagcg aggagctggt ggtgcagact    1440
gaggaagacg ttccaggagc tgttcctcta gaatccatcc aagggggcc ctttgaggag     1500 aagatctaca tccagtggaa acctcccaat gagaccaatg ggtcatcac gctctacgag    1560 atcaactaca ggctgtcgg ctcgctggac ccaagtgctg acctctcgag ccagagggg     1620 aaagtgttca gctccggaa tgaaacccac cacctctttg tgggtctgta cccagggacc    1680
acctattcct tcaccatcaa ggccagcaca gcaaagggct ttgggccccc tgtcaccact    1740
cggattgcca ccaaaatttc agctccatcc atgcctgagt acgacacaga caccccattg    1800
aatgagacag acacgaccat cacagtgatg ctgaaaccg ctcagtcccg gggagctcct     1860
gtcagtgttt atcagctggt tgtcaaggag gagcgacttc agaagtcacg gagggcagct    1920
```

```
gacattattg agtgcttttc ggtgcccgtg agctatcgga atgcctccag cctcgattct   1980
ctacactact ttgctgctga gttgaagcct gccaacctgc ctgtcaccca gccatttaca   2040
gtgggtgaca ataagacata caatggctac tggaaccctc ctctctctcc cctgaaaagc   2100
tacagcatct acttccaggc actcagcaaa gccaatggag agaccaaaat caactgtgtt   2160
cgtctggcta caaaagcacc aatgggcagc gcccaggtga ccccggggac tccactctgc   2220
ctcctcacca caggtgcctc cacccagaat tctaacactg tggagccaga gaagcaggtg   2280
gacaacaccg tgaagatggc tggcgtgatc gctggcctcc tcatgttcat catcattctc   2340
ctgggcgtga tgctcaccat caaaaggaga agaaatgctt attcctactc ctattacttg   2400
tcccaaagga agctggccaa gaagcagaag gagacccaga gtggagccca gagggagatg   2460
gggcctgtgg cctctgccga caaacccacc accaagctca cgccagccg caatgatgaa   2520
ggcttctctt ctagttctca ggacgtcaac ggattcacag atggcagccg cggggagctt   2580
tcccagccca ccctcacgat ccagactcat ccctaccgca cctgtgaccc tgtggagatg   2640
agctaccccc gggaccagtt ccaactcgcc atccgggtgg ctgacttgct gcagcacatc   2700
acgcagatga agagaggcca gggctacggg ttcaaggagg aatacgaggc cttaccagag   2760
gggcagacag cttcgtggga cacagccaag gaggatgaaa accgcaataa gaatcgatat   2820
gggaacatca tatcctacga ccattcccgg gtgaggctgc tggtgctgga tggagacccg   2880
cactctgact acatcaatgc caactacatt gacggatacc atcgacctcg gcactacatt   2940
gcgactcaag gtccgatgca ggagactgta aaggacttt ggagaatgat ctggcaggag   3000
aactccgcca gcatcgtcat ggtcacaaac ctggtggaag tgggcagggt gaaatgtgtg   3060
cgatactggc cagatgacac ggaggtctac ggagacatta aagtcaccct gattgaaaca   3120
gagcccctgg cagaatacgt catacgcacc ttcacagtcc agaagaaagg ctaccatgag   3180
atccgggagc tccgcctctt ccacttcacc agctggcctg accacggcgt tccctgctat   3240
gccactggcc ttctgggctt cgtccgccag gtcaagttcc tcaaccccc ggaagctggg   3300
cccatagtgg tccactgcag tgctgggct gggcggactg gctgcttcat tgccattgac   3360
accatgcttg acatggccga gaatgaaggg gtggtggaca tcttcaactg cgtgcgtgag   3420
ctccgggccc aaagggtcaa cctggtacag acagaggagc aatatgtgtt tgtgcacgat   3480
gccatcctgg aagcgtgcct ctgtggcaac actgccatcc ctgtgtgtga gttccgttct   3540
ctctactaca atatcagcag gctggaccc cagacaaact ccagccaaat caaagatgaa   3600
tttcagaccc tcaacattgt gacacccgt gtgcggcccg aggactgcag cattgggctc   3660
ctgccccgga accatgataa gaatcgaagt atggacgtgc tgcctctgga ccgctgcctg   3720
ccccttcctta tctcagtgga cggagaatcc agcaattaca tcaacgcagc actgatggat   3780
agccacaagc agcctgccgc cttcgtggtc acccagcacc ctctacccaa caccgtggca   3840
gacttctgga ggctggtgtt cgattacaac tgctcctctg tggtgatgct gaatgagatg   3900
gacactgccc agttctgtat gcagtattgg cctgagaaga cctccgggtg ctatgggccc   3960
atccaggtgg agttcgtctc cgcagacatc gacgaggaca tcatccacag aatattccgc   4020
atctgtaaca tggcccggcc acaggatggt tatcgtatag tccagcacct ccagtacatt   4080
ggctggcctg cctaccggga cacgccccc tccaagcgct ctctgctcaa agtggtccga   4140
cgactggaga agtggcagga gcagtatgac gggagggagg gacgtactgt ggtccactgc   4200
ctaaatgggg gaggccgtag tggaacctc tgtgccatct gcagtgtgtg tgagatgatc   4260
```

```
cagcagcaaa acatcattga cgtgttccac atcgtgaaaa cactgcgtaa caacaaatcc    4320
aacatggtgg agaccctgga acagtataaa tttgtatacg aggtggcact ggaatattta    4380
agctcctttt agctcaatgg gatggggaac ctgccggagt ccagaggctg ctgtgaccaa    4440
gccccctttt gtgtgaatgg cagtaactgg gctcaggagc tctgaggtgg caccctgcct    4500
gactccaagg agaagactgg tggccctgtg ttccacgggg ggctctgcac cttctgaggg    4560
gtctcctgtt gccgtgggag atgctgctcc aaaaggccca ggcttccttt tcaacctaac    4620
cagccacagc caagggccca agcagaagta cacccacaag caaggccttg gatttctggc    4680
tcccagacca cctgcttttg ttctgagttt gtggatctct tggcaagcca actgtgcagg    4740
tgctggggag tgggaggctc ccctgccctc cttctcctta ggagtggagg agatgtgtgt    4800
tctgctcctc tacgtcatgg aaaagattga ggctcttggg ggtcactgct ctgctgcccc    4860
ctgcaacctc cttcaggggc ctctggcacc agacatttgc agtctggacc agtgtgacct    4920
tacgatgttc cctaggccac aagagaggcc cccatcctc acacctaacc tgcatggggc    4980
ttcgcccaca accattctgt accccttccc cagcctgggc cttgaccgtc cagcattcac    5040
tggccggcca gctgtgtcca cagcagtttt tgataaaggt gttctttgct ttttttgtgtg    5100 gtcagtggga ggggtggaa ctgcaggaa cttctctgct cctccttgtc tttgtaaaaa    5160
gggaccacct ccctggggca gggcttgggc tgacctgtag gatgtaaccc ctgtgtttct    5220
ttggtggtag ctttctttgg aagagacaaa caagataaga tttgattatt ttccaaagtg    5280
tatgtgaaaa gaaactttct tttggagggt gtaaaatctt agtctcttat gtcaaaaaga    5340
agggggcggg ggagtttgag tatgtacctc taagacaaat ctctcgggcc ttttattttt    5400
tcctggcaat gtccttaaaa gctcccaccc tgggacagca tgccactgag caaggagaga    5460
tgggtgagcc tgaagatggt cccttttggt tctggggcaa atagagcacc agctttgtgc    5520
ataatttgga tgtccaaatt tgaactcctt cctaagaaa cccagcagcc accttgaaaa    5580
aggccattgt ggagcccatt atactttgat ttaaaatagg ccaagagaat caggcctgga    5640
gatctagggt cttgtccaaa gtgtgagtga gtcaatgaga gggaaccaac atttgctaag    5700
tctctactgt atgccaggga tcatgcttgg cactttccat aggacatttc acacagtcct    5760
tagaaccccc aggagagagc tactgacttg ttatcatctc catttgatca tctcctccaa    5820
tgaggaaacc cacgcacctt ccttagtaat gaaatcctgg gttccaaagg ggcaggtaat    5880
ggcaatgaga cttctccgtg ctgttttctt catcttctct aagccaagca attatttat    5940 ggagggaaaa taaggccaga aacttctgag cagataactc cacaaatgga aatttagtac    6000
tttcttcctg atgccagttc ttctgggaag cgcagaattt cagatatatt ttagtaacac    6060
attcccagct ccccaggaaa gccagtctca tctaatttct tagtcagtaa aaacaattcc    6120
ctgttccttc aggctatgaa tggaccagcc agggaaactc tcgaccttga tctctagcca    6180
gtgcttaggc ccaatatctg acagcctcag gtgggctggg acctaggaag ctccatcttg    6240
aaggctggtc tagccccaga cagggcatga ggggcagaga attcaagaag gtacagcttt    6300
ggccctcaag agcccactgt atgctgggga aatggaacca tggtgcagta gtgtggagtg    6360
gatgagtgtt ccatgagcct aggagcaaga agtctcttc ggcctcgggc ttcctggaga    6420
aggggacgtc cattcctgct gggtcttaac aagcataaaa aggaaaaaa ggaaactcag    6480 gcaaagggat ccatatgtgc aatggcaaag aaatgtgaaa aggcattggg agaagcagtc    6540
tgggggaggc cagcccagtg cgggcacagc acaacacggg gagcagcaag agatgagcca    6600
gggtccagga gacagatgcc catcgcgagt acagactttg tcctattggc aacaaggagt    6660
```

```
ccatggagct ttagagagat gcactcagct tcgtgttggc caagactcct tctgggccaa    6720
tggggctgcc tcttttcctt tcatcagaca ctgtgaaaac attcccttaa gcgtgcactt    6780
tttaatatca catctatttg tctgtctgct cattgttttg ttgctggaac taaatatgca    6840
atggatcatg agactcagat tctatgagaa acccagggtc tctgctttac cacggagcag    6900
ggtcaccaac ccagatctcc aggcccatga ggatggaaca tgaaaggagc cgacaaagt    6960 tgcttccatt ggcatgggct ctggagctgt ccagaagtcc agggacacca gacttgatca    7020
aggaagggct gtcactttag aggttcaaaa ggaagtgcct caaagcaaag gcaagcaaag    7080
gaaccccacg atgaacttgc tcttttcctt tgatgagcct ctccccaggt gtatttcagc    7140 agacnccgg ggacccance cccactgggc ctgctggcct ccctcggctc cagcccaatg    7200
ccccagctgg ccttccccag cctgcaagga gcctgtagca tggcaaatct gcctgctgta    7260
tgctattttc ttagatcttg gtacatccag acaggatgag ggtggaggga gagctattta    7320
acacaaatcc taagattttt ttctgctcag gaagggtga aatagctggc agatacaaaa    7380
gacagtggct tttatcattt taaatggtag gaatttaagg tgtgacttca gggagaaaca    7440
aacttgcaaa aaaaaaaaan nnntctncag gccatgttgg ggtaacccag caagggccag    7500
tgatgatttc ccccagctca tccccttatt ttcccacaac ccaaccattc tctaaagcag    7560
gacagtgaat aggtcttagg ccagtgcaca caggaagaaa ttgaggctta tggatgggga    7620
tgacttccct aagatcccat gggacaagga tgtggcaagg cttggatgag atggggcacc    7680
agtgcccagg aatttgaaca ttttcctta cccaggnaaa tctccggagc caacaccacc    7740
accccagggg ggtctncccc accccacccc atttacaggg tgagctcagc ctgtncatng    7800
agncagagga aaatattnat tnaatgctct ctngagtctt tnnacaacag gnagctcttn    7860
accntcatag natgtngggc tctgtttggg gaagatgcaa ggaagtaatg agaagcccag    7920
gaaatttctc cacctgtgtt tatggcctaa atagcttcag gatgtatctt agctgcactc    7980
caacattgca tcctttctgg ggtgaagaat ctgggccaac caggggtcct tgggcctcta    8040
gaaggccaca gtaggcctct ctttgtggga atggaaaggg gacagtttgc ttttagtgc    8100 tggccctctc tgtgggtgtg gcctgccaaa ggaaccaaca ngaccctatg cctggggact    8160
cctaacatgt gagcctccat taaattcctt cccagcattc ctaaaggagg gtttgtgatt    8220
gtcaccattt actgatgagg aaactaaggc tcctagggga gaaatcactt gcccacagtt    8280
cccacagcta gtgagtgaat gaaccaggat ttaaaccggt ttttctcac tacagagaca    8340 atatttttcc accattgtat ctcacatttt tcccaggagg ttacccataa cagaagagac    8400
tagagtggaa cagatacgtc agtggataaa gctcaaagca aacaacagta agcttaaaat    8460 tccttccatag tctcatgttt tacgttcaca attcatgcaa aatttgcatt ccactttctg    8520
atttagcctt gttggtttta atatgactct atgaatattt caaaaaaaaa tgtgctctgt    8580
tcctcatgtt gttctgttct gttcaccccg ctatgacgga ccctaggtca gctggtcttc    8640
agcttgaccc tagaattgac tctaggagca gtgaccctgc tgcctcccag agccagttat    8700
aggctcaaga tcaagaccaa ctgaccttct cctaggcagc tcctttggtg tgtgggtgct    8760
ctgacctcac tgttcatgag gggacctcaa ctaaggcatc ttccagttgg gtgctggaag    8820
gaacccatta actcacacta gaatgatgag gatttgctca tctggcgtgg agaaggatga    8880
gcccacaaaa ccctaaaggg aaaagagaag ctggacacag ctgtactcag cagattcctg    8940
aatgctaggc tggaaagtgg tgcctgttgt ccaagtggag tcacatggtt gctaatgtgg    9000
```

```
gcaagtctga ggacacactt catgagcagc tggggtctgg aaggctcctc actttaccct    9060
agccacacat aattactggg tgcctacagc acctagcacc ttggagggg cactattagg     9120 aaatcgagat tactatggca caattaattc ctgggtaagg catggggttg tggtggacag    9180
agctcagtct ttagtttgaa cgaaaacata catacatgaa aaacatacat gaaaaaagga    9240
ccctcatcaa cattagaagg ggtagatttg gagcacttta ggcaggaaaa caggaacgca    9300
aggccaggaa actggaaccc agtgaatact cagaaccgag gatgcagatg acttatttag    9360
caaaatggtc acttctgtga catagctgga gaaaggatgg gtaacagctt gccagagcca    9420
cttggaacaa gggcaaatct cagtgtctgg ggcaaaagat gatgcatttc cctctgaccc    9480
atcatgttta ttcatcctcc actccccatt gccacactag ctcttgctgt aagtcctcac    9540
caggatctac atttcctcgt cgctggtggg aacccttag agtacataga ggtatcagtc     9600
cagtaagact gctctacaca acagaagtga ggcccaggga gtagcagcca ggcccttatc    9660
ctgttacctc tgcaggagtg actgcccaac ccagatccag agacattgaa ggaaatgata    9720
attccttggt acctcactgc cttgggacaa aatgaagaaa gccacccttc cttaggctgc    9780
agcttgccac tcctgggctg ggtaaacagg tcatcagcac caggctcaac caggagtaac    9840
attctggaag acatgggtga gcccaagagg aagcatgaac aggacgctgt tcctaagtca    9900
tgtcaacagg ttgtgctggg ccaggatccc cagggaaaaa aatggtcaac ccaactggag    9960
ggtaggttag aagaaaaaaa acataaacgt ggatagtcat gtcatctcaa atccctgact   10020
tggcttcccc attacttgac agtctgagct ccttcttagc ctgtgaccag cttcaaatca   10080
cagccaagta aaacaaggaa ataggaaaag taaatccaac tagaagagac aagctgagat   10140
tcagatttgt ttactcctcc catgcaaagt ttccctgttg gaggttttcc atgtatacat   10200
gtctagaagt gatagaatgc aaggccttgg ctttgtcttg cagggatctg cctttgaggt   10260
catagactga acagcaggga gagaggttag tggtggagtg tgggggagc tgttctagct    10320 ccagtttctt ctgacacatt tttcaggatc atggatctga tcctccgaag cacagcagag   10380
atatctaagc catatttgtg cacatgagca gactcttcta gttttttagt aaccagggat   10440
gggcttttgc atggcactga ctatagagat gtcttgtaga gatcaagcca gtcttttgca   10500
tcccacctgc ccacctccag aagagatggg aaaaggtcat caagggcat tcaccaactg    10560 aaatccactc atgaatgtta ggtctctaaa aggaggcatc aacactcaca atggtagcct   10620
ccaaacctag catcccacct atctaagagc tcaggggtgg tccactgggg cagatacaag   10680
ggaagtgcaa gggctcagga tgaaagaaaa tctattggga agagttttag ggcttgatc    10740 attatgggc ttccttctat atctgagaac tgctctgggt ggtgagatgt ggactctgat    10800
ccttaattgg aatgttcgga gaatgagtgt ctggtggcct tgaagtgttg gacagaaaag   10860
tatcagtata aaagcctgga gctcagggta attaatgtag ttcatggttc cttagtgagc   10920
aggactcttg gatgtggagg agaaagggtc ataggaagta aaccaccaaa attacaaaat   10980
tgagtctctg tacaattact tcagtgcctt tgggcttatg aatacaaatc agtgggcctt   11040
ctctatgatg gtccaacaaa ctctcagtgt ccaccctgtc cctgtatctc ccatggaaga   11100
tgaataatgt caggtgttct ttgggtcaaa ggccccaggg cagtctggag cttagaggg    11160 cagagtggtg tcattccatg taaagttagg cttctgaggg gtcaggcaga atatggtgtc   11220
catatcttcc atagctctgc agattcttgg natgaagtca agcacagttt gctagaccca   11280
ggntcactcc tctngagtat naactaggna cccatgagtg aaacttaata gctgtnaagg   11340
naagnaacct gnctgtnctg ccnagagagg atnaagctgn cccatctcag ncagctgtnc   11400
```

```
tnaaaagaag gncaggtgtc tctnttnnaa agggnaagag gaagncattg gtggaaatgg    11460
nattttcagg tncacttncc attcccangn atgggtngag atcttgtgga gctgggatnc    11520
atgtttngaa ctcattcata cctgtagnag ncacgaattc caagtagatt gtgtttggtc    11580
tgtacaggct gaagccccct gctctcccac ccaagtgccc ccactgagca ggccaacatg    11640
ctgttgtggc cacatatact gggctgatcc aggctggtta tcaccaaaca gcaaaccata    11700
gggaacagtg gctttgccat agacccaata cccatgtaga tctctcatga gagcagccat    11760
aactcagacc cactgaccaa cagggccatg agtgacagcc agaaccagtg aaggtccaag    11820
taggacacag agcagggctt ttcttaccat acacattatc tccagaggtt atttctaccc    11880
cactccctat tcaaggcctg ttggagcaca ctgcaaaagc aaaagcacag taactcaatt    11940
tacacatgat tataatcatt tccagtgcac acatttcatc accaggtgga tcctgagcta    12000
gcccatgtaa atccgggtta acccatattg gtaatcatac tcaaaagcac ttttcaccct    12060
acattctact agccaatcaa agacaaagag ttgtggcctc taccattgcc ttggcttctg    12120
gacaccctca caagctatcc caaggttccc ggctcaaccc ccagggrggc cggacatcct    12180
tcacatccca ckgggccata aaatattgc catgagaccc aaagtcctcc cacactcttt    12240
gcagccctcc tcccatgaat ccccaatggc ctgcacttgt nacagtttgg gtgtttgnat    12300
agataaagca cgtatgagaa gagaaaacaa aataaatcaa cttttaaaa aagccagcac    12360 tgtgctgtca atgtttttttt tttcttttca attnctagct cagaaaagca gaaggtaaat    12420
aatgtcaggt caatgaatat cagatatatt ttttgactgt acattacagt gaagtgtaat    12480 cttttacac ctgcaagtcc atcttattta ttcttgtaaa tgttccctga caatgtttgt    12540
aatatggctg tgttaaaaaa tctatacaat aaagctgtga ccctgagaww matgttttcc    12600
taagataaaa aaaangnnan nstnyknnnc tknnnnngtn hg                      12642
```

<210> SEQ ID NO 22
<211> LENGTH: 1463
<212> TYPE: PRT
<213> ORGANISM: Homo sapiens

<400> SEQUENCE: 22

```
Met Ala Ser Leu Ala Ala Leu Ala Leu Ser Leu Leu Leu Arg Leu Gln
1               5                   10                  15

Leu Pro Pro Leu Pro Gly Ala Arg Ala Gln Ser Ala Pro Gly Gly Cys
                20                  25                  30

Ser Phe Asp Glu His Tyr Ser Asn Cys Gly Tyr Ser Val Ala Leu Gly
            35                  40                  45

Thr Asn Gly Phe Thr Trp Glu Gln Ile Asn Thr Thr Glu Lys Pro Met
        50                  55                  60

Leu Asp Gln Ala Val Pro Thr Gly Ser Phe Met Met Val Asn Ser Ser
65                  70                  75                  80

Gly Arg Ala Ser Gly Gln Lys Ala His Leu Leu Pro Thr Leu Lys
                85                  90                  95

Glu Asn Asp Thr His Cys Ile Asp Phe His Tyr Tyr Phe Ser Ser Arg
            100                 105                 110

Asp Arg Ser Ser Pro Gly Ala Leu Asn Val Tyr Val Lys Val Asn Gly
        115                 120                 125

Gly Pro Gln Gly Asn Pro Val Trp Asn Val Ser Gly Val Val Thr Glu
    130                 135                 140

Gly Trp Val Lys Ala Glu Leu Ala Ile Ser Thr Phe Trp Pro His Phe
```

```
            145                 150                 155                 160
Tyr Gln Val Ile Phe Glu Ser Val Ser Leu Lys Gly His Pro Gly Tyr
                    165                 170                 175
Ile Ala Val Asp Glu Val Arg Val Leu Ala His Pro Cys Arg Lys Ala
                    180                 185                 190
Pro His Phe Leu Arg Leu Gln Asn Val Glu Val Asn Val Gly Gln Asn
                    195                 200                 205
Ala Thr Phe Gln Cys Ile Ala Gly Gly Lys Trp Ser Gln His Asp Lys
                    210                 215                 220
Leu Trp Leu Gln Gln Trp Asn Gly Arg Asp Thr Ala Leu Met Val Thr
225                 230                 235                 240
Arg Val Val Asn His Arg Arg Phe Ser Ala Thr Val Ser Val Ala Asp
                    245                 250                 255
Thr Ala Gln Arg Ser Val Ser Lys Tyr Arg Cys Val Ile Arg Ser Asp
                    260                 265                 270
Gly Gly Ser Gly Val Ser Asn Tyr Ala Glu Leu Ile Val Lys Glu Pro
                    275                 280                 285
Pro Thr Pro Ile Ala Pro Pro Glu Leu Leu Ala Val Gly Ala Thr Tyr
    290                 295                 300
Leu Trp Ile Lys Pro Asn Ala Asn Ser Ile Ile Gly Asp Gly Pro Ile
305                 310                 315                 320
Ile Leu Lys Glu Val Glu Tyr Arg Thr Thr Thr Gly Thr Trp Ala Glu
                    325                 330                 335
Thr His Ile Val Asp Ser Pro Asn Tyr Lys Leu Trp His Leu Asp Pro
                    340                 345                 350
Asp Val Glu Tyr Glu Ile Arg Val Leu Leu Thr Arg Pro Gly Glu Gly
                    355                 360                 365
Gly Thr Gly Pro Pro Gly Ala Pro Leu Thr Thr Arg Thr Lys Cys Ala
                    370                 375                 380
Asp Pro Val His Gly Pro Gln Asn Val Glu Ile Val Asp Ile Arg Ala
385                 390                 395                 400
Arg Gln Leu Thr Leu Gln Trp Glu Pro Phe Gly Tyr Ala Val Thr Arg
                    405                 410                 415
Cys His Ser Tyr Asn Leu Thr Val Gln Tyr Gln Tyr Val Phe Asn Gln
                    420                 425                 430
Gln Gln Tyr Glu Ala Glu Glu Val Ile Gln Thr Ser Ser His Tyr Thr
                    435                 440                 445
Leu Arg Gly Leu Arg Pro Phe Met Thr Ile Arg Leu Arg Leu Leu Leu
450                 455                 460
Ser Asn Pro Glu Gly Arg Met Glu Ser Glu Glu Leu Val Val Gln Thr
465                 470                 475                 480
Glu Glu Asp Val Pro Gly Ala Val Pro Leu Glu Ser Ile Gln Gly Gly
                    485                 490                 495
Pro Phe Glu Glu Lys Ile Tyr Ile Gln Trp Lys Pro Pro Asn Glu Thr
                    500                 505                 510
Asn Gly Val Ile Thr Leu Tyr Glu Ile Asn Tyr Lys Ala Val Gly Ser
                    515                 520                 525
Leu Asp Pro Ser Ala Asp Leu Ser Ser Gln Arg Gly Lys Val Phe Lys
                    530                 535                 540
Leu Arg Asn Glu Thr His His Leu Phe Val Gly Leu Tyr Pro Gly Thr
545                 550                 555                 560
Thr Tyr Ser Phe Thr Ile Lys Ala Ser Thr Ala Lys Gly Phe Gly Pro
                    565                 570                 575
```

```
Pro Val Thr Thr Arg Ile Ala Thr Lys Ile Ser Ala Pro Ser Met Pro
            580                 585                 590

Glu Tyr Asp Thr Asp Thr Pro Leu Asn Glu Thr Asp Thr Thr Ile Thr
            595                 600                 605

Val Met Leu Lys Pro Ala Gln Ser Arg Gly Ala Pro Val Ser Val Tyr
610                 615                 620

Gln Leu Val Val Lys Glu Glu Arg Leu Gln Lys Ser Arg Arg Ala Ala
625                 630                 635                 640

Asp Ile Ile Glu Cys Phe Ser Val Pro Val Ser Tyr Arg Asn Ala Ser
                645                 650                 655

Ser Leu Asp Ser Leu His Tyr Phe Ala Ala Glu Leu Lys Pro Ala Asn
            660                 665                 670

Leu Pro Val Thr Gln Pro Phe Thr Val Gly Asp Asn Lys Thr Tyr Asn
            675                 680                 685

Gly Tyr Trp Asn Pro Pro Leu Ser Pro Leu Lys Ser Tyr Ser Ile Tyr
            690                 695                 700

Phe Gln Ala Leu Ser Lys Ala Asn Gly Glu Thr Lys Ile Asn Cys Val
705                 710                 715                 720

Arg Leu Ala Thr Lys Ala Pro Met Gly Ser Ala Gln Val Thr Pro Gly
                725                 730                 735

Thr Pro Leu Cys Leu Leu Thr Thr Gly Ala Ser Thr Gln Asn Ser Asn
            740                 745                 750

Thr Val Glu Pro Glu Lys Gln Val Asp Asn Thr Val Lys Met Ala Gly
            755                 760                 765

Val Ile Ala Gly Leu Leu Met Phe Ile Ile Leu Leu Gly Val Met
770                 775                 780

Leu Thr Ile Lys Arg Arg Arg Asn Ala Tyr Ser Tyr Ser Tyr Tyr Leu
785                 790                 795                 800

Ser Gln Arg Lys Leu Ala Lys Lys Gln Lys Glu Thr Gln Ser Gly Ala
            805                 810                 815

Gln Arg Glu Met Gly Pro Val Ala Ser Ala Asp Lys Pro Thr Thr Lys
            820                 825                 830

Leu Ser Ala Ser Arg Asn Asp Glu Gly Phe Ser Ser Ser Gln Asp
            835                 840                 845

Val Asn Gly Phe Thr Asp Gly Ser Arg Gly Glu Leu Ser Gln Pro Thr
            850                 855                 860

Leu Thr Ile Gln Thr His Pro Tyr Arg Thr Cys Asp Pro Val Glu Met
865                 870                 875                 880

Ser Tyr Pro Arg Asp Gln Phe Gln Leu Ala Ile Arg Val Ala Asp Leu
                885                 890                 895

Leu Gln His Ile Thr Gln Met Lys Arg Gly Gln Gly Tyr Gly Phe Lys
            900                 905                 910

Glu Glu Tyr Glu Ala Leu Pro Glu Gly Gln Thr Ala Ser Trp Asp Thr
            915                 920                 925

Ala Lys Glu Asp Glu Asn Arg Asn Lys Asn Arg Tyr Gly Asn Ile Ile
            930                 935                 940

Ser Tyr Asp His Ser Arg Val Arg Leu Leu Val Leu Asp Gly Asp Pro
945                 950                 955                 960

His Ser Asp Tyr Ile Asn Ala Asn Tyr Ile Asp Gly Tyr His Arg Pro
                965                 970                 975

Arg His Tyr Ile Ala Thr Gln Gly Pro Met Gln Glu Thr Val Lys Asp
            980                 985                 990
```

-continued

Phe Trp Arg Met Ile Trp Gln Glu Asn Ser Ala Ser Ile Val Met Val
    995                 1000                1005

Thr Asn Leu Val Glu Val Gly Arg Val Lys Cys Val Arg Tyr Trp
    1010            1015            1020

Pro Asp Asp Thr Glu Val Tyr Gly Asp Ile Lys Val Thr Leu Ile
    1025            1030            1035

Glu Thr Glu Pro Leu Ala Glu Tyr Val Ile Arg Thr Phe Thr Val
    1040            1045            1050

Gln Lys Lys Gly Tyr His Glu Ile Arg Glu Leu Arg Leu Phe His
    1055            1060            1065

Phe Thr Ser Trp Pro Asp His Gly Val Pro Cys Tyr Ala Thr Gly
    1070            1075            1080

Leu Leu Gly Phe Val Arg Gln Val Lys Phe Leu Asn Pro Pro Glu
    1085            1090            1095

Ala Gly Pro Ile Val Val His Cys Ser Ala Gly Ala Gly Arg Thr
    1100            1105            1110

Gly Cys Phe Ile Ala Ile Asp Thr Met Leu Asp Met Ala Glu Asn
    1115            1120            1125

Glu Gly Val Val Asp Ile Phe Asn Cys Val Arg Glu Leu Arg Ala
    1130            1135            1140

Gln Arg Val Asn Leu Val Gln Thr Glu Glu Gln Tyr Val Phe Val
    1145            1150            1155

His Asp Ala Ile Leu Glu Ala Cys Leu Cys Gly Asn Thr Ala Ile
    1160            1165            1170

Pro Val Cys Glu Phe Arg Ser Leu Tyr Tyr Asn Ile Ser Arg Leu
    1175            1180            1185

Asp Pro Gln Thr Asn Ser Ser Gln Ile Lys Asp Glu Phe Gln Thr
    1190            1195            1200

Leu Asn Ile Val Thr Pro Arg Val Arg Pro Glu Asp Cys Ser Ile
    1205            1210            1215

Gly Leu Leu Pro Arg Asn His Asp Lys Asn Arg Ser Met Asp Val
    1220            1225            1230

Leu Pro Leu Asp Arg Cys Leu Pro Phe Leu Ile Ser Val Asp Gly
    1235            1240            1245

Glu Ser Ser Asn Tyr Ile Asn Ala Ala Leu Met Asp Ser His Lys
    1250            1255            1260

Gln Pro Ala Ala Phe Val Val Thr Gln His Pro Leu Pro Asn Thr
    1265            1270            1275

Val Ala Asp Phe Trp Arg Leu Val Phe Asp Tyr Asn Cys Ser Ser
    1280            1285            1290

Val Val Met Leu Asn Glu Met Asp Thr Ala Gln Phe Cys Met Gln
    1295            1300            1305

Tyr Trp Pro Glu Lys Thr Ser Gly Cys Tyr Gly Pro Ile Gln Val
    1310            1315            1320

Glu Phe Val Ser Ala Asp Ile Asp Glu Asp Ile Ile His Arg Ile
    1325            1330            1335

Phe Arg Ile Cys Asn Met Ala Arg Pro Gln Asp Gly Tyr Arg Ile
    1340            1345            1350

Val Gln His Leu Gln Tyr Ile Gly Trp Pro Ala Tyr Arg Asp Thr
    1355            1360            1365

Pro Pro Ser Lys Arg Ser Leu Leu Lys Val Val Arg Arg Leu Glu
    1370            1375            1380

Lys Trp Gln Glu Gln Tyr Asp Gly Arg Glu Gly Arg Thr Val Val

His Cys Leu Asn Gly Gly Gly Arg Ser Gly Thr Phe Cys Ala Ile
       1400                1405                 1410

Cys Ser Val Cys Glu Met Ile Gln Gln Gln Asn Ile Ile Asp Val
    1415                1420                1425

Phe His Ile Val Lys Thr Leu Arg Asn Asn Lys Ser Asn Met Val
    1430                1435                1440

Glu Thr Leu Glu Gln Tyr Lys Phe Val Tyr Glu Val Ala Leu Glu
    1445                1450                1455

Tyr Leu Ser Ser Phe
    1460

<210> SEQ ID NO 23
<211> LENGTH: 1297
<212> TYPE: DNA
<213> ORGANISM: Homo sapiens

<400> SEQUENCE: 23

```
gtcgacccac gcgtccgtgc tcagcctggt gaaccacaca ggcccgagtt tcacccagtc      60
cccactccac ggtgcagctg cggcttatct ctcagcccag cgagatgcca gccttcctgt     120
cccgggccag cgctctgaca tgcagaaggt gaccctgggc ctgcttgtgt tcctggcagg     180
ctttcctgtc ctggacgcca atgacctaga agataaaaac agtcctttct actatgactg     240
gcacagcctc caggttggcg ggctcatctg cgctggggtt ctgtgcgcca tgggcatcat     300
catcgtcatg agtgcaaaat gcaaatgcaa gtttggccag aagtccggtc accatccagg     360
ggagactcca cctctcatca ccccaggctc agcccaaagc tgatgaggac agaccagctg     420
aaattgggtg gaggaccgtt ctctgtcccc aggtcctgtc tctgcacaga aacttgaact     480
ccaggatgga attcttcctc ctctgctggg actcctttgc atggcagggc tcatctcac      540
ctctcgcaag agggtctctt tgttcaattt tttttaatct aaaatgattg tgcctctgcc     600
caagcagcct ggagacttcc tatgtgtgca ttggggtggg gcttgggca ccatgagaag      660
gttggcgtgc cctggaggct gacacagagg ctggcactga gcctgcttgt tgggaaaagc     720
ccacaggcct gttcccttgt ggcttgggac atggcacagg cccgccctct gcctcctcag     780
ccatgggaac tcatatgca atttgggatt tactagtagc caaaaggaat gaaagagagc     840
tctaaccaga tggaacactg gaacattcca gtggaccctg gaccattcca ggaaaactgg     900
gacataggat cgtcccgcta tgatggaagt gttcagacag tttataatag taagcccctg     960
tgaccctctc acttaccccg agacctcact ttattacaag atctttccaa atacccaaat    1020
gtccctgcaa gcccgttaaa taattcccta tgctaccctt aataacatac aatgaccaca    1080
tagtgtgaga acttccaaca agcctcaaag tcccttgaga ctccccaata cctaataagg    1140
catgcgaaat gttctcatga actaccccac aacacgccta aaactcaaaa cacccaaaaa    1200
tatctcctcc aatgtcctga acatgaacc caaaagaga cccacaataa actcgtgact      1260
tgtcccctca aaaaaaaaa aaaaaaggg cggccgc                              1297
```

<210> SEQ ID NO 24
<211> LENGTH: 87
<212> TYPE: PRT
<213> ORGANISM: Homo sapiens

<400> SEQUENCE: 24

Met Gln Lys Val Thr Leu Gly Leu Leu Val Phe Leu Ala Gly Phe Pro
1               5                   10                  15

```
Val Leu Asp Ala Asn Asp Leu Glu Asp Lys Asn Ser Pro Phe Tyr Tyr
         20                  25                  30

Asp Trp His Ser Leu Gln Val Gly Gly Leu Ile Cys Ala Gly Val Leu
         35                  40                  45

Cys Ala Met Gly Ile Ile Val Met Ser Ala Lys Cys Lys Cys Lys
 50                  55                  60

Phe Gly Gln Lys Ser Gly His His Pro Gly Glu Thr Pro Pro Leu Ile
 65                  70                  75                  80

Thr Pro Gly Ser Ala Gln Ser
                 85

<210> SEQ ID NO 25
<211> LENGTH: 1888
<212> TYPE: DNA
<213> ORGANISM: Homo sapiens
<220> FEATURE:
<221> NAME/KEY: modified_base
<222> LOCATION: (1814)..(1814)
<223> OTHER INFORMATION: a, c, t or g
<220> FEATURE:
<221> NAME/KEY: modified_base
<222> LOCATION: (1834)..(1834)
<223> OTHER INFORMATION: a, c, t or g
<220> FEATURE:
<221> NAME/KEY: modified_base
<222> LOCATION: (1850)..(1850)
<223> OTHER INFORMATION: a, c, t or g

<400> SEQUENCE: 25
```

| | | | | | |
|---|---|---|---|---|---|
| aggtacgcgg | gggaataatg | tgtggcttct | gttggattgc | ttttctttcc | aaaattccta | 60 |
| ggcaatgctt | ccccgaggtg | tgcacctttg | tgaggtgttt | gtggggttgg | gggagcttca | 120 |
| ggcgctactc | gcgggacgcc | gtcacgtgat | ccgggacgag | gtggagttcg | gctttaagga | 180 |
| ggcgtctctt | cctagcttca | tcaatcttta | ggatctgagc | aggagaaata | ccagcggatc | 240 |
| ttccccactc | tgctcccttc | cattcccacc | cttccttctt | taataagcag | gagcgaaaaa | 300 |
| gacaaattcc | aaagaggatt | gttcagttca | agggaatgaa | gaattcagaa | taattttggt | 360 |
| aaatggattc | caatatgggg | aataagaata | agctgaacag | ttgacctgct | ttgaagaaac | 420 |
| atactgtcca | tttgtctaaa | ataatctata | acaaccaaac | caatcaaaat | gaattcaaca | 480 |
| ttattttccc | aggttgaaaa | tcattcagtc | cactctaatt | tctcagagaa | gaatgcccag | 540 |
| cttctggctt | ttgaaaatga | tgattgtcat | ctgcccttgg | ccatgatatt | taccttagct | 600 |
| cttgcttatg | gagctgtgat | cattcttggt | gtctctggaa | acctggcctt | gatcataatc | 660 |
| atcttgaaac | aaaaggagat | gagaaatgtt | accaacatcc | tgattgtgaa | cctttccttc | 720 |
| tcagacttgc | ttgttgccat | catgtgtctc | cccttacat | ttgtctacac | attaatggac | 780 |
| cactgggtct | ttggtgaggc | gatgtgtaag | ttgaatcctt | ttgtgcaatg | tgtttcaatc | 840 |
| actgtgtcca | ttttctctct | ggttctcatt | gctgtggaac | gacatcagct | gataatcaac | 900 |
| cctcgagggt | ggagaccaaa | taatagacat | gcttatgtag | gtattgctgt | gatttgggtc | 960 |
| cttgctgtgg | cttcttcttt | gccttcctg | atctaccaag | taatgactga | tgagccgttc | 1020 |
| caaaatgtaa | cacttgatgc | gtacaaagac | aaatacgtgt | gctttgatca | atttccatcg | 1080 |
| gactctcata | ggttgtctta | taccactctc | ctcttggtgc | tgcagtattt | tggtccactt | 1140 |
| tgttttatat | ttatttgcta | cttcaagata | tatatacgcc | taaaaggag | aaacaacatg | 1200 |
| atggacaaga | tgagagacaa | taagtacagg | tccagtgaaa | ccaaaagaat | caatatcatg | 1260 |
| ctgctctcca | ttgtggtagc | atttgcagtc | tgctggctcc | ctcttaccat | ctttaacact | 1320 |

-continued

```
gtgtttgatt ggaatcatca gatcattgct acctgcaacc acaatctgtt attcctgctc    1380
tgccacctca cagcaatgat atccacttgt gtcaaccca tattttatgg gttcctgaac     1440
aaaaacttcc agagagactt gcagttcttc ttcaactttt gtgatttccg gtctcgggat    1500
gatgattatg aaacaatagc catgtccacg atgcacacag atgtttccaa aacttctttg    1560
aagcaagcaa gcccagtcgc atttaaaaaa atcaacaaca atgatgataa tgaaaaaatc    1620
tgaaactact tatagcctat ggtcccggat gacatctgtt taaaaacaag cacaacctgc    1680
aacatacttt gattacctgt tctcccaagg amtggggttg aaatcatttg aaaatgacta    1740
agattttctt gtcttggctt tttactgctt ttgttgtagt tgtcataatt tacatttggg    1800
aacaaaaggg tgtngggctt tkgggatctt tctnggrrat tagkkgttgn accmgacatc    1860
tttgaagtgc ttttttgtgaa tttaccag                                     1888
```

<210> SEQ ID NO 26
<211> LENGTH: 384
<212> TYPE: PRT
<213> ORGANISM: Homo sapiens

<400> SEQUENCE: 26

```
Met Asn Ser Thr Leu Phe Ser Gln Val Glu Asn His Ser Val His Ser
1               5                   10                  15

Asn Phe Ser Glu Lys Asn Ala Gln Leu Leu Ala Phe Glu Asn Asp Asp
            20                  25                  30

Cys His Leu Pro Leu Ala Met Ile Phe Thr Leu Ala Leu Ala Tyr Gly
        35                  40                  45

Ala Val Ile Ile Leu Gly Val Ser Gly Asn Leu Ala Leu Ile Ile Ile
    50                  55                  60

Ile Leu Lys Gln Lys Glu Met Arg Asn Val Thr Asn Ile Leu Ile Val
65                  70                  75                  80

Asn Leu Ser Phe Ser Asp Leu Leu Val Ala Ile Met Cys Leu Pro Phe
                85                  90                  95

Thr Phe Val Tyr Thr Leu Met Asp His Trp Val Phe Gly Glu Ala Met
            100                 105                 110

Cys Lys Leu Asn Pro Phe Val Gln Cys Val Ser Ile Thr Val Ser Ile
        115                 120                 125

Phe Ser Leu Val Leu Ile Ala Val Glu Arg His Gln Leu Ile Ile Asn
    130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
            180                 185                 190

Lys Asp Lys Tyr Val Cys Phe Asp Gln Phe Pro Ser Asp Ser His Arg
        195                 200                 205

Leu Ser Tyr Thr Thr Leu Leu Leu Val Leu Gln Tyr Phe Gly Pro Leu
    210                 215                 220

Cys Phe Ile Phe Ile Cys Tyr Phe Lys Ile Tyr Ile Arg Leu Lys Arg
225                 230                 235                 240

Arg Asn Asn Met Met Asp Lys Met Arg Asp Asn Lys Tyr Arg Ser Ser
                245                 250                 255

Glu Thr Lys Arg Ile Asn Ile Met Leu Leu Ser Ile Val Val Ala Phe
            260                 265                 270
```

Ala Val Cys Trp Leu Pro Leu Thr Ile Phe Asn Thr Val Phe Asp Trp
        275                 280                 285

Asn His Gln Ile Ile Ala Thr Cys Asn His Asn Leu Leu Phe Leu Leu
        290                 295                 300

Cys His Leu Thr Ala Met Ile Ser Thr Cys Val Asn Pro Ile Phe Tyr
305                 310                 315                 320

Gly Phe Leu Asn Lys Asn Phe Gln Arg Asp Leu Gln Phe Phe Asn
                325                 330                 335

Phe Cys Asp Phe Arg Ser Arg Asp Asp Tyr Glu Thr Ile Ala Met
                340                 345                 350

Ser Thr Met His Thr Asp Val Ser Lys Thr Ser Leu Lys Gln Ala Ser
        355                 360                 365

Pro Val Ala Phe Lys Lys Ile Asn Asn Asn Asp Asn Glu Lys Ile
        370                 375                 380

<210> SEQ ID NO 27
<211> LENGTH: 852
<212> TYPE: DNA
<213> ORGANISM: Homo sapiens

<400> SEQUENCE: 27
ctagtcctga cttcacttct gatgaggaag cctctctcct tagccttcag cctttcctcc     60
cacccctgcca taagtaattt gatcctcaag aagttaaacc acacctcatt ggtccctggc   120
taattcacca atttacaaac agcaggaaat agaaacttaa gagaaataca cacttctgag   180
aaaactgaaac gacaggggaa aggaggtctc actgagcacc gtcccagcat ccggacacca   240
cagcggccct tcgctccacg cagaaaacca cacttctcaa accttcactc aacacttcct   300
tccccaaagc cagaagatgc acaaggagga acatgaggtg gctgtgctgg gggcaccccc   360
cagcaccatc cttccaaggt ccaccgtgat caacatccac agcgagacct ccgtgcccga   420
ccatgtcgtc tggtccctgt tcaacaccct cttcttgaac tggtgctgtc tgggcttcat   480
agcattcgcc tactccgtga agtctaggga caggaagatg gttggcgacg tgaccggggc   540
ccaggcctat gcctccaccg ccaagtgcct gaacatctgg gccctgattc tgggcatcct   600
catgaccatt ggattcatcc tgttactggt attcggctct gtgacagtct accatattat   660
gttacagata atacaggaaa aacggggtta ctagtagccg cccatagcct gcaacctttg   720
cactccactg tgcaatgctg gccctgcacc tggggctgtt gccctgccc ccttggtcct    780
gccctagat acagcagttt atacccacac acctgtctac agtgtcattc aataaagtgc    840
acgtgcttgt ga                                                       852

<210> SEQ ID NO 28
<211> LENGTH: 125
<212> TYPE: PRT
<213> ORGANISM: Homo sapiens

<400> SEQUENCE: 28

Met His Lys Glu Glu His Glu Val Ala Val Leu Gly Ala Pro Pro Ser
1               5                   10                  15

Thr Ile Leu Pro Arg Ser Thr Val Ile Asn Ile His Ser Glu Thr Ser
            20                  25                  30

Val Pro Asp His Val Val Trp Ser Leu Phe Asn Thr Leu Phe Leu Asn
        35                  40                  45

Trp Cys Cys Leu Gly Phe Ile Ala Phe Ala Tyr Ser Val Lys Ser Arg
    50                  55                  60

Asp Arg Lys Met Val Gly Asp Val Thr Gly Ala Gln Ala Tyr Ala Ser
65                  70                  75                  80

Thr Ala Lys Cys Leu Asn Ile Trp Ala Leu Ile Leu Gly Ile Leu Met
            85                  90                  95

Thr Ile Gly Phe Ile Leu Leu Val Phe Gly Ser Val Thr Val Tyr
        100                 105                 110

His Ile Met Leu Gln Ile Ile Gln Glu Lys Arg Gly Tyr
    115                 120                 125

<210> SEQ ID NO 29
<211> LENGTH: 1106
<212> TYPE: DNA
<213> ORGANISM: Homo sapiens

<400> SEQUENCE: 29
cagagctgct gtcatggcgg ccgctctgtg gggcttcttt cccgtcctgc tgctgctgct    60
gctatcgggg gatgtccaga gctcggaggt gcccggggct gctgctgagg gatcgggagg   120
gagtggggtc ggcataggag atcgcttcaa gattgagggg cgtgcagttg ttccaggggt   180
gaagcctcag gactggatct cggcggcccg agtgctggta gacggagaag agcacgtcgg   240
tttccttaag acagatggga gttttgtggt tcatgatata ccttctggat cttatgtagt   300
ggaagttgta tctccagctt acagatttga tcccgttcga gtggatatca cttcgaaagg   360
aaaaatgaga gcaagatatg tgaattacat caaaacatca gaggttgtca gactgcccta   420
tcctctccaa atgaaatctt caggtccacc ttcttacttt attaaaaggg aatcgtgggg   480
ctggacagac tttctaatga acccaatggt tatgatgatg gttcttcctt tattgatatt   540
tgtgcttctg cctaaagtgg tcaacacaag tgatcctgac atgagacggg aaatggagca   600
gtcaatgaat atgctgaatt ccaaccatga gttgcctgat gtttctgagt tcatgacaag   660
actcttctct tcaaaatcat ctggcaaatc tagcagcggc agcagtaaaa caggcaaaag   720
tggggctggc aaaaggaggt agtcaggccg tccagagctg gcatttgcac aaacacggca   780
acactgggtg gcatccaagt cttggaaaac cgtgtgaagc aactactata aacttgagtc   840
atcccgacgt tgatctctta caactgtgta tgttaacttt ttagcacatg ttttgtactt   900
ggtacacgag aaaacccagc tttcatcttt tgtctgtatg aggtcaatat tgatgtcact   960
gaattaatta cagtgtccta tagaaaatgc cattaataaa ttatatgaac tactatacat  1020
tatgtatatt aattaaaaca tcttaatcca gaaaaaaaaa aaaaaaaaa aaaaaaaaa   1080 armaaamgcg ggcgcggggg cgasky                                      1106

<210> SEQ ID NO 30
<211> LENGTH: 242
<212> TYPE: PRT
<213> ORGANISM: Homo sapiens

<400> SEQUENCE: 30

Met Ala Ala Ala Leu Trp Gly Phe Phe Pro Val Leu Leu Leu Leu
1               5                   10                  15

Leu Ser Gly Asp Val Gln Ser Ser Glu Val Pro Gly Ala Ala Ala Glu
                20                  25                  30

Gly Ser Gly Gly Ser Gly Val Gly Ile Gly Asp Arg Phe Lys Ile Glu
            35                  40                  45

Gly Arg Ala Val Val Pro Gly Val Lys Pro Gln Asp Trp Ile Ser Ala
        50                  55                  60

```
Ala Arg Val Leu Val Asp Gly Glu Glu His Val Gly Phe Leu Lys Thr
 65                  70                  75                  80

Asp Gly Ser Phe Val Val His Asp Ile Pro Ser Gly Ser Tyr Val Val
                 85                  90                  95

Glu Val Val Ser Pro Ala Tyr Arg Phe Asp Pro Val Arg Val Asp Ile
            100                 105                 110

Thr Ser Lys Gly Lys Met Arg Ala Arg Tyr Val Asn Tyr Ile Lys Thr
        115                 120                 125

Ser Glu Val Val Arg Leu Pro Tyr Pro Leu Gln Met Lys Ser Ser Gly
130                 135                 140

Pro Pro Ser Tyr Phe Ile Lys Arg Glu Ser Trp Gly Trp Thr Asp Phe
145                 150                 155                 160

Leu Met Asn Pro Met Val Met Met Val Leu Pro Leu Leu Ile Phe
                165                 170                 175

Val Leu Leu Pro Lys Val Val Asn Thr Ser Asp Pro Asp Met Arg Arg
                180                 185                 190

Glu Met Glu Gln Ser Met Asn Met Leu Asn Ser Asn His Glu Leu Pro
            195                 200                 205

Asp Val Ser Glu Phe Met Thr Arg Leu Phe Ser Ser Lys Ser Ser Gly
        210                 215                 220

Lys Ser Ser Ser Gly Ser Ser Lys Thr Gly Lys Ser Gly Ala Gly Lys
225                 230                 235                 240

Arg Arg

<210> SEQ ID NO 31
<211> LENGTH: 2795
<212> TYPE: DNA
<213> ORGANISM: Homo sapiens

<400> SEQUENCE: 31
ggagctgaat accctcccag gcacacacag gtgggacaca aataagggtt ttggaaccac     60
tattttctca tcacgacagc aacttaaaat gcctgggaag atggtcgtga tccttggagc    120
ctcaaatata ctttggataa tgtttgcagc ttctcaagct tttaaaatcg agaccacccc    180
agaatctaga tatcttgctc agattggtga ctccgtctca ttgacttgca gcaccacagg    240
ctgtgagtcc ccattttttct cttggagaac ccagatagat agtccactga atgggaaggt    300
gacgaatgag gggaccacat ctacgctgac aatgaatcct gttagttttg gaacgaaca    360 ctcttacctg tgcacagcaa cttgtgaatc taggaaattg gaaaaaggaa tccaggtgga    420
gatctactct tttcctaagg atccagagat tcatttgagt ggccctctgg aggctgggaa    480
gccgatcaca gtcaagtgtt cagttgctga tgtatacccca tttgacaggc tggagataga    540
cttactgaaa ggagatcatc tcatgaagag tcaggaattt ctggaggatg cagacaggaa    600
gtccctggaa accaagagtt tggaagtaac ctttactcct gtcattgagg atattggaaa    660
agttcttgtt tgccgagcta aattacacat tgatgaaatg gattctgtgc cacagtaag    720 gcaggctgta aaagaattgc aagtctacat atcacccaag aatacagtta tttctgtgaa    780
tccatccaca aagctgcaag aaggtggctc tgtgaccatg acctgttcca gcgagggtct    840
accagctcca gagattttct ggagtaagaa attagataat gggaatctac agcacctttc    900
tggaaatgca actctcacct taattgctat gaggatggaa gattctggaa tttatgtgtg    960
tgaaggagtt aatttgattg ggaaaaacag aaaagaggtg gaattaattg ttcaagcatt   1020
ccctagagat ccagaaatcg agatgagtgg tggcctcgtg aatgggagct ctgtcactgt   1080
```

```
aagctgcaag gttcctagcg tgtaccccct tgaccggctg agattgaat tacttaaggg      1140 ggagactatt ctggagaata tagagttttt ggaggatacg gatatgaaat ctctagagaa      1200
caaaagtttg gaaatgacct tcatccctac cattgaagat actggaaaag ctcttgtttg      1260
tcaggctaag ttacatattg atgacatgga attcgaaccc aaacaaaggc agagtacgca      1320
aacactttat gtcaatgttg cccccagaga tacaaccgtc ttggtcagcc cttcctccat      1380
cctggaggaa ggcagttctg tgaatatgac atgcttgagc cagggctttc ctgctccgaa      1440
aatcctgtgg agcaggcagc tccctaacgg ggagctacag cctctttctg agaatgcaac      1500
tctcacccta atttctacaa aaatggaaga ttctggggtt tatttatgtg aaggaattaa      1560
ccaggctgga agaagcagaa aggaagtgga attaattatc caagttactc caaaagacat      1620
aaaacttaca gcttttcctt ctgagagtgt caaagaagga gacactgtca tcatctcttg      1680
tacatgtgga aatgttccag aaacatggat aatcctgaag aaaaaagcgg agacaggaga      1740
cacagtacta aaatctatag atggcgccta taccatccga aaggcccagt gaaggatgc       1800 gggagtatat gaatgtgaat ctaaaaacaa agttggctca caattaagaa gtttaacact      1860
tgatgttcaa ggaagagaaa acaacaaaga ctatttttct cctgagcttc tcgtgctcta      1920
ttttgcatcc tccttaataa tacctgccat tggaatgata atttactttg caagaaaagc      1980
caacatgaag gggtcatata gtcttgtaga agcacagaaa tcaaaagtgt agctaatgct      2040
tgatatgttc aactggagac actatttatc tgtgcaaatc cttgatactg ctcatcattc      2100
cttgagaaaa acaatgagct gagaggcaga cttccctgaa tgtattgaac ytggaaagaa      2160
atgcccatct atgtcccttg ctgtgagcaa gaagtcaaag taaaacttgc tgcctgaaga      2220
acagtaactg ccatcaagat gagagaactg gaggagttcc ttgatctgta tatacaataa      2280
cataatttgt acatatgtaa aataaaatta tgccatagca agattgctta aaatagcaac      2340
actctatatt tagawtgtta aaawaamyag tgttgcytgg actattataa tttaatgcat      2400
gttaggaaaa ttycacatta awatttgckg acagctgacc yttgtcatct ttctyctatt      2460
ttatycccct ycacaaaatt ttatycctat atagtttatt gacaataatt tcaggttttg      2520
taaagatgcc gggtttttata ttttttataga caaataataa gcaaagggag cactgggttg      2580
actttcaggt actaaatacc tcaacctatg gtataatggt tgactgggtt tctctgtata      2640
gtactggcat ggtacggaga tgtttcacga agtttgttca tcagactcct gtgcaacttt      2700
cccaatgtgg cctaaaaatg caacttcttt ttatttttctt ttgtaaatgt ttaggttttt      2760
ttgtatagta aagtgataat ttctggaaww aaaaa                                 2795
```

<210> SEQ ID NO 32
<211> LENGTH: 647
<212> TYPE: PRT
<213> ORGANISM: Homo sapiens

<400> SEQUENCE: 32

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
            20                  25                  30

Ser Arg Tyr Leu Ala Gln Ile Gly Asp Ser Val Ser Leu Thr Cys Ser
        35                  40                  45

Thr Thr Gly Cys Glu Ser Pro Phe Phe Ser Trp Arg Thr Gln Ile Asp
    50                  55                  60

Ser Pro Leu Asn Gly Lys Val Thr Asn Glu Gly Thr Thr Ser Thr Leu

```
               65                  70                  75                  80
Thr Met Asn Pro Val Ser Phe Gly Asn Glu His Ser Tyr Leu Cys Thr
                    85                  90                  95
Ala Thr Cys Glu Ser Arg Lys Leu Glu Lys Gly Ile Gln Val Glu Ile
                   100                 105                 110
Tyr Ser Phe Pro Lys Asp Pro Glu Ile His Leu Ser Gly Pro Leu Glu
                   115                 120                 125
Ala Gly Lys Pro Ile Thr Val Lys Cys Ser Val Ala Asp Val Tyr Pro
                130                 135                 140
Phe Asp Arg Leu Glu Ile Asp Leu Leu Lys Gly Asp His Leu Met Lys
145                 150                 155                 160
Ser Gln Glu Phe Leu Glu Asp Ala Asp Arg Lys Ser Leu Glu Thr Lys
                    165                 170                 175
Ser Leu Glu Val Thr Phe Thr Pro Val Ile Glu Asp Ile Gly Lys Val
                   180                 185                 190
Leu Val Cys Arg Ala Lys Leu His Ile Asp Glu Met Asp Ser Val Pro
               195                 200                 205
Thr Val Arg Gln Ala Val Lys Glu Leu Gln Val Tyr Ile Ser Pro Lys
               210                 215                 220
Asn Thr Val Ile Ser Val Asn Pro Ser Thr Lys Leu Gln Glu Gly Gly
225                 230                 235                 240
Ser Val Thr Met Thr Cys Ser Ser Glu Gly Leu Pro Ala Pro Glu Ile
                   245                 250                 255
Phe Trp Ser Lys Lys Leu Asp Asn Gly Asn Leu Gln His Leu Ser Gly
                   260                 265                 270
Asn Ala Thr Leu Thr Leu Ile Ala Met Arg Met Glu Asp Ser Gly Ile
                   275                 280                 285
Tyr Val Cys Glu Gly Val Asn Leu Ile Gly Lys Asn Arg Lys Glu Val
               290                 295                 300
Glu Leu Ile Val Gln Ala Phe Pro Arg Asp Pro Glu Ile Glu Met Ser
305                 310                 315                 320
Gly Gly Leu Val Asn Gly Ser Ser Val Thr Val Ser Cys Lys Val Pro
                   325                 330                 335
Ser Val Tyr Pro Leu Asp Arg Leu Glu Ile Glu Leu Leu Lys Gly Glu
                   340                 345                 350
Thr Ile Leu Glu Asn Ile Glu Phe Leu Glu Asp Thr Asp Met Lys Ser
                355                 360                 365
Leu Glu Asn Lys Ser Leu Glu Met Thr Phe Ile Pro Thr Ile Glu Asp
                   370                 375                 380
Thr Gly Lys Ala Leu Val Cys Gln Ala Lys Leu His Ile Asp Asp Met
385                 390                 395                 400
Glu Phe Glu Pro Lys Gln Arg Gln Ser Thr Gln Thr Leu Tyr Val Asn
                   405                 410                 415
Val Ala Pro Arg Asp Thr Thr Val Leu Val Ser Pro Ser Ser Ile Leu
               420                 425                 430
Glu Glu Gly Ser Ser Val Asn Met Thr Cys Leu Ser Gln Gly Phe Pro
               435                 440                 445
Ala Pro Lys Ile Leu Trp Ser Arg Gln Leu Pro Asn Gly Glu Leu Gln
               450                 455                 460
Pro Leu Ser Glu Asn Ala Thr Leu Thr Leu Ile Ser Thr Lys Met Glu
465                 470                 475                 480
Asp Ser Gly Val Tyr Leu Cys Glu Gly Ile Asn Gln Ala Gly Arg Ser
                   485                 490                 495
```

```
Arg Lys Glu Val Glu Leu Ile Ile Gln Val Thr Pro Lys Asp Ile Lys
            500                 505                 510
Leu Thr Ala Phe Pro Ser Glu Ser Val Lys Glu Gly Asp Thr Val Ile
            515                 520                 525
Ile Ser Cys Thr Cys Gly Asn Val Pro Glu Thr Trp Ile Ile Leu Lys
            530                 535                 540
Lys Lys Ala Glu Thr Gly Asp Thr Val Leu Lys Ser Ile Asp Gly Ala
545                 550                 555                 560
Tyr Thr Ile Arg Lys Ala Gln Leu Lys Asp Ala Gly Val Tyr Glu Cys
                565                 570                 575
Glu Ser Lys Asn Lys Val Gly Ser Gln Leu Arg Ser Leu Thr Leu Asp
            580                 585                 590
Val Gln Gly Arg Glu Asn Asn Lys Asp Tyr Phe Ser Pro Glu Leu Leu
            595                 600                 605
Val Leu Tyr Phe Ala Ser Ser Leu Ile Ile Pro Ala Ile Gly Met Ile
            610                 615                 620
Ile Tyr Phe Ala Arg Lys Ala Asn Met Lys Gly Ser Tyr Ser Leu Val
625                 630                 635                 640
Glu Ala Gln Lys Ser Lys Val
                645
```

<210> SEQ ID NO 33
<211> LENGTH: 1375
<212> TYPE: DNA
<213> ORGANISM: Homo sapiens
<220> FEATURE:
<221> NAME/KEY: modified_base
<222> LOCATION: (1327)..(1372)
<223> OTHER INFORMATION: a, c, t or g

<400> SEQUENCE: 33

```
gagtcgaccc acgcgtccgc ccacgcgtcc gagcggtctg dacagcgcgt ggccggcgcc      60
gctgtgggga cagcatgagc ggcggttgga tggcgcaggt tggagcgtgg cgaacagggg     120
ctctgggcct ggcgctgctg ctgctgctcg gcctcggact aggcctggag gccgccgcga     180
gcccgctttc caccccgacc tctgcccagg ccgcaggccc cagctcaggc tcgtgcccac     240
ccaccaagtt ccagtgccgc accagtggct tatgcgtgcc cctcacctgg cgctgcgaca     300
gggacttgga ctgcagcgat ggcagcgatg aggaggagtg caggattgag ccatgtaccc     360
agaaagggca atgcccaccg cccctggcc tccctgccc ctgcaccggc gtcagtgact     420
gctctggggg aactgacaag aaactgcgca actgcagccg cctggcctgc ctagcaggcg     480
agctccgttg cacgctgagc gatgactgca ttccactcac gtggcgctgc gacggccacc     540
cagactgtcc cgactccagc gacgagctcg gctgtggaac caatgagatc ctcccggaag     600
gggatgccac aaccatgggg cccctgtga ccctggagag tgtcacctct ctcaggaatg     660
ccacaaccat gggccccct gtgacccgg agagtgtccc ctctgtcggg aatgccacat     720
cctcctctgc cggagaccag tctggaagcc caactgccta tgggttatt gcagctgctg     780
cggtgctcag tgcaagcctg gtcaccgcca ccctcctcct tttgtcctgg ctccagcccc     840
aggagcgcct ccgcccactg gggttactgg tggccatgaa ggagtccctg ctgctgtcag     900
aacagaagac ctcgctgccc tgaggacaag cacttgccac caccgtcact cagccctggg     960
cgtagccgga caggaggaga gcagtgatgc ggatgggtac ccgggcacac cagccctcag    1020
agacctgagc tcttctggcc acgtggaacc tcgaacccga gctcctgcag gaagtggccc    1080
```

-continued

```
tggagattga gggtccctgg acactcccta tggagatccg gggagctagg atggggaacc    1140
tgccacagcc agaactgagg ggctggcccc aggcagctcc caggggtag aacggccctg     1200 tgcttaagac actcctgctg ccccgtctga gggtggcgat taaagttgct tcacatcctc   1260
aaaaaaaaaa aaaaaaaaaa aaaaaaaaaa aaaaaaaaaa aaaaaaargg gcggcccgct   1320
agactannnn nnnnnnnnnn nnnnnnnnnn nnnnnnnnnn nnnnnnnnnn nngaa         1375
```

<210> SEQ ID NO 34
<211> LENGTH: 282
<212> TYPE: PRT
<213> ORGANISM: Homo sapiens

<400> SEQUENCE: 34

```
Met Ser Gly Gly Trp Met Ala Gln Val Gly Ala Trp Arg Thr Gly Ala
1               5                   10                  15

Leu Gly Leu Ala Leu Leu Leu Leu Gly Leu Gly Leu Gly Leu Glu
                20                  25                  30

Ala Ala Ala Ser Pro Leu Ser Thr Pro Thr Ser Ala Gln Ala Ala Gly
                35                  40                  45

Pro Ser Ser Gly Ser Cys Pro Pro Thr Lys Phe Gln Cys Arg Thr Ser
50                  55                  60

Gly Leu Cys Val Pro Leu Thr Trp Arg Cys Asp Arg Asp Leu Asp Cys
65                  70                  75                  80

Ser Asp Gly Ser Asp Glu Glu Cys Arg Ile Glu Pro Cys Thr Gln
                85                  90                  95

Lys Gly Gln Cys Pro Pro Pro Gly Leu Pro Cys Pro Cys Thr Gly
                100                 105                 110

Val Ser Asp Cys Ser Gly Gly Thr Asp Lys Lys Leu Arg Asn Cys Ser
            115                 120                 125

Arg Leu Ala Cys Leu Ala Gly Glu Leu Arg Cys Thr Leu Ser Asp Asp
130                 135                 140

Cys Ile Pro Leu Thr Trp Arg Cys Asp Gly His Pro Asp Cys Pro Asp
145                 150                 155                 160

Ser Ser Asp Glu Leu Gly Cys Gly Thr Asn Glu Ile Leu Pro Glu Gly
                165                 170                 175

Asp Ala Thr Thr Met Gly Pro Pro Val Thr Leu Glu Ser Val Thr Ser
                180                 185                 190

Leu Arg Asn Ala Thr Thr Met Gly Pro Pro Val Thr Leu Glu Ser Val
            195                 200                 205

Pro Ser Val Gly Asn Ala Thr Ser Ser Ser Ala Gly Asp Gln Ser Gly
            210                 215                 220

Ser Pro Thr Ala Tyr Gly Val Ile Ala Ala Ala Val Leu Ser Ala
225                 230                 235                 240

Ser Leu Val Thr Ala Thr Leu Leu Leu Ser Trp Leu Arg Ala Gln
                245                 250                 255

Glu Arg Leu Arg Pro Leu Gly Leu Val Ala Met Lys Glu Ser Leu
                260                 265                 270

Leu Leu Ser Glu Gln Lys Thr Ser Leu Pro
                275                 280
```

<210> SEQ ID NO 35
<211> LENGTH: 1798
<212> TYPE: DNA
<213> ORGANISM: Homo sapiens
<220> FEATURE:
<221> NAME/KEY: modified_base
<222> LOCATION: (6)..(7)
<223> OTHER INFORMATION: a, c, t or g

<400> SEQUENCE: 35

```
ttcganngge cgcccgggca ggtacctcaa attttaggg gagggtgggt tagggactga    60
tactcagatt gtggataata attgaattgg tttttaaagg caacatagca ttctacagca   120
gggttaatct attatcaaga acagtcaccc tggttaataa caagttttac tgatcagttg   180
ctggttggtt ggttggttgg catgtgggtg tgtgggtgta taggtgtgtg tgggtgtgtg   240
tgtgtatttt tccccatgag tccttttttt aatcctgtgg cttttcact tacaactagc   300
ctaaccctgt aatttccta catccaagaa acaatcaca aagtagtggt ttaaatactt    360
tgttgtatt ggctaatttt gctgtcttaa tgcagcctat taagagttgg gttaaaaatc   420
agtaatcagt actttattac atcactgaac taaaatatgg agacatcctc attgaaaatg   480
gagggcactc tatcagtcta taactatcaa cgtagtgcaa cagggtgttt tgatacctttt  540
gttttcacct cttgacataa tgctatttaa aggcttgaat ttttccttt atataatttt   600
caccttact ttcaaagtgt tttgttgtag ttggctattg cagagagtgc attgtcctat   660
cattcctaaa cctggtctgc tttctacatt catggtatgg aaaccatgtg attctttgta   720
cagtttatcc tgatgttgct tgtaatgcag tagaggctat ttcgccttcg ctttctttc   780
tcgaccttt tgtaaaccct ataattatga agcgattgct tgagaaaata acatataaac   840
atagaataga atagactgac caagatggtt cacagtttct ttttttaact aggttattta   900
taatgtattt ctgaaccact tggcagacaa attcacaaca cttaatgttc atattttgag   960
taaaggaagc taaaaccatg tttgctttct ggtactacat gcattagcga aaggttaagt  1020
aagtttgtt ctccactgaa gtaatactta acatctcaga aaaatttg catgttctgt    1080
agttttgtat taaatcagtc atttcatatg cactatatca agtacaaaca ggtagtttac  1140
ctgtttatag tagtgtacta acaaagtctc ccttgcagct tcagactgtt atctataggc  1200
ttatcgttca aatacagcac ttgaatatcc caagtagttc ttctacgcat agctcacctt  1260
tctaaaccca gttaagcatg gaagagaggt agtaggtagg tgcagtgtgt ggaagctgca  1320
aacaagtagg ccttttattc attgatatct ttcccaagt actggattt aaatctgwat    1380
gtatctgttt gatttttt tctaatattt cagttgagct gctgttttct tccatgcaat   1440
attgtatact caattgtgta tagaagaagc tggtgagagt gccctcctac ataaataagc  1500
aattgcagtg ttttgcatgc aaaatataaa aaatttaaat tgtcctgatt ctattttgta  1560
aatggagaaa caatcatatc tttctaagcg gtaatggagg aagactagtg ctttgtgcat  1620
tttgatatat ttgagttcat ttttccaca atgtcatact tttgacgcag ttgggtttct   1680
catargtatc ctagttcatg tacatccgaa tgctaaataa tactgtgttt taagttttgt  1740
gttgcaagaa caaatggaat aaacttgaat tgtgctacaa aaaaaaaaaa aaaaaaa    1798
```

<210> SEQ ID NO 36
<211> LENGTH: 57
<212> TYPE: PRT
<213> ORGANISM: Homo sapiens

<400> SEQUENCE: 36

```
Met Leu Phe Lys Gly Leu Asn Phe Ser Leu Tyr Ile Ile Phe Thr Phe
1               5                   10                  15

Thr Phe Lys Val Phe Cys Cys Ser Trp Leu Leu Gln Arg Val His Cys
            20                  25                  30
```

```
Pro Ile Ile Pro Lys Pro Gly Leu Leu Ser Thr Phe Met Val Trp Lys
        35                  40                  45

Pro Cys Asp Ser Leu Tyr Ser Leu Ser
        50                  55

<210> SEQ ID NO 37
<211> LENGTH: 3113
<212> TYPE: DNA
<213> ORGANISM: Homo sapiens
<220> FEATURE:
<221> NAME/KEY: modified_base
<222> LOCATION: (68)..(68)
<223> OTHER INFORMATION: a, c, t or g
<220> FEATURE:
<221> NAME/KEY: modified_base
<222> LOCATION: (92)..(92)
<223> OTHER INFORMATION: a, c, t or g
<220> FEATURE:
<221> NAME/KEY: modified_base
<222> LOCATION: (94)..(94)
<223> OTHER INFORMATION: a, c, t or g
<220> FEATURE:
<221> NAME/KEY: modified_base
<222> LOCATION: (106)..(106)
<223> OTHER INFORMATION: a, c, t or g
<220> FEATURE:
<221> NAME/KEY: modified_base
<222> LOCATION: (145)..(145)
<223> OTHER INFORMATION: a, c, t or g

<400> SEQUENCE: 37
gacccacgms yccgcgtcgt ccgcgcgtcg ccggaagggg aagtttcgcc tcagaaggct      60
gcctcgcntg gtccgaattc ggtggcgcca cngntccgcc cgtctnccgc cttctgcatc    120
gcggcttcgg cggcttccac ctagnacacc taacagtcgc ggagccggcc gcgtcgtgag    180
ggggtcggca cggggagtcg ggcggtcttg tgcatcttgg ctacctgtgg gtcgaagatg    240
tcggacatcg gagactggtt caggagcatc ccggcgatca cgcgctattg gttcgccgcc    300
accgtcgccg tgcccttggt cggcaaactc ggcctcatca gcccggccta cctcttcctc    360
tggcccgaag ccttcctttta tcgctttcag atttggaggc caatcactgc cacctttttat    420 ttccctgtgg gtccaggaac tggatttctt tatttggtca atttatattt cttatatcag    480
tattctacgc gacttgaaac aggagctttt gatgggaggc cagcagacta tttattcatg    540 ctcctctttta actggatttg catcgtgatt actggcttag caatggatat gcagttgctg    600
atgattcctc tgatcatgtc agtactttat gtctgggccc agctgaacag agacatgatt    660
gtatcatttt ggtttggaac acgatttaag gcctgctatt tacccctgggt tatccttgga    720 ttcaactata tcatcggagg ctcggtaatc aatgagctta ttggaaatct ggttggacat    780
ctttattttt tcctaatgtt cagatacccca atggacttgg gaggaagaaa ttttctatcc    840
acacctcagt ttttgtaccg ctggctgccc agtaggagag gaggagtatc aggatttggt    900
gtgccccctg ctagcatgag gcgagctgct gatcagaatg gcggaggcgg gagacacaac    960
tggggccagg gctttcgact tggagaccag tgaaggggcg gcctcgggca gccgctcctc    1020
tcaagccaca tttcctccca gtgctgggtg cgcttaacaa ctgcgttctg gctaacactg    1080
ttggacctga cccacactga atgtagtctt tcagtacgag acaaagtttc ttaaatcccg    1140
aagaaaaata taagtgttcc acaagtttca cgattctcat tcaagtcctt actgctgtga    1200
agaacaaata ccaactgtgc aaattgcaaa actgactaca ttttttggtg tcttctcttc    1260 tccccttttcc gtctgaataa tgggttttag cgggtcctag tctgctggca ttgagctggg    1320
gctgggtcac caaacccttc ccaaaaggac ccttatctct ttcttgcaca catgcctctc    1380
```

```
tcccactttt cccaaccccc acatttgcaa ctagaagagg ttgcccataa aattgctctg    1440
cccttgacag gttctgttat ttattgactt ttgccaaggc ttggtcacaa caatcatatt    1500
cacgtaattt tcccccttg gtggcagaac tgtagcaata gggggagaag acaagcagcg    1560
gatgaagcgt tttctcagct tttggaattg cttcgacctg acatccgttg taaccgtttg    1620
ccacttcttc agatatttt ataaaaaagt accactgagt cagtgagggc cacagattgg    1680
tattaatgag atacgagggt tgttgctggg tgtttgtttc ctgagctaag tgatcaagac    1740
tgtagtggag ttgcagctaa catgggttag gtttaaacca tggggatgc aaccccttg    1800 cgtttcatat gtaggcctac tggctttgtg tagctggagt agttgggttg ctttgtgtta    1860
ggaggatcca gatcatgttg gctacaggga gatgctctct ttgagaggct cctgggcatt    1920
gattccattt caatctcatt ctggatatgt gttcattgag taaaggagga gagaccctca    1980
tacgctattt aaatgtcact ttttgccta tcccccgttt tttggtcatg tttcaattaa    2040
ttgtgaggaa ggcgcagctc ctctctgcac gtagatcatt ttttaaagct aatgtaagca    2100
catctaaggg aataacatga tttaaggttg aaatggcttt agaatcattt gggtttgagg    2160
gtgtgttatt ttgagtcatg aatgtacaag ctctgtgaat cagaccagct taaataccca    2220 caccttttt tcgtaggtgg cttttccta tcagagcttg gctcataacc aaataaagtt    2280
ttttgaaggc catggctttt cacacagtta ttttatttta tgacgttatc tgaaagcaga    2340
ctgttaggag cagtattgag tggctgtcac actttgaggc aactaaaaag gcttcaaacg    2400
ttttgatcag tttcttttca ggaaacattg tgctctaaca gtatgactat tctttccccc    2460
actcttaaac agtgtgatgt gtgttatcct aggaaatgag agttggcaaa caacttctca    2520
ttttgaatag agtttgtgtg tacctctcca tatttaattt atatgataaa ataggtgggg    2580
agagtctgaa ccttaactgt catgttttgt tgttcatctg tggccacaat aaagtttact    2640
tgtaaaattt tagaggccat tactccaatt atgttgcacg tacactcatt gtacaggcgt    2700
ggagactcat tgtatgtata agaatattct gacagtgagt gacccggagt ctctggtgta    2760
ccctcttacc agtcagctgc ctgcgagcag tcattttttc ctaaaggtt acaagtattt    2820 agaactcttc agttcagggc aaaatgttca tgaagttatt cctcttaaac atggttagga    2880
agctgatgac gttattgatt ttgtctggat tatgtttctg gaataatttt accaaaacaa    2940
gctatttgag ttttgacttg acaaggcaaa acatgacagt ggattctctt tacaaatgga    3000 aaaaaaaat ccttatttg tataaaggac ttcccttttt gtaaactaat cctttttatt    3060
ggtaaaaatt gtaaattaaa atgtgcaact tgaaaaaaaa aaaaaaaaa aaa           3113
```

<210> SEQ ID NO 38
<211> LENGTH: 251
<212> TYPE: PRT
<213> ORGANISM: Homo sapiens

<400> SEQUENCE: 38

```
Met Ser Asp Ile Gly Asp Trp Phe Arg Ser Ile Pro Ala Ile Thr Arg
1               5                   10                  15

Tyr Trp Phe Ala Ala Thr Val Ala Val Pro Leu Val Gly Lys Leu Gly
            20                  25                  30

Leu Ile Ser Pro Ala Tyr Leu Phe Leu Trp Pro Glu Ala Phe Leu Tyr
        35                  40                  45

Arg Phe Gln Ile Trp Arg Pro Ile Thr Ala Thr Phe Tyr Phe Pro Val
    50                  55                  60
```

Gly Pro Gly Thr Gly Phe Leu Tyr Leu Val Asn Leu Tyr Phe Leu Tyr
65                  70                  75                  80

Gln Tyr Ser Thr Arg Leu Glu Thr Gly Ala Phe Asp Gly Arg Pro Ala
                85                  90                  95

Asp Tyr Leu Phe Met Leu Leu Phe Asn Trp Ile Cys Ile Val Ile Thr
            100                 105                 110

Gly Leu Ala Met Asp Met Gln Leu Leu Met Ile Pro Leu Ile Met Ser
        115                 120                 125

Val Leu Tyr Val Trp Ala Gln Leu Asn Arg Asp Met Ile Val Ser Phe
    130                 135                 140

Trp Phe Gly Thr Arg Phe Lys Ala Cys Tyr Leu Pro Trp Val Ile Leu
145                 150                 155                 160

Gly Phe Asn Tyr Ile Ile Gly Gly Ser Val Ile Asn Glu Leu Ile Gly
                165                 170                 175

Asn Leu Val Gly His Leu Tyr Phe Phe Leu Met Phe Arg Tyr Pro Met
            180                 185                 190

Asp Leu Gly Gly Arg Asn Phe Leu Ser Thr Pro Gln Phe Leu Tyr Arg
        195                 200                 205

Trp Leu Pro Ser Arg Arg Gly Gly Val Ser Gly Phe Gly Val Pro Pro
210                 215                 220

Ala Ser Met Arg Arg Ala Ala Asp Gln Asn Gly Gly Gly Arg His
225                 230                 235                 240

Asn Trp Gly Gln Gly Phe Arg Leu Gly Asp Gln
                245                 250

<210> SEQ ID NO 39
<211> LENGTH: 3599
<212> TYPE: DNA
<213> ORGANISM: Homo sapiens
<220> FEATURE:
<221> NAME/KEY: modified_base
<222> LOCATION: (3390)..(3390)
<223> OTHER INFORMATION: a, c, t or g
<220> FEATURE:
<221> NAME/KEY: modified_base
<222> LOCATION: (3420)..(3420)
<223> OTHER INFORMATION: a, c, t or g

<400> SEQUENCE: 39
cagtttggga ccaaagccaa agataaccag gttcatatta attacacgga ataggcaaga      60
aagcatgagc cctgaggagg aaggaaaggg actgtcccag gtgtacttac ctcaaagatg     120
aagaaatatc aaagacagga aaccctaggt tcttgccctt cagtcgctat ctccttgccc     180
attagtaaaa tgcggccgat gaatgtcctc acttctgtcc atctgggcag gaggtgggaa     240
gggtgacgtg caaatggatg ggaggaaccc ttttttcggc agcacccacc acacccagcc     300
tagtgccacg caccgcaagc gctccataaa cgcacacagc gtcgcswcya csmgkmyscc     360
gggcggcctt cgcgggattt ctcctggcgt cggctttcag actcccgagg gtgggataaa     420
tcgagagggt ggcatccttt ggcttttctt ctcccaggca gctctgaacc atgtttatgc     480
aacgtttaat gggctctaat aaaacggcta ataatttga tccgcggaag caccgactcg     540
ctcgctaagc cgagtctgcg agggtgaagc tgcaactcca acgccggaaa gcgcggctac     600
cgaaaagcgc atgcgccacg gggtggcacg aagctagagt aagctgagga ggtgggcgga     660
aaccatggca accatgggtg atgacgacat ggggagcgtc tctagcgctg gattatgacg     720
ctggattatg acgcatgcag tgggcgcccg ctctgcggtt cgcttgactg acggcgcagc     780
ctccgggcct agccacagca gcaacggcag aggccagcgg gcgaggtcaa gatggtggct     840

```
ccgcgggcgg gggaggcagt ggagggagga ggagtcagac cttagccagc cggaaacacc      900
gaaacccaga gacctcctgg ggagccgtcg ccgccgccgc cctctcggcc atcgctgcct      960
ccgccgcctg ctccacctcg agggacgcga gcgggcggcg gggctggccg tgagagagac     1020
aggagaggaa ggagggcagg ggcggagttg cccgccttag cccccgcccc cggccgcggc     1080
cccgggccct gccccgcgcg gccctgcccg gcccaccgag ccctggtgtg gcagcggctc     1140
atggcggccg tggggccccc gcagcagcag gtgcggatgg cccatcagca ggtctgggcg     1200
gcgctcgaag tggcgctccg ggtgccctgc ctttacatca tcgacgccat cttcaactcc     1260
tacccggatt ccagccaaag ccggttctgc atcgtgctcc agatcttcct ccggctcttt     1320
ggtgtatttg catccagtat tgttctgatc ttgtcacaac gatcactttt caagttttac     1380
acgtacagct cagcctttct gttagctgca acttcagtgt tggtgaatta ttatgcttct     1440
ttgcacattg acttctatgg tgcctacaac acgtcagctt ttggaattga gctgcttcct     1500
cgaaaaggtc cctcgctgtg gatggcactt atcgttctac agctaacatt tggaattgga     1560
tacgttacac tactccagat tcattccatc tattcacaat taattatttt ggatctcttg     1620
gttcctgtaa taggcttaat cacagagcta ccattacaca tcagagagac tttactgttt     1680
acttcttcct tgattctcac attaaataca gtgtttgtcc tggcagtgaa actgaagtgg     1740
ttttattatt ccacacgata tgtttatctt ttggtgaggc acatgtatcg aatttatgga     1800
ttacagttat tgatggagga cacatggaag aggattcgtt tcccagacat actacgagtc     1860
ttttggctaa caagagttac agctcaggct acagtgttaa tgtacatctt aaggatggca     1920
aatgaaactg attccttctt tatttcttgg gatgattttt gggacctcat ttgcaatctt     1980
ataattagtg ggtgcgattc tacactaact gtactgggca tgagtgctgt aatttcctca     2040
gtagcccatt atttggggct tggaatattg gcctttattg gatcaactga ggaagatgac     2100
aggcgtcttg gctttgttgc acctgtttta tttttttatt tggctcttca gactgggtta     2160
agtgggctaa gaccagaaga gagacttatt cgcttaagta gaaacatgtg cctttt atta     2220 actgcagtcc tgcattttat ccatggaatg acagaccctg tattaatgtc tctcagtgcc     2280
tctcatgtgt catcttttcg tagacatttt cctgtgctgt ttgtctctgc ttgcctgttt     2340
attcttcctg tcttactcag ttatgttctt tggcatcact atgcactaaa tacatggttg     2400
tttgcagtta cagcattttg tgtggaactg tgcttaaaag taattgtttc tctcactgtt     2460
tatacgttat tcatgattga tggctactat aatgtcctct gggaaaagct tgacgattat     2520
gtctactacg ttcgttcaac aggcagtatt attgaattta tatttggagt tgtaatgttt     2580
ggaaatgggg cttacactat gatgtttgag tcgggaagta aaattcgggc ttttatgatg     2640
tgcctacatg catattttaa catctactta caagccaaaa atggctggaa gacatttatg     2700
aatcgtagga ctgctgtgaa gaaattaat tcacttcctg aaataaaagg gagccgctta      2760
caagaaataa atgatgtatg tgcaatctgc tatcatgagt ttacaacatc tgctcgtatt     2820
acaccgtgta atcattattt ccatgcactt tgccttcgga atggctgta cattcaagat     2880 acttgtccaa tgtgccatca gaaagtatac atcgaagatg atatcaagga taattcaaat     2940
gtatctaaca caatggatt tattccaccc aatgaaactc cagaggaagc tgtaagagaa     3000
gctgctgctg aatctgacag ggaattgaac gaagatgaca gtacagattg tgatgatgat     3060
gttcaaagag aaagaaatgg agtgattcag cacacaggcg cagcagctga gaatttaat      3120 gatgatactg actgatgaaa atagcattta ttaatgattg aggtatttgt ttaaaattca     3180
```

-continued

```
gttcatccaa atggagtaa tatccttcac cttcagtgtg taaccaagca caaaaacagt    3240
atcaatgttg aatctgtgaa tggttttccg tttactgtga tgtgctactg taaatatacc    3300
tctttaatta cttctggtct ctttggtgac ctgtttaaat ttgtgtacat tattgtacat    3360
agaataaaat gttttcacat ttttatgacn aaaawwwraa caaatagctt tttaatagan    3420
tgtaatgatc atatggtgcg tcacctgtgc caaatattct tcaatgaaat tatataatgt    3480
aactttggac ctcagttttt ctttagaaat gggtgggaga atgaaaatgc aaatcaggaa    3540
accacattaa agtcaaggaa ataaaataat ttgaccagag gataaaggac atgagagag    3599
```

<210> SEQ ID NO 40
<211> LENGTH: 664
<212> TYPE: PRT
<213> ORGANISM: Homo sapiens

<400> SEQUENCE: 40

```
Met Ala Ala Val Gly Pro Pro Gln Gln Gln Val Arg Met Ala His Gln
 1               5                  10                  15

Gln Val Trp Ala Ala Leu Glu Val Ala Leu Arg Val Pro Cys Leu Tyr
             20                  25                  30

Ile Ile Asp Ala Ile Phe Asn Ser Tyr Pro Asp Ser Ser Gln Ser Arg
         35                  40                  45

Phe Cys Ile Val Leu Gln Ile Phe Leu Arg Leu Phe Gly Val Phe Ala
     50                  55                  60

Ser Ser Ile Val Leu Ile Leu Ser Gln Arg Ser Leu Phe Lys Phe Tyr
 65                  70                  75                  80

Thr Tyr Ser Ser Ala Phe Leu Leu Ala Ala Thr Ser Val Leu Val Asn
                 85                  90                  95

Tyr Tyr Ala Ser Leu His Ile Asp Phe Tyr Gly Ala Tyr Asn Thr Ser
            100                 105                 110

Ala Phe Gly Ile Glu Leu Leu Pro Arg Lys Gly Pro Ser Leu Trp Met
        115                 120                 125

Ala Leu Ile Val Leu Gln Leu Thr Phe Gly Ile Gly Tyr Val Thr Leu
    130                 135                 140

Leu Gln Ile His Ser Ile Tyr Ser Gln Leu Ile Ile Leu Asp Leu Leu
145                 150                 155                 160

Val Pro Val Ile Gly Leu Ile Thr Glu Leu Pro Leu His Ile Arg Glu
                165                 170                 175

Thr Leu Leu Phe Thr Ser Ser Leu Ile Leu Thr Leu Asn Thr Val Phe
            180                 185                 190

Val Leu Ala Val Lys Leu Lys Trp Phe Tyr Ser Thr Arg Tyr Val
        195                 200                 205

Tyr Leu Leu Val Arg His Met Tyr Arg Ile Tyr Gly Leu Gln Leu Leu
    210                 215                 220

Met Glu Asp Thr Trp Lys Arg Ile Arg Phe Pro Asp Ile Leu Arg Val
225                 230                 235                 240

Phe Trp Leu Thr Arg Val Thr Ala Gln Ala Thr Val Leu Met Tyr Ile
                245                 250                 255

Leu Arg Met Ala Asn Glu Thr Asp Ser Phe Phe Ile Ser Trp Asp Asp
            260                 265                 270

Phe Trp Asp Leu Ile Cys Asn Leu Ile Ile Ser Gly Cys Asp Ser Thr
        275                 280                 285

Leu Thr Val Leu Gly Met Ser Ala Val Ile Ser Ser Val Ala His Tyr
    290                 295                 300
```

Leu Gly Leu Gly Ile Leu Ala Phe Ile Gly Ser Thr Glu Glu Asp Asp
305                 310                 315                 320

Arg Arg Leu Gly Phe Val Ala Pro Val Leu Phe Phe Ile Leu Ala Leu
                325                 330                 335

Gln Thr Gly Leu Ser Gly Leu Arg Pro Glu Glu Arg Leu Ile Arg Leu
            340                 345                 350

Ser Arg Asn Met Cys Leu Leu Leu Thr Ala Val Leu His Phe Ile His
        355                 360                 365

Gly Met Thr Asp Pro Val Leu Met Ser Leu Ser Ala Ser His Val Ser
    370                 375                 380

Ser Phe Arg Arg His Phe Pro Val Leu Phe Val Ser Ala Cys Leu Phe
385                 390                 395                 400

Ile Leu Pro Val Leu Leu Ser Tyr Val Leu Trp His His Tyr Ala Leu
                405                 410                 415

Asn Thr Trp Leu Phe Ala Val Thr Ala Phe Cys Val Glu Leu Cys Leu
            420                 425                 430

Lys Val Ile Val Ser Leu Thr Val Tyr Thr Leu Phe Met Ile Asp Gly
        435                 440                 445

Tyr Tyr Asn Val Leu Trp Glu Lys Leu Asp Asp Tyr Val Tyr Tyr Val
    450                 455                 460

Arg Ser Thr Gly Ser Ile Ile Glu Phe Ile Phe Gly Val Val Met Phe
465                 470                 475                 480

Gly Asn Gly Ala Tyr Thr Met Met Phe Glu Ser Gly Ser Lys Ile Arg
                485                 490                 495

Ala Phe Met Met Cys Leu His Ala Tyr Phe Asn Ile Tyr Leu Gln Ala
            500                 505                 510

Lys Asn Gly Trp Lys Thr Phe Met Asn Arg Arg Thr Ala Val Lys Lys
        515                 520                 525

Ile Asn Ser Leu Pro Glu Ile Lys Gly Ser Arg Leu Gln Glu Ile Asn
    530                 535                 540

Asp Val Cys Ala Ile Cys Tyr His Glu Phe Thr Thr Ser Ala Arg Ile
545                 550                 555                 560

Thr Pro Cys Asn His Tyr Phe His Ala Leu Cys Leu Arg Lys Trp Leu
                565                 570                 575

Tyr Ile Gln Asp Thr Cys Pro Met Cys His Gln Lys Val Tyr Ile Glu
            580                 585                 590

Asp Asp Ile Lys Asp Asn Ser Asn Val Ser Asn Asn Gly Phe Ile
        595                 600                 605

Pro Pro Asn Glu Thr Pro Glu Glu Ala Val Arg Glu Ala Ala Ala Glu
    610                 615                 620

Ser Asp Arg Glu Leu Asn Glu Asp Ser Thr Asp Cys Asp Asp Asp
625                 630                 635                 640

Val Gln Arg Glu Arg Asn Gly Val Ile Gln His Thr Gly Ala Ala Ala
                645                 650                 655

Glu Glu Phe Asn Asp Asp Thr Asp
            660

<210> SEQ ID NO 41
<211> LENGTH: 2080
<212> TYPE: DNA
<213> ORGANISM: Homo sapiens
<220> FEATURE:
<221> NAME/KEY: modified_base
<222> LOCATION: (34)..(34)
<223> OTHER INFORMATION: a, c, t or g
<220> FEATURE:

<221> NAME/KEY: modified_base
<222> LOCATION: (85)..(85)
<223> OTHER INFORMATION: a, c, t or g
<220> FEATURE:
<221> NAME/KEY: modified_base
<222> LOCATION: (95)..(95)
<223> OTHER INFORMATION: a, c, t or g

<400> SEQUENCE: 41

```
cgaccccgcs tccrcmgssr rkkgcgtccg cggnggcgcg gggagagtag ggtgctgtgg      60
tctgagctag agggtgaagc tggcnggagc agganggatg ggcgagcagt ctgaatgcca     120
gaatggataa ccgttttgct acagcatttg taattgcttg tgtgcttagc ctcatttcca     180
ccatctacat ggcagcctcc attggcacag acttctggta tgaatatcga agtccagttc     240
aagaaaattc cagtgatttg aataaaagca tctgggatga attcattagt gatgaggcag     300
atgaaaagac ttataatgat gcacttttc gatacaatgg cacagtggga ttgtggagac      360
ggtgtatcac catacccaaa aacatgcatt ggtatagccc accagaaagg acagagtcat     420
ttgatgtggt cacaaaatgt gtgagtttca cactaactga gcagttcatg gagaaatttg     480
ttgatcccgg aaaccacaat agcgggattg atctccttag gacctatctt tggcgttgcc     540
agttcctttt accttttgtg agtttaggtt tgatgtgctt tggggctttg atcggacttt     600
gtgcttgcat tgccgaagc ttatatccca ccattgccac gggcattctc catctccttg      660
caggtctgtg tacactgggc tcagtaagtt gttatgttgc tggaattgaa ctactccacc     720
agaaactaga gctccctgac aatgtatccg gtgaatttgg atggtccttc tgcctggctt     780
gtgtctctgc tcccttacag ttcatggctt ctgctctctt catctgggct gctcacacca     840
accggaaaga gtacacctta atgaaggcat atcgtgtggc atgagcaaga aactgcctgc     900
tttacaattg ccattttat ttttttaaaa taatactgat attttcccca cctctcaatt      960
gttttaatt tttatttgtg gatataccat tttattatga aaatctattt tatttataca     1020
cattcaccac taaatacaca cttaatacca ctaaaattta tgtggtttac tttaagcgat    1080
gccatctttc aaataaacta atctaggtct agacagaaag aaatggatag agacttgaca    1140
caaatttatg aaagaaaatt gggagtagga atgtgaccga aaacaagttg tgctaatgtc    1200
tgttagactt ttcagtaaaa ctaaagtaac tgtatctgtt caactaaaaa ctctatatta    1260
gtttctttgg gaaacctctc atcgtcaaaa ctttatgttc actttgctgt tgtagatagc    1320
cagtcaacca gcagtattag tgctgttttc aaagatttaa gctctataaa attgggaaat    1380
tatctaagat cattttccct aagcattgac acatagcttc atctgaggtg agatatggca    1440
gctgtttgta tctgcactgt gtctgtctac aaaagtgaa aaatacagtg tttacttgaa     1500
atttaacctt tgtaactgca agaattccag ttcagccggg cgaggattag tattattttt    1560
aactctccgt aagattttca gtaccaccaa attgttttgg attttttttc tttcctcttc    1620
acataccagg gttattaaaa gtgtgctttc ttttacatt atattacagt tacaaggtaa     1680
aattcctcaa ctgctattta tttattccag cccagtacta taagaacgt ttcaccataa     1740
tgaccctcca gagctgggaa acctaccaca agatctaaag ttctggctgt ccattaacct    1800
ccaactatgg tctttatttc ttgtggtaat atgatgtgcc tttccttgcc taaatccctt    1860
cctggtgtgt atcaacatta tttaatgtct tctaattcag tcatttttttt ataagtatgt   1920
ctataaacat tgaactttaa aaaacttatt tatttattcc actactgtag caattgacag    1980
attaaaaaaa tgtaacttca taattctta ccataacctc aatgtctttt ttaaaaaata     2040
aaattaaaaa tgaaaagaga aaaaaaaaa aaaaaaaaac                            2080
```

<210> SEQ ID NO 42
<211> LENGTH: 253
<212> TYPE: PRT
<213> ORGANISM: Homo sapiens

<400> SEQUENCE: 42

```
Met Asp Asn Arg Phe Ala Thr Ala Phe Val Ile Ala Cys Val Leu Ser
1               5                   10                  15

Leu Ile Ser Thr Ile Tyr Met Ala Ala Ser Ile Gly Thr Asp Phe Trp
            20                  25                  30

Tyr Glu Tyr Arg Ser Pro Val Gln Glu Asn Ser Ser Asp Leu Asn Lys
        35                  40                  45

Ser Ile Trp Asp Glu Phe Ile Ser Asp Glu Ala Asp Glu Lys Thr Tyr
    50                  55                  60

Asn Asp Ala Leu Phe Arg Tyr Asn Gly Thr Val Gly Leu Trp Arg Arg
65                  70                  75                  80

Cys Ile Thr Ile Pro Lys Asn Met His Trp Tyr Ser Pro Pro Glu Arg
                85                  90                  95

Thr Glu Ser Phe Asp Val Val Thr Lys Cys Val Ser Phe Thr Leu Thr
            100                 105                 110

Glu Gln Phe Met Glu Lys Phe Val Asp Pro Gly Asn His Asn Ser Gly
        115                 120                 125

Ile Asp Leu Leu Arg Thr Tyr Leu Trp Arg Cys Gln Phe Leu Leu Pro
    130                 135                 140

Phe Val Ser Leu Gly Leu Met Cys Phe Gly Ala Leu Ile Gly Leu Cys
145                 150                 155                 160

Ala Cys Ile Cys Arg Ser Leu Tyr Pro Thr Ile Ala Thr Gly Ile Leu
                165                 170                 175

His Leu Leu Ala Gly Leu Cys Thr Leu Gly Ser Val Ser Cys Tyr Val
            180                 185                 190

Ala Gly Ile Glu Leu Leu His Gln Lys Leu Glu Leu Pro Asp Asn Val
        195                 200                 205

Ser Gly Glu Phe Gly Trp Ser Phe Cys Leu Ala Cys Val Ser Ala Pro
    210                 215                 220

Leu Gln Phe Met Ala Ser Ala Leu Phe Ile Trp Ala Ala His Thr Asn
225                 230                 235                 240

Arg Lys Glu Tyr Thr Leu Met Lys Ala Tyr Arg Val Ala
                245                 250
```

<210> SEQ ID NO 43
<211> LENGTH: 2015
<212> TYPE: DNA
<213> ORGANISM: Homo sapiens

<400> SEQUENCE: 43

```
cttcacccgt ccgtgataag gagatttaag aagtctgagg gtggtgttaa gtttctcaga      60
acagacgcat atttgcggat gcaattgcag aacaggaaac agaaccaggg agaattttag     120 gtaccccccaa atctcattgg ccctccgcac aagccaagcc acagccactc ctgccacaca    180
atcggatcgc tttcagcact cgcagccgtg acagctccc tcgccgcgcg gtcctttcct      240
ctgcagtgag ctgatttgct ctgccagcag ctgtcggtgc cgcgctcgac accgagtcct    300
agctagcgct cacagaatac gcgctcccct cctccccctt ctctgtcccc cgcctctcgc    360
tcaccccggc ccactccagc ggcgactttg agggattccc tctctggcgg cctctgcagc   420
```

-continued

```
agcacagccg gcctcattcg gggcactgcg agtatggatc tccaaggaag aggggtcccc    480
agcatcgaca gacttcgagt tctcctgatg ttgttccata caatggctca aatcatggca    540
gaacaagaag tggaaaatct ctcaggcctt tccactaacc ctgaaaaaga tatatttgtg    600
gtgcggaaaa tgggacgac gtgtctcatg gcagagtttg cagccaaatt tattgtacct    660
tatgatgtgt gggccagcaa ctacgtagat ctgatcacag aacaggccga tatcgcattg    720
acccggggag ctgaggtgaa gggccgctgt ggccacagcg agtcggagct gcaagtgttc    780
tgggtggatc gcgcatatgc actcaaaatg ctctttgtaa aggaaagcca acatgtcc     840 aagggacctg aggcgacttg gaggctgagc aaagtgcagt ttgtctacga ctcctcggag    900
aaaacccact tcaaagacgc agtcagtgct gggaagcaca cagccaactc gcaccacctc    960
tctgccttgg tcaccccgc tgggaagtcc atgagtgtc aagctcaaca aaccatttca    1020
ctggcctcta gtgatccgca aagacggtc accatgatcc tgtctgcggt ccacatccaa    1080
ccttttgaca ttatctcaga ttttgtcttc agtgaagagc ataaatgccc agtggatgag    1140
cgggagcaac tggaagaaac cttgcccctg attttggggc tcatcttggg cctcgtcatc    1200
atggtaacac tcgcgattta ccacgtccac cacaaaatga ctgccaacca ggtgcagatc    1260
cctcgggaca gatcccagta taagcacatg ggctagaggc cgttaggcag gcaccccta    1320 ttcctgctcc cccaactgga tcaggtagaa caacaaaagc acttttccat cttgtacacg    1380
agatacacca acatagctac aatcaaacag gcctgggtat ctgaggcttg cttggcttgt    1440
gtccatgctt aaacccacgg aaggggggaga ctctttcgga tttgtagggt gaaatggcaa    1500
ttattctctc catgctgggg aggaggggag gagggtctca gacagctttc gtgctcatgg    1560
tggcttggct ttgactctcc aaagagcaat aaatgccact tggagctgta tctggcccca    1620
aagtttaggg attgaaaaca tgcttctttg aggaggaaac ccctttaggt tcagaagaat    1680
atggggtgct ttgctcccctt ggacacagct ggcttatcct atacagttgt caatgcacac    1740
agaatacaac ctcatgctcc ctgcagcaag acccctgaaa gtgattcatg cttctggctg    1800
gcattctgca tgtttagtga ttgtcttggg aatgtttcac tgctacccgc atccagcgac    1860
tgcagcacca gaaaacgact aatgtaacta tgcagagttg tttggacttc ttcctgtgcc    1920
aggtccaagt cgggggacct gaagaatcaa tctgtgtgag tctgttttc aaaatgaaat    1980 aaaacacact attctctggc aaaaaaaaaa aaaaa                              2015
```

<210> SEQ ID NO 44
<211> LENGTH: 280
<212> TYPE: PRT
<213> ORGANISM: Homo sapiens

<400> SEQUENCE: 44

```
Met Asp Leu Gln Gly Arg Gly Val Pro Ser Ile Asp Arg Leu Arg Val
1               5                   10                  15

Leu Leu Met Leu Phe His Thr Met Ala Gln Ile Met Ala Glu Gln Glu
            20                  25                  30

Val Glu Asn Leu Ser Gly Leu Ser Thr Asn Pro Glu Lys Asp Ile Phe
        35                  40                  45

Val Val Arg Glu Asn Gly Thr Thr Cys Leu Met Ala Glu Phe Ala Ala
    50                  55                  60

Lys Phe Ile Val Pro Tyr Asp Val Trp Ala Ser Asn Tyr Val Asp Leu
65                  70                  75                  80

Ile Thr Glu Gln Ala Asp Ile Ala Leu Thr Arg Gly Ala Glu Val Lys
            85                  90                  95
```

Gly Arg Cys Gly His Ser Glu Ser Glu Leu Gln Val Phe Trp Val Asp
            100                 105                 110

Arg Ala Tyr Ala Leu Lys Met Leu Phe Val Lys Glu Ser His Asn Met
        115                 120                 125

Ser Lys Gly Pro Glu Ala Thr Trp Arg Leu Ser Lys Val Gln Phe Val
    130                 135                 140

Tyr Asp Ser Ser Glu Lys Thr His Phe Lys Asp Ala Val Ser Ala Gly
145                 150                 155                 160

Lys His Thr Ala Asn Ser His His Leu Ser Ala Leu Val Thr Pro Ala
                165                 170                 175

Gly Lys Ser Tyr Glu Cys Gln Ala Gln Gln Thr Ile Ser Leu Ala Ser
            180                 185                 190

Ser Asp Pro Gln Lys Thr Val Thr Met Ile Leu Ser Ala Val His Ile
        195                 200                 205

Gln Pro Phe Asp Ile Ile Ser Asp Phe Val Phe Ser Glu Glu His Lys
    210                 215                 220

Cys Pro Val Asp Glu Arg Glu Gln Leu Glu Glu Thr Leu Pro Leu Ile
225                 230                 235                 240

Leu Gly Leu Ile Leu Gly Leu Val Ile Met Val Thr Leu Ala Ile Tyr
                245                 250                 255

His Val His His Lys Met Thr Ala Asn Gln Val Gln Ile Pro Arg Asp
                260                 265                 270

Arg Ser Gln Tyr Lys His Met Gly
            275                 280

<210> SEQ ID NO 45
<211> LENGTH: 2937
<212> TYPE: DNA
<213> ORGANISM: Homo sapiens

<400> SEQUENCE: 45

```
ttagggagtc gacccacgcg tccgcggacg cgtgggcgga cgcgtgggtt cggggactaa      60
ctgcaacgga gagactcaag atgattccct ttttacccat gttttctcta ctattgctgc     120
ttattgttaa ccctataaac gccaacaatc attatgacaa gatcttggct catagtcgta     180
tcaggggtcg ggaccaaggc ccaaatgtct gtgcccttca acagattttg ggcaccaaaa     240
agaaatactt cagcacttgt aagaactggt ataaaaagtc catctgtgga cagaaaacga     300
ctgtgttata tgaatgttgc cctggttata tgagaatgga aggaatgaaa ggctgcccag     360
cagttttgcc cattgaccat gtttatggca ctctgggcat cgtgggagcc accacaacgc     420
agcgctattc tgacgcctca aaactgaggg aggagatcga gggaagggga tccttcactt     480
actttgcacc gagtaatgag gcttgggaca acttggattc tgatatccgt agaggtttgg     540
agagcaacgt gaatgttgaa ttactgaatg ctttacatag tcacatgatt aataagagaa     600
tgttgaccaa ggacttaaaa aatggcatga ttattccttc aatgtataac aatttggggc     660
ttttcattaa ccattatcct aatggggttg tcactgttaa ttgtgctcga atcatccatg     720
ggaaccagat tgcaacaaat ggtgttgtcc atgtcattga ccgtgtgctt acacaaattg     780
gtacctcaat tcaagacttc attgaagcag aagatgacct tcatcttttt agagcagctg     840
ccatcacatc ggacatattg gaggcccttg aagagacgg tcacttcaca ctctttgctc     900
ccaccaatga ggcttttgag aaacttccac gaggtgtcct agaaaggatc atgggagaca     960
aagtggcttc cgaagctctt atgaagtacc acatcttaaa tactctccag tgttctgagt    1020
```

```
ctattatggg aggagcagtc tttgagacgc tggaaggaaa tacaattgag ataggatgtg    1080
acggtgacag tataacagta aatggaatca aatggtgaa caaaaaggat attgtgacaa     1140
ataatggtgt gatccatttg attgatcagg tcctaattcc tgattctgcc aaacaagtta   1200
ttgagctggc tggaaaacag caaaccacct tcacggatct tgtggcccaa ttaggcttgg   1260
catctgctct gaggccagat ggagaataca ctttgctggc acctgtgaat aatgcatttt   1320
ctgatgatac tctcagcatg gatcagcgcc tccttaaatt aattctgcag aatcacatat   1380
tgaaagtaaa agttggcctt aatgagcttt acaacgggca aatactggaa accatcggag   1440
gcaaacagct cagagtcttc gtatatcgta cagctgtctg cattgaaaat tcatgcatgg   1500
agaaagggag taagcaaggg agaaacggtg cgattcacat attccgcgag atcatcaagc   1560
cagcagagaa atccctccat gaaaagttaa acaagataa gcgctttagc accttcctca    1620
gcctacttga agctgcagac ttgaaagagc tcctgacaca acctggagac tggacattat   1680
ttgtgccaac caatgatgct tttaaggaa tgactagtga agaaaagaa attctgatac      1740 gggacaaaaa tgctcttcaa aacatcattc tttatcacct gacaccagga gttttcattg   1800
gaaaaggatt tgaacctggt gttactaaca ttttaaagac cacacaagga agcaaaatct   1860
ttctgaaaga agtaaatgat acacttctgg tgaatgaatt gaaatcaaaa gaatctgaca   1920
tcatgacaac aaatggtgta attcatgttg tagataaact cctctatcca gcagacacac   1980
ctgttggaaa tgatcaactg ctggaaatac ttaataaatt aatcaaatac atccaaatta   2040
agtttgttcg tggagaaaca gaagaaactc tgaagaaatt gttacaagaa gacacacccg   2100
tgaggaagtt gcaagccaac aaaaaagttc aaggatctag aagacgatta agggaaggtc   2160
gttctcagtg aaaatccaaa aaccagaaaa aaatgtttat acaaccctaa gtcaataacc   2220
tgaccttaga aaattgtgag agccaagttg acttcaggaa ctgaaacatc agcacaaga    2280 agcaatcatc aaataattct gaacacaaat ttaatatttt tttttctgaa tgagaaacat   2340
gagggaaatt gtggagttag cctcctgtgg taaaggaatt gaagaaaata taacacctta   2400 caccctttt catcttgaca ttaaaagttc tggctaactt tggaatccat tagagaaaaa    2460
tccttgtcac cagattcatt acaattcaaa tcgaagagtt gtgaactgtt atcccattga   2520
aaagaccgag ccttgtatgt atgttatgga tacataaaat gcacgcaagc cattatctct   2580
ccatgggaag ctaagttata aaataggtg cttggtgtac aaactttttt atatcaaaag    2640
gctttgcaca tttctatatg agtgggttta ctggtaaatt atgttatttt ttacaactaa   2700
ttttgtactc tcagaatgtc atatgcttct tgcaatgcat atttttaat ctcaaacgtt    2760 tcaataaaac cattttcag atataaagag aattacttca aattgagtaa ttcagaaaaa    2820
ctcaagattt aagttaaaaa gtggtttgga cttgggaaca ggactttata cctcttttac   2880
tgtaacaagt actcattaaa ggaaattgaa tgaaaaaaaa aaaaaaaggg cggccgc      2937
```

<210> SEQ ID NO 46
<211> LENGTH: 696
<212> TYPE: PRT
<213> ORGANISM: Homo sapiens

<400> SEQUENCE: 46

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln

```
                   35                  40                  45
Ile Leu Gly Thr Lys Lys Lys Tyr Phe Ser Thr Cys Lys Asn Trp Tyr
 50                  55                  60
Lys Lys Ser Ile Cys Gly Gln Lys Thr Thr Val Leu Tyr Glu Cys Cys
 65                  70                  75                  80
Pro Gly Tyr Met Arg Met Glu Gly Met Lys Gly Cys Pro Ala Val Leu
                 85                  90                  95
Pro Ile Asp His Val Tyr Gly Thr Leu Gly Ile Val Gly Ala Thr Thr
                100                 105                 110
Thr Gln Arg Tyr Ser Asp Ala Ser Lys Leu Arg Glu Glu Ile Glu Gly
                115                 120                 125
Lys Gly Ser Phe Thr Tyr Phe Ala Pro Ser Asn Glu Ala Trp Asp Asn
130                 135                 140
Leu Asp Ser Asp Ile Arg Arg Gly Leu Glu Ser Asn Val Asn Val Glu
145                 150                 155                 160
Leu Leu Asn Ala Leu His Ser His Met Ile Asn Lys Arg Met Leu Thr
                165                 170                 175
Lys Asp Leu Lys Asn Gly Met Ile Ile Pro Ser Met Tyr Asn Asn Leu
                180                 185                 190
Gly Leu Phe Ile Asn His Tyr Pro Asn Gly Val Val Thr Val Asn Cys
                195                 200                 205
Ala Arg Ile Ile His Gly Asn Gln Ile Ala Thr Asn Gly Val Val His
210                 215                 220
Val Ile Asp Arg Val Leu Thr Gln Ile Gly Thr Ser Ile Gln Asp Phe
225                 230                 235                 240
Ile Glu Ala Glu Asp Asp Leu Ser Ser Phe Arg Ala Ala Ile Thr
                245                 250                 255
Ser Asp Ile Leu Glu Ala Leu Gly Arg Asp Gly His Phe Thr Leu Phe
                260                 265                 270
Ala Pro Thr Asn Glu Ala Phe Glu Lys Leu Pro Arg Gly Val Leu Glu
                275                 280                 285
Arg Ile Met Gly Asp Lys Val Ala Ser Glu Ala Leu Met Lys Tyr His
                290                 295                 300
Ile Leu Asn Thr Leu Gln Cys Ser Glu Ser Ile Met Gly Gly Ala Val
305                 310                 315                 320
Phe Glu Thr Leu Glu Gly Asn Thr Ile Glu Ile Gly Cys Asp Gly Asp
                325                 330                 335
Ser Ile Thr Val Asn Gly Ile Lys Met Val Asn Lys Asp Ile Val
                340                 345                 350
Thr Asn Asn Gly Val Ile His Leu Ile Asp Gln Val Leu Ile Pro Asp
                355                 360                 365
Ser Ala Lys Gln Val Ile Glu Leu Ala Gly Lys Gln Gln Thr Thr Phe
                370                 375                 380
Thr Asp Leu Val Ala Gln Leu Gly Leu Ala Ser Ala Leu Arg Pro Asp
385                 390                 395                 400
Gly Glu Tyr Thr Leu Leu Ala Pro Val Asn Asn Ala Phe Ser Asp Asp
                405                 410                 415
Thr Leu Ser Met Asp Gln Arg Leu Leu Lys Leu Ile Leu Gln Asn His
                420                 425                 430
Ile Leu Lys Val Lys Val Gly Leu Asn Glu Leu Tyr Asn Gly Gln Ile
                435                 440                 445
Leu Glu Thr Ile Gly Gly Lys Gln Leu Arg Val Phe Val Tyr Arg Thr
450                 455                 460
```

```
Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
610                 615                 620

Asp Lys Leu Leu Tyr Pro Ala Asp Thr Pro Val Gly Asn Asp Gln Leu
                625                 630                 635                 640

Leu Glu Ile Leu Asn Lys Leu Ile Lys Tyr Ile Gln Ile Lys Phe Val
                645                 650                 655

Arg Gly Glu Thr Glu Thr Leu Lys Leu Leu Gln Glu Asp Thr
            660                 665                 670

Pro Val Arg Lys Leu Gln Ala Asn Lys Lys Val Gln Gly Ser Arg Arg
        675                 680                 685

Arg Leu Arg Glu Gly Arg Ser Gln
    690                 695

<210> SEQ ID NO 47
<211> LENGTH: 3417
<212> TYPE: DNA
<213> ORGANISM: Homo sapiens

<400> SEQUENCE: 47
gccccgcgtc cgcgcctccg ggctccttcg gccccgccat gggctgctgc agctccgcct      60
cctccgccgc gcagagctcc aaacgagaat ggaagccgct ggaggaccgt agctgcacag     120
acataccatg gctgctgctc ttcatcctct tctgcattgg gatgggattt atttgtggct     180
tttcaatagc aacaggtgca gcagcaagac tagtgtcagg atacgacagc tatggaaata     240
tctgtgggca gaaaaataca aagttggaag caataccaaa cagtggcatg gaccacaccc     300
agcggaagta tgtattcttt ttggatccat gcaacctgga cttgataaac cggaagatta     360
agtctgtagc actgtgtgta gcagcgtgtc caaggcaaga actgaaaact ctgagtgatg     420
ttcagaagtt tgcagagata aatggttcag ccctatgtag ctacaaccta aagccttctg     480
aatacactac atctccaaaa tcttctgttc tctgccccaa actaccagtt ccagcgagtg     540
cacctattcc attcttccat cgctgtgctc ctgtgaacat ttcctgctat gccaagtttg     600
cagaggccct gatcaccttt gtcagtgaca atagtgtctt acacaggctg attagtggag     660
taatgaccag caaagaaatt atattgggac tttgcttgtt atcactagtt ctatccatga     720
ttttgatggt gataatcagg tatatatcaa gagtacttgt gtggatctta acgattctgg     780
```

```
tcatactcgg ttcacttgga ggcacaggtg tactatggtg gctgtatgca aagcaaagaa    840
ggtctcccaa agaaactgtt actcctgagc agcttcagat agctgaagac aatcttcggg    900
ccctcctcat ttatgccatt tcagctacag tgttcacagt gatcttattc ctgataatgt    960
tggttatgcg caaacgtgtt gctcttacca tcgccttgtt ccacgtagct ggcaaggtct   1020
tcattcactt gccactgcta gtcttccaac ccttctggac tttctttgct cttgtcttgt   1080
tttgggtgta ctggatcatg acacttcttt tccttggcac taccggcagt cctgttcaga   1140
atgagcaagg ctttgtggag ttcaaaattt ctgggcctct gcagtacatg tggtggtacc   1200
atgtggtggg cctgatttgg atcagtgaat ttattctagc atgtcagcag atgacagtgg   1260
caggagctgt ggtaacatac tattttacta gggataaaag gaatttgcca tttacaccta   1320
ttttggcatc agtaaatcgc cttattcgtt accacctagg tacggtggca aaaggatctt   1380
tcattatcac attagtcaaa attccgcgaa tgatccttat gtatattcac agtcagctca   1440
aaggaaagga aaatgcttgt gcacgatgtg tgctgaaatc ttgcatttgt tgcctttggt   1500
gtcttgaaaa gtgcctaaat tatttaaatc agaatgcata cacagccaca gctatcaaca   1560
gcaccaactt ctgcacctca gcaaaggatg cctttgtcat tctggtggag aatgcttttg   1620
gagtggctac catcaacaca gtaggagatt ttatgttatt ccttggcaag gtgctgatag   1680
tctgcagcac aggtttagct gggattatgc tgctcaacta ccagcaggac tacacagtat   1740
gggtgctgcc tctgatcatc gtctgcctct ttgctttcct agtcgctcat tgcttcctgt   1800
ctatttatga atggtagtg gatgtattat tcttgtgttt tgccattgat acaaaataca   1860
atgatgggag ccctggcaga gaattctata tggataaagt gctgatggag tttgtggaaa   1920
acagtaggaa agcaatgaaa gaagctggta agggaggcgt cgctgattcc agagagctaa   1980
agccgatggc ttcgggagca agttctgctt gaacctagcc gacggttatg gaaacccatt   2040
gacattccaa aacaatatat acacataact atgtatttgt gtgtgtgggt gtgtgtatat   2100
atgtatatgt atgtgtgtat atatgtatat gtatatacac acacacacat aaatcagcca   2160
aaatcagaga aaaggaacag ggatttaata cctttttat gcttattttt gtcaaacatg    2220
tactcctttc atacgggtgg cttttacaag gcaacttccg tcatttaatg ttttcaactg   2280
taattgtctt aatggaaatg ttaaaattca tatctgatta acatttttaa taacttagag   2340
gagattttaa ctttatttaa aaataggtaa aattattgta cctaattatg tctaaagttt   2400
attcaggggt aatttccctg atgtctgtat aaaatcaaga tcttatttta ctgatgcata   2460
agtcctagtg ggtcaagact aggcatatgc tttcagataa ataaggaatt actccaatca   2520
gttttcccca atcaaagaag ccatgtcatt ttactttag aaacatacaa ttgggcccaa    2580
tatgggaatt tcataatag ttcatacatt tgtcagccaa cattaaaagg taaccaactc    2640
ctcaggtatt tgtagtttac cctaacgctt ctttaaaaga aagtaggtaa aaaaagaaaa   2700
gggtagataa tctttcgtat gcaaactttt cccttatatt ttgtctttct ttccttttg    2760 actttagtag catcctccac acatttgtgt gcctgatttg aaaggaagct ggggcaccca   2820
gcgagtttag cctttaagtt tctgtgtatt gatttgcaga ttaagtaatg ctgagaggaa   2880
taaagaaggg acagaaacat ggaacataaa gcattgaaaa ttccggtgct gggcttcgg    2940 cttcagagta acgtcagtgg cttagggtta aacggccatt ttattcaaat gcttgctata   3000
caatctgaaa acacactggc aggtgctcct ctccttggca attcattgag tatccagagt   3060
tctacgatgt ttaactgaag aattggctaa tgttttgatc ctccagtgtg actgttgttt   3120
```

```
ttgtttgggg gtgggtttgg ggttttttgc ttttttattc ctgaagctta ccagatatga   3180
atggctaata ctccattgtt ctgcttgttg taatggtgaa tgctttaaga aaaaaaagtg   3240
taatttgcta agaataattc atgatctgtt tatgcgataa ctcctttttg ttacaatttt   3300
tttaaaaaaa gctattttg ttaatgtaaa gtaaatattt cagagcaaat tttttaaact    3360
tattgcacta atacaggct ctgtacaaaa aaaaaaaaa agggcggccg ctagact        3417
```

```
<210> SEQ ID NO 48
<211> LENGTH: 657
<212> TYPE: PRT
<213> ORGANISM: Homo sapiens

<400> SEQUENCE: 48
```

```
Met Gly Cys Cys Ser Ser Ala Ser Ser Ala Ala Gln Ser Ser Lys Arg
1               5                   10                  15

Glu Trp Lys Pro Leu Glu Asp Arg Ser Cys Thr Asp Ile Pro Trp Leu
            20                  25                  30

Leu Leu Phe Ile Leu Phe Cys Ile Gly Met Gly Phe Ile Cys Gly Phe
        35                  40                  45

Ser Ile Ala Thr Gly Ala Ala Arg Leu Val Ser Gly Tyr Asp Ser
    50                  55                  60

Tyr Gly Asn Ile Cys Gly Gln Lys Asn Thr Lys Leu Glu Ala Ile Pro
65                  70                  75                  80

Asn Ser Gly Met Asp His Thr Gln Arg Lys Tyr Val Phe Phe Leu Asp
                85                  90                  95

Pro Cys Asn Leu Asp Leu Ile Asn Arg Lys Ile Lys Ser Val Ala Leu
            100                 105                 110

Cys Val Ala Ala Cys Pro Arg Gln Glu Leu Lys Thr Leu Ser Asp Val
        115                 120                 125

Gln Lys Phe Ala Glu Ile Asn Gly Ser Ala Leu Cys Ser Tyr Asn Leu
    130                 135                 140

Lys Pro Ser Glu Tyr Thr Thr Ser Pro Lys Ser Ser Val Leu Cys Pro
145                 150                 155                 160

Lys Leu Pro Val Pro Ala Ser Ala Pro Ile Pro Phe Phe His Arg Cys
                165                 170                 175

Ala Pro Val Asn Ile Ser Cys Tyr Ala Lys Phe Ala Glu Ala Leu Ile
            180                 185                 190

Thr Phe Val Ser Asp Asn Ser Val Leu His Arg Leu Ile Ser Gly Val
        195                 200                 205

Met Thr Ser Lys Glu Ile Ile Leu Gly Leu Cys Leu Leu Ser Leu Val
    210                 215                 220

Leu Ser Met Ile Leu Met Val Ile Ile Arg Tyr Ile Ser Arg Val Leu
225                 230                 235                 240

Val Trp Ile Leu Thr Ile Leu Val Ile Leu Gly Ser Leu Gly Gly Thr
                245                 250                 255

Gly Val Leu Trp Trp Leu Tyr Ala Lys Gln Arg Arg Ser Pro Lys Glu
            260                 265                 270

Thr Val Thr Pro Glu Gln Leu Gln Ile Ala Glu Asp Asn Leu Arg Ala
        275                 280                 285

Leu Leu Ile Tyr Ala Ile Ser Ala Thr Val Phe Thr Val Ile Leu Phe
    290                 295                 300

Leu Ile Met Leu Val Met Arg Lys Arg Val Ala Leu Thr Ile Ala Leu
305                 310                 315                 320

Phe His Val Ala Gly Lys Val Phe Ile His Leu Pro Leu Leu Val Phe
```

```
                    325               330               335
       Gln Pro Phe Trp Thr Phe Phe Ala Leu Val Leu Phe Trp Val Tyr Trp
                340               345               350

Ile Met Thr Leu Leu Phe Leu Gly Thr Thr Gly Ser Pro Val Gln Asn
                355               360               365

Glu Gln Gly Phe Val Glu Phe Lys Ile Ser Gly Pro Leu Gln Tyr Met
                370               375               380

Trp Trp Tyr His Val Val Gly Leu Ile Trp Ile Ser Glu Phe Ile Leu
       385               390               395               400

Ala Cys Gln Gln Met Thr Val Ala Gly Ala Val Val Thr Tyr Tyr Phe
                        405               410               415

Thr Arg Asp Lys Arg Asn Leu Pro Phe Thr Pro Ile Leu Ala Ser Val
                    420               425               430

Asn Arg Leu Ile Arg Tyr His Leu Gly Thr Val Ala Lys Gly Ser Phe
                    435               440               445

Ile Ile Thr Leu Val Lys Ile Pro Arg Met Ile Leu Met Tyr Ile His
                450               455               460

Ser Gln Leu Lys Gly Lys Glu Asn Ala Cys Ala Arg Cys Val Leu Lys
       465               470               475               480

Ser Cys Ile Cys Cys Leu Trp Cys Leu Glu Lys Cys Leu Asn Tyr Leu
                        485               490               495

Asn Gln Asn Ala Tyr Thr Ala Thr Ala Ile Asn Ser Thr Asn Phe Cys
                    500               505               510

Thr Ser Ala Lys Asp Ala Phe Val Ile Leu Val Glu Asn Ala Leu Arg
                    515               520               525

Val Ala Thr Ile Asn Thr Val Gly Asp Phe Met Leu Phe Leu Gly Lys
                530               535               540

Val Leu Ile Val Cys Ser Thr Gly Leu Ala Gly Ile Met Leu Leu Asn
       545               550               555               560

Tyr Gln Gln Asp Tyr Thr Val Trp Val Leu Pro Leu Ile Ile Val Cys
                        565               570               575

Leu Phe Ala Phe Leu Val Ala His Cys Phe Leu Ser Ile Tyr Glu Met
                    580               585               590

Val Val Asp Val Leu Phe Leu Cys Phe Ala Ile Asp Thr Lys Tyr Asn
                    595               600               605

Asp Gly Ser Pro Gly Arg Glu Phe Tyr Met Asp Lys Val Leu Met Glu
                610               615               620

Phe Val Glu Asn Ser Arg Lys Ala Met Lys Glu Ala Gly Lys Gly Gly
       625               630               635               640

Val Ala Asp Ser Arg Glu Leu Lys Pro Met Ala Ser Gly Ala Ser Ser
                        645               650               655

Ala

<210> SEQ ID NO 49
<211> LENGTH: 3758
<212> TYPE: DNA
<213> ORGANISM: Homo sapiens

<400> SEQUENCE: 49
cctcgcgtcc gcgcacaccg gggtggcagc gccgcagcgg gcagggcgcc cgcactccgc      60
cgcctctgcc cgcaaccgct gagccatcca tgggggtcgc gggccgcaac cgtcccgggg     120
cggcctgggc ggtgctgctg ctgctgctgc cgccactgct gctgctggcg ggggccgtcc     180
cgccgggtcg gggccgtgcc gcggggccgc aggaggatgt agatgagtgt ccgcaagggc     240
```

```
tagatgactg ccatgccgac gccctgtgtc agaacacacc cacctcctac aagtgctcct    300
gcaagcctgg ctaccaaggg gaaggcaggc agtgtgagga catcgatgaa tgtggaaatg    360
agctcaatgg aggctgtgtc catgactgtt tgaatattcc aggcaattat cgttgcactt    420
gttttgatgc cttcatgttg gctcatgacg gtcataattg tcttgatgtg gacgagtgcc    480
tggagaacaa tggcggctgc cagcatacct gtgtcaacgt catggggagc tatgagtgct    540
gctgcaagga ggggttttttc ctgagtgaca atcagcacac ctgcattcac cgctcggaag    600
agggcctgag ctgcatgaat aaggatcacg gctgtagtca catctgcaag gaggcccccaa    660
ggggcagcgt cgcctgtgag tgcaggcctg gttttgagct ggccaagaac cagagagact    720
gcatcttgac ctgtaaccat gggaacggtg ggtgccagca ctcctgtgac gatacagccg    780
atggcccaga gtgcagctgc catccacagt acaagatgca cacagatggg aggagctgcc    840
ttgagcgaga ggacactgtc ctggaggtga cagagagcaa caccacatca gtggtggatg    900
gggataaacg ggtgaaacgg cggctgctca tggaaacgtg tgctgtcaac aatggaggct    960
gtgaccgcac ctgtaaggat acttcgacag gtgtccactg cagttgtcct gttggattca   1020
ctctccagtt ggatgggaag acatgtaaag atattgatga gtgccagacc cgcaatggag   1080
gttgtgatca tttctgcaaa aacatcgtgg gcagttttga ctgcggctgc aagaaggat    1140
ttaaattatt aacagatgag aagtcttgcc aagatgtgga tgagtgctct ttggataggaa   1200
cctgtgacca cagctgcatc aaccaccctg gcacatttgc ttgtgcttgc aaccgagggt   1260
acaccctgta tggcttcacc cactgtggag acaccaatga gtgcagcatc aacaacggag   1320
gctgtcagca ggtctgtgtg aacacagtgg gcagctatga atgccagtgc caccctgggt   1380
acaagctcca ctggaataaa aaagactgtg tggaagtgaa ggggctcctg cccacaagtg   1440
tgtcaccccg tgtgtccctg cactgcggta agagtggtgg aggagacggg tgcttcctca   1500
gatgtcactc tggcattcac ctctcttcag atgtcaccac catcaggaca agtgtaacct   1560
ttaagctaaa tgaaggcaag tgtagtttga aaaatgctga gctgttttccc gagggtctgc   1620
gaccagcact accagagaag cacagctcag taaaagagag cttccgctac gtaaaccttta   1680
catgcagctc tggcaagcaa gtcccaggag ccctggccg accaagcacc cctaaggaaa   1740
tgtttatcac tgttgagttt gagcttgaaa ctaaccaaaa ggaggtgaca gcttcttgtg   1800
acctgagctg catcgtaaag cgaaccgaga agcggctccg taaagccatc cgcacgctca   1860
gaaaggccgt ccacgggag cagtttcacc tccagctctc aggcatgaac ctcgacgtgg   1920
ctaaaagcc tccagaaca tctgaacgcc aggcagagtc ctgtggagtg gccagggtc   1980
atgcagaaaa ccaatgtgtc agttgcaggg ctgggaccta ttatgatgga gcacgagaac   2040
gctgcatttt atgtccaaat ggaaccttcc aaaatgagga aggacaaatg acttgtgaac   2100
catgcccaag accaggaaat tctggggccc tgaagacccc agaagcttgg aatatgtctg   2160
aatgtggagg tctgtgtcaa cctggtgaat attctgcaga tggctttgca ccttgccagc   2220
tctgtgccct gggcacgttc agcctgaag ctggtcgaac ttcctgcttc ccctgtggag   2280
gaggccttgc caccaaacat cagggagcta cttcctttca ggactgtgaa accagagttc   2340
aatgttcacc tggacatttc tacaacacca ccactcaccg atgtattcgt tgcccagtgg   2400
gaacatacca gcctgaattt ggaaaaaata attgtgtttc ttgcccagga aatactacga   2460
ctgactttga tggctccaca aacataaccc agtgtaaaaa cagaagatgt ggaggggagc   2520
tgggagattt cactgggtac attgaatccc caaactaccc aggcaattac ccagccaaca   2580
```

-continued

```
ccgagtgtac gtggaccatc aacccacccc ccaagcgccg catcctgatc gtggtccctg    2640
agatcttcct gcccatagag gacgactgtg gggactatct ggtgatgcgg aaaacctctt    2700
catccaattc tgtgacaaca tatgaaacct gccagaccta cgaacgcccc atcgccttca    2760
cctccaggtc aaagaagctg tggattcagt tcaagtccaa tgaagggaac agcgctagag    2820
ggttccaggt cccatacgtg acatatgatg aggactacca ggaactcatt gaagacatag    2880
ttcgagatgg caggctctat gcatctgaga accatcagga aatacttaag gataagaaac    2940
ttatcaaggc tctgtttgat gtcctggccc atccccagaa ctatttcaag tacacagccc    3000
aggagtcccg agagatgttt ccaagatcgt tcatccgatt gctacgttcc aaagtgtcca    3060 ggttttgag accttacaaa tgactcagcc cacgtgccac tcaatacaaa tgttctgcta    3120
tagggttggt gggacagagc tgtcttcctt ctgcatgtca gcacagtcgg gtattgctgc    3180
ctcccgtatc agtgactcat tagagttcaa ttttttataga taatacagat attttggtaa    3240
attgaacttg gtttttcttt cccagcatcg tggatgtaga ctgagaatgg ctttgagtgg    3300
catcagcttc tcactgctgt gggcggatgt cttggataga tcacgggctg gctgagctgg    3360
actttggtca gcctaggtga gactcacctg tccttctggg gtcttactcc tcctcaagga    3420
gtctgtagtg gaaaggaggc cacagaataa gctgcttatt ctgaaacttc agcttcctct    3480
agcccggccc tctctaaggg agccctctgc actcgtgtgc aggctctgac caggcagaac    3540
aggcaagagg ggagggaagg agaccccctgc aggctccctc cacccacctt gagacctggg    3600
aggactcagt ttctccacag ccttctccag cctgtgtgat acaagtttga tcccaggaac    3660
ttgagttcta agcagtgctc gtgaaaaaaa aaagcagaaa gaattagaaa taaataaaaa    3720
ctaagcactt ctggagacac ctataggagt cgtattac                             3758
```

<210> SEQ ID NO 50
<211> LENGTH: 997
<212> TYPE: PRT
<213> ORGANISM: Homo sapiens

<400> SEQUENCE: 50

```
Met Gly Val Ala Gly Arg Asn Arg Pro Gly Ala Ala Trp Ala Val Leu
1               5                   10                  15

Leu Leu Leu Leu Pro Pro Leu Leu Leu Ala Gly Ala Val Pro Pro
            20                  25                  30

Gly Arg Gly Arg Ala Ala Gly Pro Gln Glu Asp Val Asp Glu Cys Pro
        35                  40                  45

Gln Gly Leu Asp Asp Cys His Ala Asp Ala Leu Cys Gln Asn Thr Pro
    50                  55                  60

Thr Ser Tyr Lys Cys Ser Cys Lys Pro Gly Tyr Gln Gly Glu Gly Arg
65                  70                  75                  80

Gln Cys Glu Asp Ile Asp Glu Cys Gly Asn Glu Leu Asn Gly Cys
                85                  90                  95

Val His Asp Cys Leu Asn Ile Pro Gly Asn Tyr Arg Cys Thr Cys Phe
            100                 105                 110

Asp Gly Phe Met Leu Ala His Asp Gly His Asn Cys Leu Asp Val Asp
        115                 120                 125

Glu Cys Leu Glu Asn Asn Gly Gly Cys Gln His Thr Cys Val Asn Val
    130                 135                 140

Met Gly Ser Tyr Glu Cys Cys Cys Lys Glu Gly Phe Phe Leu Ser Asp
145                 150                 155                 160

Asn Gln His Thr Cys Ile His Arg Ser Glu Glu Gly Leu Ser Cys Met
```

```
                165                 170                 175
Asn Lys Asp His Gly Cys Ser His Ile Cys Lys Glu Ala Pro Arg Gly
                180                 185                 190

Ser Val Ala Cys Glu Cys Arg Pro Gly Phe Glu Leu Ala Lys Asn Gln
            195                 200                 205

Arg Asp Cys Ile Leu Thr Cys Asn His Gly Asn Gly Gly Cys Gln His
        210                 215                 220

Ser Cys Asp Asp Thr Ala Asp Gly Pro Glu Cys Ser Cys His Pro Gln
225                 230                 235                 240

Tyr Lys Met His Thr Asp Gly Arg Ser Cys Leu Glu Arg Glu Asp Thr
                245                 250                 255

Val Leu Glu Val Thr Glu Ser Asn Thr Thr Ser Val Val Asp Gly Asp
            260                 265                 270

Lys Arg Val Lys Arg Leu Leu Met Glu Thr Cys Ala Val Asn Asn
        275                 280                 285

Gly Gly Cys Asp Arg Thr Cys Lys Asp Thr Ser Thr Gly Val His Cys
        290                 295                 300

Ser Cys Pro Val Gly Phe Thr Leu Gln Leu Asp Gly Lys Thr Cys Lys
305                 310                 315                 320

Asp Ile Asp Glu Cys Gln Thr Arg Asn Gly Gly Cys Asp His Phe Cys
                325                 330                 335

Lys Asn Ile Val Gly Ser Phe Asp Cys Gly Cys Lys Lys Gly Phe Lys
            340                 345                 350

Leu Leu Thr Asp Glu Lys Ser Cys Gln Asp Val Asp Glu Cys Ser Leu
        355                 360                 365

Asp Arg Thr Cys Asp His Ser Cys Ile Asn His Pro Gly Thr Phe Ala
        370                 375                 380

Cys Ala Cys Asn Arg Gly Tyr Thr Leu Tyr Gly Phe Thr His Cys Gly
385                 390                 395                 400

Asp Thr Asn Glu Cys Ser Ile Asn Asn Gly Gly Cys Gln Gln Val Cys
                405                 410                 415

Val Asn Thr Val Gly Ser Tyr Glu Cys Gln Cys His Pro Gly Tyr Lys
            420                 425                 430

Leu His Trp Asn Lys Lys Asp Cys Val Glu Val Lys Gly Leu Leu Pro
        435                 440                 445

Thr Ser Val Ser Pro Arg Val Ser Leu His Cys Gly Lys Ser Gly Gly
        450                 455                 460

Gly Asp Gly Cys Phe Leu Arg Cys His Ser Gly Ile His Leu Ser Ser
465                 470                 475                 480

Asp Val Thr Thr Ile Arg Thr Ser Val Thr Phe Lys Leu Asn Glu Gly
                485                 490                 495

Lys Cys Ser Leu Lys Asn Ala Glu Leu Phe Pro Glu Gly Leu Arg Pro
            500                 505                 510

Ala Leu Pro Glu Lys His Ser Ser Val Lys Glu Ser Phe Arg Tyr Val
        515                 520                 525

Asn Leu Thr Cys Ser Ser Gly Lys Gln Val Pro Gly Ala Pro Gly Arg
        530                 535                 540

Pro Ser Thr Pro Lys Glu Met Phe Ile Thr Val Glu Phe Glu Leu Glu
545                 550                 555                 560

Thr Asn Gln Lys Glu Val Thr Ala Ser Cys Asp Leu Ser Cys Ile Val
                565                 570                 575

Lys Arg Thr Glu Lys Arg Leu Arg Lys Ala Ile Arg Thr Leu Arg Lys
            580                 585                 590
```

-continued

```
Ala Val His Arg Glu Gln Phe His Leu Gln Leu Ser Gly Met Asn Leu
    595                 600                 605
Asp Val Ala Lys Lys Pro Pro Arg Thr Ser Glu Arg Gln Ala Glu Ser
610                 615                 620
Cys Gly Val Gly Gln Gly His Ala Glu Asn Gln Cys Val Ser Cys Arg
625                 630                 635                 640
Ala Gly Thr Tyr Tyr Asp Gly Ala Arg Glu Arg Cys Ile Leu Cys Pro
                645                 650                 655
Asn Gly Thr Phe Gln Asn Glu Glu Gly Gln Met Thr Cys Glu Pro Cys
                660                 665                 670
Pro Arg Pro Gly Asn Ser Gly Ala Leu Lys Thr Pro Glu Ala Trp Asn
    675                 680                 685
Met Ser Glu Cys Gly Gly Leu Cys Gln Pro Gly Glu Tyr Ser Ala Asp
    690                 695                 700
Gly Phe Ala Pro Cys Gln Leu Cys Ala Leu Gly Thr Phe Gln Pro Glu
705                 710                 715                 720
Ala Gly Arg Thr Ser Cys Phe Pro Cys Gly Gly Leu Ala Thr Lys
                725                 730                 735
His Gln Gly Ala Thr Ser Phe Gln Asp Cys Glu Thr Arg Val Gln Cys
                740                 745                 750
Ser Pro Gly His Phe Tyr Asn Thr Thr Thr His Arg Cys Ile Arg Cys
    755                 760                 765
Pro Val Gly Thr Tyr Gln Pro Glu Phe Gly Lys Asn Asn Cys Val Ser
    770                 775                 780
Cys Pro Gly Asn Thr Thr Thr Asp Phe Asp Gly Ser Thr Asn Ile Thr
785                 790                 795                 800
Gln Cys Lys Asn Arg Arg Cys Gly Gly Glu Leu Gly Asp Phe Thr Gly
                805                 810                 815
Tyr Ile Glu Ser Pro Asn Tyr Pro Gly Asn Tyr Pro Ala Asn Thr Glu
                820                 825                 830
Cys Thr Trp Thr Ile Asn Pro Pro Lys Arg Arg Ile Leu Ile Val
    835                 840                 845
Val Pro Glu Ile Phe Leu Pro Ile Glu Asp Asp Cys Gly Asp Tyr Leu
    850                 855                 860
Val Met Arg Lys Thr Ser Ser Ser Asn Ser Val Thr Thr Tyr Glu Thr
865                 870                 875                 880
Cys Gln Thr Tyr Glu Arg Pro Ile Ala Phe Thr Ser Arg Ser Lys Lys
                885                 890                 895
Leu Trp Ile Gln Phe Lys Ser Asn Glu Gly Asn Ser Ala Arg Gly Phe
                900                 905                 910
Gln Val Pro Tyr Val Thr Tyr Asp Glu Asp Tyr Gln Glu Leu Ile Glu
                915                 920                 925
Asp Ile Val Arg Asp Gly Arg Leu Tyr Ala Ser Glu Asn His Gln Glu
    930                 935                 940
Ile Leu Lys Asp Lys Lys Leu Ile Lys Ala Leu Phe Asp Val Leu Ala
945                 950                 955                 960
His Pro Gln Asn Tyr Phe Lys Tyr Thr Ala Gln Glu Ser Arg Glu Met
                965                 970                 975
Phe Pro Arg Ser Phe Ile Arg Leu Leu Arg Ser Lys Val Ser Arg Phe
                980                 985                 990
Leu Arg Pro Tyr Lys
            995
```

<210> SEQ ID NO 51
<211> LENGTH: 3586
<212> TYPE: DNA
<213> ORGANISM: Homo sapiens

<400> SEQUENCE: 51

| | | | | | |
|---|---|---|---|---|---|
| ccgcggcgct | gcgcgcggcg | gtaattagtg | attgtcttcc | agcttcgcga | aggctagggg | 60 |
| cgcggctgcc | gggtggctgc | gcggcgctgc | ccccggaccg | aggggcagcc | aatccaatga | 120 |
| aaccaccgcg | tgttcgcgcc | tggtagagat | ttctcgaaga | caccagtggg | cccgttccga | 180 |
| gccctctgga | ccgcccgtgt | ggaaccaaac | ctgcgcgcgt | ggccgggccg | tgggacaacg | 240 |
| aggccgcgga | gacgaaggcg | caatggcgag | gaagttatct | gtaatcttga | tcctgacctt | 300 |
| tgccctctct | gtcacaaatc | cccttcatga | actaaaagca | gctgctttcc | cccagaccac | 360 |
| tgagaaaatt | agtccgaatt | gggaatctgg | cattaatgtt | gacttggcaa | tttccacacg | 420 |
| gcaatatcat | ctacaacagc | ttttctaccg | ctatggagaa | aataattctt | tgtcagttga | 480 |
| agggttcaga | aaattacttc | aaaatatagg | catagataag | attaaaagaa | tccatataca | 540 |
| ccatgaccac | gaccatcact | cagaccacga | gcatcactca | gaccatgagc | gtcactcaga | 600 |
| ccatgagcat | cactcagacc | acgagcatca | ctctgaccat | gatcatcact | cttctggtaa | 660 |
| aaataagcga | aaagctcttt | gcccagacca | tgactcagat | agttcaggta | aagatcctag | 720 |
| aaacagccag | gggaaaggag | ctcaccgacc | agaaacatgcc | agtggtagaa | ggaatgtcaa | 780 |
| ggacagtgtt | agtgctagtg | aagtgacctc | aactgtgtac | aacactgtct | ctgaaggaac | 840 |
| tcactttcta | gagacaatag | agactccaag | acctggaaaa | ctcttcccca | agatgtaag | 900 |
| cagctccact | ccacccagtg | tcacatcaaa | gagccgggtg | agccggctgg | ctggtaggaa | 960 |
| aacaaatgaa | tctgtgagtg | agccccgaaa | aggctttatg | tattccagaa | acacaaatga | 1020 |
| aaatcctcag | gagtgtttca | atgcatcaaa | gctactgaca | tctcatggca | tgggcatcca | 1080 |
| ggttccgctg | aatgcaacag | agttcaacta | tctctgtcca | gccatcatca | accaaattga | 1140 |
| tgctagatct | tgtctgattc | atacaagtga | aagaaggct | gaaatccctc | caaagaccta | 1200 |
| ttcattacaa | atagcctggg | ttggtggttt | tatagccatt | tccatcatca | gtttcctgtc | 1260 |
| tctgctgggg | gttatcttag | tgcctctcat | gaatcgggtg | ttttttcaaat | ttctcctgag | 1320 |
| tttccttgtg | gcactggccg | ttgggactt | gagtggtgat | gcttttttac | accttcttcc | 1380 |
| acattctcat | gcaagtcacc | accatagtca | tagccatgaa | gaaccagcaa | tggaaatgaa | 1440 |
| aagaggacca | cttttcagtc | atctgtcttc | tcaaaacata | gaagaaagtg | cctatttga | 1500 |
| ttccacgtgg | aagggtctaa | cagctctagg | aggcctgtat | ttcatgtttc | ttgttgaaca | 1560 |
| tgtcctcaca | ttgatcaaac | aatttaaaga | taagaagaaa | aagaatcaga | agaaacctga | 1620 |
| aaatgatgat | gatgtggaga | ttaagaagca | gttgtccaag | tatgaatctc | aactttcaac | 1680 |
| aaatgaggag | aaagtagata | cagatgatcg | aactgaaggc | tatttacgag | cagactcaca | 1740 |
| agagccctcc | cactttgatt | ctcagcagcc | tgcagtcttg | gaagaagaag | aggtcatgat | 1800 |
| agctcatgct | catccacagg | aagtctacaa | tgaatatgta | cccagagggt | gcaagaataa | 1860 |
| atgccattca | catttccacg | atacactcgg | ccagtcagac | gatctcattc | accaccatca | 1920 |
| tgactaccat | catattctcc | atcatcacca | ccaccaaaac | caccatcctc | acagtcacag | 1980 |
| ccagcgctac | tctcgggagg | agctgaaaga | tgccggcgtc | gccactttgg | cctggatggt | 2040 |
| gataatgggt | gatggcctgc | acaatttcag | cgatggccta | gcaattggtg | ctgcttttac | 2100 |
| tgaaggctta | tcaagtggtt | taagtacttc | tgttgctgtg | ttctgtcatg | agttgcctca | 2160 |

```
tgaattaggt gactttgctg ttctactaaa ggctggcatg accgttaagc aggctgtcct    2220
ttataatgca ttgtcagcca tgctggcgta tcttggaatg gcaacaggaa ttttcattgg    2280
tcattatgct gaaaatgttt ctatgtggat atttgcactt actgctggct tattcatgta    2340
tgttgctctg gttgatatgg tacctgaaat gctgcacaat gatgctagtg accatggatg    2400
tagccgctgg gggtatttct ttttacagaa tgctgggatg cttttgggtt ttggaattat    2460
gttacttatt ccatatttga acataaaatc gtgttcgtat aaatttctag ttaaggttta    2520
aatgctagag tagcttaaaa agttgtcata gtttcagtag gtcataggga gatgagtttg    2580
tatgctgtac tatgcagcgt ttaaagttag tgggttttgt gattttttgta ttgaatattg    2640 ctgtctgtta caaagtcagt taaaggtacg ttttaatatt taagttattc tatcttggag    2700
ataaaatctg tatgtgcaat tcaccggtat taccagtttta ttatgtaaac aagagatttg    2760
gcatgacatg ttctgtatgt ttcagggaaa aatgtcttta atgcttttc aagaactaac    2820 acagttattc ctatactgga ttttaggtct ctgaagaact gctggtgttt aggaataaga    2880
atgtgcatga agcctaaaat accaagaaag cttatactga atttaagcaa agaaataaag    2940
gagaaaagag aagaatctga gaattgggga ggcatagatt cttataaaaa tcacaaaatt    3000
tgttgtaaat tagaggggag aaatttagaa ttaagtataa aaaggcagaa ttagtataga    3060
gtacattcat taaacatttt tgtcaggatt atttcccgta aaaacgtagt gagcactctc    3120
atatactaat tagtgtacat ttaactttgt ataatacaga aatctaaata tatttaatga    3180
attcaagcaa tatacacttg accaagaaat tggaatttca aaatgttcgt gcgggttata    3240
taccagatga gtacagtgag tagtttatgt atcaccagac tgggttattg ccaagttata    3300
tatcaccaaa agctgtatga ctggatgttc tggttacctg gtttacaaaa ttatcagagt    3360
agtaaaactt tgatatatat gaggatatta aaactacact aagtatcatt tgattcgatt    3420
cagaaagtac tttgatatct ctcagtgctt cagtgctatc attgtgagca attgtcttta    3480
tatacggtac tgtagccata ctaggcctgt ctgtggcatt ctctagatgt ttcttttta    3540 cacaataaat tccttatatc agcttgaaaa aaaaaaaaa aaaaaa                    3586
```

<210> SEQ ID NO 52
<211> LENGTH: 752
<212> TYPE: PRT
<213> ORGANISM: Homo sapiens

<400> SEQUENCE: 52

Met Ala Arg Lys Leu Ser Val Ile Leu Ile Leu Thr Phe Ala Leu Ser
1               5                   10                  15

Val Thr Asn Pro Leu His Glu Leu Lys Ala Ala Ala Phe Pro Gln Thr
            20                  25                  30

Thr Glu Lys Ile Ser Pro Asn Trp Glu Ser Gly Ile Asn Val Asp Leu
        35                  40                  45

Ala Ile Ser Thr Arg Gln Tyr His Leu Gln Gln Leu Phe Tyr Arg Tyr
    50                  55                  60

Gly Glu Asn Asn Ser Leu Ser Val Gly Phe Arg Lys Leu Leu Gln
65                  70                  75                  80

Asn Ile Gly Ile Asp Lys Ile Lys Arg Ile His Ile His His Asp His
                85                  90                  95

Asp His His Ser Asp His Glu His Ser Asp His Glu Arg His Ser
            100                 105                 110

Asp His Glu His His Ser Asp His Glu His His Ser Asp His Asp His

```
            115                 120                 125
His Ser Ser Gly Lys Asn Lys Arg Lys Ala Leu Cys Pro Asp His Asp
    130                 135                 140

Ser Asp Ser Ser Gly Lys Asp Pro Arg Asn Ser Gln Gly Lys Gly Ala
145                 150                 155                 160

His Arg Pro Glu His Ala Ser Gly Arg Arg Asn Val Lys Asp Ser Val
                165                 170                 175

Ser Ala Ser Glu Val Thr Ser Thr Val Tyr Asn Thr Val Ser Glu Gly
            180                 185                 190

Thr His Phe Leu Glu Thr Ile Glu Thr Pro Arg Pro Gly Lys Leu Phe
        195                 200                 205

Pro Lys Asp Val Ser Ser Thr Pro Pro Ser Val Thr Ser Lys Ser
    210                 215                 220

Arg Val Ser Arg Leu Ala Gly Arg Lys Thr Asn Glu Ser Val Ser Glu
225                 230                 235                 240

Pro Arg Lys Gly Phe Met Tyr Ser Arg Asn Thr Asn Glu Asn Pro Gln
                245                 250                 255

Glu Cys Phe Asn Ala Ser Lys Leu Leu Thr Ser His Gly Met Gly Ile
            260                 265                 270

Gln Val Pro Leu Asn Ala Thr Glu Phe Asn Tyr Leu Cys Pro Ala Ile
        275                 280                 285

Ile Asn Gln Ile Asp Ala Arg Ser Cys Leu Ile His Thr Ser Glu Lys
    290                 295                 300

Lys Ala Glu Ile Pro Pro Lys Thr Tyr Ser Leu Gln Ile Ala Trp Val
305                 310                 315                 320

Gly Gly Phe Ile Ala Ile Ser Ile Ile Ser Phe Leu Ser Leu Leu Gly
                325                 330                 335

Val Ile Leu Val Pro Leu Met Asn Arg Val Phe Phe Lys Phe Leu Leu
            340                 345                 350

Ser Phe Leu Val Ala Leu Ala Val Gly Thr Leu Ser Gly Asp Ala Phe
        355                 360                 365

Leu His Leu Leu Pro His Ser His Ala Ser His His Ser His Ser
    370                 375                 380

His Glu Glu Pro Ala Met Glu Met Lys Arg Gly Pro Leu Phe Ser His
385                 390                 395                 400

Leu Ser Ser Gln Asn Ile Glu Glu Ser Ala Tyr Phe Asp Ser Thr Trp
                405                 410                 415

Lys Gly Leu Thr Ala Leu Gly Gly Leu Tyr Phe Met Phe Leu Val Glu
            420                 425                 430

His Val Leu Thr Leu Ile Lys Gln Phe Lys Asp Lys Lys Lys Asn
        435                 440                 445

Gln Lys Lys Pro Glu Asn Asp Asp Val Glu Ile Lys Lys Gln Leu
    450                 455                 460

Ser Lys Tyr Glu Ser Gln Leu Ser Thr Asn Glu Glu Lys Val Asp Thr
465                 470                 475                 480

Asp Asp Arg Thr Glu Gly Tyr Leu Arg Ala Asp Ser Gln Glu Pro Ser
                485                 490                 495

His Phe Asp Ser Gln Gln Pro Ala Val Leu Glu Glu Glu Val Met
            500                 505                 510

Ile Ala His Ala His Pro Gln Glu Val Tyr Asn Glu Tyr Val Pro Arg
        515                 520                 525

Gly Cys Lys Asn Lys Cys His Ser His Phe His Asp Thr Leu Gly Gln
    530                 535                 540
```

Ser Asp Asp Leu Ile His His His Asp Tyr His His Ile Leu His
545                 550                 555                 560

His His His His Gln Asn His His Pro His Ser His Ser Gln Arg Tyr
                565                 570                 575

Ser Arg Glu Glu Leu Lys Asp Ala Gly Val Ala Thr Leu Ala Trp Met
            580                 585                 590

Val Ile Met Gly Asp Gly Leu His Asn Phe Ser Asp Gly Leu Ala Ile
        595                 600                 605

Gly Ala Ala Phe Thr Glu Gly Leu Ser Ser Gly Leu Ser Thr Ser Val
    610                 615                 620

Ala Val Phe Cys His Glu Leu Pro His Glu Leu Gly Asp Phe Ala Val
625                 630                 635                 640

Leu Leu Lys Ala Gly Met Thr Val Lys Gln Ala Val Leu Tyr Asn Ala
                645                 650                 655

Leu Ser Ala Met Leu Ala Tyr Leu Gly Met Ala Thr Gly Ile Phe Ile
            660                 665                 670

Gly His Tyr Ala Glu Asn Val Ser Met Trp Ile Phe Ala Leu Thr Ala
        675                 680                 685

Gly Leu Phe Met Tyr Val Ala Leu Val Asp Met Val Pro Glu Met Leu
    690                 695                 700

His Asn Asp Ala Ser Asp His Gly Cys Ser Arg Trp Gly Tyr Phe Phe
705                 710                 715                 720

Leu Gln Asn Ala Gly Met Leu Leu Gly Phe Gly Ile Met Leu Leu Ile
                725                 730                 735

Pro Tyr Leu Asn Ile Lys Ser Cys Ser Tyr Lys Phe Leu Val Lys Val
            740                 745                 750

<210> SEQ ID NO 53
<211> LENGTH: 9646
<212> TYPE: DNA
<213> ORGANISM: Homo sapiens
<220> FEATURE:
<221> NAME/KEY: modified_base
<222> LOCATION: (9026)..(9026)
<223> OTHER INFORMATION: a, c, t or g
<220> FEATURE:
<221> NAME/KEY: modified_base
<222> LOCATION: (9030)..(9030)
<223> OTHER INFORMATION: a, c, t or g

<400> SEQUENCE: 53

| | | | |  |
|---|---|---|---|---|
| atgcccaagc | gcgcgcactg | gggggccctc | tccgtggtgc tgatcctgct ttggggccat | 60 |
| ccgcgagtgg | cgctggcctg | cccgcatcct | tgtgcctgct acgtcccag cgaggtccac | 120 |
| tgcacgttcc | gatccctggc | ttccgtgccc | gctggcattg ctagacacgt ggaaagaatc | 180 |
| aatttggggt | taatagcat | acaggccctg | tcagaaacct catttgcagg actgaccaag | 240 |
| ttggagctac | ttatgattca | cggcaatgag | atcccaagca tccccgatgg agctttaaga | 300 |
| gacctcagct | ctcttcaggt | tttcaagttc | agctacaaca agctgagagt gatcacagga | 360 |
| cagaccctcc | agggtctctc | taacttaatg | aggctgcaca ttgaccacaa caagatcgag | 420 |
| tttatccacc | ctcaagcttt | caacggctta | acgtctctga ggctactcca tttggaagga | 480 |
| aatctcctcc | accagctgca | ccccagcacc | ttctccacgt tcacattttt ggattatttc | 540 |
| agactctcca | ccataaggca | cctctactta | gcagagaaca tggttagaac tcttcctgcc | 600 |
| agcatgcttc | ggaacatgcc | gcttctggag | aatctttact tgcagggaaa tcgtggaccc | 660 |
| tgcgattgtg | agatgagatg | gttttttggaa | tgggatgcaa aatccagagg aattctgaag | 720 |

```
tgtaaaaagg acaaagctta tgaaggcggt cagttgtgtg caatgtgctt cagtccaaag    780
aagttgtaca aacatgagat acacaagctg aaggacatga cttgtctgaa gccttcaata    840
gagtcccctc tgagacagaa caggagcagg agtattgagg aggagcaaga acaggaagag    900
gatggtggca gccagctcat cctggagaaa ttccaactgc cccagtggag catctctttg    960
aatatgaccg acgagcacgg gaacatggtg aacttggtct gtgacatcaa gaaccaatg   1020 gatgtgtaca agattcactt gaaccaaacg gatcctccag atattgacat aaatgcaaca   1080
gttgccttgg actttgagtg tccaatgacc cgagaaaact atgaaaagct atggaaattg   1140
atagcatact acagtgaagt tcccgtgaag ctacacagag agctcatgct cagcaaagac   1200
cccagagtca gctaccagta caggcaggat gctgatgagg aagctctttta ctacacaggt   1260 gtgagagccc agattcttgc agaaccagaa tgggtcatgc agccatccat agatatccag   1320
ctgaaccgac gtcagagtac ggccaagaag gtgctacttt cctactacac ccagtattct   1380
caaacaatat ccaccaaaga tacaaggcag gctcggggca gaagctgggt aatgattgag   1440
cctagtggag ctgtgcaaag agatcagact gtcctggaag ggggtccatg ccagttgagc   1500
tgcaacgtga aagcttctga gagtccatct atcttctggg tgcttccaga tggctccatc   1560
ctgaaagcgc ccatggatga cccagacagc aagttctcca ttctcagcag tggctggctg   1620
aggatcaagt ccatggagcc atctgactca ggccttgtacc agtgcattgc tcaagtgagg   1680
gatgaaatgg accgcatggt atatagggta cttgtgcagt ctccctccac tcagccagcc   1740
gagaaagaca cagtgacaat tggcaagaac ccaggggagt cggtgacatt gccttgcaat   1800
gctttagcaa tacccgaagc ccaccttagc tggattcttc caaacagaag gataattaat   1860
gatttggcta acacatcaca tgtatacatg ttgccaaatg gaactctttc catcccaaag   1920
gtccaagtca gtgatagtgg ttactacaga tgtgtggctg tcaaccagca aggggcagac   1980 catttttacgg tgggaatcac agtgaccaag aaagggtctg gcttgccatc caaaagaggc   2040
agacgcccag gtgcaaaggc tcttttccaga gtcagagaag acatcgtgga ggatgaaggg   2100
ggctcgggca tggagatga agagaacact tcaaggagac ttctgcatcc aaaggaccaa   2160
gaggtgttcc tcaaaacaaa ggatgatgcc atcaatgagg acaagaaagc caagaaaggg   2220
agaagaaagc tgaaactctg gaagcattcg gaaaaagaac cagagaccaa tgttgcagaa   2280
ggtcgcagag tgtttgaatc tagacgaagg ataaacatgg caaacaaaca gattaatccg   2340
gagcgctggg ctgatatttt agccaaagtc cgtgggaaaa atctccctaa gggcacagaa   2400 gtaccccgt tgattaaaac cacaagtcct ccatccttga gcctagaagt cacaccacct   2460
tttcctgctg tttctccccc ctcagcatct cctgtgcaga cagtaaccag tgctgaagaa   2520
tcctcagcag atgtacctct acttggtgaa gaagagcacg ttttgggtac catttcctca   2580
gccagcatgg ggctagaaca caaccacaat ggagttattc ttgttgaacc tgaagtaaca   2640
agcacacctc tggaggaagt tgttgatgac ctttctgaga agactgagga gataacttcc   2700
actgaaggag acctgaaggg gacagcagcc cctacactta tatctgagcc ttatgaacca   2760
tctcctactc tgcacacatt agacacagtc tatgaaaagc ccacccatga agagacggca   2820
acagagggtt ggtctgcagc agatgttgga tcgtcaccag agcccacatc cagtgagtat   2880
gagcctccat tggatgctgt ctccttggct gagtctgagc ccatgcaata ctttgaccca   2940
gatttggaga ctaagtcaca accagatgag gataagatga agaagacac ctttgcacac   3000 cttactccaa ccccccaccat ctgggttaat gactccagta catcacagtt atttgaggat   3060
```

```
tctactatag gggaaccagg tgtcccaggc caatcacatc tacaaggact gacagacaac    3120
atccaccttg tgaaaagtag tctaagcact caagacacct tactgattaa aaagggtatg    3180
aaagagatgt ctcagacact acagggagga aatatgctag agggagaccc cacacactcc    3240
agaagttctg agagtgaggg ccaagagagc aaatccatca ctttgcctga ctccacactg    3300
ggtataatga gcagtatgtc tccagttaag aagcctgcgg aaaccacagt tggtaccctc    3360
ctagacaaag acaccacaac agtaacaaca acaccaaggc aaaaagttgc tccgtcatcc    3420
accatgagca ctcacccttc tcgaaggaga cccaacggga aaggagatt acgcccaac     3480 aaattccgcc accggcacaa gcaaccccca cccacaactt ttgccccatc agagactttt    3540
tctactcaac caactcaagc acctgacatt aagatttcaa gtcaagtgga gagttctctg    3600
gttcctacag cttgggtgga taacacagtt aataccccca aacagttgga aatggagaag    3660
aatgcagaac ccacatccaa gggaacacca cggagaaaac acgggaagag gccaaacaaa    3720
catcgatata cccttctac agtgagctca agagcgtccg gatccaagcc cagcccttct    3780
ccagaaaata aacatagaaa cattgttact cccagttcag aaactatact tttgcctaga    3840
actgtttctc tgaaaactga gggcccttat gattccttag attacatgac aaccaccaga    3900
aaaatatatt catcttaccc taaagtccaa gagacacttc cagtcacata taaacccaca    3960
tcagatggaa aagaaattaa ggatgatgtt gccacaaatg ttgacaaaca taaaagtgac    4020
attttagtca ctggtgaatc aattactaat gccataccaa cttctcgctc cttggtctcc    4080
actatgggag aatttaagga agaatcctct cctgtaggct ttccaggaac tccaacctgg    4140
aatccctcaa ggacggccca gcctggagg ctacagacag acatacctgt taccacttct    4200
ggggaaaatc ttacagaccc tccccttctt aaagagcttg aggatgtgga tttcacttcc    4260 gagttttgt cctcttgac agtctccaca ccatttcacc aggaagaagc tggttcttcc    4320
acaactctct caagcataaa agtggaggtg gcttcaagtc aggcagaaac caccacctt    4380 gatcaagatc atcttgaaac cactgtggct attctccttt ctgaaactag accacagaat    4440 cacacccta ctgctgcccg gatgaaggag ccagcatcct cgtccccatc acaattctc    4500 atgtctttgg gacaaaccac caccactaag ccagcacttc ccagtccaag aatatctcaa    4560
gcatctagag attccaagga aaatgttttc ttgaattatg tggggaatcc agaaacagaa    4620
gcaaccccag tcaacaatga aggaacacag catatgtcag ggccaaatga attatcaaca    4680
ccctcttccg accgggatgc atttaacttg tctacaaagc tggaattgga aaagcaagta    4740
tttggtagta ggagtctacc acgtggccca gatagccaac gccaggatgg aagagttcat    4800
gcttctcatc aactaaccag agtccctgcc aaacccatcc taccaacagc aacagtgagg    4860
ctacctgaaa tgtccacaca aagcgcttcc agatactttg taacttccca gtcacctcgt    4920
cactggacca acaaaccgga ataactaca tatccttctg gggctttgcc agagaacaaa    4980
cagtttacaa ctccaagatt atcaagtaca acaattcctc tcccattgca catgtccaaa    5040
cccagcattc ctagtaagtt tactgaccga agaactgacc aattcaatgg ttactccaaa    5100
gtgtttggaa ataacaacat ccctgaggca agaaacccag ttggaaagcc tcccagtcca    5160
agaattcctc attattccaa tggaagactc cctttcttta ccaacaagac tctttctttt    5220
ccacagttgg gagtcacccg gagaccccag atacccactt ctcctgcccc agtaatgaga    5280
gagagaaaag ttattccagg ttcctacaac aggatacatt cccatagcac cttccatctg    5340
gactttggcc ctccggcacc tccgttgttg cacactccgc agaccacggg atcaccctca    5400
actaacttac agaatatccc tatggtctct tccacccaga gttctatctc ctttataaca    5460
```

-continued

```
tcttctgtcc agtcctcagg aagcttccac cagagcagct caaagttctt tgcaggagga    5520
cctcctgcat ccaaattctg gtctcttggg gaaaagcccc aaatcctcac caagtcccca    5580
cagactgtgt ccgtcaccgc tgagacagac actgtgttcc cctgtgaggc aacaggaaaa    5640
ccaaagcctt tcgttacttg gacaaaggtt tccacaggag ctcttatgac tccgaatacc    5700
aggatacaac ggtttgaggt tctcaagaac ggtaccttag tgatacggaa ggttcaagta    5760
caagatcgag gccagtatat gtgcaccgcc agcaacctgc acggcctgga caggatggtg    5820
gtcttgcttt cggtcaccgt gcagcaacct caaatcctag cctcccacta ccaggacgtc    5880
actgtctacc tgggagacac cattgcaatg gagtgtctgg ccaaagggac cccagccccc    5940
caaatttcct ggatcttccc tgacaggagg gtgtggcaaa ctgtgtcccc cgtggagagc    6000
cgcatcaccc tgcacgaaaa ccggacccct tccatcaagg aggcgtcctt ctcagacaga    6060
ggcgtctata agtgcgtggc cagcaatgca gccggggcgg acagcctggc catccgcctg    6120
cacgtggcgg cactgccccc cgttatccac caggagaagc tggagaacat ctcgctgccc    6180
ccggggctca gcattcacat tcactgcact gccaaggctg cgcccctgcc cagcgtgcgc    6240
tgggtgctcg gggacggtac ccagatccgc ccctcgcagt tcctccacgg gaacttgttt    6300
gttttcccca acgggacgct ctacatccgc aacctcgcgc ccaaggacag cgggcgctat    6360
gagtgcgtgg ccgccaacct ggtaggctcc gcgcgcagga cggtgcagct gaacgtgcag    6420
cgtgcagcag ccaacgcgcg catcacgggc acctcccgc ggaggacgga cgtcaggtac    6480
ggaggaaccc tcaagctgga ctgcagcgcc tcggggacc cctggccgcg catcctctgg    6540
aggctgccgt ccaagaggat gatcgacgcg ctcttcagtt ttgatagcag aatcaaggtg    6600
tttgccaatg ggaccctggt ggtgaaatca gtgacggaca agatgccgg agattacctg    6660 tgcgtagctc gaaataaggt tggtgatgac tacgtggtgc tcaaagtgga tgtggtgatg    6720
aaaccggcca agattgaaca caaggaggag aacgaccaca aagtcttcta cggggtgac    6780 ctgaaagtgg actgtgtggc caccgggctt cccaatcccg agatctcctg gagcctccca    6840
gacgggagtc tggtgaactc cttcatgcag tcggatgaca gcggtggacg caccaagcgc    6900
tatgtcgtct tcaacaatgg gacactctac tttaacgaag tggggatgag ggaggaagga    6960
gactacacct gctttgctga aaatcaggtc gggaaggacg agatgagagt cagagtcaag    7020
gtggtgacag cgcccgccac catccggaac aagacttact ggcggttca ggtgccctat    7080 ggagacgtgg tcactgtagc ctgtgaggcc aaaggagaac ccatgcccaa ggtgacttgg    7140
ttgtccccaa ccaacaaggt gatccccacc tcctctgaga agtatcagat ataccaagat    7200
ggcactctcc ttattcagaa agcccagcgt tctgacagcg gcaactacac ctgcttggtc    7260
aggaacagcg cgggagagga taggaagacg gtgtggatt acgtcaacgt ccagccaccc    7320
aagatcaacg gtaaccccaa ccccatcacc accgtgcggg agatagcagc cggggcagt    7380 cggaaactga ttgactgcaa agctgaaggc atccccaccc cgagggtgtt atgggctttt    7440
cccgagggtg tggttctgcc agctccatac tatggaaacc ggatcactgt ccatggcaac    7500
ggttccctgg acatcaggag tttgaggaag agcgactccg tccagctggt atgcatggca    7560
cgcaacgagg aggggaggc gaggttgatc gtgcagctca ctgtcctgga gcccatggag    7620
aaacccatct tccacgaccc gatcagcgag aagatcacgg ccatggcggg ccacaccatc    7680
agcctcaact gctctgccgc ggggacccg acacccagcc tggtgtgggt ccttcccaat    7740
ggcaccgatc tgcagagtgg acagcagctg cagcgcttct accacaaggc tgacggcatg    7800
```

```
ctacacatta gcggtctctc ctcggtggac gcygggggcct accgctgcgt ggcccgcaat      7860
gccgctggcc acacggagag gctggtctcc ctgaaggtgg gactgaagcc agaagcaaac      7920
aagcagtatc ataacctggt cagcatcatc aatggtgaga ccctgaagct cccctgcacc      7980
cctcccgggg ctgggcaggg acgtttctcc tggacgctcc caatggcat gcatctggag       8040
ggcccccaaa ccctgggacg cgtttctctt ctggacaatg gcaccctcac ggttcgtgag      8100
gcctcggtgt ttgacagggg tacctatgta tgcaggatgg agacggagta cggcccttcg      8160
gtcaccagca tccccgtgat tgtgatcgcc tatcctcccc ggatcaccag cgagcccacc      8220
ccggtcatct acacccggcc cgggaacacc gtgaaactga actgcatggc tatgggggatt     8280
cccaaagctg acatcacgtg ggagttaccg gataagtcgc atctgaaggc aggggttcag      8340
gctcgtctgt atggaaacag atttcttcac ccccagggat cactgaccat ccagcatgcc      8400
acacagagag atgccggctt ctacaagtgc atggcaaaaa acattctcgg cagtgactcc      8460
aaaacaactt catccacgt cttctgaaat gtggattcca gaatgattgc ttaggaactg       8520
acaacaaagc ggggtttgta agggaagcca ggttggggaa taggagctct taaataatgt      8580
gtcacagtgc atggtggcct ctggtgggtt tcaagttgag gttgatcttg atctacaatt      8640
gttgggaaaa ggaagcaatg cagacacgag aaggagggct cagccttgct gagacacttt      8700
cttttgtgtt tacatcatgc caggggcttc attcagggtg tctgtgctct gactgcaatt      8760
tttcttttt tgcaaatgcc actcgactgc cttcataagc gtccatagga tatctgagga      8820
acattcatca aaataagcc atagacatga caacacctc actaccccat gaagacgca       8880
tcacctagtt aacctgctgc agttttaca tgatagactt tgttccagat tgacaagtca      8940
tctttcagtt atttcctctg tcacttcaaa actccagctt gcccaataag gatttagaac      9000
cagagtgact gatatatata tatatntttn aattcagagt tacatacata cagctaccat      9060
tttatatgaa aaagaaaaa catttcttcc tggaactcac ttttatata atgtttata         9120
tatatatttt tkcctttcaa atcagacgat gagactagaa ggagaaatac tttctgtctt      9180
attaaaatta ataaattatt ggtctttaca agacttggat acattacagc agacatggaa      9240
aatataattt taaaaaattt ctctccaacc tccttcaaat tcagtcacca ctgttatatt      9300
accttctcca ggaaccctcc agtggggaag gctgcgatat tagatttcct tgtatgcaaa      9360
gtttttgttg aaagctgtgc tcagaggagg tgagaggaga ggaaggagaa aactgcatca     9420
taactttaca gaattgaatc tagagtcttc cccgaaaagc ccagaaactt ctctgcagta      9480
tctggcttgt ccatctggtc taaggtggct gcttcttccc cagccatgag tcagtttgtg      9540
cccatgaata atacacgacc tgttatttcc atgactgctt tactgtatt ttaaggtcaa       9600
tatactgtac atttgataat aaaataatat tctcccaaaa aaaaaa                   9646
```

<210> SEQ ID NO 54
<211> LENGTH: 2828
<212> TYPE: PRT
<213> ORGANISM: Homo sapiens

<400> SEQUENCE: 54

Met Pro Lys Arg Ala His Trp Gly Ala Leu Ser Val Val Leu Ile Leu
1               5                   10                  15

Leu Trp Gly His Pro Arg Val Ala Leu Ala Cys Pro His Pro Cys Ala
            20                  25                  30

Cys Tyr Val Pro Ser Glu Val His Cys Thr Phe Arg Ser Leu Ala Ser
        35                  40                  45

Val Pro Ala Gly Ile Ala Arg His Val Glu Arg Ile Asn Leu Gly Phe
 50                  55                  60

Asn Ser Ile Gln Ala Leu Ser Glu Thr Ser Phe Ala Gly Leu Thr Lys
 65                  70                  75                  80

Leu Glu Leu Leu Met Ile His Gly Asn Glu Ile Pro Ser Ile Pro Asp
                 85                  90                  95

Gly Ala Leu Arg Asp Leu Ser Ser Leu Gln Val Phe Lys Phe Ser Tyr
                100                 105                 110

Asn Lys Leu Arg Val Ile Thr Gly Gln Thr Leu Gln Gly Leu Ser Asn
            115                 120                 125

Leu Met Arg Leu His Ile Asp His Asn Lys Ile Glu Phe Ile His Pro
130                 135                 140

Gln Ala Phe Asn Gly Leu Thr Ser Leu Arg Leu Leu His Leu Glu Gly
145                 150                 155                 160

Asn Leu Leu His Gln Leu His Pro Ser Thr Phe Ser Thr Phe Thr Phe
                165                 170                 175

Leu Asp Tyr Phe Arg Leu Ser Thr Ile Arg His Leu Tyr Leu Ala Glu
            180                 185                 190

Asn Met Val Arg Thr Leu Pro Ala Ser Met Leu Arg Asn Met Pro Leu
            195                 200                 205

Leu Glu Asn Leu Tyr Leu Gln Gly Asn Pro Trp Thr Cys Asp Cys Glu
210                 215                 220

Met Arg Trp Phe Leu Glu Trp Asp Ala Lys Ser Arg Gly Ile Leu Lys
225                 230                 235                 240

Cys Lys Lys Asp Lys Ala Tyr Glu Gly Gly Gln Leu Cys Ala Met Cys
                245                 250                 255

Phe Ser Pro Lys Lys Leu Tyr Lys His Glu Ile His Lys Leu Lys Asp
            260                 265                 270

Met Thr Cys Leu Lys Pro Ser Ile Glu Ser Pro Leu Arg Gln Asn Arg
            275                 280                 285

Ser Arg Ser Ile Glu Glu Gln Glu Gln Glu Glu Asp Gly Gly Ser
290                 295                 300

Gln Leu Ile Leu Glu Lys Phe Gln Leu Pro Gln Trp Ser Ile Ser Leu
305                 310                 315                 320

Asn Met Thr Asp Glu His Gly Asn Met Val Asn Leu Val Cys Asp Ile
                325                 330                 335

Lys Lys Pro Met Asp Val Tyr Lys Ile His Leu Asn Gln Thr Asp Pro
            340                 345                 350

Pro Asp Ile Asp Ile Asn Ala Thr Val Ala Leu Asp Phe Glu Cys Pro
            355                 360                 365

Met Thr Arg Glu Asn Tyr Glu Lys Leu Trp Lys Leu Ile Ala Tyr Tyr
370                 375                 380

Ser Glu Val Pro Val Lys Leu His Arg Glu Leu Met Leu Ser Lys Asp
385                 390                 395                 400

Pro Arg Val Ser Tyr Gln Tyr Arg Gln Asp Ala Asp Glu Glu Ala Leu
            405                 410                 415

Tyr Tyr Thr Gly Val Arg Ala Gln Ile Leu Ala Glu Pro Glu Trp Val
            420                 425                 430

Met Gln Pro Ser Ile Asp Ile Gln Leu Asn Arg Arg Gln Ser Thr Ala
            435                 440                 445

Lys Lys Val Leu Leu Ser Tyr Tyr Thr Gln Tyr Ser Gln Thr Ile Ser
450                 455                 460

Thr Lys Asp Thr Arg Gln Ala Arg Gly Arg Ser Trp Val Met Ile Glu

-continued

```
465                 470                 475                 480

Pro Ser Gly Ala Val Gln Arg Asp Gln Thr Val Leu Glu Gly Pro
                485                 490                 495

Cys Gln Leu Ser Cys Asn Val Lys Ala Ser Glu Ser Pro Ser Ile Phe
                500                 505                 510

Trp Val Leu Pro Asp Gly Ser Ile Leu Lys Ala Pro Met Asp Asp Pro
                515                 520                 525

Asp Ser Lys Phe Ser Ile Leu Ser Ser Gly Trp Leu Arg Ile Lys Ser
        530                 535                 540

Met Glu Pro Ser Asp Ser Gly Leu Tyr Gln Cys Ile Ala Gln Val Arg
545                 550                 555                 560

Asp Glu Met Asp Arg Met Val Tyr Arg Val Leu Val Gln Ser Pro Ser
                565                 570                 575

Thr Gln Pro Ala Glu Lys Asp Thr Val Thr Ile Gly Lys Asn Pro Gly
                580                 585                 590

Glu Ser Val Thr Leu Pro Cys Asn Ala Leu Ala Ile Pro Glu Ala His
        595                 600                 605

Leu Ser Trp Ile Leu Pro Asn Arg Arg Ile Ile Asn Asp Leu Ala Asn
        610                 615                 620

Thr Ser His Val Tyr Met Leu Pro Asn Gly Thr Leu Ser Ile Pro Lys
625                 630                 635                 640

Val Gln Val Ser Asp Ser Gly Tyr Tyr Arg Cys Val Ala Val Asn Gln
                645                 650                 655

Gln Gly Ala Asp His Phe Thr Val Gly Ile Thr Val Thr Lys Lys Gly
                660                 665                 670

Ser Gly Leu Pro Ser Lys Arg Gly Arg Pro Gly Ala Lys Ala Leu
        675                 680                 685

Ser Arg Val Arg Glu Asp Ile Val Glu Asp Gly Gly Ser Gly Met
        690                 695                 700

Gly Asp Glu Glu Asn Thr Ser Arg Arg Leu Leu His Pro Lys Asp Gln
705                 710                 715                 720

Glu Val Phe Leu Lys Thr Lys Asp Asp Ala Ile Asn Gly Asp Lys Lys
                725                 730                 735

Ala Lys Lys Gly Arg Arg Lys Leu Lys Leu Trp Lys His Ser Glu Lys
                740                 745                 750

Glu Pro Glu Thr Asn Val Ala Glu Gly Arg Arg Val Phe Glu Ser Arg
                755                 760                 765

Arg Arg Ile Asn Met Ala Asn Lys Gln Ile Asn Pro Glu Arg Trp Ala
770                 775                 780

Asp Ile Leu Ala Lys Val Arg Gly Lys Asn Leu Pro Lys Gly Thr Glu
785                 790                 795                 800

Val Pro Pro Leu Ile Lys Thr Thr Ser Pro Ser Leu Ser Leu Glu
                805                 810                 815

Val Thr Pro Pro Phe Pro Ala Val Ser Pro Ser Ala Ser Pro Val
                820                 825                 830

Gln Thr Val Thr Ser Ala Glu Glu Ser Ser Ala Asp Val Pro Leu Leu
                835                 840                 845

Gly Glu Glu Glu His Val Leu Gly Thr Ile Ser Ser Ala Ser Met Gly
                850                 855                 860

Leu Glu His Asn His Asn Gly Val Ile Leu Val Glu Pro Glu Val Thr
865                 870                 875                 880

Ser Thr Pro Leu Glu Glu Val Val Asp Asp Leu Ser Glu Lys Thr Glu
                885                 890                 895
```

```
Glu Ile Thr Ser Thr Glu Gly Asp Leu Lys Gly Thr Ala Ala Pro Thr
           900                 905                 910

Leu Ile Ser Glu Pro Tyr Glu Pro Ser Pro Thr Leu His Thr Leu Asp
           915                 920                 925

Thr Val Tyr Glu Lys Pro Thr His Glu Thr Ala Thr Glu Gly Trp
       930                 935                 940

Ser Ala Ala Asp Val Gly Ser Ser Pro Glu Pro Thr Ser Ser Glu Tyr
945                 950                 955                 960

Glu Pro Pro Leu Asp Ala Val Ser Leu Ala Glu Ser Glu Pro Met Gln
               965                 970                 975

Tyr Phe Asp Pro Asp Leu Glu Thr Lys Ser Gln Pro Asp Glu Asp Lys
           980                 985                 990

Met Lys Glu Asp Thr Phe Ala His Leu Thr Pro Thr Pro Thr Ile Trp
       995                 1000                1005

Val Asn Asp Ser Ser Thr Ser Gln Leu Phe Glu Asp Ser Thr Ile
    1010                1015                1020

Gly Glu Pro Gly Val Pro Gly Gln Ser His Leu Gln Gly Leu Thr
    1025                1030                1035

Asp Asn Ile His Leu Val Lys Ser Ser Leu Ser Thr Gln Asp Thr
    1040                1045                1050

Leu Leu Ile Lys Lys Gly Met Lys Glu Met Ser Gln Thr Leu Gln
    1055                1060                1065

Gly Gly Asn Met Leu Glu Gly Asp Pro Thr His Ser Arg Ser Ser
    1070                1075                1080

Glu Ser Glu Gly Gln Glu Ser Lys Ser Ile Thr Leu Pro Asp Ser
    1085                1090                1095

Thr Leu Gly Ile Met Ser Ser Met Ser Pro Val Lys Lys Pro Ala
    1100                1105                1110

Glu Thr Thr Val Gly Thr Leu Leu Asp Lys Asp Thr Thr Thr Val
    1115                1120                1125

Thr Thr Thr Pro Arg Gln Lys Val Ala Pro Ser Ser Thr Met Ser
    1130                1135                1140

Thr His Pro Ser Arg Arg Arg Pro Asn Gly Arg Arg Arg Leu Arg
    1145                1150                1155

Pro Asn Lys Phe Arg His Arg His Lys Gln Thr Pro Pro Thr Thr
    1160                1165                1170

Phe Ala Pro Ser Glu Thr Phe Ser Thr Gln Pro Thr Gln Ala Pro
    1175                1180                1185

Asp Ile Lys Ile Ser Ser Gln Val Glu Ser Ser Leu Val Pro Thr
    1190                1195                1200

Ala Trp Val Asp Asn Thr Val Asn Thr Pro Lys Gln Leu Glu Met
    1205                1210                1215

Glu Lys Asn Ala Glu Pro Ser Lys Gly Thr Pro Arg Arg Lys
    1220                1225                1230

His Gly Lys Arg Pro Asn Lys His Arg Tyr Thr Pro Ser Thr Val
    1235                1240                1245

Ser Ser Arg Ala Ser Gly Ser Lys Pro Ser Pro Ser Pro Glu Asn
    1250                1255                1260

Lys His Arg Asn Ile Val Thr Pro Ser Ser Glu Thr Ile Leu Leu
    1265                1270                1275

Pro Arg Thr Val Ser Leu Lys Thr Glu Gly Pro Tyr Asp Ser Leu
    1280                1285                1290
```

Asp Tyr Met Thr Thr Thr Arg Lys Ile Tyr Ser Ser Tyr Pro Lys
1295                1300                1305

Val Gln Glu Thr Leu Pro Val Thr Tyr Lys Pro Thr Ser Asp Gly
1310                1315                1320

Lys Glu Ile Lys Asp Asp Val Ala Thr Asn Val Asp Lys His Lys
1325                1330                1335

Ser Asp Ile Leu Val Thr Gly Glu Ser Ile Thr Asn Ala Ile Pro
1340                1345                1350

Thr Ser Arg Ser Leu Val Ser Thr Met Gly Glu Phe Lys Glu Glu
1355                1360                1365

Ser Ser Pro Val Gly Phe Pro Gly Thr Pro Thr Trp Asn Pro Ser
1370                1375                1380

Arg Thr Ala Gln Pro Gly Arg Leu Gln Thr Asp Ile Pro Val Thr
1385                1390                1395

Thr Ser Gly Glu Asn Leu Thr Asp Pro Pro Leu Leu Lys Glu Leu
1400                1405                1410

Glu Asp Val Asp Phe Thr Ser Glu Phe Leu Ser Ser Leu Thr Val
1415                1420                1425

Ser Thr Pro Phe His Gln Glu Glu Ala Gly Ser Ser Thr Thr Leu
1430                1435                1440

Ser Ser Ile Lys Val Glu Val Ala Ser Ser Gln Ala Glu Thr Thr
1445                1450                1455

Thr Leu Asp Gln Asp His Leu Glu Thr Thr Val Ala Ile Leu Leu
1460                1465                1470

Ser Glu Thr Arg Pro Gln Asn His Thr Pro Thr Ala Ala Arg Met
1475                1480                1485

Lys Glu Pro Ala Ser Ser Ser Pro Ser Thr Ile Leu Met Ser Leu
1490                1495                1500

Gly Gln Thr Thr Thr Thr Lys Pro Ala Leu Pro Ser Pro Arg Ile
1505                1510                1515

Ser Gln Ala Ser Arg Asp Ser Lys Glu Asn Val Phe Leu Asn Tyr
1520                1525                1530

Val Gly Asn Pro Glu Thr Glu Ala Thr Pro Val Asn Asn Glu Gly
1535                1540                1545

Thr Gln His Met Ser Gly Pro Asn Glu Leu Ser Thr Pro Ser Ser
1550                1555                1560

Asp Arg Asp Ala Phe Asn Leu Ser Thr Lys Leu Glu Leu Glu Lys
1565                1570                1575

Gln Val Phe Gly Ser Arg Ser Leu Pro Arg Gly Pro Asp Ser Gln
1580                1585                1590

Arg Gln Asp Gly Arg Val His Ala Ser His Gln Leu Thr Arg Val
1595                1600                1605

Pro Ala Lys Pro Ile Leu Pro Thr Ala Thr Val Arg Leu Pro Glu
1610                1615                1620

Met Ser Thr Gln Ser Ala Ser Arg Tyr Phe Val Thr Ser Gln Ser
1625                1630                1635

Pro Arg His Trp Thr Asn Lys Pro Glu Ile Thr Thr Tyr Pro Ser
1640                1645                1650

Gly Ala Leu Pro Glu Asn Lys Gln Phe Thr Thr Pro Arg Leu Ser
1655                1660                1665

Ser Thr Thr Ile Pro Leu Pro Leu His Met Ser Lys Pro Ser Ile
1670                1675                1680

Pro Ser Lys Phe Thr Asp Arg Arg Thr Asp Gln Phe Asn Gly Tyr

```
                1685                1690                1695

Ser Lys Val Phe Gly Asn Asn Ile Pro Glu Ala Arg Asn Pro
    1700                1705                1710

Val Gly Lys Pro Pro Ser Pro Arg Ile Pro His Tyr Ser Asn Gly
    1715                1720                1725

Arg Leu Pro Phe Phe Thr Asn Lys Thr Leu Ser Phe Pro Gln Leu
    1730                1735                1740

Gly Val Thr Arg Arg Pro Gln Ile Pro Thr Ser Pro Ala Pro Val
    1745                1750                1755

Met Arg Glu Arg Lys Val Ile Pro Gly Ser Tyr Asn Arg Ile His
    1760                1765                1770

Ser His Ser Thr Phe His Leu Asp Phe Gly Pro Pro Ala Pro Pro
    1775                1780                1785

Leu Leu His Thr Pro Gln Thr Thr Gly Ser Pro Ser Thr Asn Leu
    1790                1795                1800

Gln Asn Ile Pro Met Val Ser Ser Thr Gln Ser Ser Ile Ser Phe
    1805                1810                1815

Ile Thr Ser Ser Val Gln Ser Ser Gly Ser Phe His Gln Ser Ser
    1820                1825                1830

Ser Lys Phe Phe Ala Gly Gly Pro Pro Ala Ser Lys Phe Trp Ser
    1835                1840                1845

Leu Gly Glu Lys Pro Gln Ile Leu Thr Lys Ser Pro Gln Thr Val
    1850                1855                1860

Ser Val Thr Ala Glu Thr Asp Thr Val Phe Pro Cys Glu Ala Thr
    1865                1870                1875

Gly Lys Pro Lys Pro Phe Val Thr Trp Thr Lys Val Ser Thr Gly
    1880                1885                1890

Ala Leu Met Thr Pro Asn Thr Arg Ile Gln Arg Phe Glu Val Leu
    1895                1900                1905

Lys Asn Gly Thr Leu Val Ile Arg Lys Val Gln Val Gln Asp Arg
    1910                1915                1920

Gly Gln Tyr Met Cys Thr Ala Ser Asn Leu His Gly Leu Asp Arg
    1925                1930                1935

Met Val Val Leu Leu Ser Val Thr Val Gln Gln Pro Gln Ile Leu
    1940                1945                1950

Ala Ser His Tyr Gln Asp Val Thr Val Tyr Leu Gly Asp Thr Ile
    1955                1960                1965

Ala Met Glu Cys Leu Ala Lys Gly Thr Pro Ala Pro Gln Ile Ser
    1970                1975                1980

Trp Ile Phe Pro Asp Arg Arg Val Trp Gln Thr Val Ser Pro Val
    1985                1990                1995

Glu Ser Arg Ile Thr Leu His Glu Asn Arg Thr Leu Ser Ile Lys
    2000                2005                2010

Glu Ala Ser Phe Ser Asp Arg Gly Val Tyr Lys Cys Val Ala Ser
    2015                2020                2025

Asn Ala Ala Gly Ala Asp Ser Leu Ala Ile Arg Leu His Val Ala
    2030                2035                2040

Ala Leu Pro Pro Val Ile His Gln Glu Lys Leu Glu Asn Ile Ser
    2045                2050                2055

Leu Pro Pro Gly Leu Ser Ile His Ile His Cys Thr Ala Lys Ala
    2060                2065                2070

Ala Pro Leu Pro Ser Val Arg Trp Val Leu Gly Asp Gly Thr Gln
    2075                2080                2085
```

```
Ile Arg Pro Ser Gln Phe Leu His Gly Asn Leu Phe Val Phe Pro
2090                2095                2100

Asn Gly Thr Leu Tyr Ile Arg Asn Leu Ala Pro Lys Asp Ser Gly
2105                2110                2115

Arg Tyr Glu Cys Val Ala Ala Asn Leu Val Gly Ser Ala Arg Arg
2120                2125                2130

Thr Val Gln Leu Asn Val Gln Arg Ala Ala Ala Asn Ala Arg Ile
2135                2140                2145

Thr Gly Thr Ser Pro Arg Arg Thr Asp Val Arg Tyr Gly Gly Thr
2150                2155                2160

Leu Lys Leu Asp Cys Ser Ala Ser Gly Asp Pro Trp Pro Arg Ile
2165                2170                2175

Leu Trp Arg Leu Pro Ser Lys Arg Met Ile Asp Ala Leu Phe Ser
2180                2185                2190

Phe Asp Ser Arg Ile Lys Val Phe Ala Asn Gly Thr Leu Val Val
2195                2200                2205

Lys Ser Val Thr Asp Lys Asp Ala Gly Asp Tyr Leu Cys Val Ala
2210                2215                2220

Arg Asn Lys Val Gly Asp Asp Tyr Val Val Leu Lys Val Asp Val
2225                2230                2235

Val Met Lys Pro Ala Lys Ile Glu His Lys Glu Asn Asp His
2240                2245                2250

Lys Val Phe Tyr Gly Gly Asp Leu Lys Val Asp Cys Val Ala Thr
2255                2260                2265

Gly Leu Pro Asn Pro Glu Ile Ser Trp Ser Leu Pro Asp Gly Ser
2270                2275                2280

Leu Val Asn Ser Phe Met Gln Ser Asp Asp Ser Gly Gly Arg Thr
2285                2290                2295

Lys Arg Tyr Val Val Phe Asn Asn Gly Thr Leu Tyr Phe Asn Glu
2300                2305                2310

Val Gly Met Arg Glu Glu Gly Asp Tyr Thr Cys Phe Ala Glu Asn
2315                2320                2325

Gln Val Gly Lys Asp Glu Met Arg Val Arg Val Lys Val Val Thr
2330                2335                2340

Ala Pro Ala Thr Ile Arg Asn Lys Thr Tyr Leu Ala Val Gln Val
2345                2350                2355

Pro Tyr Gly Asp Val Val Thr Val Ala Cys Glu Ala Lys Gly Glu
2360                2365                2370

Pro Met Pro Lys Val Thr Trp Leu Ser Pro Thr Asn Lys Val Ile
2375                2380                2385

Pro Thr Ser Ser Glu Lys Tyr Gln Ile Tyr Gln Asp Gly Thr Leu
2390                2395                2400

Leu Ile Gln Lys Ala Gln Arg Ser Asp Ser Gly Asn Tyr Thr Cys
2405                2410                2415

Leu Val Arg Asn Ser Ala Gly Glu Asp Arg Lys Thr Val Trp Ile
2420                2425                2430

His Val Asn Val Gln Pro Pro Lys Ile Asn Gly Asn Pro Asn Pro
2435                2440                2445

Ile Thr Thr Val Arg Glu Ile Ala Ala Gly Gly Ser Arg Lys Leu
2450                2455                2460

Ile Asp Cys Lys Ala Glu Gly Ile Pro Thr Pro Arg Val Leu Trp
2465                2470                2475
```

| | | | | | | | | | |
|---|---|---|---|---|---|---|---|---|---|
| Ala | Phe | Pro | Glu | Gly | Val | Val | Leu | Pro | Ala | Pro | Tyr | Tyr | Gly | Asn |
| | 2480 | | | | 2485 | | | | 2490 | | | | | |

Ala Phe Pro Glu Gly Val Val Leu Pro Ala Pro Tyr Tyr Gly Asn
    2480                2485                2490

Arg Ile Thr Val His Gly Asn Gly Ser Leu Asp Ile Arg Ser Leu
    2495                2500                2505

Arg Lys Ser Asp Ser Val Gln Leu Val Cys Met Ala Arg Asn Glu
    2510                2515                2520

Gly Gly Glu Ala Arg Leu Ile Val Gln Leu Thr Val Leu Glu Pro
    2525                2530                2535

Met Glu Lys Pro Ile Phe His Asp Pro Ile Ser Glu Lys Ile Thr
    2540                2545                2550

Ala Met Ala Gly His Thr Ile Ser Leu Asn Cys Ser Ala Ala Gly
    2555                2560                2565

Thr Pro Thr Pro Ser Leu Val Trp Val Leu Pro Asn Gly Thr Asp
    2570                2575                2580

Leu Gln Ser Gly Gln Gln Leu Gln Arg Phe Tyr His Lys Ala Asp
    2585                2590                2595

Gly Met Leu His Ile Ser Gly Leu Ser Ser Val Asp Ala Gly Ala
    2600                2605                2610

Tyr Arg Cys Val Ala Arg Asn Ala Ala Gly His Thr Glu Arg Leu
    2615                2620                2625

Val Ser Leu Lys Val Gly Leu Lys Pro Glu Ala Asn Lys Gln Tyr
    2630                2635                2640

His Asn Leu Val Ser Ile Ile Asn Gly Glu Thr Leu Lys Leu Pro
    2645                2650                2655

Cys Thr Pro Pro Gly Ala Gly Gln Gly Arg Phe Ser Trp Thr Leu
    2660                2665                2670

Pro Asn Gly Met His Leu Glu Gly Pro Gln Thr Leu Gly Arg Val
    2675                2680                2685

Ser Leu Leu Asp Asn Gly Thr Leu Thr Val Arg Glu Ala Ser Val
    2690                2695                2700

Phe Asp Arg Gly Thr Tyr Val Cys Arg Met Glu Thr Glu Tyr Gly
    2705                2710                2715

Pro Ser Val Thr Ser Ile Pro Val Ile Val Ile Ala Tyr Pro Pro
    2720                2725                2730

Arg Ile Thr Ser Glu Pro Thr Pro Val Ile Tyr Thr Arg Pro Gly
    2735                2740                2745

Asn Thr Val Lys Leu Asn Cys Met Ala Met Gly Ile Pro Lys Ala
    2750                2755                2760

Asp Ile Thr Trp Glu Leu Pro Asp Lys Ser His Leu Lys Ala Gly
    2765                2770                2775

Val Gln Ala Arg Leu Tyr Gly Asn Arg Phe Leu His Pro Gln Gly
    2780                2785                2790

Ser Leu Thr Ile Gln His Ala Thr Gln Arg Asp Ala Gly Phe Tyr
    2795                2800                2805

Lys Cys Met Ala Lys Asn Ile Leu Gly Ser Asp Ser Lys Thr Thr
    2810                2815                2820

Tyr Ile His Val Phe
    2825

<210> SEQ ID NO 55
<211> LENGTH: 6763
<212> TYPE: DNA
<213> ORGANISM: Homo sapiens

<400> SEQUENCE: 55

```
atggtgctga cgccctctga agagcagtcg ggtccttggg aactgtgcca gcttctctgt    60
aagcggggca catgcacatc ttgccagggc gtcctggtgc tgcccaccac atccttcgcc   120
agtgtgattt gggaggcacc aagaggacct tccctggag aaggtgtgat gcttgtgcca   180
cacatggcta ctggtgacac caactctgca accaccatga gcttctcaac aagagctgct   240
acggagagag ctagggctac cgatccgaca gatgggtgc gaattctggc ttcggcttcc   300
tgctgtctgg ttttgagatg ttcccttagc ctttctgagc ctcacttctt tggtcagcag   360
atgggctgtg attgggtgcc ttcaaggatg gctgccaaat tggtgtccac agttataatg   420
gaggctggtc tggggatgg tggggcagct gcctggggta aggtcacggg atagagatc   480
aggaccatct ttgtgaagtt ggtggtcagc gcagtggggt gtcagatcgg tcagtgggac   540
aaaccagaca aattgcggct cttcaaggct gtagatggag tgaaacctca cattctgctg   600
ggaaaaaagg aagtgcccaa caagcccttg cgtgtgcgtg tccggtcctc agatgacagg   660
ctgtccgttg cgtggaaggc accacgcctg tctggagcca agagtccacg cagatcacgg   720
ggttttctcc tgggctacgg ggagagtggc cggaagatga attatgttcc actgacaaga   780
gatgaacgga cacacgaaat taaaaagcta gagcacttgc ttggacggaa gcccggcgag   840
cccacactcc taggcgctct gagagctcct aactctgagg aaggcacagc catgcatttc   900
ggagcctgga taagcagctc tgtgctcttc agtacctccg aggccagccc cctgggtcca   960
gttcttgggc tcgcccttca tagtcctcaa gaagtgggaa taccccaga aagaggaaac  1020
ggaaaaaggg gaaggggagg aggaatgcag aacccccgct ccagcccag gggatgtgtg  1080
ttcctgagaa atggaagtca gaatctcatc cctcactccc tggtccacag cctcggaatc  1140
cgtgtatgtg gtctccctgc agtccatgaa ctctcagggc cggagccaac cagtctacag  1200
ggctgcccta acaaagcgaa agatttcaga cagtacaccg tgcgctatcg agagaagggg  1260
gaattggcca ggtgggatta taagcagatc gctaacaggc gtgtgctgat tgagaacctg  1320
attccagaca ctgtgtatga atttgcagtc cgtatttcac agggtgaaag agatggcaaa  1380
tggagtacgt cagtcttcca aagaacacca gaatctgccc ctaccacagc tcctgaaaac  1440
ttgaacgtct ggccagtcaa tggcaaacct acagttgtcg ctgcatcttg ggatgcgcta  1500
ccagagactg aggggaaagt gaaagaatac attctttcat acgccccggc tctcaaacca  1560
tttgagcaa agtccctcac ctatcctgga gacactactt ctgccctggt ggatggtctg  1620
cagcctgggg aacgctatct tttcaaaatc cgggccacaa acaggagagg cctgggacct  1680
cactccaaag ccttcattgt cgctatgcca acaagcaatt ctttaaaatc tgttgcagcc  1740
agtaaggcgg atgttcagca gaacacggag gacaatggga aacccgaaaa acctgagcct  1800
tcctcacctt ctcccagagc tccagcttcc tcccaacacc cctctgtgcc tgcttctccc  1860
caagggagaa atgccaagga ccttcttctt gacttgaaga acaaaatatt ggctaatggt  1920
ggggcgcccc gaaaacccca gcttcgcgcc aagaaggcag aggagctgga tcttcagtcg  1980
acagaaatca ctggggagga ggagctgggt tcccgggagg actcgcccat gtcaccctca  2040
gacacccaag accagaaacg gaccctgagg ccgccaagta gacacggcca ctcggtggtt  2100
gctcccggca ggactgcagt gagggcccgg atgccagcgc tgccccgaag gaaggcgta  2160
gataagcctg gcttttccct ggccacgcag cccgcccag gggcgccccc ctcggcttcg  2220
gcctctcctg cccaccacgc gtccaccag ggcacctctc atcgtccttc cctgcctgcc  2280
agcttgaatg acaacgactt ggtggactca gacgaagatg agcgcgctgt gggctcccctc  2340
```

```
caccccaagg gcgccttcgc ccagccccgg ccagccctgt cccccagccg ccagtccccg    2400
tccagcgttc tccgcgacag aagctctgtg caccccggcg caaagccagc ctcgccggcg    2460
cggaggaccc cccattcagg ggccgcagag gaagattcca gtgcctcagc cccaccctca    2520
agactttctc cacccatgg gggatcatct cggctgctgc ccaccagcc acacctgagc       2580 tctccacttt ccaagggcgg gaaggatggt gaggacgccc cagccaccaa ctccaatgcg    2640 ccatcacgt ccaccatgtc ctcctccgtc tcttctcatc tctcgtccag gacgcaggtc      2700
tctgagggag cggaggcttc tgatggtgaa agccacggtg acggcgatag ggaagacggc    2760
ggaaggcagg cggaggccac ggcccagacg ctgcgggccc ggcctgcctc tggacacttc    2820
catttgctca gacacaaacc ctttgctgcc aacgggaggt ctccaagcag gttcagcatt    2880
gggcggggac ctcggctgca gccctccagc tccccacagt cgactgtgcc ctcccgagcc    2940
caccccaggg ttccctctca ctctgattcc caccctaagc ttagctcagg tatccatgga   3000
gacgaggagg atgagaagcc gcttcctgcc accgttgtca atgaccacgt gccttcctcc    3060
tccaggcagc ccatctcccg gggctgggag gacttaagga gaagcccgca gagagggcc    3120 agcctgcatc ggaaggaacc catcccagag aaccccaaat ccacaggggc agatacacat    3180
cctcagggca agtactcctc cctggcctcc aaggctcagg atgttcaaca gagcacagac    3240
gcggacacgg agggtcattc tcccaaagca cagccagggt ccacagaccg ccacgcgtcc    3300
cctgctcgtc ctcccgcagc acggtcacag cagcatccca gtgttcccag aaggatgaca    3360
cccggccggg ccccagaaca gcagccccct cctcccgtcg ccacgtccca gcaccaccccg   3420 ggaccccaga gcagagacgc gggtcggtca ccttcccagc ccaggctctc actgacccag    3480
gccgggcggc cccgcccac gtcgcagggc cgctcccact cctcctcgga cccttacacg      3540
gcgagctcca gagggatgct ccccacgccc ctccagaacc aggacgagga tgcccagggc    3600
agctacgacg acgacagcac agaagtcgag gcccaggatg tgcgggcccc cgcgcacgcc    3660
gcgcgcgcca aggaggcagc tgcgtcccctt cccaagcacc agcaggtgga gtctcccaca   3720
ggcgcagggg caggtggcga ccacaggtcc cagcgcggac atgcggcctc ccccgccagg    3780
cccagccgac ccggcggccc ccagtcccgc gcccgggtcc ccagcagggc agcgccgggg    3840
aagtcggagc ctccttccaa gcggcccctg tcctccaagt cccagcagtc ggtctcagcc    3900
gaggacgagg aggaggagga cgcggggttt tttaaaggcg ggaaagaaga ccttctgtct    3960
tcctctgtgc caaagtggcc ctcttcctcc actcccaggg gcggcaaaga cgccgatggg    4020
agcctcgcca aggaagagag ggagcctgcc atcgcgcttg cccctcgcgg agggagcctg    4080
gctcctgtga agcgacctct cccccacct ccaggcagct ccccagggc ctcccacgtc       4140 ccttcccgac cgccgcctcg cagcgctgcc accgtgagcc ccgtcgcggg cacccacccc    4200
tggccgcagt acaccacgcg cgcccacct ggcgacttct ccaccacccc gatgctgtcc      4260
ttgcgccaga ggatgatgca tgccagattc cgtaaccctc tctcccgaca gcctgccaga    4320
ccctcttaca gacaaggtta taatggcaga ccaaatgtag aagggaaagt ccttcctggt    4380
agtaatggaa aaccgaatgg acagagaatt atcaatggcc ctcaaggaac aaagtgggtt    4440
gtggaccttg atcgtgggtt agtattgaat gcagaaggaa ggtacctcca agattcacat    4500
ggaaatcctc ttcggattaa actaggagga gatggtcgaa ccattgtaga tctggaaggg    4560 accccgtgg tgagtcctga cggcctccca ctctttgggc aggggcgaca tggcacacct     4620
ctggccaatg cccaagataa gccaattttg agtcttggag gaaagccgct ggtgggcttg    4680
gaggtcatca aaaaaaccac ccatcccct accactacca tgcagcccac cactactacg     4740
```

-continued

```
acgcccctgc ctaccactac aaccccgagg cccaccactg ccaccacccg ccgcacgacc    4800
accaggcgtc caacaaccac agtccgaacc actacgcgga caaccaccac cacccccccc    4860
aaacccacca ctcccatccc cacctgtccc cctgggacct tggaacggca cgacgatgat    4920
ggcaacctga taatgagctc caatgggatc ccagagtgct acgctgaaga agatgagttc    4980
tcaggcttgg agactgacac tgcagtacct acggaagagg cctacgttat atatgatgaa    5040
gattatgaat ttgagacgtc aaggccacca accaccactg agccttcgac cactgctacc    5100
acaccgaggg tgatcccaga ggaaggcgcc atcagttcct ttcctgaaga agaatttgat    5160
ctggctggaa ggaaacgatt tgttgctcct tacgtgacgt acctaaataa agacccatca    5220
gccccgtgct ctctgactga tgcactggat cacttccaag tggacagcct ggatgaaatc    5280
atccccaatg acctgaagaa gagtgatctg cctccccagc atgctccccg caacatcacc    5340
gtggtggccg tggaaggttg ccactcattt gtcattgtgg actgggacaa agccacccca    5400
ggagatgtgg tcacaggtta cttggtttac agtgcatcct atgaagactt catcaggaac    5460
aagtggtcca ctcaagcttc atcagtaact cacttgccca ttgagaacct aaagcccaac    5520
acgaggtatt attttaaagt gcaagcacaa aatcctcatg gctacggacc tatcagccct    5580
tcggtctcat ttgtcaccga atcagataat cctctgcttg ttgtgaggcc cccaggcggt    5640
gagcctatct ggatcccatt cgctttcaaa catgatccca gctacacgga ctgccatgga    5700
cggcaatatg tgaagcgcac gtggtatcga aagttcgtgg gagttgttct ttgtaattca    5760
ctgaggtata aaatctacct cagtgacaac ctgaaagata cattctacag cattggagac    5820
agctggggaa gaggtgaaga ccattgccaa tttgtggatt cacaccttga tggaagaaca    5880
gggcctcagt cctatgtaga agccctccct actattcaag gctactatcg ccagtatcgt    5940
caggagcctg tcaggtttgg gaacatcggc ttcggaaccc cctactacta tgtgggctgg    6000
tacgagtgtg gggtctccat ccctggaaag tggtaatcac aggaccgtca tgctgcaagc    6060
ttgccctgcc cagccccacc aactaagtcg cactaggggc tgtgagcaaa gacagccagc    6120
atgctcagcc ccgctgccct aggtgccagg aaggtcacag atggacactg gccattctgg    6180
tcatctcagt ctggaactca gtcccacttc ttggcctgga caatgaacag gattcagttt    6240
tgctgttaac tttgcttctc tactttttt tgtttgtttg taatagcaca tcccagagac    6300
atcagaaacc agcaactgat tcagtgtgat tccagactt tttaggcatg aaattcggac    6360
acttcagtat ttccaggaat agcatatgca cgctgttctt gcttcatgga atgctacatg    6420
ctttctgttt ttctcatttt ggattctcc aaaactaact gaatttaagc ttcaggtccc    6480
tttgtatgca gtagaaagga attattaaaa acaccaccaa agaaaataaa tatatcctac    6540
ttgaaattta ctctatggac ttaccccactg ctagaataaa tgtatcaaat cttatttgta    6600
aattctcaat tttgatatat atatgtatat atgcatatac atatccacac ttgtctgcaa    6660
gaatattgat taaaattgct aaatttgtac ttgttcacca ggaaaaaaaa aaaaaaaaaa    6720
aaaaggggc ggccrttccc tttaggaggg ttaattttag cgg                       6763
```

<210> SEQ ID NO 56
<211> LENGTH: 2011
<212> TYPE: PRT
<213> ORGANISM: Homo sapiens

<400> SEQUENCE: 56

```
Met Val Leu Thr Pro Ser Glu Glu Gln Ser Gly Pro Trp Glu Leu Cys
1               5                   10                  15
```

Gln Leu Leu Cys Lys Arg Gly Thr Cys Thr Ser Cys Gln Gly Val Leu
             20                  25                  30

Val Leu Pro Thr Thr Ser Phe Ala Ser Val Ile Trp Glu Ala Pro Arg
         35                  40                  45

Gly Pro Ser Pro Gly Glu Gly Val Met Leu Val Pro His Met Ala Thr
     50                  55                  60

Gly Asp Thr Asn Ser Ala Thr Thr Met Ser Phe Ser Thr Arg Ala Ala
 65                  70                  75                  80

Thr Glu Arg Ala Arg Ala Thr Asp Pro Thr Asp Gly Val Arg Ile Leu
                 85                  90                  95

Ala Ser Ala Ser Cys Cys Leu Val Leu Arg Cys Ser Leu Ser Leu Ser
             100                 105                 110

Glu Pro His Phe Phe Gly Gln Gln Met Gly Cys Asp Trp Val Pro Ser
         115                 120                 125

Arg Met Ala Ala Lys Leu Val Ser Thr Val Ile Met Glu Ala Gly Ala
     130                 135                 140

Gly Asp Gly Gly Ala Ala Ala Trp Gly Lys Val Thr Gly Ile Glu Ile
145                 150                 155                 160

Arg Thr Ile Phe Val Lys Leu Val Ser Ala Val Gly Cys Gln Ile
                 165                 170                 175

Gly Gln Trp Asp Lys Pro Asp Lys Leu Arg Leu Phe Lys Ala Val Asp
             180                 185                 190

Gly Val Lys Pro His Ile Leu Leu Gly Lys Lys Glu Val Pro Asn Lys
         195                 200                 205

Pro Leu Arg Val Arg Val Arg Ser Ser Asp Asp Arg Leu Ser Val Ala
     210                 215                 220

Trp Lys Ala Pro Arg Leu Ser Gly Ala Lys Ser Pro Arg Arg Ser Arg
225                 230                 235                 240

Gly Phe Leu Leu Gly Tyr Gly Glu Ser Gly Arg Lys Met Asn Tyr Val
                 245                 250                 255

Pro Leu Thr Arg Asp Glu Arg Thr His Glu Ile Lys Lys Leu Glu His
             260                 265                 270

Leu Leu Gly Arg Lys Pro Gly Pro Thr Leu Leu Gly Ala Leu Arg
         275                 280                 285

Ala Pro Asn Ser Glu Glu Gly Thr Ala Met His Phe Gly Ala Trp Ile
     290                 295                 300

Ser Ser Ser Val Leu Phe Ser Thr Ser Glu Ala Ser Pro Leu Gly Pro
305                 310                 315                 320

Val Leu Gly Leu Ala Leu His Ser Pro Gln Glu Val Gly Ile Pro Pro
                 325                 330                 335

Glu Arg Gly Asn Gly Lys Arg Gly Arg Gly Gly Met Gln Asn Pro
             340                 345                 350

Arg Ser Ser Pro Arg Gly Cys Val Phe Leu Arg Asn Gly Ser Gln Asn
     355                 360                 365

Leu Ile Pro His Ser Leu Val His Ser Leu Gly Ile Arg Val Cys Gly
370                 375                 380

Leu Pro Ala Val His Glu Leu Ser Gly Pro Glu Pro Thr Ser Leu Gln
385                 390                 395                 400

Gly Cys Pro Asn Lys Ala Lys Asp Phe Arg Gln Tyr Thr Val Arg Tyr
                 405                 410                 415

Arg Glu Lys Gly Glu Leu Ala Arg Trp Asp Tyr Lys Gln Ile Ala Asn
             420                 425                 430

-continued

Arg Arg Val Leu Ile Glu Asn Leu Ile Pro Asp Thr Val Tyr Glu Phe
        435                 440                 445

Ala Val Arg Ile Ser Gln Gly Glu Arg Asp Gly Lys Trp Ser Thr Ser
450                 455                 460

Val Phe Gln Arg Thr Pro Glu Ser Ala Pro Thr Thr Ala Pro Glu Asn
465             470                 475                 480

Leu Asn Val Trp Pro Val Asn Gly Lys Pro Thr Val Val Ala Ala Ser
            485                 490                 495

Trp Asp Ala Leu Pro Glu Thr Glu Gly Lys Val Lys Glu Tyr Ile Leu
        500                 505                 510

Ser Tyr Ala Pro Ala Leu Lys Pro Phe Gly Ala Lys Ser Leu Thr Tyr
        515                 520                 525

Pro Gly Asp Thr Thr Ser Ala Leu Val Asp Gly Leu Gln Pro Gly Glu
        530                 535                 540

Arg Tyr Leu Phe Lys Ile Arg Ala Thr Asn Arg Arg Gly Leu Gly Pro
545                 550                 555                 560

His Ser Lys Ala Phe Ile Val Ala Met Pro Thr Ser Asn Ser Leu Lys
                565                 570                 575

Ser Val Ala Ala Ser Lys Ala Asp Val Gln Gln Asn Thr Glu Asp Asn
            580                 585                 590

Gly Lys Pro Glu Lys Pro Glu Pro Ser Ser Pro Ser Pro Arg Ala Pro
            595                 600                 605

Ala Ser Ser Gln His Pro Ser Val Pro Ala Ser Pro Gln Gly Arg Asn
            610                 615                 620

Ala Lys Asp Leu Leu Leu Asp Leu Lys Asn Lys Ile Leu Ala Asn Gly
625                 630                 635                 640

Gly Ala Pro Arg Lys Pro Gln Leu Arg Ala Lys Lys Ala Glu Glu Leu
                645                 650                 655

Asp Leu Gln Ser Thr Glu Ile Thr Gly Glu Glu Leu Gly Ser Arg
        660                 665                 670

Glu Asp Ser Pro Met Ser Pro Ser Asp Thr Gln Asp Gln Lys Arg Thr
        675                 680                 685

Leu Arg Pro Pro Ser Arg His Gly His Ser Val Ala Pro Gly Arg
        690                 695                 700

Thr Ala Val Arg Ala Arg Met Pro Ala Leu Pro Arg Arg Glu Gly Val
705                 710                 715                 720

Asp Lys Pro Gly Phe Ser Leu Ala Thr Gln Pro Arg Pro Gly Ala Pro
                725                 730                 735

Pro Ser Ala Ser Ala Ser Pro Ala His His Ala Ser Thr Gln Gly Thr
            740                 745                 750

Ser His Arg Pro Ser Leu Pro Ala Ser Leu Asn Asp Asn Asp Leu Val
        755                 760                 765

Asp Ser Asp Glu Asp Glu Arg Ala Val Gly Ser Leu His Pro Lys Gly
        770                 775                 780

Ala Phe Ala Gln Pro Arg Pro Ala Leu Ser Pro Ser Arg Gln Ser Pro
785                 790                 795                 800

Ser Ser Val Leu Arg Asp Arg Ser Ser Val His Pro Gly Ala Lys Pro
            805                 810                 815

Ala Ser Pro Ala Arg Arg Thr Pro His Ser Gly Ala Ala Glu Glu Asp
            820                 825                 830

Ser Ser Ala Ser Ala Pro Pro Ser Arg Leu Ser Pro His Gly Gly
            835                 840                 845

Ser Ser Arg Leu Leu Pro Thr Gln Pro His Leu Ser Ser Pro Leu Ser

```
                850                 855                 860
Lys Gly Gly Lys Asp Gly Glu Asp Ala Pro Ala Thr Asn Ser Asn Ala
865                 870                 875                 880

Pro Ser Arg Ser Thr Met Ser Ser Val Ser Ser His Leu Ser Ser
                885                 890                 895

Arg Thr Gln Val Ser Glu Gly Ala Glu Ala Ser Asp Gly Glu Ser His
                    900                 905                 910

Gly Asp Gly Asp Arg Glu Asp Gly Gly Arg Gln Ala Glu Ala Thr Ala
                915                 920                 925

Gln Thr Leu Arg Ala Arg Pro Ala Ser Gly His Phe His Leu Leu Arg
                930                 935                 940

His Lys Pro Phe Ala Ala Asn Gly Arg Ser Pro Ser Arg Phe Ser Ile
945                 950                 955                 960

Gly Arg Gly Pro Arg Leu Gln Pro Ser Ser Pro Gln Ser Thr Val
                    965                 970                 975

Pro Ser Arg Ala His Pro Arg Val Pro Ser His Ser Asp Ser His Pro
                980                 985                 990

Lys Leu Ser Ser Gly Ile His Gly Asp Glu Glu Asp Glu Lys Pro Leu
            995                 1000                1005

Pro Ala Thr Val Val Asn Asp His Val Pro Ser Ser Ser Arg Gln
            1010                1015                1020

Pro Ile Ser Arg Gly Trp Glu Asp Leu Arg Arg Ser Pro Gln Arg
            1025                1030                1035

Gly Ala Ser Leu His Arg Lys Glu Pro Ile Pro Glu Asn Pro Lys
            1040                1045                1050

Ser Thr Gly Ala Asp Thr His Pro Gln Gly Lys Tyr Ser Ser Leu
            1055                1060                1065

Ala Ser Lys Ala Gln Asp Val Gln Gln Ser Thr Asp Ala Asp Thr
            1070                1075                1080

Glu Gly His Ser Pro Lys Ala Gln Pro Gly Ser Thr Asp Arg His
            1085                1090                1095

Ala Ser Pro Ala Arg Pro Ala Ala Arg Ser Gln Gln His Pro
            1100                1105                1110

Ser Val Pro Arg Arg Met Thr Pro Gly Arg Ala Pro Glu Gln Gln
            1115                1120                1125

Pro Pro Pro Val Ala Thr Ser Gln His His Pro Gly Pro Gln
            1130                1135                1140

Ser Arg Asp Ala Gly Arg Ser Pro Ser Gln Pro Arg Leu Ser Leu
            1145                1150                1155

Thr Gln Ala Gly Arg Pro Arg Pro Thr Ser Gln Gly Arg Ser His
            1160                1165                1170

Ser Ser Ser Asp Pro Tyr Thr Ala Ser Ser Arg Gly Met Leu Pro
            1175                1180                1185

Thr Ala Leu Gln Asn Gln Asp Glu Asp Ala Gln Gly Ser Tyr Asp
            1190                1195                1200

Asp Asp Ser Thr Glu Val Glu Ala Gln Asp Val Arg Ala Pro Ala
            1205                1210                1215

His Ala Ala Arg Ala Lys Glu Ala Ala Ala Ser Leu Pro Lys His
            1220                1225                1230

Gln Gln Val Glu Ser Pro Thr Gly Ala Gly Ala Gly Gly Asp His
            1235                1240                1245

Arg Ser Gln Arg Gly His Ala Ala Ser Pro Ala Arg Pro Ser Arg
            1250                1255                1260
```

```
Pro Gly Gly Pro Gln Ser Arg Ala Arg Val Pro Ser Arg Ala Ala
1265                 1270                1275

Pro Gly Lys Ser Glu Pro Pro Ser Lys Arg Pro Leu Ser Ser Lys
1280                 1285                1290

Ser Gln Gln Ser Val Ser Ala Glu Asp Glu Glu Glu Glu Asp Ala
1295                 1300                1305

Gly Phe Phe Lys Gly Gly Lys Glu Asp Leu Leu Ser Ser Ser Val
1310                 1315                1320

Pro Lys Trp Pro Ser Ser Ser Thr Pro Arg Gly Gly Lys Asp Ala
1325                 1330                1335

Asp Gly Ser Leu Ala Lys Glu Arg Glu Pro Ala Ile Ala Leu
1340                 1345                1350

Ala Pro Arg Gly Gly Ser Leu Ala Pro Val Lys Arg Pro Leu Pro
1355                 1360                1365

Pro Pro Pro Gly Ser Ser Pro Arg Ala Ser His Val Pro Ser Arg
1370                 1375                1380

Pro Pro Pro Arg Ser Ala Ala Thr Val Ser Pro Val Ala Gly Thr
1385                 1390                1395

His Pro Trp Pro Gln Tyr Thr Thr Arg Ala Pro Pro Gly Asp Phe
1400                 1405                1410

Ser Thr Thr Pro Met Leu Ser Leu Arg Gln Arg Met Met His Ala
1415                 1420                1425

Arg Phe Arg Asn Pro Leu Ser Arg Gln Pro Ala Arg Pro Ser Tyr
1430                 1435                1440

Arg Gln Gly Tyr Asn Gly Arg Pro Asn Val Glu Gly Lys Val Leu
1445                 1450                1455

Pro Gly Ser Asn Gly Lys Pro Asn Gly Gln Arg Ile Ile Asn Gly
1460                 1465                1470

Pro Gln Gly Thr Lys Trp Val Val Asp Leu Asp Arg Gly Leu Val
1475                 1480                1485

Leu Asn Ala Glu Gly Arg Tyr Leu Gln Asp Ser His Gly Asn Pro
1490                 1495                1500

Leu Arg Ile Lys Leu Gly Gly Asp Gly Arg Thr Ile Val Asp Leu
1505                 1510                1515

Glu Gly Thr Pro Val Val Ser Pro Asp Gly Leu Pro Leu Phe Gly
1520                 1525                1530

Gln Gly Arg His Gly Thr Pro Leu Ala Asn Ala Gln Asp Lys Pro
1535                 1540                1545

Ile Leu Ser Leu Gly Gly Lys Pro Leu Val Gly Leu Glu Val Ile
1550                 1555                1560

Lys Lys Thr Thr His Pro Pro Thr Thr Thr Met Gln Pro Thr Thr
1565                 1570                1575

Thr Thr Thr Pro Leu Pro Thr Thr Thr Thr Pro Arg Pro Thr Thr
1580                 1585                1590

Ala Thr Thr Arg Arg Thr Thr Thr Arg Arg Pro Thr Thr Thr Val
1595                 1600                1605

Arg Thr Thr Thr Arg Thr Thr Thr Thr Thr Pro Lys Pro Thr
1610                 1615                1620

Thr Pro Ile Pro Thr Cys Pro Pro Gly Thr Leu Glu Arg His Asp
1625                 1630                1635

Asp Asp Gly Asn Leu Ile Met Ser Ser Asn Gly Ile Pro Glu Cys
1640                 1645                1650
```

Tyr Ala Glu Glu Asp Glu Phe Ser Gly Leu Glu Thr Asp Thr Ala
    1655            1660                1665

Val Pro Thr Glu Glu Ala Tyr Val Ile Tyr Asp Glu Asp Tyr Glu
    1670            1675                1680

Phe Glu Thr Ser Arg Pro Pro Thr Thr Thr Glu Pro Ser Thr Thr
    1685            1690                1695

Ala Thr Thr Pro Arg Val Ile Pro Glu Glu Gly Ala Ile Ser Ser
    1700            1705                1710

Phe Pro Glu Glu Glu Phe Asp Leu Ala Gly Arg Lys Arg Phe Val
    1715            1720                1725

Ala Pro Tyr Val Thr Tyr Leu Asn Lys Asp Pro Ser Ala Pro Cys
    1730            1735                1740

Ser Leu Thr Asp Ala Leu Asp His Phe Gln Val Asp Ser Leu Asp
    1745            1750                1755

Glu Ile Ile Pro Asn Asp Leu Lys Lys Ser Asp Leu Pro Pro Gln
    1760            1765                1770

His Ala Pro Arg Asn Ile Thr Val Val Ala Val Glu Gly Cys His
    1775            1780                1785

Ser Phe Val Ile Val Asp Trp Asp Lys Ala Thr Pro Gly Asp Val
    1790            1795                1800

Val Thr Gly Tyr Leu Val Tyr Ser Ala Ser Tyr Glu Asp Phe Ile
    1805            1810                1815

Arg Asn Lys Trp Ser Thr Gln Ala Ser Ser Val Thr His Leu Pro
    1820            1825                1830

Ile Glu Asn Leu Lys Pro Asn Thr Arg Tyr Tyr Phe Lys Val Gln
    1835            1840                1845

Ala Gln Asn Pro His Gly Tyr Gly Pro Ile Ser Pro Ser Val Ser
    1850            1855                1860

Phe Val Thr Glu Ser Asp Asn Pro Leu Leu Val Val Arg Pro Pro
    1865            1870                1875

Gly Gly Glu Pro Ile Trp Ile Pro Phe Ala Phe Lys His Asp Pro
    1880            1885                1890

Ser Tyr Thr Asp Cys His Gly Arg Gln Tyr Val Lys Arg Thr Trp
    1895            1900                1905

Tyr Arg Lys Phe Val Gly Val Val Leu Cys Asn Ser Leu Arg Tyr
    1910            1915                1920

Lys Ile Tyr Leu Ser Asp Asn Leu Lys Asp Thr Phe Tyr Ser Ile
    1925            1930                1935

Gly Asp Ser Trp Gly Arg Gly Glu Asp His Cys Gln Phe Val Asp
    1940            1945                1950

Ser His Leu Asp Gly Arg Thr Gly Pro Gln Ser Tyr Val Glu Ala
    1955            1960                1965

Leu Pro Thr Ile Gln Gly Tyr Tyr Arg Gln Tyr Arg Gln Glu Pro
    1970            1975                1980

Val Arg Phe Gly Asn Ile Gly Phe Gly Thr Pro Tyr Tyr Tyr Val
    1985            1990                1995

Gly Trp Tyr Glu Cys Gly Val Ser Ile Pro Gly Lys Trp
    2000            2005                2010

<210> SEQ ID NO 57
<211> LENGTH: 1441
<212> TYPE: DNA
<213> ORGANISM: Homo sapiens

<400> SEQUENCE: 57

```
gtcgacccac gcgtccgccc ttacatcctc ctaggacccg gtcggtagtc gtcgccccag    60
cccgccgggg gcgcagcgcc cgagccgcgg ccctcgagac gggaccgaga gcatcatggg   120
cagcactgtc ccgcgctccg cctccgtgct gcttctgctg ctgctcctgc gcgggccga    180
gcagccctgc ggggccgagc tcaccttcga gctgccggac aacgccaagc agtgcttcca   240
cgaggaggtg gagcagggcg tgaagttctc cctggattac caggtcatca ctggaggcca   300
ctacgatgtt gactgctatg taggaccc ccaggggaac accatctaca gagaaacgaa    360
gaagcagtac gacagcttca cgtaccgggc tgaagtcaag ggcgtttatc agttttgctt   420
cagtaatgag ttttccacct tctctcacaa gaccgtctac tttgactttc aagtgggcga   480
tgagcctccc attctcccag acatggggaa cagggtcaca gctctcaccc agatggagtc   540
cgcctgcgtg accatccatg aggctctgaa aacggtgatt gactcccaga cgcattaccg   600
gctgcgggag gcccaggacc gggcccgagc ggaagacctt aatagccgag tctcttactg   660
gtctgttggc gagacgattg ccctgttcgt ggtcagcttc agtcaggtgc tactgttgaa   720
aagcttcttc acagaaaaac gacccatcag cagggcagtc cactcctagc cccggcatcc   780
tgctctaggg cccctcatgc cccaggctgg agcagctctc ctaggtcaca gcctgctggg   840
ctgggtcgcg tagcccaggg tggaggcaga acgatgctgc tgtggtagcc ctttgccttt   900
catgcccatg cttgattctt gcacctcagc agctgaaggt ctcagagacc agtaatcaga   960
aggcatccga ctgcattaag tgtgcagcgc tgaaaagaca tttacaacta ggccagggat  1020
tagccactgt gggagggtgg acaggcaatg gttcagtggc ctggctgttg gcaggaactc  1080
caagtgccca ggcctcttgg gcagcttagg gccctgcctc tgtttcatga tgcatgggtc  1140
atttgtcttg ggtgtcctat cccatatgga gaagaaaggg gctctaagtt ctggctcttc  1200
tttctttggg gttctctgta cctgaggaaa ccaggccctg ggtgactttg cagatctgct  1260
caccctcggt gagcaacagt gtcagccatg caagcaggac agaatggtga ctgggtgccc  1320
ttggtgagct gtgtatttcc tagaagtaga aaactgtggg aaactgtggc taataaaaac  1380
taagtgtgag cgtcaaaaaa aaaaaaaaaa aaaaaaaaaa aaaaaaaaaa agggcggccg  1440
c                                                                 1441
```

<210> SEQ ID NO 58
<211> LENGTH: 217
<212> TYPE: PRT
<213> ORGANISM: Homo sapiens

<400> SEQUENCE: 58

```
Met Gly Ser Thr Val Pro Arg Ser Ala Ser Val Leu Leu Leu Leu Leu
1               5                   10                  15

Leu Leu Arg Arg Ala Glu Gln Pro Cys Gly Ala Glu Leu Thr Phe Glu
            20                  25                  30

Leu Pro Asp Asn Ala Lys Gln Cys Phe His Glu Glu Val Glu Gln Gly
        35                  40                  45

Val Lys Phe Ser Leu Asp Tyr Gln Val Ile Thr Gly Gly His Tyr Asp
    50                  55                  60

Val Asp Cys Tyr Val Glu Asp Pro Gln Gly Asn Thr Ile Tyr Arg Glu
65                  70                  75                  80

Thr Lys Lys Gln Tyr Asp Ser Phe Thr Tyr Arg Ala Glu Val Lys Gly
                85                  90                  95

Val Tyr Gln Phe Cys Phe Ser Asn Glu Phe Ser Thr Phe Ser His Lys
            100                 105                 110
```

```
           Thr Val Tyr Phe Asp Phe Gln Val Gly Asp Glu Pro Pro Ile Leu Pro
               115                 120                 125

Asp Met Gly Asn Arg Val Thr Ala Leu Thr Gln Met Glu Ser Ala Cys
           130                 135                 140

Val Thr Ile His Glu Ala Leu Lys Thr Val Ile Asp Ser Gln Thr His
           145                 150                 155                 160

Tyr Arg Leu Arg Glu Ala Gln Asp Arg Ala Arg Ala Glu Asp Leu Asn
                           165                 170                 175

Ser Arg Val Ser Tyr Trp Ser Val Gly Glu Thr Ile Ala Leu Phe Val
                       180                 185                 190

Val Ser Phe Ser Gln Val Leu Leu Leu Lys Ser Phe Phe Thr Glu Lys
                   195                 200                 205

Arg Pro Ile Ser Arg Ala Val His Ser
               210                 215

<210> SEQ ID NO 59
<211> LENGTH: 2316
<212> TYPE: DNA
<213> ORGANISM: Homo sapiens

<400> SEQUENCE: 59
ccacgcgtcc ggtctccccc agcactgagg agctcgcctg ctgccctctt gcgcgcggga      60
agcagcacca agttcacggc caacgccttg cactagggt ccagaatggc tacaacagtc     120
cctgatggtt gccgcaatgg cctgaaatcc aagtactaca actttgtga taaggctgaa     180 gcttggggca tcgtcctaga aacggtggcc acagccgggg ttgtgacctc ggtggccttc     240
atgctcactc tcccgatcct cgtctgcaag gtgcaggact ccaacaggcg aaaaatgctg     300
cctactcagt ttctcttcct cctgggtgtg ttgggcatct ttggcctcac cttcgccttc     360
atcatcggac tggacgggag cacagggccc acacgcttct tcctctttgg gatcctcttt     420
tccatctgct tctcctgcct gctggctcat gctgtcagtc tgaccaagct cgtccggggg     480
aggaagcccc tttccctgtt ggtgattctg ggtctggccg tgggcttcag cctagtccag     540
gatgttatcg ctattgaata tattgtcctg accatgaata ggaccaacgt caatgtcttt     600
tctgagcttt ccgctcctcg tcgcaatgaa gactttgtcc tcctgctcac ctacgtcctc     660
ttcttgatgg cgctgacctt cctcatgtcc tccttcacct tctgtggttc cttcacgggc     720
tggaagagac atggggccca catctaccct cacgatgctcc tctccattgc catctgggtg     780
gcctggatca ccctgctcat gcttcctgac tttgaccgca ggtgggatga caccatcctc     840
agctccgcct ggctgccaa tggctgggtg ttcctgttgg cttatgttag tcccgagttt     900
tggctgctca caaagcaacg aaaccccatg gattatcctg ttgaggatgc tttctgtaaa     960
cctcaactcg tgaagaagag ctatggtgtg gagaacagag cctactctca agaggaaatc    1020
actcaaggtt ttgaagagac aggggacacg ctctatgccc cctattccac acattttcag    1080
ctgcagaacc agcctcccca aaaggaattc tccatcccac gggcccacgc ttggccgagc    1140
ccttacaaag actatgaagt aaagaaagag ggcagctaac tctgtcctga gagtgggac    1200 aaatgcagcc gggcggcaga tctagcggga gctcaaaggg atgtgggcga atctgagtc    1260 ttctgagaaa actgtacaag acactacggg aacagtttgc ctccctccca gcctcaacca    1320
caattcttcc atgctggggc tgatgtgggc tagtaagact ccagttctta gaggcgctgt    1380
agtatttttt ttttttgtc tcatcctttg gatacttctt ttaagtggga gtctcaggca    1440
actcaagttt agacccttac tcttttttgtt tgttttttga aacaggatct tgctctgtca    1500
```

-continued

```
cccaggcttg agtgcagtgg tgcgatcaca gcccagtgca gcctcgacca cctgtgctca    1560
agcaatcctc ccatctccat ctcccaaagt gctgggatga caggcgtgag ccacagctcc    1620
cagcctaggc ccttaatctt gctgttattt tccatggact aaaggtctgg tcatctgagc    1680
tcacgctggc tcacacagct ctaggggcct gctcctctaa ctcacagtgg gttttgtgag    1740
gctctgtggc cagagcaga cctgcatatc tgagcaaaaa tagcaaaagc ctctctcagc     1800
ccactggcct gaatctacac tggaagccaa cttgctggca ccccgctcc ccaacccttc     1860 ttgcctgggt aggagaggct aaagatcacc ctaaatttac tcatctctct agtgctgcct    1920
cacattgggc tcagcagct ccccagcacc aattcacagg tcacccctct cttcttgcac     1980
tgtccccaaa cttgctgtca attccgagat ctaatctccc cctacgctct gccaggaatt    2040
ctttcagacc tcactagcac aagcccggtt gctccttgtc aggagaattt gtagatcatt    2100
ctcacttcaa attcctgggg ctgatacttc tctcatcttg caccccaacc tctgtaaata    2160
gatttaccgc atttacggct gcattctgta agtgggcatg gtctcctaat ggaggagtgt    2220
tcattgtata ataagttatt cacctgagta tgcaataaag atgtggtggc cactctttca    2280
tggtggtggc agcaaaaaaa aaaaaaaaaa aaaaaa                              2316
```

<210> SEQ ID NO 60
<211> LENGTH: 357
<212> TYPE: PRT
<213> ORGANISM: Homo sapiens

<400> SEQUENCE: 60

```
Met Ala Thr Thr Val Pro Asp Gly Cys Arg Asn Gly Leu Lys Ser Lys
1               5                   10                  15

Tyr Tyr Arg Leu Cys Asp Lys Ala Glu Ala Trp Gly Ile Val Leu Glu
            20                  25                  30

Thr Val Ala Thr Ala Gly Val Val Thr Ser Val Ala Phe Met Leu Thr
        35                  40                  45

Leu Pro Ile Leu Val Cys Lys Val Gln Asp Ser Asn Arg Arg Lys Met
    50                  55                  60

Leu Pro Thr Gln Phe Leu Phe Leu Gly Val Leu Gly Ile Phe Gly
65                  70                  75                  80

Leu Thr Phe Ala Phe Ile Ile Gly Leu Asp Gly Ser Thr Gly Pro Thr
                85                  90                  95

Arg Phe Phe Leu Phe Gly Ile Leu Phe Ser Ile Cys Phe Ser Cys Leu
            100                 105                 110

Leu Ala His Ala Val Ser Leu Thr Lys Leu Val Arg Gly Arg Lys Pro
        115                 120                 125

Leu Ser Leu Leu Val Ile Leu Gly Leu Ala Val Gly Phe Ser Leu Val
    130                 135                 140

Gln Asp Val Ile Ala Ile Glu Tyr Ile Val Leu Thr Met Asn Arg Thr
145                 150                 155                 160

Asn Val Asn Val Phe Ser Glu Leu Ser Ala Pro Arg Arg Asn Glu Asp
                165                 170                 175

Phe Val Leu Leu Leu Thr Tyr Val Leu Phe Leu Met Ala Leu Thr Phe
            180                 185                 190

Leu Met Ser Ser Phe Thr Phe Cys Gly Ser Phe Thr Gly Trp Lys Arg
        195                 200                 205

His Gly Ala His Ile Tyr Leu Thr Met Leu Leu Ser Ile Ala Ile Trp
    210                 215                 220
```

Val Ala Trp Ile Thr Leu Leu Met Leu Pro Asp Phe Asp Arg Arg Trp
225                 230                 235                 240

Asp Asp Thr Ile Leu Ser Ser Ala Leu Ala Ala Asn Gly Trp Val Phe
            245                 250                 255

Leu Leu Ala Tyr Val Ser Pro Glu Phe Trp Leu Leu Thr Lys Gln Arg
            260                 265                 270

Asn Pro Met Asp Tyr Pro Val Glu Asp Ala Phe Cys Lys Pro Gln Leu
            275                 280                 285

Val Lys Lys Ser Tyr Gly Val Glu Asn Arg Ala Tyr Ser Gln Glu Glu
290                 295                 300

Ile Thr Gln Gly Phe Glu Glu Thr Gly Asp Thr Leu Tyr Ala Pro Tyr
305                 310                 315                 320

Ser Thr His Phe Gln Leu Gln Asn Gln Pro Pro Gln Lys Glu Phe Ser
            325                 330                 335

Ile Pro Arg Ala His Ala Trp Pro Ser Pro Tyr Lys Asp Tyr Glu Val
            340                 345                 350

Lys Lys Glu Gly Ser
            355

<210> SEQ ID NO 61
<211> LENGTH: 4651
<212> TYPE: DNA
<213> ORGANISM: Homo sapiens
<220> FEATURE:
<221> NAME/KEY: modified_base
<222> LOCATION: (2270)..(2270)
<223> OTHER INFORMATION: a, c, t or g
<220> FEATURE:
<221> NAME/KEY: modified_base
<222> LOCATION: (3639)..(3639)
<223> OTHER INFORMATION: a, c, t or g
<220> FEATURE:
<221> NAME/KEY: modified_base
<222> LOCATION: (3724)..(3724)
<223> OTHER INFORMATION: a, c, t or g
<220> FEATURE:
<221> NAME/KEY: modified_base
<222> LOCATION: (4265)..(4265)
<223> OTHER INFORMATION: a, c, t or g
<220> FEATURE:
<221> NAME/KEY: modified_base
<222> LOCATION: (4638)..(4638)
<223> OTHER INFORMATION: a, c, t or g
<220> FEATURE:
<221> NAME/KEY: modified_base
<222> LOCATION: (4644)..(4645)
<223> OTHER INFORMATION: a, c, t or g
<220> FEATURE:
<221> NAME/KEY: modified_base
<222> LOCATION: (4647)..(4647)
<223> OTHER INFORMATION: a, c, t or g
<220> FEATURE:
<221> NAME/KEY: modified_base
<222> LOCATION: (4649)..(4651)
<223> OTHER INFORMATION: a, c, t or g

<400> SEQUENCE: 61 tttttagtt   ttacctagtt   ttatttgtct   atttgagtat   tgtccttgaa   tttaaaattt      60
ttttcagccc  caactgatac   acacacatat   acatacataa   cacatgtgtg   tgtgtgtagc     120
ttacagagtg  tttataggaa   actgattttg   tatactttgg   ctactttgtt   gtaagttcta    180
gttttttttc  ttttattatt   aaactagtgc   acgacatcaa   tgctatatga   ttggtgtttc    240
gttgacctag  aaataatgca   tgccatcttc   ttttcacagc   tgtgtgccaa   ccacgatgca    300
aacatggtga  atgtatcggg   ccaaacaagt   gcaagtgtca   tcctggttat   gctggaaaaa    360

| | | |
|---|---|---|
| ccttctaact cgtgtgaaga cgagcacatc ccagctcctc ttgaccaagg cagtgaacag | 420 |
| cctctttttcc aaccccctgga tcaccaagcc acaagtttgc cttcaaggga tctaaatgag | 480 |
| tgtggcctga agccccggcc ctgtaagcac aggtgcatga acacttacgg cagctacaag | 540 |
| tgctactgtc tcaacggata tatgctcatg ccggatggtt cctgctcaag tgccctgacc | 600 |
| tgctccatgg caaactgtca gtatggctgt gatgttgtta aaggacaaat acggtgccag | 660 |
| tgcccatccc ctggcctgca cctggctcct gatggggagga cctgtgtaga tgttgatgaa | 720 |
| tgtgctacag gaagagcctc ctgccctaga tttaggcaat gtgtcaacac ttttgggagc | 780 |
| tacatctgca agtgtcataa aggcttcgat ctcatgcata ttggaggcaa atatcaatgt | 840 |
| catgacatag acgaatgctc acttggtcag tatcagtgca gcagctttgc tcgatgttat | 900 |
| aacgtacgtg ggtcctacaa gtgcaaatgt aaagaaggat accagggtga tggactgact | 960 |
| tgtgtgtata tcccaaaagt tatgattgaa ccttcaggtc caattcatgt accaaaggga | 1020 |
| aatggtacca ttttaaaggg tgacacagga ataataatt ggattcctga tgttggaagt | 1080 |
| acttggtggc ctccgaagac accatatatt cctcctatca ttaccaacag gcctacttct | 1140 |
| aagccaacaa caagacctac accaaagcca acaccaattc ctactccacc accaccacca | 1200 |
| cccctgccaa cagagctcag aacacctcta ccacctacaa ccccagaaag gccaaccacc | 1260 |
| ggactgacaa ctatagcacc agctgccagt acacctccag gagggattac agttgacaac | 1320 |
| agggtacaga cagaccctca gaaacccaga ggagatgtgt tcattccacg caaccttca | 1380 |
| aatgacttgt ttgaaatatt tgaaatagaa agaggagtca gtgcagacga tgaagcaaag | 1440 |
| gatgatccag gtgttctggt acacagttgt aattttgacc atggactttg tggatggatc | 1500 |
| agggagaaag acaatgactt gcactgggaa ccaatcaggg acccagcagg tggacaatat | 1560 |
| ctgacagtgt cggcagccaa agccccaggg ggaaaagctg cacgcttggt gctacctctc | 1620 |
| ggccgcctca tgcattcagg ggacctgtgc ctgtcattca ggcacaaggt gacggggctg | 1680 |
| cactctggca cactccaggt gtttgtgaga aaacacggtg cccacggagc agccctgtgg | 1740 |
| ggaagaaatg gtggccatgg ctggaggcaa acacagatca ccttgcgagg ggctgacatc | 1800 |
| aagagcgtcg tcttcaaagg tgaaaaaagg cgtggtcaca ctggggagat tggattagat | 1860 |
| gatgtgagct tgaaaaaagg ccactgctct gaagaacgct aacaactcca gaactaacaa | 1920 |
| tgaactccta tgttgctcta tcctctttt ccaattctca tcttctctcc tcttctccct | 1980 |
| tttatcaggc ctaggagaag agtgggtcag tgggtcagaa ggaagtctat ttggtgaccc | 2040 |
| aggttttttct ggcctgcttt tgtgcaatcc caatgaacag tgatacctc cttgaaatac | 2100 |
| aggggcatcg cagacacatc aaagccatct gtgggtgttg ccttccatcc tgtgtctctt | 2160 |
| tcaggaaggc attcagcatg cgtgagccat accatcctcc atcctgatta caaggtgctc | 2220 |
| cttgtagcaa attatgagag tgagttacgg gagcagtttt taaaagaaan tctttkcara | 2280 |
| kggstwtraw gtwwtkkgty cggkgttgkm cccawgrgkr gkwttgrcct tcccttgrra | 2340 |
| wawrawrwac aawagkgctk gkgaaawwra mwatmccty ttcmytttaa rwwarwtytg | 2400 |
| gccygmccys aamatytkwy ttttaygtgs crkctcmytt twttaaaawa arggtgtgta | 2460 |
| acatatcaag atacatttat ttttatctgt tttttttttt cctgttaaag acaattatgt | 2520 |
| agagtgggca cgtaatccct ccttagtagt attgtgtttt gtgtaaatgt gctattgata | 2580 |
| ttaagtattt acatgttcca aatatttaca gactctagtt gcaaggtaaa gggcagcttg | 2640 |
| tgatctcaaa aaaatacatg gtgaaatgtc atccagttcc atgacctat attggcagca | 2700 |
| gtaggaaatt ggcagaagtg ttgggttgtg gtaacggagt gatgaatttt tttttaatgg | 2760 |

```
ccttgagttt gatctctgca aaggatagga aacctttagg aagacaagaa actgcagtta    2820
atttagaact gtcactgttt caagttacac tttaaaacca cagcttttac catcataaca    2880
tggctctggt aatatgtagg aagctttata aaagttttgg ttgattcaga aaaaggatcc    2940
tgttgcagag tgagaggaag catagggggaa aactccattg aacagatttt tcacacaacg    3000
ttttaaattg atataagttt aggcagttgt agttcataac ttatgttgct catgttgtgc    3060
tgtgtcagga tgggatagga agcaagtccc atgcttagag gcatgggatg tgttggaacg    3120
ggatttacac acactggagg agcagggcaa gttggaattc taagatccat gaaccccccaa   3180 ctgtatttcc tccctgcata ttttaccaat atattaaaaa acaatgtaac ttttaaaagg    3240
catcattcct gaggtttgtc ttaatttctg attaagtaat cagaatattt tctgctatttt   3300 ttgccaggaa tcacaaagat gattaaaggg ttggaaaaaa agatctatga tggaaaatta   3360
aaggaactgg gattattgag cctggagaag agaagactga ggggcaaacc attgatggtt    3420
ttcaagtata tgaaggggttg gcacagagag ggtggcgacc agctgttctc catatgccac   3480
taagaataga acaagaggaa actggcttag actagagtat aagggagcat tcttggcag    3540 gggccattgt tagaatactt cataaaaaaa gaagtgtgaa atctcagta tctctctctc    3600 tttctaaaaa attagataaa aatttgtcta tttaagatng gttaaagatg ttcttaccca    3660
aggaaaagta acaaattata gaatttccca aaagatgttt tgatcctact agtagtatgc    3720
agtngaaaat ctttagaact aaataatttg gacaaggctt aatttaggca tttccctctt    3780
gacctcctaa tggagaggga ttgaaagggg aagagcccac caaatgctga gctcactgaa    3840
atatctctcc cttatggcaa tcctagcagt attaaagaaa aaggaaact atttattcca    3900 aatgagagta tgatggacag atattttagt atctccagtaa tgtcctagtg tggcggtggt   3960
tttcaatgtt tcttcatggt aaaggtataa gcctttcatt tgttcaatgg atgatgtttc    4020
ggattttttt tttttaagag atccttcaag gaacacagtt cagagagatt ttcatcgggt   4080
gcattctctc tgcttcgtgt gtgacaagtt atcttggctg ctgagaaaga gtgccctgcc    4140
ccacaccggc agacctttcc ttcacctcat cagtatgatt cagtttctct tatcaattgg    4200
actctcccag gttccacaga acagtaatat ttttttgaaca ataggtacaa tagaaggtct   4260
tctgntcatt taacctggta aaggcagggc tggaggggga aaataaatca ttaagccttt    4320
gagtaacggc agaatatatg gctgtagatc catttttaat ggttcatttc ctttatggtc   4380
atataactgc acagctgaag atgaaagggg aaaataaatg aaaattttac ttttcgatgc    4440
caatgataca ttgcactaaa ctgatggaag aagttatcca aagtactgta taacatcttg    4500
tttattattt aatgttttct aaaataaaaaa atgttagtgg ttttccaaat ggcctaataa    4560
aaacaattat ttgtaaataa aaacactgtt agtaataaaa aaaaaaaaaa aaaaaaaaaa    4620
aarrrrmmra ammmmaancc gccnntngnn n                                  4651
```

<210> SEQ ID NO 62
<211> LENGTH: 560
<212> TYPE: PRT
<213> ORGANISM: Homo sapiens

<400> SEQUENCE: 62

Met Leu Tyr Asp Trp Cys Phe Val Asp Leu Glu Ile Met His Ala Ile
1               5                   10                  15

Phe Phe Ser Gln Leu Cys Ala Asn His Asp Ala Asn Met Val Asn Val
            20                  25                  30

```
Ser Gly Gln Thr Ser Ala Ser Val Ile Leu Val Met Leu Glu Lys Pro
            35                  40                  45

Ser Asn Ser Cys Glu Asp Glu His Ile Pro Ala Pro Leu Asp Gln Gly
        50                  55                  60

Ser Glu Gln Pro Leu Phe Gln Pro Leu Asp His Gln Ala Thr Ser Leu
65                  70                  75                  80

Pro Ser Arg Asp Leu Asn Glu Cys Gly Leu Lys Pro Arg Pro Cys Lys
                85                  90                  95

His Arg Cys Met Asn Thr Tyr Gly Ser Tyr Lys Cys Tyr Cys Leu Asn
            100                 105                 110

Gly Tyr Met Leu Met Pro Asp Gly Ser Cys Ser Ser Ala Leu Thr Cys
        115                 120                 125

Ser Met Ala Asn Cys Gln Tyr Gly Cys Asp Val Val Lys Gly Gln Ile
    130                 135                 140

Arg Cys Gln Cys Pro Ser Pro Gly Leu His Leu Ala Pro Asp Gly Arg
145                 150                 155                 160

Thr Cys Val Asp Val Asp Glu Cys Ala Thr Gly Arg Ala Ser Cys Pro
                165                 170                 175

Arg Phe Arg Gln Cys Val Asn Thr Phe Gly Ser Tyr Ile Cys Lys Cys
            180                 185                 190

His Lys Gly Phe Asp Leu Met His Ile Gly Gly Lys Tyr Gln Cys His
        195                 200                 205

Asp Ile Asp Glu Cys Ser Leu Gly Gln Tyr Gln Cys Ser Ser Phe Ala
    210                 215                 220

Arg Cys Tyr Asn Val Arg Gly Ser Tyr Lys Cys Lys Cys Lys Glu Gly
225                 230                 235                 240

Tyr Gln Gly Asp Gly Leu Thr Cys Val Tyr Ile Pro Lys Val Met Ile
                245                 250                 255

Glu Pro Ser Gly Pro Ile His Val Pro Lys Gly Asn Gly Thr Ile Leu
            260                 265                 270

Lys Gly Asp Thr Gly Asn Asn Trp Ile Pro Asp Val Gly Ser Thr
        275                 280                 285

Trp Trp Pro Pro Lys Thr Pro Tyr Ile Pro Pro Ile Ile Thr Asn Arg
290                 295                 300

Pro Thr Ser Lys Pro Thr Thr Arg Pro Thr Pro Lys Pro Thr Pro Ile
305                 310                 315                 320

Pro Thr Pro Pro Pro Pro Pro Leu Pro Thr Glu Leu Arg Thr Pro
                325                 330                 335

Leu Pro Pro Thr Thr Pro Glu Arg Pro Thr Thr Gly Leu Thr Thr Ile
            340                 345                 350

Ala Pro Ala Ala Ser Thr Pro Gly Gly Ile Thr Val Asp Asn Arg
        355                 360                 365

Val Gln Thr Asp Pro Gln Lys Pro Arg Gly Asp Val Phe Ile Pro Arg
370                 375                 380

Gln Pro Ser Asn Asp Leu Phe Glu Ile Phe Glu Ile Glu Arg Gly Val
385                 390                 395                 400

Ser Ala Asp Asp Glu Ala Lys Asp Asp Pro Gly Val Leu Val His Ser
                405                 410                 415

Cys Asn Phe Asp His Gly Leu Cys Gly Trp Ile Arg Glu Lys Asp Asn
            420                 425                 430

Asp Leu His Trp Glu Pro Ile Arg Asp Pro Ala Gly Gly Gln Tyr Leu
        435                 440                 445

Thr Val Ser Ala Ala Lys Ala Pro Gly Gly Lys Ala Ala Arg Leu Val
```

|     |     |     | 450 |     |     |     | 455 |     |     |     | 460 |
|-----|-----|-----|-----|-----|-----|-----|-----|-----|-----|-----|-----|

Leu Pro Leu Gly Arg Leu Met His Ser Gly Asp Leu Cys Leu Ser Phe
465                 470                 475                 480

Arg His Lys Val Thr Gly Leu His Ser Gly Thr Leu Gln Val Phe Val
                485                 490                 495

Arg Lys His Gly Ala His Gly Ala Ala Leu Trp Gly Arg Asn Gly Gly
            500                 505                 510

His Gly Trp Arg Gln Thr Gln Ile Thr Leu Arg Gly Ala Asp Ile Lys
        515                 520                 525

Ser Val Val Phe Lys Gly Glu Lys Arg Gly His Thr Gly Glu Ile
    530                 535                 540

Gly Leu Asp Asp Val Ser Leu Lys Lys Gly His Cys Ser Glu Glu Arg
545                 550                 555                 560

<210> SEQ ID NO 63
<211> LENGTH: 4461
<212> TYPE: DNA
<213> ORGANISM: Homo sapiens

<400> SEQUENCE: 63

```
cgaccccgcg tccgggggca ttgcgtggtg gaaagttgcg tgcggcagag aaccgaaggt      60
gcagcgccac agcccagggg acggtgtgtc tgggagaaga cgctgcccct gcgtcgggac     120
cgccagcgc gcgggcaccg cggggcccgg gacgacgccc cctcctgcgg cgtggactcc     180
gtcagtggcc caccaagaag gaggaggaat atggaatcca agggggccag ttcctgccgt     240
ctgctcttct gcctcttgat ctccgccacc gtcttcaggc caggccttgg atggtatact     300
gtaaattcag catatggaga taccattatc ataccttgcc gacttgacgt acctcagaat     360
ctcatgtttg gcaaatggaa atatgaaaag cccgatggct ccccagtatt tattgccttc     420
agatcctcta caagaaaag tgtgcagtac gacgatgtac cagaatacaa agacagattg     480
aacctctcag aaaactacac tttgtctatc agtaatgcaa ggatcagtga tgaaaagaga     540
tttgtgtgca tgctagtaac tgaggacaac gtgtttgagg cacctacaat agtcaaggtg     600
ttcaagcaac catctaaacc tgaaattgta agcaaagcac tgtttctcga aacagagcag     660
ctaaaaaagt tgggtgactg catttcagaa gacagttatc cagatggcaa tatcacatgg     720
tacaggaatg gaaagtgct acatccccctt gaaggagcgg tggtcataat tttttaaaaag     780
gaaatggacc cagtgactca gctctatacc atgacttcca ccctggagta caagacaacc     840
aaggctgaca tacaaatgcc attcacctgc tcggtgacat attatggacc atctggccag     900
aaaacaattc attctgaaca ggcagtattt gatatttact atcctacaga gcaggtgaca     960
atacaagtgc tgccaccaaa aaatgccatc aagaagggg ataacatcac tcttaaatgc    1020
ttagggaatg gcaaccctcc cccagaggaa tttttgtttt acttaccagg acagcccgaa    1080
ggaataagaa gctcaaatac ttacacactg atggatgtga gcgcaatgc aacaggagac    1140
tacaagtgtt ccctgataga caaaaaaagc atgattgctt caacagccat cacagttcac    1200
tatttggatt tgtccttaaa cccaagtgga gaagtgacta cagagattgg tgatgcccta    1260
cccgtgtcat gcacaatatc tgctagcagg aatgcaactg tggtatggat gaaagataac    1320
atcaggcttc gatctagccc gtcatttttct agtcttcatt atcaggatgc tggaaactat    1380
gtctgcgaaa ctgctctgca ggaggttgaa ggactaaaga aagagagtc attgactctc    1440
attgtagaag gcaaacctca aataaaaatg acaaagaaaa ctgatcccag tggactatct    1500
aaaacaataa tctgccatgt ggaaggtttt ccaaagccag ccattcagtg gacaattact    1560
```

```
ggcagtggaa gcgtcataaa ccaaacagag gaatctcctt atattaatgg caggtattat    1620
agtaaaatta tcatttcccc tgaagagaat gttacattaa cttgcacagc agaaaaccaa    1680
ctggagagaa cagtaaactc cttgaatgtc tctgctataa gtattccaga acacgatgag    1740
gcagacgaga taagtgatga aaacagagaa aaggtgaatg accaggcaaa actaattgtg    1800
ggaatcgttg ttggtctcct ccttgctgcc cttgttgctg gtgtcgtcta ctggctgtac    1860
atgaagaagt caaagactgc atcaaaacat gtaaacaagg acctcggtaa tatggaagaa    1920
aacaaaaagt tagaagaaaa caatcacaaa actgaagcct aagagagaaa ctgtcctagt    1980
tgtccagaga taaaaatcat atagaccaat tgaagcatga acgtggattg tatttaagac    2040
ataaacaaag acattgacag caattcatgg ttcaagtatt aagcagttca ttctaccaag    2100
ctgtcacagg ttttcagaga attatctcaa gtaaaacaaa tgaaatttaa ttacaaacaa    2160
taagaacaag ttttggcagc catgataata ggtcatatgt tgtgtttggt tcaattttt     2220
ttccgtaaat gtctgcactg aggatttctt tttggtttgc cttttatgta aatttttac    2280
gtagctattt ttatacactg taagctttgt tctgggagtt gctgttaatc tgatgtataa    2340
tgtaatgttt ttatttcaat tgtttatatg gataatctga gcaggtacat ttctgattct    2400
gattgctatc agcaatgccc caaactttct cataagcacc taaaacccaa aggtggcagc    2460
ttgtgaagat tggggacact catattgccc taattaaaaa ctgtgatttt tatcacaagg    2520
gaggggaggc cgagagtcag actgatagac accataggag ccgactcttt gatatgccac    2580
cagcgaactc tcagaaataa atcacagatg catatagaca cacatacata atggtactcc    2640
caaactgaca attttaccta ttctgaaaaa gacataaaac agaatttggt agcacttacc    2700
tctacagaca cctgctaata aattattttc tgtcaaaaga aaaaacacaa gcatgtgtga    2760
gagacagttt ggaaaaatca tggtcaacat tcccattttc atagatcaca atgtaaatca    2820
ctataattac aaattggtgt taaatccttt gggttatcca ctgccttaaa attataccta    2880
tttcatgttt aaaaagatat caatcagaat tggagttttt aacagtggtc attatcaaag    2940
ctgtgttatt ttccacagaa tatagaatat atattttttt cgtgtgtgtt tttgttaact    3000
accctacaga tattgaatgc accttgagat aatttagtgt ttttaactga tacataattt    3060
atcaagcagt acatgaaagt gtaataataa aatgtctatg tatctttagt tacattcaaa    3120
tttgtaactt tataaacatg ttttatgctt gaggaaattt ttaaggtggt agtataaatg    3180
gaaactttt gaagtagacc ggatatgggc tacttgtgac tagacttttta aactttgctc     3240
tttcaagcag aagcctggtt tctgggagaa cactgcacag cgatttcttt cccaggattt    3300
acacaacttt aaagggaaga taaatgaaca tcagatttct aggtatagaa ctatgttatt    3360
gaaaggaaaa ggaaaactgg tgtttgtttc ttagactcat gaaataaaaa attatgaagg    3420
caatgaaaaa taaattgaaa attaaagtca gatgagaata ggaataatac tttgccactt    3480
ctgcattatt tagaaacata cgttattgta catttgtaaa ccatttactg tctgggcaat    3540
agtgactccg tttaataaaa gcttccgtag tgcattggta tggattaaat gcataaaata    3600
ttcttagact cgatgctgta taaaatatta tgggaaaaaa aagaaaatac gttattttgc    3660
ctctaaactt ttattgaagt tttatttggc aggaaaaaaa attgaatctt ggtcaacatt    3720
taaaccaaag taaagggga aaaccaaag ttatttgttt tgcatggcta agccattctg      3780
ttatctctgt aaatactgtg atttctttt tattttctct ttagaatttt gttaaagaaa    3840
ttctaaaatt tttaaacacc tgctctccac aataaatcac aaacactaaa ataaaattac    3900
```

-continued

```
ttccatataa atattatttt ctcttttggt gtgggagatc aaaggtttaa agtctaactt    3960
ctaagatata tttgcagaaa gaagcaacat gacaatagag agagttatgc tacaattatt    4020
tcttggtttc cacttgcaat ggttaattaa gtccaaaaac agctgtcaga acctcgagag    4080
cagaacatga gaaactcaga gctctggacc gaaagcagaa agtttgccag gaaaaaaaaa    4140
gacaacatta ttaccatcga ttcagtgcct ggataaagag gaaagcttac ttgtttaatg    4200
gcagccacat gcacgaagat gctaagaaga aaaagaattc caaatcctca acttttgagg    4260
tttcggctct ccaatttaac tctttggcaa caggaaacag gttttgcaag ttcaaggttc    4320
actccctata tgtgattata ggaattgttt gtggaaatgg attaacatac ccgtctatgc    4380
ctaaaagata ataaaactga aatatgtctt caaaaaaaaa aaaaaaaaaa aaaaaaaaa    4440 aaaaaaaaaa gggcggccgc t                                              4461
```

<210> SEQ ID NO 64
<211> LENGTH: 583
<212> TYPE: PRT
<213> ORGANISM: Homo sapiens

<400> SEQUENCE: 64

```
Met Glu Ser Lys Gly Ala Ser Ser Cys Arg Leu Leu Phe Cys Leu Leu
1               5                   10                  15

Ile Ser Ala Thr Val Phe Arg Pro Gly Leu Gly Trp Tyr Thr Val Asn
            20                  25                  30

Ser Ala Tyr Gly Asp Thr Ile Ile Pro Cys Arg Leu Asp Val Pro
        35                  40                  45

Gln Asn Leu Met Phe Gly Lys Trp Lys Tyr Glu Lys Pro Asp Gly Ser
    50                  55                  60

Pro Val Phe Ile Ala Phe Arg Ser Ser Thr Lys Lys Ser Val Gln Tyr
65                  70                  75                  80

Asp Asp Val Pro Glu Tyr Lys Asp Arg Leu Asn Leu Ser Glu Asn Tyr
                85                  90                  95

Thr Leu Ser Ile Ser Asn Ala Arg Ile Ser Asp Glu Lys Arg Phe Val
            100                 105                 110

Cys Met Leu Val Thr Glu Asp Asn Val Phe Glu Ala Pro Thr Ile Val
        115                 120                 125

Lys Val Phe Lys Gln Pro Ser Lys Pro Glu Ile Val Ser Lys Ala Leu
    130                 135                 140

Phe Leu Glu Thr Glu Gln Leu Lys Lys Leu Gly Asp Cys Ile Ser Glu
145                 150                 155                 160

Asp Ser Tyr Pro Asp Gly Asn Ile Thr Trp Tyr Arg Asn Gly Lys Val
                165                 170                 175

Leu His Pro Leu Glu Gly Ala Val Val Ile Phe Lys Lys Glu Met
            180                 185                 190

Asp Pro Val Thr Gln Leu Tyr Thr Met Thr Ser Thr Leu Glu Tyr Lys
        195                 200                 205

Thr Thr Lys Ala Asp Ile Gln Met Pro Phe Thr Cys Ser Val Thr Tyr
    210                 215                 220

Tyr Gly Pro Ser Gly Gln Lys Thr Ile His Ser Glu Gln Ala Val Phe
225                 230                 235                 240

Asp Ile Tyr Tyr Pro Thr Glu Gln Val Thr Ile Gln Val Leu Pro Pro
                245                 250                 255

Lys Asn Ala Ile Lys Glu Gly Asp Asn Ile Thr Leu Lys Cys Leu Gly
            260                 265                 270
```

Asn Gly Asn Pro Pro Glu Glu Phe Leu Phe Tyr Leu Pro Gly Gln
            275                 280                 285

Pro Glu Gly Ile Arg Ser Ser Asn Thr Tyr Thr Leu Met Asp Val Arg
290                 295                 300

Arg Asn Ala Thr Gly Asp Tyr Lys Cys Ser Leu Ile Asp Lys Lys Ser
305                 310                 315                 320

Met Ile Ala Ser Thr Ala Ile Thr Val His Tyr Leu Asp Leu Ser Leu
                325                 330                 335

Asn Pro Ser Gly Glu Val Thr Arg Gln Ile Gly Asp Ala Leu Pro Val
            340                 345                 350

Ser Cys Thr Ile Ser Ala Ser Arg Asn Ala Thr Val Val Trp Met Lys
        355                 360                 365

Asp Asn Ile Arg Leu Arg Ser Ser Pro Ser Phe Ser Ser Leu His Tyr
370                 375                 380

Gln Asp Ala Gly Asn Tyr Val Cys Glu Thr Ala Leu Gln Glu Val Glu
385                 390                 395                 400

Gly Leu Lys Lys Arg Glu Ser Leu Thr Leu Ile Val Glu Gly Lys Pro
                405                 410                 415

Gln Ile Lys Met Thr Lys Lys Thr Asp Pro Ser Gly Leu Ser Lys Thr
            420                 425                 430

Ile Ile Cys His Val Glu Gly Phe Pro Lys Pro Ala Ile Gln Trp Thr
        435                 440                 445

Ile Thr Gly Ser Gly Ser Val Ile Asn Gln Thr Glu Glu Ser Pro Tyr
450                 455                 460

Ile Asn Gly Arg Tyr Tyr Ser Lys Ile Ile Ser Pro Glu Glu Asn
465                 470                 475                 480

Val Thr Leu Thr Cys Thr Ala Glu Asn Gln Leu Glu Arg Thr Val Asn
                485                 490                 495

Ser Leu Asn Val Ser Ala Ile Ser Ile Pro Glu His Asp Glu Ala Asp
            500                 505                 510

Glu Ile Ser Asp Glu Asn Arg Glu Lys Val Asn Asp Gln Ala Lys Leu
        515                 520                 525

Ile Val Gly Ile Val Gly Leu Leu Leu Ala Ala Leu Val Ala Gly
530                 535                 540

Val Val Tyr Trp Leu Tyr Met Lys Lys Ser Lys Thr Ala Ser Lys His
545                 550                 555                 560

Val Asn Lys Asp Leu Gly Asn Met Glu Glu Asn Lys Lys Leu Glu Glu
                565                 570                 575

Asn Asn His Lys Thr Glu Ala
            580

<210> SEQ ID NO 65
<211> LENGTH: 2174
<212> TYPE: DNA
<213> ORGANISM: Homo sapiens
<220> FEATURE:
<221> NAME/KEY: modified_base
<222> LOCATION: (1910)..(1910)
<223> OTHER INFORMATION: a, c, t or g
<220> FEATURE:
<221> NAME/KEY: modified_base
<222> LOCATION: (1941)..(1941)
<223> OTHER INFORMATION: a, c, t or g

<400> SEQUENCE: 65
agcaccacgc gtccgtgaag atggagacca acgagtctac ggagggatcg cggtcgcggt    60
cgcggtgaga gccgcagctc tggctgcagg cataagggga cgaggaaggt cagctgactt   120

```
cctctgctgc gcttttgaca gccatgtcgt gtttgctttc tttcagatct ttagacatac      180
agcccagctc cgaaggactg gggcccactt cggaaccgtt tccttcttca gatgacagtc      240
ccaggtcggc cctggcagct gcaaccgcag cagctgcagc ggctgcatca gctgctgcag      300
ctactgcagc cttcaccact gccaaagcag ctgcattatc tacaaagacc ccagcgccct      360
gttctgagtt catggagccg tcctctgacc ccagccttct tggggagccc tgtgcgggac      420
ccggctttac ccacaatata gcccatggga gtcttggctt tgagcccgtc tatgtttcct      480
gtattgctca ggacacttgc actacaactg accatagttc taatcctggc cctgttccag      540
gctctagctc tgggcctgtt cttggttcca gctcaggtgc tggccatggc tctggctctg      600
gctctggtcc tggctgtggc tctgtccctg gctctggctc tggtcctggt cctggctctg      660
gtcctggtca tggctctggc tctcatcctg gtcctgcctc tgggcctggt ccagacactg      720
gccctgactc tgagctcagc ccctgtattc ctccagggtt cagaaacctg gtggcagatc      780
gggtccctaa ctatacctcc tggagtcagc actgcccctg ggagcccag aaacaaccac       840 cttgggaatt tttgcaagtc ttagaaccgg gtgcccgagg actatggaaa cccccagaca      900
ttaaagggaa gcttatggtt tgctatgaaa ctttgccacg gggccagtgc ctcctctaca      960
actgggagga agaggtatta aagttttggc ctgctccctt ttcttgaagg ctgccctcag     1020
tttcttaggg gaggcagtag tttacatgag ggtgggtacc agaagggata ttatagtcat     1080
tcaacttggg atccacagag agccaccaac cacctggatc aagtcccaag catgcaggat     1140
ggctctgaga gttttttctt ccgacacgga caccggggac tgctgactat gcaactaaag     1200
tcacccatgc cctccagcac cacccagaaa gactcgtacc agccaccagg aaacgtctat     1260
tggccacttc gagggaagcg tgaagccatg ctggagatgc tcctgcagca tcagatctgg     1320
taagggattg ggtaaagggg aagagggatg gggaggagaa aaattgggtg agaatggcct     1380
tgacacccct cgggctacat agtaaagagg tgcaggcaga acaggaaccc acaaggaagc     1440
tcttcgaggt tgagtctgtg acacaccatg actaccgaat ggagctggca caagcaggga     1500
ctcctgcccc aacaaaggtg agaacccacc cccatcccc cgccacttgc accagctggg      1560
ctctgacagg ctgtggccaa gtaccaagcc cagaggttga gagagaggc tgaaggccag      1620 gagttactca gtaccctccc tcacagcctc acgactaccg ccaggagcaa cctgagacct     1680
tctggataca gagggcacca cagctgccgg tgtgtgaggg tgactaggtg ttgggggcag     1740
agcggggcag gaaaggtagg gcagagttgt tttgttctgg cttggggaga gtgggatcca     1800
tcctcatcct ggcactcctc cagggtgtca gtaacatcag gacattggac acaccattcc     1860
ggaagaactg cagcttctca acacccagta cccttgtctc tggggaaacn ttttgcccta     1920
tgaacctgag aattacccct naccaattgg gagaaaatat cttcccttcc ctgtcccgga     1980
ggaaggctgg gtggtggagg ggggagaatg actcctttct gaggggtgag gagggaagtg     2040
gggtatggaa tatggaatct atttctgtct gcactagaga ggtcgggagg aagttaattc     2100
tcactgymct tgaagaggct ttacataaag ggttctctct craaaaaaaa rawaraaaaa     2160
aaaagggcgg ccgs                                                       2174
```

<210> SEQ ID NO 66
<211> LENGTH: 287
<212> TYPE: PRT
<213> ORGANISM: Homo sapiens

<400> SEQUENCE: 66

```
Met Ser Cys Leu Leu Ser Phe Arg Ser Leu Asp Ile Gln Pro Ser Ser
1               5                   10                  15

Glu Gly Leu Gly Pro Thr Ser Glu Pro Phe Pro Ser Ser Asp Asp Ser
            20                  25                  30

Pro Arg Ser Ala Leu Ala Ala Ala Thr Ala Ala Ala Ala Ala Ala Ala
        35                  40                  45

Ser Ala Ala Ala Ala Thr Ala Ala Phe Thr Thr Ala Lys Ala Ala Ala
50                  55                  60

Leu Ser Thr Lys Thr Pro Ala Pro Cys Ser Glu Phe Met Glu Pro Ser
65                  70                  75                  80

Ser Asp Pro Ser Leu Leu Gly Glu Pro Cys Ala Gly Pro Gly Phe Thr
                85                  90                  95

His Asn Ile Ala His Gly Ser Leu Gly Phe Glu Pro Val Tyr Val Ser
            100                 105                 110

Cys Ile Ala Gln Asp Thr Cys Thr Thr Thr Asp His Ser Ser Asn Pro
        115                 120                 125

Gly Pro Val Pro Gly Ser Ser Gly Pro Val Leu Gly Ser Ser Ser
    130                 135                 140

Gly Ala Gly His Gly Ser Gly Ser Gly Ser Gly Pro Gly Cys Gly Ser
145                 150                 155                 160

Val Pro Gly Ser Gly Ser Gly Pro Gly Ser Gly Pro Gly His
            165                 170                 175

Gly Ser Gly Ser His Pro Gly Pro Ala Ser Gly Pro Gly Pro Asp Thr
                180                 185                 190

Gly Pro Asp Ser Glu Leu Ser Pro Cys Ile Pro Pro Gly Phe Arg Asn
            195                 200                 205

Leu Val Ala Asp Arg Val Pro Asn Tyr Thr Ser Trp Ser Gln His Cys
        210                 215                 220

Pro Trp Glu Pro Gln Lys Gln Pro Pro Trp Glu Phe Leu Gln Val Leu
225                 230                 235                 240

Glu Pro Gly Ala Arg Gly Leu Trp Lys Pro Pro Asp Ile Lys Gly Lys
                245                 250                 255

Leu Met Val Cys Tyr Glu Thr Leu Pro Arg Gly Gln Cys Leu Leu Tyr
            260                 265                 270

Asn Trp Glu Glu Glu Val Leu Lys Phe Trp Pro Ala Pro Phe Ser
        275                 280                 285

<210> SEQ ID NO 67
<211> LENGTH: 4305
<212> TYPE: DNA
<213> ORGANISM: Homo sapiens

<400> SEQUENCE: 67
cccttaataa gatttgccac gtacactcga gccatcgcga gtgtccttga gccgcgggtg      60
acggtggctc tcgctgctcg cgccccctcc tcccgcgggg ggagcctgat gccacgttcc     120
ctatgaatta tttatcgccg gcctaaaaat accccgaact tcacagcccg agtgaccctc     180
cggtggacat gggtggggcc ctggggccgg ccctgttgct cacctcgctc ttcggtgcct     240
gggcagggct gggtccgggg cagggcgagc agggcatgac ggtggccgtg gtgtttagca     300
gctcagggcc gccccaggcc cagttccgtg cccgcctcac ccccagagc ttcctggacc      360 taccctgga gatccagccg ctcacagttg gggtcaacac caccaacccc agcagcctcc     420 tcacccgat ctgcggcctc ctgggtgctg cccacgtcca cggcattgtc tttgaggaca     480
acgtggacac cgaggcggtg gcccagatcc ttgacttcat ctcctcccag acccatgtgc     540
```

```
ccatcctcag catcagcgga ggctctgctg tggtcctcac ccccaaggag ccgggctccg    600
ccttcctgca gctgggcgtg tccctggagc agcagctgca ggtgctgttc aaggtgctgg    660
aagagtacga ctggagcgcc ttcgccgtca tcaccagcct gcacccgggc cacgcgctct    720
tcctggaggg cgtgcgcgcc gtcgccgacg ccagccacgt gagttggcgg ctgctggacg    780
tggtcacgct ggagctgggc ccgggagggc cgcgcgcgcg cacgcagcgc ctgctgcgcc    840
agctcgacgc gcccgtgttt gtggcctact gctcgcgcga ggaggccgag gtgctcttcg    900
ccgaggcggc gcaggccggt ctggtggggc ccggccacgt gtggctggtg cccaacctgg    960
cgctgggcag caccgatgcg ccccccgcca ccttccccgt gggcctcatc agcgtcgtca   1020
ccgagagctg gcgcctcagc ctgcgccaga aggtgcgcga cggcgtggcc attctggccc   1080
tgggcgccca cagctactgg cgccagcatg aaccccgcc agccccggcc ggggactgcc    1140
gtgttcaccc tgggcccgtc agccctgccc ggaggccctt ctacaggcac ctactgaatg   1200
tcacctggga gggccgagac ttctccttca gccctggtgg gtacctggtc cagcccacca   1260
tggtggtgat cgccctcaac cggcaccgcc tctgggagat ggtggggcgc tgggagcatg   1320
gcgtcctata catgaagtac cctgtgtggc ctcgctacag tgcctctctg cagcccgtgg   1380
tggacagtcg gcacctgacg gtggccacgc tggaagagag gcccttttgtc atcgtggaga   1440 gccccgaccc tggcacagga ggctgcgtcc caacaccgt gccctgccgc aggcagagca   1500
accacacctt cagcagcggg gacgtggccc cctacaccaa gctctgttgt aagggattct   1560
gcatcgacat cctcaagaag ctggccgagt tggtcaaatt ctcctacgac ctgtacctgg   1620
tgaccaacgg caagcatggc aagcgggtgc gcggcgtatg gaacggcatg attggggagg   1680
tgtactacaa gcgggcagac atggccatcg gctccctcac catcaatgag gaacgctccg   1740
agatcgtaga cttctctgta ccctttgtgg agacgggcat cagtgtgatg gtggctcgca   1800
gcaatggcac cgtctccccc tcggccttct tggagccata tagccctgca gtgtgggtga   1860
tgatgtttgt catgtgcctc actgtggtgg ccatcaccgt cttcatgttc gagtacttca   1920
gccctgtcag ctacaaccag aacctcacca gaggcaagaa gtccggggc ccagcttttca    1980 ctatcggcaa gtccgtgtgg ctgctgtggg cgctggtctt caacaactca gtgcccatcg   2040
agaacccgcg gggcaccacc agcaagatca tggttctggt ctgggccttc tttgctgtca   2100
tcttcctcgc cagctacacg gccaacctgg ccgccttcat gatccaagag caatacatcg   2160
acactgtgtc gggcctcagt gacaagaagt tcagcggcc tcaagatcag tacccaccctt   2220 tccgcttcgg cacggtgccc aacgcagca cggagcggaa catccgcagt aactaccgtg   2280
acatgcacac ccacatggtc aagttcaacc agcgctcggt ggaggacgcg ctcaccagcc   2340
tcaagatggg gaagctggat gccttcatct atgatgctgc tgtcctcaac tacatggcag   2400
gcaaggacga gggctgcaag ctggtcacca ttgggtctgg caaggtctttt gctaccactg   2460 gctacggcat cgccatgcag aaggactccc actggaagcg ggccatagac ctggcgctct   2520
tgcagttcct gggggacgga gagacacaga aactggagac agtgtggctc tcagggatct   2580
gccagaatga aagaacgag gtgatgagca gcaagctgga catcgacaac atggcaggcg   2640
tcttctacat gctgctggtg gccatggggc tggccctgct ggtcttcgcc tgggagcacc   2700
tggtctactg gaagctgcgc cactcggtgc ccaactcatc ccagctggac ttcctgctgg   2760
ctttcagcag gggcatctac agctgcttca gcggggtgca gagcctcgcc agcccaccgc   2820
ggcaggccag cccggacctc acggccagct cggcccaggc cagcgtgctc aagatgctgc   2880
```

| | |
|---|---|
| aggcagcccg cgacatggtg accacggcgg gcgtaagcag ctccctggac cgcgccactc | 2940 |
| gcaccatcga gaattggggt ggcggccgcc gtgcgccccc accgtccccc tgcccgaccc | 3000 |
| cgcggtctgg ccccagccca tgcctgccca ccccgaccc gccccagag ccgagcccca | 3060 |
| cgggctgggg accgccagac gggggtcgcg cggcgcttgt gcgcagggct ccgcagcccc | 3120 |
| cgggccgccc cccgacgccg gggccgcccc tgtccgacgt ctcccgagtg tcgcgccgcc | 3180 |
| cagcctggga ggcgcggtgg ccggtgcgga ccgggcactg cgggaggcac ctctcggcct | 3240 |
| ccgagcggcc cctgtcgccc gcgcgctgtc actacagctc ctttcctcga gccgaccgat | 3300 |
| ccggccgccc cttcctcccg ctcttcccgg agccccgga gctggaggac ctgccgctgc | 3360 |
| tcggtccgga gcagctggcc cggcgggagg ccctgctgca cgcggcctgg gcccggggct | 3420 |
| cgcgcccgcg tcacgcttcc ctgcccagct ccgtggccga ggccttcgct cggcccagct | 3480 |
| cgctgcccgc tgggtgcacc ggccccgcct gcgcccgccc cgacgccac tcggcctgca | 3540 |
| ggcgcttggc gcaggcgcag tcgatgtgct tgccgatcta ccgggaggcc tgccaggagg | 3600 |
| gcgagcaggc aggggccccc gcctggcagc acagacagca cgtctgcctg cacgcccacg | 3660 |
| cccacctgcc attttgctgg ggggctgtct gtcctcacct tccaccctgt gccagccacg | 3720 |
| gctcctggct ctccggggcc tggggcctc tgggcacag gggcaggact ctggggctgg | 3780 |
| gcacaggcta cagagacagt gggggactgg acgagatcag cagtgtagcc cgtgggacgc | 3840 |
| aaggcttccc gggaccctgc acctggagac ggatctccag tctggagtca gaagtgtgag | 3900 |
| ttatcagcca ctcaggctcc gagccagctg gattctctgc ctgccactgt cagggttaag | 3960 |
| cggcaggcag gattgggctt ttctggcttc taccatgaaa tcctggccat gggacccag | 4020 |
| tgacagatga tgtcttccat ggtcatcagt gacctcagta gcctcaaatc atggtgaggg | 4080 |
| ctgggctttt gctgtcctct tctcacgcag agttctgcca ggagggtgtg ctgtgggggt | 4140 |
| cagactcctg aggctctccc ttccctgggg ctagccagtt actggtcatg gctgctgtgg | 4200 |
| gcatggaggc tggaacttgt ggttgaggca gggccatccc gatccttgct ctacctggct | 4260 |
| agagtttctt ctcatcagag cactgggaca ttaaaccaac cttttt | 4305 |

<210> SEQ ID NO 68
<211> LENGTH: 1236
<212> TYPE: PRT
<213> ORGANISM: Homo sapiens

<400> SEQUENCE: 68

Met Gly Gly Ala Leu Gly Pro Ala Leu Leu Leu Thr Ser Leu Phe Gly
1               5                   10                  15

Ala Trp Ala Gly Leu Gly Pro Gly Gln Gly Glu Gln Gly Met Thr Val
            20                  25                  30

Ala Val Val Phe Ser Ser Gly Pro Pro Gln Ala Gln Phe Arg Ala
        35                  40                  45

Arg Leu Thr Pro Gln Ser Phe Leu Asp Leu Pro Leu Glu Ile Gln Pro
    50                  55                  60

Leu Thr Val Gly Val Asn Thr Thr Asn Pro Ser Ser Leu Leu Thr Gln
65                  70                  75                  80

Ile Cys Gly Leu Leu Gly Ala Ala His Val His Gly Ile Val Phe Glu
                85                  90                  95

Asp Asn Val Asp Thr Glu Ala Val Ala Gln Ile Leu Asp Phe Ile Ser
            100                 105                 110

Ser Gln Thr His Val Pro Ile Leu Ser Ile Ser Gly Gly Ser Ala Val
        115                 120                 125

```
Val Leu Thr Pro Lys Glu Pro Gly Ser Ala Phe Leu Gln Leu Gly Val
    130                 135                 140

Ser Leu Glu Gln Gln Leu Gln Val Leu Phe Lys Val Leu Glu Glu Tyr
145                 150                 155                 160

Asp Trp Ser Ala Phe Ala Val Ile Thr Ser Leu His Pro Gly His Ala
                165                 170                 175

Leu Phe Leu Glu Gly Val Arg Ala Val Ala Asp Ala Ser His Val Ser
            180                 185                 190

Trp Arg Leu Leu Asp Val Val Thr Leu Glu Leu Gly Pro Gly Gly Pro
        195                 200                 205

Arg Ala Arg Thr Gln Arg Leu Leu Arg Gln Leu Asp Ala Pro Val Phe
210                 215                 220

Val Ala Tyr Cys Ser Arg Glu Glu Ala Glu Val Leu Phe Ala Glu Ala
225                 230                 235                 240

Ala Gln Ala Gly Leu Val Gly Pro Gly His Val Trp Leu Val Pro Asn
                245                 250                 255

Leu Ala Leu Gly Ser Thr Asp Ala Pro Pro Ala Thr Phe Pro Val Gly
            260                 265                 270

Leu Ile Ser Val Val Thr Glu Ser Trp Arg Leu Ser Leu Arg Gln Lys
        275                 280                 285

Val Arg Asp Gly Val Ala Ile Leu Ala Leu Gly Ala His Ser Tyr Trp
290                 295                 300

Arg Gln His Gly Thr Leu Pro Ala Pro Ala Gly Asp Cys Arg Val His
305                 310                 315                 320

Pro Gly Pro Val Ser Pro Ala Arg Glu Ala Phe Tyr Arg His Leu Leu
                325                 330                 335

Asn Val Thr Trp Glu Gly Arg Asp Phe Ser Phe Ser Pro Gly Gly Tyr
            340                 345                 350

Leu Val Gln Pro Thr Met Val Val Ile Ala Leu Asn Arg His Arg Leu
        355                 360                 365

Trp Glu Met Val Gly Arg Trp Glu His Gly Val Leu Tyr Met Lys Tyr
370                 375                 380

Pro Val Trp Pro Arg Tyr Ser Ala Ser Leu Gln Pro Val Val Asp Ser
385                 390                 395                 400

Arg His Leu Thr Val Ala Thr Leu Glu Glu Arg Pro Phe Val Ile Val
                405                 410                 415

Glu Ser Pro Asp Pro Gly Thr Gly Gly Cys Val Pro Asn Thr Val Pro
            420                 425                 430

Cys Arg Arg Gln Ser Asn His Thr Phe Ser Ser Gly Asp Val Ala Pro
        435                 440                 445

Tyr Thr Lys Leu Cys Cys Lys Gly Phe Cys Ile Asp Ile Leu Lys Lys
450                 455                 460

Leu Ala Arg Val Val Lys Phe Ser Tyr Asp Leu Tyr Leu Val Thr Asn
465                 470                 475                 480

Gly Lys His Gly Lys Arg Val Arg Gly Val Trp Asn Gly Met Ile Gly
                485                 490                 495

Glu Val Tyr Tyr Lys Arg Ala Asp Met Ala Ile Gly Ser Leu Thr Ile
            500                 505                 510

Asn Glu Glu Arg Ser Glu Ile Val Asp Phe Ser Val Pro Phe Val Glu
        515                 520                 525

Thr Gly Ile Ser Val Met Val Ala Arg Ser Asn Gly Thr Val Ser Pro
530                 535                 540
```

```
Ser Ala Phe Leu Glu Pro Tyr Ser Pro Ala Val Trp Val Met Met Phe
545                 550                 555                 560

Val Met Cys Leu Thr Val Val Ala Ile Thr Val Phe Met Phe Glu Tyr
            565                 570                 575

Phe Ser Pro Val Ser Tyr Asn Gln Asn Leu Thr Arg Gly Lys Lys Ser
            580                 585                 590

Gly Gly Pro Ala Phe Thr Ile Gly Lys Ser Val Trp Leu Leu Trp Ala
            595                 600                 605

Leu Val Phe Asn Asn Ser Val Pro Ile Glu Asn Pro Arg Gly Thr Thr
            610                 615                 620

Ser Lys Ile Met Val Leu Val Trp Ala Phe Phe Ala Val Ile Phe Leu
625                 630                 635                 640

Ala Ser Tyr Thr Ala Asn Leu Ala Ala Phe Met Ile Gln Glu Gln Tyr
            645                 650                 655

Ile Asp Thr Val Ser Gly Leu Ser Asp Lys Lys Phe Gln Arg Pro Gln
            660                 665                 670

Asp Gln Tyr Pro Pro Phe Arg Phe Gly Thr Val Pro Asn Gly Ser Thr
            675                 680                 685

Glu Arg Asn Ile Arg Ser Asn Tyr Arg Asp Met His Thr His Met Val
690                 695                 700

Lys Phe Asn Gln Arg Ser Val Glu Asp Ala Leu Thr Ser Leu Lys Met
705                 710                 715                 720

Gly Lys Leu Asp Ala Phe Ile Tyr Asp Ala Ala Val Leu Asn Tyr Met
            725                 730                 735

Ala Gly Lys Asp Glu Gly Cys Lys Leu Val Thr Ile Gly Ser Gly Lys
            740                 745                 750

Val Phe Ala Thr Thr Gly Tyr Gly Ile Ala Met Gln Lys Asp Ser His
            755                 760                 765

Trp Lys Arg Ala Ile Asp Leu Ala Leu Leu Gln Phe Leu Gly Asp Gly
            770                 775                 780

Glu Thr Gln Lys Leu Glu Thr Val Trp Leu Ser Gly Ile Cys Gln Asn
785                 790                 795                 800

Glu Lys Asn Glu Val Met Ser Ser Lys Leu Asp Ile Asp Asn Met Ala
            805                 810                 815

Gly Val Phe Tyr Met Leu Leu Val Ala Met Gly Leu Ala Leu Leu Val
            820                 825                 830

Phe Ala Trp Glu His Leu Val Tyr Trp Lys Leu Arg His Ser Val Pro
            835                 840                 845

Asn Ser Ser Gln Leu Asp Phe Leu Leu Ala Phe Ser Arg Gly Ile Tyr
850                 855                 860

Ser Cys Phe Ser Gly Val Gln Ser Leu Ala Ser Pro Pro Arg Gln Ala
865                 870                 875                 880

Ser Pro Asp Leu Thr Ala Ser Ser Ala Gln Ala Ser Val Leu Lys Met
            885                 890                 895

Leu Gln Ala Ala Arg Asp Met Val Thr Thr Ala Gly Val Ser Ser Ser
            900                 905                 910

Leu Asp Arg Ala Thr Arg Thr Ile Glu Asn Trp Gly Gly Arg Arg
            915                 920                 925

Ala Pro Pro Pro Ser Pro Cys Pro Thr Pro Arg Ser Gly Pro Ser Pro
            930                 935                 940

Cys Leu Pro Thr Pro Asp Pro Pro Glu Pro Ser Pro Thr Gly Trp
945                 950                 955                 960

Gly Pro Pro Asp Gly Gly Arg Ala Ala Leu Val Arg Arg Ala Pro Gln
```

|   |   |   |
|---|---|---|
| 965 | 970 | 975 |

Pro Pro Gly Arg Pro Pro Thr Pro Gly Pro Pro Leu Ser Asp Val Ser
           980                  985                  990

Arg Val Ser Arg Arg Pro Ala Trp Glu Ala Arg Trp Pro Val Arg Thr
           995                  1000               1005

Gly His Cys Gly Arg His Leu Ser Ala Ser Glu Arg Pro Leu Ser
          1010                 1015               1020

Pro Ala Arg Cys His Tyr Ser Ser Phe Pro Arg Ala Asp Arg Ser
          1025                 1030               1035

Gly Arg Pro Phe Leu Pro Leu Phe Pro Glu Pro Pro Glu Leu Glu
          1040                 1045               1050

Asp Leu Pro Leu Leu Gly Pro Glu Gln Leu Ala Arg Arg Glu Ala
          1055                 1060               1065

Leu Leu His Ala Ala Trp Ala Arg Gly Ser Arg Pro Arg His Ala
          1070                 1075               1080

Ser Leu Pro Ser Ser Val Ala Glu Ala Phe Ala Arg Pro Ser Ser
          1085                 1090               1095

Leu Pro Ala Gly Cys Thr Gly Pro Ala Cys Ala Arg Pro Asp Gly
          1100                 1105               1110

His Ser Ala Cys Arg Arg Leu Ala Gln Ala Gln Ser Met Cys Leu
          1115                 1120               1125

Pro Ile Tyr Arg Glu Ala Cys Gln Glu Gly Glu Gln Ala Gly Ala
          1130                 1135               1140

Pro Ala Trp Gln His Arg Gln His Val Cys Leu His Ala His Ala
          1145                 1150               1155

His Leu Pro Phe Cys Trp Gly Ala Val Cys Pro His Leu Pro Pro
          1160                 1165               1170

Cys Ala Ser His Gly Ser Trp Leu Ser Gly Ala Trp Gly Pro Leu
          1175                 1180               1185

Gly His Arg Gly Arg Thr Leu Gly Leu Gly Thr Gly Tyr Arg Asp
          1190                 1195               1200

Ser Gly Gly Leu Asp Glu Ile Ser Ser Val Ala Arg Gly Thr Gln
          1205                 1210               1215

Gly Phe Pro Gly Pro Cys Thr Trp Arg Arg Ile Ser Ser Leu Glu
          1220                 1225               1230

Ser Glu Val
          1235

```
<210> SEQ ID NO 69
<211> LENGTH: 1725
<212> TYPE: DNA
<213> ORGANISM: Homo sapiens

<400> SEQUENCE: 69
gtcgacccac gcgtccggct ggaaggaact ggtctgctca cacttgctgg cttgcgcatc      60
aggactggct ttatctcctg actcacggtg caaaggtgca ctctgcgaac gttaagtccg     120
tccccagcgc ttggaatcct acggccccca cagccggatc ccctcagcct tccaggtcct     180
caactcccgc ggacgctgaa caatggcctc atgggggcta caggtaatgg gcatcgcgct     240
ggccgtcctg ggctggctgg ccgtcatgct gtgctgcgcg ctgcccatgt ggcgcgtgac     300
ggccttcatc ggcagcaaca ttgtcacctc gcagaccatc tgggagggcc tatggatgaa     360
ctgcgtggtg cagagcaccg gccagatgca gtgcaaggtg tacgactcgc tgctggcact     420
gccgcaggac ctgcaggcgg cccgcgccct cgtcatcatc agcatcatcg tggctgctct     480
```

```
gggcgtgctg ctgtccgtgg tgggggcaa gtgtaccaac tgcctggagg atgaaagcgc      540
caaggccaag accatgatcg tggcgggcgt ggtgttcctg ttggccggcc ttatggtgat      600
agtgccggtg tcctggacgg cccacaacat catccaagac ttctacaatc cgctggtggc      660
ctccgggcag aagcgggaga tgggtgcctc gctctacgtc ggctgggccg cctccggcct      720
gctgctcctt ggcggggggc tgctttgctg caactgtcca ccccgcacag acaagcctta      780
ctccgccaag tattctgctg cccgctctgc tgctgccagc aactacgtgt aaggtgccac      840
ggctccactc tgttcctctc tgctttgttc ttccctggac tgagctcagc gcaggctgtg      900
accccaggag ggccctgcca cgggccactg gctgctgggg actggggact gggcagagac      960
tgagccaggc aggaaggcag cagccttcag cctctctggc ccactcggac aacttcccaa     1020
ggccgcctcc tgctagcaag aacagagtcc accctcctct ggatattggg gagggacgga     1080
agtgacaggg tgtggtggtg gagtggggag ctggcttctg ctggccagga tggcttaacc     1140
ctgactttgg gatctgcctg catcggtgtt ggccactgtc cccatttaca ttttccccac     1200
tctgtctgcc tgcatctcct ctgttgcggg taggccttga tatcacctct gggactgtgc     1260
cttgctcacc gaaacccgcg cccaggagta tggctgaggc cttgcccacc cacctgcctg     1320
ggaagtgcag agtggatgga cgggtttaga ggggaggggc gaaggtgctg taaacaggtt     1380
tgggcagtgg tgggggaggg ggccagagag gcggctcagg ttgcccagct ctgtggcctc     1440
aggactctct gcctcacccg cttcagccca gggccctgg agactgatcc cctctgagtc      1500
ctctgcccct tccaaggaca ctaatgagcc tgggagggtg gcaggagga ggggacagct      1560 tcacccttgg aagtcctggg gttttcctc ttccttcttt gtggtttctg ttttgtaatt      1620
taagaagagc tattcatcac tgtaattatt attattttct acaataaatg ggacctgtgc     1680
acaggaggaa aaaaaaaaa aaaaaaaaa aaaaagggcg gccgc                        1725
```

<210> SEQ ID NO 70
<211> LENGTH: 206
<212> TYPE: PRT
<213> ORGANISM: Homo sapiens

<400> SEQUENCE: 70

```
Met Gly Leu Gln Val Met Gly Ile Ala Leu Ala Val Leu Gly Trp Leu
1               5                   10                  15

Ala Val Met Leu Cys Cys Ala Leu Pro Met Trp Arg Val Thr Ala Phe
                20                  25                  30

Ile Gly Ser Asn Ile Val Thr Ser Gln Thr Ile Trp Glu Gly Leu Trp
            35                  40                  45

Met Asn Cys Val Val Gln Ser Thr Gly Gln Met Gln Cys Lys Val Tyr
        50                  55                  60

Asp Ser Leu Leu Ala Leu Pro Gln Asp Leu Gln Ala Ala Arg Ala Leu
65                  70                  75                  80

Val Ile Ile Ser Ile Ile Val Ala Ala Leu Gly Val Leu Leu Ser Val
                85                  90                  95

Val Gly Gly Lys Cys Thr Asn Cys Leu Glu Asp Glu Ser Ala Lys Ala
                100                 105                 110

Lys Thr Met Ile Val Ala Gly Val Val Phe Leu Leu Ala Gly Leu Met
            115                 120                 125

Val Ile Val Pro Val Ser Trp Thr Ala His Asn Ile Ile Gln Asp Phe
        130                 135                 140

Tyr Asn Pro Leu Val Ala Ser Gly Gln Lys Arg Glu Met Gly Ala Ser
```

|     |     |     |     |     |     |     |     |     |     |     |     |     |     |     |     |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |
| Leu | Tyr | Val | Gly | Trp | Ala | Ala | Ser | Gly | Leu | Leu | Leu | Gly | Gly | Gly |     |
|     |     |     |     | 165 |     |     |     |     | 170 |     |     |     |     | 175 |     |
| Leu | Leu | Cys | Cys | Asn | Cys | Pro | Pro | Arg | Thr | Asp | Lys | Pro | Tyr | Ser | Ala |
|     |     |     |     | 180 |     |     |     |     | 185 |     |     |     |     | 190 |     |
| Lys | Tyr | Ser | Ala | Ala | Arg | Ser | Ala | Ala | Ala | Ser | Asn | Tyr | Val |     |     |
|     |     |     |     | 195 |     |     |     |     | 200 |     |     |     |     | 205 |     |

<210> SEQ ID NO 71
<211> LENGTH: 5410
<212> TYPE: DNA
<213> ORGANISM: Homo sapiens

<400> SEQUENCE: 71

| | | | | | |
|---|---|---|---|---|---|
| gtcgacccac | gcgtccggct | accgccgcgt | tctattctcc | gaagccggcg | accgccccac | 60 |
| ctcctccctc | cctcccgccc | gcttcctctg | cccacagcgc | cggccagagc | gagctagaca | 120 |
| agggcacgcg | gggcctcgcc | tagacccgag | aagactgcgg | gcgcgcgcaa | gcggcggcgt | 180 |
| ggaagctgtg | agcgcccca | tcccggaggt | ctccgccggc | tcccgggtga | atcagctccc | 240 |
| ggccgacttt | aggattcttc | tggattttaa | attttttctt | tttaaaaaaa | cttggacgga | 300 |
| taaaagatgt | gccatggcag | gatagcacca | aagagcacct | cagtgtttgc | cgtggcctcc | 360 |
| gtgggacatg | gagtgttcct | tccgctagtg | atcctttgca | ccctgcttgg | agacggactt | 420 |
| gcttccgtgt | gcccctacc | accggagcca | gagaatggtg | gctacatctg | ccaccccgg | 480 |
| ccctgcagag | acccctgac | agcaggcagt | gtcatcgaat | acctgtgtgc | tgaaggctac | 540 |
| atgttgaagg | gcgattacaa | atacctgacg | tgtaagaatg | gcgagtggaa | accagccatg | 600 |
| gagattagct | gccgtctcaa | cgaggataaa | gacacccaca | catcacttgg | ggtccccacg | 660 |
| ctgtctatag | tggcttctac | tgccagctcc | gtggcgctca | ttctcctcct | cgtggtgctg | 720 |
| tttgtgctgc | tgcagccaaa | gctgaagtct | ttccatcata | gcaggcgtga | ccaggggta | 780 |
| tctggggacc | aggtctccat | catggtggat | ggagtccagg | ttgcactacc | atcatacgag | 840 |
| gaggctgtat | atggcagttc | tggtcactgt | gtgccacctg | ctgacccag | agtacagatt | 900 |
| gtgctgtcag | aagggtctgg | gcccagtggg | aggagcgtgc | caaggagca | acagctgccg | 960 |
| gaccaagggg | cctgctcctc | tgcaggtgga | gaagatgagg | ccccaggcca | gtctggacta | 1020 |
| tgtgaagcct | gggctctcg | ggcctcgag | actgtgatgg | tgcatcaggc | aaccacctct | 1080 |
| tcctgggtgg | ccggctcagg | gaaccgccaa | ctggcacaca | agaaactgc | agattcagag | 1140 |
| aacagtgaca | tacaaagcct | tttatccctc | acgtcagagg | agtacacaga | tgatattcca | 1200 |
| ctgttgaaag | aagcatgagg | gcagcggcca | gcctttcctc | tctgcgaggt | tctctcagcc | 1260 |
| cttcctccct | ctccctgtgg | gattgagcac | cctgtactct | ccagccacct | tacctggata | 1320 |
| cctgagctgc | cacctgtgta | tctgtgtatc | tctgagggcc | ctataggccc | accttgctgg | 1380 |
| aaactcaagg | aagattctcg | ccatctgcct | gttggacagc | tggaggagct | ggctctttgc | 1440 |
| ctggccccgc | cttcccatct | gtcagagaca | tatttgaatg | tgctggatca | aaccctccct | 1500 |
| tttcctaagc | ctctgggtcc | cctccagcca | gctcttttggc | ggcagccccc | accagctcct | 1560 |
| gtgggcctga | gtgctgctgt | gtttacttgt | gccttttcccc | cacctgtcc | agtttccctg | 1620 |
| tcatgcagac | ttgttgctgt | ccacaagcct | tagtggctgc | actgctgccc | cctgccacac | 1680 |
| aggggggccgg | gcctggtct | gtcctgtttc | ctttgagggt | tgccctact | gccctttgca | 1740 |
| ggaacagatc | caggtgtgag | agctcttgag | tcaagagtgg | cagaagtggc | tctaattggg | 1800 |

```
gtgagagtgt agtccctggg cttgccctgg gttgaccctg gtggcatatt tccttggctg   1860
aggatggaag atttggagaa tcatgtccat gctggcccag gacccagcca tctggcccaa   1920
aggcacaagc tcctggccct gttgagttga gagtttccaa gaagcatcca gaagatccca   1980
agggagagaa ggaaaatggc tgataatgat tgtcttccta atatgcaagt tctcacttcc   2040
tacttccagc atcggccttc ctggccttgt cttttttttg tttccctgga gtataatggg   2100
aagttgcatg ctgcctcctg ggttttatcc cagatagctc tggctttctt gctgcccaca   2160
ggggcctggg gcaggaagga gacttgctga gatgccatgg agtgcccatc tggtcactgg   2220
cagtctgggc aggttgcccc tttctgggtt tgtggtgacg gaggggaggc cgagaggcac   2280
agaccaagtc cccgggtggc tgcaggcagc tccagcccgg tcctgaggat cctcctcacc   2340
atggtcacgt gccttagtaa ctgtgcccag gaagtggcct gctgcttgct gtgctgctgc   2400
ttttcctact tctgcccttc cctgccaccc ctcgcatgtc acagctgaca agcaattcct   2460
tgtcttccct ggcccctggg ggaagggct gagaaacagt ccgtgtgcac cccaaccta   2520
atggcctgag gtgggcagag gggtgtggag cagcctggag tacagggccc tggggaggga   2580
gcccactgat gaggggcgct ctcccatagc catgtgttga atgctaacta ggctggggtg   2640
gacgaactct gccaactgct gtcatcttag aagatagatg cagcagtaag gaatgtttgt   2700
tttgctttt tctgaaattt tctgaagcac tgtggctggg aaacttcgaa gcggaccctg   2760
tgctgcatgt ctgctcctcc cctgagcctg tctgcttggg ggtggtaaaa ataaaaatcc   2820
cagtttattt tcagtacctt acctaacagg gttggctcca ggcgtgggtg gcctagaaga   2880
tgaggggagt ggtcttctcc cagccttta ccctcttgcc tcctgcctcc gcgcttacac   2940
acgcactta ccacccggtc attccctggc ctcttgctgc cacttgtagt cttccttcct   3000
tcctctcagg gtaagggcag tgcctgctgt gcctgttggc cactcccaca cttcccctcc   3060
cccaggagcc ctcatctgct gtgctgagtc caggaaagca tagttaggta gggagctggt   3120
tggagaaggt gctagaacta gaaggcagat gagactagca tgggcccacc tggagggctg   3180
tccctaatgg ccccagtcgc cttacctcac ccacagcagt gcccttgtct tcctccaaaa   3240
cagaaagcag tgacaaaagg gggaggggtg gtaatctgaa gtctcactgc tgagccttca   3300
gcttttattt ttcactgttt caaaacccgc attctattct agaatggttt ttaaaatgga   3360
agatcttacc ttttctatc ttgttactct gggttttgt cccctaaga gattgcactt      3420
tttgtttggg gtttattcag ctgcatagat gaccagcttg atccctggtg aaatgaaaag   3480
ccttccttct cctgaagcct cttttccgccc tgccctccac taacaacact gaggagcaca   3540
agcccaggct tgcccacctg gtaggaaagg aagaaattag aacaatggga gccttggctc   3600
ccctctcgtc tcctcccctc cttcttgtca ctggctttga tgaggccac ttcccagagg   3660
ctcctgggcc tgtgagtgca ggagctcatt ctcccctcac tgctgaagtc tgtgacagct   3720
tcttcctcca gttatgtctt tcttccaaag caatttctta accatcagcc atgtgctgct   3780
atttctaggg cttctgggct ttgtcccta ctgagagatt agggactcca cagctgcctt    3840
gaggtagggt ctggctgaga gacaagggta gcagcaggtg gcaggctgtt aaaagacagg   3900
ctgcctgagg agcctggagc aggtggaaac aggtggaaga aaccggccac agccctgctt   3960
taccgggctc acctctaggg cattccagca agaggctgat gcaggagaat ggccagcacc   4020
aaaggacatt taaagagtt ttgggttttt tttgtttgtt tgttgttggt gtttgttttt    4080
tttttttttt tttttggca cacttgagct gactcagtgc aggtttaata tcctggtgac   4140
ttgcagtcac attctaatga ctttcaaggg ccagaatatg gtgaaaatca cttaaaatat   4200
```

```
ccgtcccttc catgccttag tttagcaggt aggctctatc ttttgccatt tctgtatttt      4260
atgtgctgtg ttcccgtttc actgggtatg aactgtgaaa tcgactgaat cctggccact      4320
ttatgagttt gtttggtttt ataaggcatt tcaatgtaca ttctataaat acaagcactc      4380
catttgcaaa cagatcttaa gctaatattt tctttcccat tcatcttgcc ctcccctcc       4440 tcccgccagc tttaaagttc agtggagaag ccagatggca attcagacaa aggtatactc      4500
ttcctgcttc atgggtggtg gcacgggaat agatagccct tagccctttc cctcccagtc      4560
ccagctgagc cctcagacca cttgcttccc acataacaat gtcgcctcca tttccgagga      4620
acatccttgc gtagagaatg aaatatgctg caatcatttc tgcatcctta ctcctcaccc      4680
ccaaagaaaa aaaaaaggcc tagcagggaa gcagcatgca ggcttcacag cttaatgcca      4740
aggacagcga gtgaggctgg gagcttctct tgggcctgct gggtctgtca gctctcggaa      4800
tagggacagt ccttactggt gccccaaggt gggacttgga gaatattttg cttggcatat      4860
gtttggtctg aatggtgtag ttgctggttc cctagagagg aaaaggtggc aggcccagct      4920
ttgctgggaa atggctctta atttccagtt gaaaccctag tagaattgtg aatgaaaacc      4980
tcaaggttga gcccctctgc caagcagcag agctagtaga aggggatgca ggggcaaagc      5040
actcagttgc caagcaagga ggagagatgt acgtgggctg tgtggcagtc cccacaccct      5100
gccctggctt cttcaggtta tcgcaccact atggaatcct ttgcagaatg gtactcatat      5160
aatggtttaa aacaacacat tcataattga ctctgtgcag gatgtcactc aatcagtttg      5220
ggtttgcttt atttttatttt atatatatat tttttggtat cctgtacatt gcagtgggtg      5280
tgaagatagt attttaatat ttgtacaaag tttaatttaa ttttaattgt tctatgtata      5340
taactgcatt tctaaataat taaaaaaaag ttcttatgaa aaaaaaaaaa aaaaaaaaa       5400 gggcggccgc                                                             5410
```

<210> SEQ ID NO 72
<211> LENGTH: 303
<212> TYPE: PRT
<213> ORGANISM: Homo sapiens

<400> SEQUENCE: 72

Met Cys His Gly Arg Ile Ala Pro Lys Ser Thr Ser Val Phe Ala Val
1               5                   10                  15

Ala Ser Val Gly His Gly Val Phe Leu Pro Leu Val Ile Leu Cys Thr
            20                  25                  30

Leu Leu Gly Asp Gly Leu Ala Ser Val Cys Pro Leu Pro Glu Pro
        35                  40                  45

Glu Asn Gly Gly Tyr Ile Cys His Pro Arg Pro Cys Arg Asp Pro Leu
    50                  55                  60

Thr Ala Gly Ser Val Ile Glu Tyr Leu Cys Ala Glu Gly Tyr Met Leu
65                  70                  75                  80

Lys Gly Asp Tyr Lys Tyr Leu Thr Cys Lys Asn Gly Glu Trp Lys Pro
                85                  90                  95

Ala Met Glu Ile Ser Cys Arg Leu Asn Glu Asp Lys Asp Thr His Thr
            100                 105                 110

Ser Leu Gly Val Pro Thr Leu Ser Ile Val Ala Ser Thr Ala Ser Ser
        115                 120                 125

Val Ala Leu Ile Leu Leu Leu Val Val Leu Phe Val Leu Leu Gln Pro
    130                 135                 140

Lys Leu Lys Ser Phe His His Ser Arg Arg Asp Gln Gly Val Ser Gly

```
                        145                 150                 155
                Asp Gln Val Ser Ile Met Val Asp Gly Val Gln Val Ala Leu Pro Ser
                                165                 170                 175

Tyr Glu Glu Ala Val Tyr Gly Ser Ser Gly His Cys Val Pro Pro Ala
                            180                 185                 190

Asp Pro Arg Val Gln Ile Val Leu Ser Glu Gly Ser Gly Pro Ser Gly
                        195                 200                 205

Arg Ser Val Pro Arg Glu Gln Gln Leu Pro Asp Gln Gly Ala Cys Ser
                210                 215                 220

Ser Ala Gly Gly Glu Asp Glu Ala Pro Gly Gln Ser Gly Leu Cys Glu
                225                 230                 235                 240

Ala Trp Gly Ser Arg Ala Ser Glu Thr Val Met Val His Gln Ala Thr
                                245                 250                 255

Thr Ser Ser Trp Val Ala Gly Ser Gly Asn Arg Gln Leu Ala His Lys
                            260                 265                 270

Glu Thr Ala Asp Ser Glu Asn Ser Asp Ile Gln Ser Leu Leu Ser Leu
                        275                 280                 285

Thr Ser Glu Glu Tyr Thr Asp Asp Ile Pro Leu Leu Lys Glu Ala
                    290                 295                 300

<210> SEQ ID NO 73
<211> LENGTH: 4392
<212> TYPE: DNA
<213> ORGANISM: Homo sapiens

<400> SEQUENCE: 73
gtcgacccac gcgtccgggc cgtccaggct agcggcggcc cgcaggcggc ggggagaaag      60
actctctcac ctggtcttgc ggctgtggcc accgccggcc aggggtgtgg agggcgtgct     120
gccggagacg tccgccgggc tctgcagttc cgccgggggt cgggcagcta tggagccgcg     180
gcccacggcg ccctcctccg cgcccccggg actggccggg gtcggggaga cgccgtcagc     240
cgctgcgctg gccgcagcca gggtggaact gcccggcacg gctgtgccct cggtgccgga     300
ggatgctgcg cccgcgagcc gggacggcgg cggggtccgc gatgagggcc ccgcggcggc     360
cggggacggg ctgggcagac ccttgggggcc caccccgagc cagagccgtt tccaggtgga     420 cctggttttcc gagaacgccg ggcgggccgc tgctgcggcg gcggcggcgg cggcggcagc     480
ggcggcggct ggtgctgggg cggggggccaa gcagacccccc gcggacgggg aagccagcgg     540
cgagagcgag ccggctaaag gcagcgagga agccaagggc cgcttccgcg tgaacttcgt     600
ggacccagct gcctcctcgt cggctgaaga cagcctgtca gatgctgccg gggtcggagt     660
cgacgggccc aacgtgagct tccagaacgg cggggacacg gtgctgagcg agggcagcag     720
cctgcactcc ggcggcggcg gcggcagtgg gcaccaccag cactactatt atgatatccca     780 caccaacacc tactacctgc gcaccttcgg ccacaacacc atggacgctg tgcccaggat     840
cgatcactac cggcacacag ccgcgcagct gggcgagaag ctgctccggc ctagcctggc     900
ggagctccac gacgagctgg aaaaggaacc ttttgaggat ggctttgcaa atgggaaga     960 aagtactcca accagagatg ctgtggtcac gtatactgca gaaagtaaag gagtcgtgaa    1020
gtttggctgg atcaagggtg tattagtacg ttgtatgtta aacatttggg gtgtgatgct    1080
tttcattaga ttgtcatgga ttgtgggtca agctggaata ggtctatcag tccttgtaat    1140
aatgatggcc actgttgtga caactatcac aggattgtct acttcagcaa tagcaactaa    1200
tggatttgta agaggaggag gagcatatta tttaatatct agaagtctag gccagaatt    1260
```

```
tggtggtgca attggtctaa tcttcgcctt tgccaacgct gttgcagttg ctatgtatgt    1320
ggttggattt gcagaaaccg tggtggagtt gcttaaggaa cattccatac ttatgataga    1380
tgaaatcaat gatatccgaa ttattggagc cattacagtc gtgattcttt taggtatctc    1440
agtagctgga atggagtggg aagcaaaagc tcagattgtt cttttggtga tcctacttct    1500
tgctattggt gatttcgtca taggaacatt tatcccactg gagagcaaga agccaaaagg    1560
gttttttggt tataaatctg aaatatttaa tgagaacttt gggcccgatt tcgagagga    1620 agagactttc ttttctgtat ttgccatctt ttttcctgct gcaactggta ttctggctgg    1680
agcaaatatc tcaggtgatc ttgcagatcc tcagtcagcc atacccaaag gaacactcct    1740
agccatttta attactacat tggtttacgt aggaattgca gtatctgtag gttcttgtgt    1800
tgttcgagat gccactggaa acgttaatga cactatcgta acagagctaa caaactgtac    1860
ttctgcagcc tgcaaattaa actttgattt ttcatcttgt gaaagcagtc cttgttccta    1920
tggcctaatg aacaacttcc aggtaatgag tatggtgtca ggatttacac cactaatttc    1980
tgcaggtata ttttcagcca ctctttcttc agcattagca tccctagtga gtgctcccaa    2040
aatatttcag gctctatgta aggacaacat ctacccagct ttccagatgt ttgctaaagg    2100
ttatgggaaa ataatgaac ctcttcgtgg ctacatctta acattcttaa ttgcacttgg    2160
attcatctta attgctgaac tgaatgttat tgcaccaatt atctcaaact tcttccttgc    2220
atcatatgca ttgatcaatt tttcagtatt ccatgcatca cttgcaaaat ctccaggatg    2280
gcgtcctgca ttcaaatact acaacatgtg gatatcactt cttggagcaa ttctttgttg    2340
catagtaatg ttcgtcatta actggtgggc tgcattgcta acatatgtga tagtccttgg    2400
gctgtatatt tatgttacct acaaaaaacc agatgtgaat tggggatcct ctacacaagc    2460
cctgacttac ctgaatgcac tgcagcattc aattcgtctt tctggagtgg aagaccacgt    2520
gaaaaacttt aggccacagt gtcttgttat gacaggtgct ccaaactcac gtccagcttt    2580
acttcatctt gttcatgatt tcacaaaaaa tgttggtttg atgatctgtg ccatgtaca    2640 tatgggtcct cgaagacaag ccatgaaaga gatgtccatc gatcaagcca aatatcagcg    2700
atggcttatt aagaacaaaa tgaaggcatt ttatgctcca gtacatgcag atgacttgag    2760
agaaggtgca cagtatttga tgcaggctgc tggtcttggt cgtatgaagc caaacacact    2820
tgtccttgga tttaagaaag attggttgca agcagatatg agggatgtgg atatgtatat    2880 aaacttatt catgatgctt ttgacataca atatggagta gtggttattc gcctaaaaga    2940
aggtctggat atatctcatc ttcaaggaca agaagaatta ttgtcatcac aagagaaatc    3000
tcctggcacc aaggatgtgg tagtaagtgt ggaatatagt aaaaagtccg atttagatac    3060
ttccaaacca ctcagtgaaa aaccaattac acacaaagtt gaggaagagg atggcaagac    3120
tgcaactcaa ccactgttga aaaagaatc caaaggccct attgtgcctt taaatgtagc    3180
tgaccaaaag cttcttgaag ctagtacaca gtttcagaaa aaacaaggaa agaatactat    3240
tgatgtctgg tggcttttg atgatggagg tttgaccctta ttgatacctt accttctgac    3300
gaccaagaaa aaatggaaag actgtaagat cagagtattc attggtggaa agataaacag    3360
aatagaccat gaccggagag cgatggctac tttgcttagc aagttccgga tagacttttc    3420
tgatatcatg gttctaggag atatcaatac caaaccaaag aaagaaaata ttatagcttt    3480
tgaggaaatc attgagccat acagacttca tgaagatgat aaagagcaag atattgcaga    3540
taaaatgaaa gaagatgaac catggcgaat aacagataat gagcttgaac tttataagac    3600
caagacatac cggcagatca ggttaaatga gttattaaag gaacattcaa gcacagctaa    3660
```

```
tattattgtc atgagtctcc cagttgcacg aaaaggtgct gtgtctagtg ctctctacat    3720
ggcatggtta gaagctctat ctaaggacct accaccaatc ctcctagttc gtgggaatca    3780
tcagagtgtc cttaccttct attcataaat gttctataca gtggacagcc ctccagaatg    3840
gtacttcagt gcctagtgta gtaactgaaa tcttcaatga cacattaaca tcacaatggc    3900
gaatggtgac ttttctttca cgatttcatt aatttgaaag cacacaggaa agttgctcca    3960
ttgataacgt gtatggagac ttcggtttta gtcaattcca tatctcaatc ttaatggtga    4020
ttcttctctg ttgaactgaa gtttgtgaga gtagttttcc tttgctactt gaatagcaat    4080
aaaagcgtgt taacttttg attgatgaaa gaagtacaaa aagcctttag ccttgaggtg     4140
ccttctgaaa ttaaccaaat ttcatccata tatcctcttt tataaactta tagaatgtca    4200
aamwwwrmmw wmaamwrwww wwawwwmwar wmwmwwmmam wwwaaaamaa aawraamact    4260
gcttgtcttc ttccattgac catttagtgt tgagtactgt atgtgttttg ttaattctat    4320
aaaggtatct gttagatatt aaaggtgaga attagggcag gttaatcaaa aatggggaag    4380
gggaaatggt aa                                                        4392

<210> SEQ ID NO 74
<211> LENGTH: 1212
<212> TYPE: PRT
<213> ORGANISM: Homo sapiens

<400> SEQUENCE: 74

Met Glu Pro Arg Pro Thr Ala Pro Ser Ser Gly Ala Pro Gly Leu Ala
1               5                   10                  15

Gly Val Gly Glu Thr Pro Ser Ala Ala Ala Leu Ala Ala Ala Arg Val
            20                  25                  30

Glu Leu Pro Gly Thr Ala Val Pro Ser Val Pro Glu Asp Ala Ala Pro
        35                  40                  45

Ala Ser Arg Asp Gly Gly Gly Val Arg Asp Glu Gly Pro Ala Ala Ala
    50                  55                  60

Gly Asp Gly Leu Gly Arg Pro Leu Gly Pro Thr Pro Ser Gln Ser Arg
65                  70                  75                  80

Phe Gln Val Asp Leu Val Ser Glu Asn Ala Gly Arg Ala Ala Ala Ala
                85                  90                  95

Ala Ala Ala Ala Ala Ala Ala Ala Ala Gly Ala Gly Ala Gly
            100                 105                 110

Ala Lys Gln Thr Pro Ala Asp Gly Glu Ala Ser Gly Glu Ser Glu Pro
        115                 120                 125

Ala Lys Gly Ser Glu Glu Ala Lys Gly Arg Phe Arg Val Asn Phe Val
    130                 135                 140

Asp Pro Ala Ala Ser Ser Ser Ala Glu Asp Leu Ser Asp Ala Ala
145                 150                 155                 160

Gly Val Gly Val Asp Gly Pro Asn Val Ser Phe Gln Asn Gly Gly Asp
                165                 170                 175

Thr Val Leu Ser Glu Gly Ser Ser Leu His Ser Gly Gly Gly Gly
            180                 185                 190

Ser Gly His His Gln His Tyr Tyr Tyr Asp Thr His Thr Asn Thr Tyr
        195                 200                 205

Tyr Leu Arg Thr Phe Gly His Asn Thr Met Asp Ala Val Pro Arg Ile
    210                 215                 220

Asp His Tyr Arg His Thr Ala Ala Gln Leu Gly Glu Lys Leu Leu Arg
225                 230                 235                 240
```

```
Pro Ser Leu Ala Glu Leu His Asp Glu Leu Glu Lys Glu Pro Phe Glu
            245                 250                 255

Asp Gly Phe Ala Asn Gly Glu Ser Thr Pro Thr Arg Asp Ala Val
            260                 265                 270

Val Thr Tyr Thr Ala Glu Ser Lys Gly Val Val Lys Phe Gly Trp Ile
            275                 280                 285

Lys Gly Val Leu Val Arg Cys Met Leu Asn Ile Trp Gly Val Met Leu
        290                 295                 300

Phe Ile Arg Leu Ser Trp Ile Val Gly Gln Ala Gly Ile Gly Leu Ser
305                 310                 315                 320

Val Leu Val Ile Met Met Ala Thr Val Val Thr Thr Ile Thr Gly Leu
                325                 330                 335

Ser Thr Ser Ala Ile Ala Thr Asn Gly Phe Val Arg Gly Gly Gly Ala
                340                 345                 350

Tyr Tyr Leu Ile Ser Arg Ser Leu Gly Pro Glu Phe Gly Gly Ala Ile
            355                 360                 365

Gly Leu Ile Phe Ala Phe Ala Asn Ala Val Ala Val Ala Met Tyr Val
        370                 375                 380

Val Gly Phe Ala Glu Thr Val Val Glu Leu Leu Lys Glu His Ser Ile
385                 390                 395                 400

Leu Met Ile Asp Glu Ile Asn Asp Ile Arg Ile Ile Gly Ala Ile Thr
                405                 410                 415

Val Val Ile Leu Leu Gly Ile Ser Val Ala Gly Met Glu Trp Glu Ala
                420                 425                 430

Lys Ala Gln Ile Val Leu Leu Val Ile Leu Leu Leu Ala Ile Gly Asp
            435                 440                 445

Phe Val Ile Gly Thr Phe Ile Pro Leu Glu Ser Lys Lys Pro Lys Gly
            450                 455                 460

Phe Phe Gly Tyr Lys Ser Glu Ile Phe Asn Glu Asn Phe Gly Pro Asp
465                 470                 475                 480

Phe Arg Glu Glu Glu Thr Phe Phe Ser Val Phe Ala Ile Phe Phe Pro
                485                 490                 495

Ala Ala Thr Gly Ile Leu Ala Gly Ala Asn Ile Ser Gly Asp Leu Ala
            500                 505                 510

Asp Pro Gln Ser Ala Ile Pro Lys Gly Thr Leu Leu Ala Ile Leu Ile
            515                 520                 525

Thr Thr Leu Val Tyr Val Gly Ile Ala Val Ser Val Gly Ser Cys Val
530                 535                 540

Val Arg Asp Ala Thr Gly Asn Val Asn Asp Thr Ile Val Thr Glu Leu
545                 550                 555                 560

Thr Asn Cys Thr Ser Ala Ala Cys Lys Leu Asn Phe Asp Phe Ser Ser
                565                 570                 575

Cys Glu Ser Ser Pro Cys Ser Tyr Gly Leu Met Asn Asn Phe Gln Val
            580                 585                 590

Met Ser Met Val Ser Gly Phe Thr Pro Leu Ile Ser Ala Gly Ile Phe
        595                 600                 605

Ser Ala Thr Leu Ser Ser Ala Leu Ala Ser Leu Val Ser Ala Pro Lys
            610                 615                 620

Ile Phe Gln Ala Leu Cys Lys Asp Asn Ile Tyr Pro Ala Phe Gln Met
625                 630                 635                 640

Phe Ala Lys Gly Tyr Gly Lys Asn Asn Glu Pro Leu Arg Gly Tyr Ile
                645                 650                 655
```

```
Leu Thr Phe Leu Ile Ala Leu Gly Phe Ile Leu Ile Ala Glu Leu Asn
            660                 665                 670

Val Ile Ala Pro Ile Ile Ser Asn Phe Phe Leu Ala Ser Tyr Ala Leu
            675                 680                 685

Ile Asn Phe Ser Val Phe His Ala Ser Leu Ala Lys Ser Pro Gly Trp
            690                 695                 700

Arg Pro Ala Phe Lys Tyr Tyr Asn Met Trp Ile Ser Leu Leu Gly Ala
705                 710                 715                 720

Ile Leu Cys Cys Ile Val Met Phe Val Ile Asn Trp Trp Ala Ala Leu
                725                 730                 735

Leu Thr Tyr Val Ile Val Leu Gly Leu Tyr Ile Tyr Val Thr Tyr Lys
            740                 745                 750

Lys Pro Asp Val Asn Trp Gly Ser Ser Thr Gln Ala Leu Thr Tyr Leu
            755                 760                 765

Asn Ala Leu Gln His Ser Ile Arg Leu Ser Gly Val Glu Asp His Val
            770                 775                 780

Lys Asn Phe Arg Pro Gln Cys Leu Val Met Thr Gly Ala Pro Asn Ser
785                 790                 795                 800

Arg Pro Ala Leu Leu His Leu Val His Asp Phe Thr Lys Asn Val Gly
            805                 810                 815

Leu Met Ile Cys Gly His Val His Met Gly Pro Arg Arg Gln Ala Met
            820                 825                 830

Lys Glu Met Ser Ile Asp Gln Ala Lys Tyr Gln Arg Trp Leu Ile Lys
            835                 840                 845

Asn Lys Met Lys Ala Phe Tyr Ala Pro Val His Ala Asp Asp Leu Arg
850                 855                 860

Glu Gly Ala Gln Tyr Leu Met Gln Ala Ala Gly Leu Gly Arg Met Lys
865                 870                 875                 880

Pro Asn Thr Leu Val Leu Gly Phe Lys Lys Asp Trp Leu Gln Ala Asp
            885                 890                 895

Met Arg Asp Val Asp Met Tyr Ile Asn Leu Phe His Ala Phe Asp
            900                 905                 910

Ile Gln Tyr Gly Val Val Val Ile Arg Leu Lys Glu Gly Leu Asp Ile
            915                 920                 925

Ser His Leu Gln Gly Gln Glu Glu Leu Leu Ser Ser Gln Glu Lys Ser
            930                 935                 940

Pro Gly Thr Lys Asp Val Val Ser Val Glu Tyr Ser Lys Lys Ser
945                 950                 955                 960

Asp Leu Asp Thr Ser Lys Pro Leu Ser Glu Lys Pro Ile Thr His Lys
            965                 970                 975

Val Glu Glu Glu Asp Gly Lys Thr Ala Thr Gln Pro Leu Leu Lys Lys
            980                 985                 990

Glu Ser Lys Gly Pro Ile Val Pro Leu Asn Val Ala Asp Gln Lys Leu
            995                 1000                1005

Leu Glu Ala Ser Thr Gln Phe Gln Lys Lys Gln Gly Lys Asn Thr
            1010                1015                1020

Ile Asp Val Trp Trp Leu Phe Asp Asp Gly Gly Leu Thr Leu Leu
            1025                1030                1035

Ile Pro Tyr Leu Leu Thr Thr Lys Lys Lys Trp Lys Asp Cys Lys
            1040                1045                1050

Ile Arg Val Phe Ile Gly Gly Lys Ile Asn Arg Ile Asp His Asp
            1055                1060                1065

Arg Arg Ala Met Ala Thr Leu Leu Ser Lys Phe Arg Ile Asp Phe
```

```
        1070                1075                 1080

Ser Asp  Ile Met Val Leu Gly  Asp Ile Asn Thr  Lys Pro Lys Lys
    1085                1090                1095

Glu Asn  Ile Ile Ala Phe Glu  Glu Ile Ile Glu  Pro Tyr Arg Leu
    1100                1105                1110

His Glu  Asp Asp Lys Glu Gln  Asp Ile Ala Asp  Lys Met Lys Glu
    1115                1120                1125

Asp Glu  Pro Trp Arg Ile Thr  Asp Asn Glu Leu  Glu Leu Tyr Lys
    1130                1135                1140

Thr Lys  Thr Tyr Arg Gln Ile  Arg Leu Asn Glu  Leu Leu Lys Glu
    1145                1150                1155

His Ser  Ser Thr Ala Asn Ile  Ile Val Met Ser  Leu Pro Val Ala
    1160                1165                1170

Arg Lys  Gly Ala Val Ser Ser  Ala Leu Tyr Met  Ala Trp Leu Glu
    1175                1180                1185

Ala Leu  Ser Lys Asp Leu Pro  Pro Ile Leu Leu  Val Arg Gly Asn
    1190                1195                1200

His Gln  Ser Val Leu Thr Phe  Tyr Ser
    1205                1210
```

<210> SEQ ID NO 75
<211> LENGTH: 2778
<212> TYPE: DNA
<213> ORGANISM: Homo sapiens

<400> SEQUENCE: 75

```
gtcgacccac gcgtccggca agaagctgac gggtcgcctc atgctggccg tgggaggagc      60
agtgcttggc tccctgcagt ttggctacaa cactggagtc atcaatgccc ccagaaggt     120
gatcgaggag ttctacaacc agacatgggt ccaccgctat ggggagagca tcctgcccac     180
cacgctcacc acgctctggt ccctctcagt ggccatcttt tctgttgggg gcatgattgg     240
ctccttctct gtgggccttt tcgttaaccg cttttggccgg cggaattcaa tgctgatgat     300
gaacctgctg gccttcgtgt ccgccgtgct catgggcttc tcgaaactgg gcaagtcctt     360
tgagatgctg atcctgggcc gcttcatcat cggtgtgtac tgcggcctga ccacaggctt     420
cgtgcccatg tatgtgggtg aagtgtcacc cacagccctt cgtgggggcc tgggcaccct     480
gcaccagctg ggcatcgtcg tcggcatcct catcgcccag tgttcggcc tggactccat     540
catgggcaac aaggacctgt ggcccctgct gctgagcatc atcttcatcc cggccctgct     600
gcagtgcatc gtgctgccct ctgccccga gagtccccgc ttcctgctca tcaaccgcaa     660
cgaggagaac cgggccaaga gtgtgctaaa gaagctgcgc gggacagctg acgtgaccca     720
tgacctgcag gagatgaagg aagagagtcg gcagatgatg cggagaagaa aggtcaccat     780
cctggagctg ttccgctccc ccgcctaccg ccagcccatc ctcatcgctg tggtgctgca     840
gctgtcccag cagctgtctg gcatcaacgc tgtcttctat tactccacga gcatcttcga     900
gaaggcgggg gtgcagcagc ctgtgtatgc caccattggc tccggtatcg tcaacacggc     960
cttcactgtc gtgtcgctgt ttgtggtgga gcgagcaggc cggcggaccc tgcacctcat    1020
aggcctcgct ggcatggcgg gttgtgccat actcatgacc atcgcgctag cactgctgga    1080
gcagctaccc tggatgtcct atctgagcat cgtggccatc tttggctttg tggccttctt    1140
tgaagtgggt cctggcccca tcccatggtt catcgtggct gaactcttca gccagggtcc    1200
acgtccagct gccattgccg ttgcaggctt ctccaactgg acctcaaatt tcattgtggg    1260
```

| | | | | | |
|---|---|---|---|---|---|
| catgtgcttc | cagtatgtgg | agcaactgtg | tggtccctac | gtcttcatca | tcttcactgt | 1320
| gctcctggtt | ctgttcttca | tcttcaccta | cttcaaagtt | cctgagacta | aaggccggac | 1380
| cttcgatgag | atcgcttccg | gcttccggca | gggggagcc | agccaaagtg | acaagacacc | 1440
| cgaggagctt | ttccatcccc | tggggctga | ttcccaagtg | tgagtcgccc | cagatcacca | 1500
| gcccggcctg | ctcccagcag | ccctaaggat | ctctcaggag | cacaggcagc | tggatgagac | 1560
| ttccaaacct | gacagatgtc | agccgagccg | ggcctgggc | tcctttctcc | agccagcaat | 1620
| gatgtccaga | agaatattca | ggacttaacg | gctccaggat | tttaacaaaa | gcaagactgt | 1680
| tgctcaaatc | tattcagaca | agcaacaggt | tttataattt | ttttattact | gattttgtta | 1740
| tttttatatc | agcctgagtc | tcctgtgccc | acatcccagg | cttcaccctg | aatggttcca | 1800
| tgcctgaggg | tggagactaa | gccctgtcga | gacacttgcc | ttcttcaccc | agctaatctg | 1860
| tagggctgga | cctatgtcct | aaggacacac | taatcgaact | atgaactaca | aagcttctat | 1920
| cccaggaggt | ggctatggcc | acccgttctg | ctggcctgga | tctccccact | ctagggtca | 1980
| ggctccatta | ggatttgccc | cttccatct | cttcctaccc | aaccactcaa | attaatcttt | 2040
| ctttacctga | gaccagttgg | gagcactgga | gtgcagggag | gagagggaa | gggccagtct | 2100
| gggctgccgg | gttctagtct | cctttgcact | gagggccaca | ctattaccat | gagaagaggg | 2160
| cctgtgggag | cctgcaaact | cactgctcaa | gaagacatgg | agactcctgc | cctgttgtgt | 2220
| atagatgcaa | gatatttata | tatattttg | gttgtcaata | ttaaatacag | acactaagtt | 2280
| atagtatatc | tggacaagcc | aacttgtaaa | tacaccacct | cactcctgtt | acttacctaa | 2340
| acagatataa | atggctggtt | tttagaaaca | tggttttgaa | atgcttgtgg | attgagggta | 2400
| ggaggtttgg | atgggagtga | gacagaagta | agtggggttg | caaccactgc | aacggcttag | 2460
| acttcgactc | aggatccagt | cccttacacg | tacctctcat | cagtgtcctc | ttgctcaaaa | 2520
| atctgtttga | tccctgttac | ccagagaata | tatacattct | ttatcttgac | attcaaggca | 2580
| tttctatcac | atatttgata | gttggtgttc | aaaaaaacac | tagttttgtg | ccagccgtga | 2640
| tgctcaggct | tgaaatgcat | tattttgaat | gtgaagtaaa | tactgtacct | ttattggaca | 2700
| ggctcaaaaa | aaaaaaaaaa | aaaaaaaaaa | aaaaaaaaaa | aaaaaaaaaa | aaaaaaaaaa | 2760
| aaaaaaaagg | gcggccgc | | | | | 2778

<210> SEQ ID NO 76
<211> LENGTH: 480
<212> TYPE: PRT
<213> ORGANISM: Homo sapiens

<400> SEQUENCE: 76

Met Leu Ala Val Gly Gly Ala Val Leu Gly Ser Leu Gln Phe Gly Tyr
1               5                   10                  15

Asn Thr Gly Val Ile Asn Ala Pro Gln Lys Val Ile Glu Glu Phe Tyr
            20                  25                  30

Asn Gln Thr Trp Val His Arg Tyr Gly Glu Ser Ile Leu Pro Thr Thr
        35                  40                  45

Leu Thr Thr Leu Trp Ser Leu Ser Val Ala Ile Phe Ser Val Gly Gly
    50                  55                  60

Met Ile Gly Ser Phe Ser Val Gly Leu Phe Val Asn Arg Phe Gly Arg
65                  70                  75                  80

Arg Asn Ser Met Leu Met Met Asn Leu Leu Ala Phe Val Ser Ala Val
                85                  90                  95

Leu Met Gly Phe Ser Lys Leu Gly Lys Ser Phe Glu Met Leu Ile Leu

```
                100                 105                 110
Gly Arg Phe Ile Ile Gly Val Tyr Cys Gly Leu Thr Thr Gly Phe Val
            115                 120                 125
Pro Met Tyr Val Gly Glu Val Ser Pro Thr Ala Leu Arg Gly Ala Leu
130                 135                 140
Gly Thr Leu His Gln Leu Gly Ile Val Val Gly Ile Leu Ile Ala Gln
145                 150                 155                 160
Val Phe Gly Leu Asp Ser Ile Met Gly Asn Lys Asp Leu Trp Pro Leu
                165                 170                 175
Leu Leu Ser Ile Ile Phe Ile Pro Ala Leu Leu Gln Cys Ile Val Leu
            180                 185                 190
Pro Phe Cys Pro Glu Ser Pro Arg Phe Leu Leu Ile Asn Arg Asn Glu
        195                 200                 205
Glu Asn Arg Ala Lys Ser Val Leu Lys Lys Leu Arg Gly Thr Ala Asp
    210                 215                 220
Val Thr His Asp Leu Gln Glu Met Lys Glu Glu Ser Arg Gln Met Met
225                 230                 235                 240
Arg Glu Lys Lys Val Thr Ile Leu Glu Leu Phe Arg Ser Pro Ala Tyr
                245                 250                 255
Arg Gln Pro Ile Leu Ile Ala Val Val Leu Gln Leu Ser Gln Gln Leu
            260                 265                 270
Ser Gly Ile Asn Ala Val Phe Tyr Tyr Ser Thr Ser Ile Phe Glu Lys
        275                 280                 285
Ala Gly Val Gln Gln Pro Val Tyr Ala Thr Ile Gly Ser Gly Ile Val
    290                 295                 300
Asn Thr Ala Phe Thr Val Val Ser Leu Phe Val Val Glu Arg Ala Gly
305                 310                 315                 320
Arg Arg Thr Leu His Leu Ile Gly Leu Ala Gly Met Ala Gly Cys Ala
                325                 330                 335
Ile Leu Met Thr Ile Ala Leu Ala Leu Leu Glu Gln Leu Pro Trp Met
            340                 345                 350
Ser Tyr Leu Ser Ile Val Ala Ile Phe Gly Phe Val Ala Phe Phe Glu
        355                 360                 365
Val Gly Pro Gly Pro Ile Pro Trp Phe Ile Val Ala Glu Leu Phe Ser
    370                 375                 380
Gln Gly Pro Arg Pro Ala Ala Ile Ala Val Ala Gly Phe Ser Asn Trp
385                 390                 395                 400
Thr Ser Asn Phe Ile Val Gly Met Cys Phe Gln Tyr Val Glu Gln Leu
                405                 410                 415
Cys Gly Pro Tyr Val Phe Ile Ile Phe Thr Val Leu Leu Val Leu Phe
            420                 425                 430
Phe Ile Phe Thr Tyr Phe Lys Val Pro Glu Thr Lys Gly Arg Thr Phe
        435                 440                 445
Asp Glu Ile Ala Ser Gly Phe Arg Gln Gly Gly Ala Ser Gln Ser Asp
    450                 455                 460
Lys Thr Pro Glu Glu Leu Phe His Pro Leu Gly Ala Asp Ser Gln Val
465                 470                 475                 480

<210> SEQ ID NO 77
<211> LENGTH: 2473
<212> TYPE: DNA
<213> ORGANISM: Homo sapiens

<400> SEQUENCE: 77
```

```
gtcgacccac gcgtccgcgc gaggcgcggg gagcctggga ccaggagcga gagccgccta    60
cctgcagccg ccgcccacgg cacggcagcc accatggcgc tcctgctgtg cttcgtgctc   120
ctgtgcggag tagtggattt cgccagaagt ttgagtatca ctactcctga agagatgatt   180
gaaaaagcca aagggaaac tgcctatctg ccatgcaaat ttacgcttag tcccgaagac   240
cagggaccgc tggacatcga gtggctgata tcaccagctg ataatcagaa ggtggatcaa   300
gtgattattt tatattctgg agacaaaatt tatgatgact actatccaga tctgaaaggc   360
cgagtacatt ttacgagtaa tgatctcaaa tctggtgatg catcaataaa tgtaacgaat   420
ttacaactgt cagatattgg cacatatcag tgcaaagtga aaaaagctcc tggtgttgca   480
aataagaaga ttcatctggt agttcttgtt aagccttcag gtgcgagatg ttacgttgat   540
ggatctgaag aaattggaag tgactttaag ataaaatgtg aaccaaaaga aggttcactt   600
ccattacagt atgagtggca aaaattgtct gactcacaga aaatgcccac ttcatggtta   660
gcagaaatga cttcatctgt tatatctgta aaaaatgcct cttctgagta ctctgggaca   720
tacagctgta cagtcagaaa cagagtgggc tctgatcagt gcctgttgcg tctaaacgtt   780
gtccctcctt caaataaagc tggactaatt gcaggagcca ttataggaac tttgcttgct   840
ctagcgctca ttggtcttat catcttttgc tgtcgtaaaa agcgcagaga agaaaaatat   900
gaaaaggaag ttcatcacga tatcagggaa gatgtgccac ctccaaagag ccgtacgtcc   960
actgccagaa gctacatcgg cagtaatcat tcatccctgg ggtccatgtc tccttccaac  1020
atggaaggat attccaagac tcagtataac caagtaccaa gtgaagactt tgaacgcact  1080
cctcagagtc cgactctccc acctgctaag gtagctgccc ctaatctaag tcgaatgggt  1140
gcgattcctg tgatgattcc agcacagagc aaggatgggt ctatagtata gagcctccat  1200
atgtctcatc tgtgctctcc gtgttccttt ccttttttg atatatgaaa acctattctg  1260
gtctaaattg tgttactagc ctcaaaatac atcaaaaaat aagttaatca ggaactgtac  1320
ggaatatatt tttaaaaatt tttgtttggt tatatcaaaa tagttacagg cactaaagtt  1380
agtaaagaaa agtttaccat ctgaaaaagc tggattttct ttaagaggtt gattataaag  1440
ttttctaaat ttatcagtac ctaagtaaga tgtagcgctt tgaatatgaa atcataggtg  1500
aagacatggg tgaacttact tgcataccaa gttgatactt gaataaccat ctgaaagtgg  1560
tacttgatca ttttaccat tattttagg atgtgtattt catttattta tggcccacca  1620
gtctccccca aattagtaca gaaatatcca tgacaaaatt acttacgtat gtttgtactt  1680
ggttttacag ctcctttgaa aactctgtgt ttggaatatc tctaaaaaca tagaaaacac  1740
tacagtggtt tagaaattac taattttact tctaagtcat tcataaacct tgtctatgaa  1800
atgacttctt aaatatttag ttgatagact gctacaggta atagggactt agcaagctct  1860
tttatatgct aaaggagcat ctatcagatt aagttagaac atttgctgtc agccacatat  1920
tgagatgaca ctaggtgcaa tagcagggat agattttgtt ggtgagtagt ctcatgcctt  1980
gagatctgtg gtggtcttca aaatggtggc cagccagatc aaggatgtag tatctcatag  2040
ttcccaggtg atatttttct tattagaaaa atattataac tcatttgttg tttgacactt  2100
atagattgaa atttcctaat ttattctaaa ttttaagtgg ttctttggtt ccagtgcttt  2160
atgttgttgt tgtttttgga tggtgttaca tattatatgt tctagaaaca tgtaatccta  2220 aatttacccct cttgaatata atccctggat gatattttt atcataaatg cagaataatc  2280
aaatacattt taagcaagtt aagtgtcctc catcaattct gtattccaga cttggggaga  2340
tgtacagttg ctgttgtgtg atcaaacatg tctctgtgta gttccagcaa atcaagctga  2400
```

```
gctttgaaaa agtttgtctt agttttgtga aggtgattta ttcttaaaaa aaaaaaaaaa    2460
aaagggcggc cgc                                                      2473
```

<210> SEQ ID NO 78
<211> LENGTH: 365
<212> TYPE: PRT
<213> ORGANISM: Homo sapiens

<400> SEQUENCE: 78

```
Met Ala Leu Leu Leu Cys Phe Val Leu Leu Cys Gly Val Val Asp Phe
1               5                   10                  15

Ala Arg Ser Leu Ser Ile Thr Thr Pro Glu Glu Met Ile Glu Lys Ala
            20                  25                  30

Lys Gly Glu Thr Ala Tyr Leu Pro Cys Lys Phe Thr Leu Ser Pro Glu
        35                  40                  45

Asp Gln Gly Pro Leu Asp Ile Glu Trp Leu Ile Ser Pro Ala Asp Asn
    50                  55                  60

Gln Lys Val Asp Gln Val Ile Ile Leu Tyr Ser Gly Asp Lys Ile Tyr
65                  70                  75                  80

Asp Asp Tyr Tyr Pro Asp Leu Lys Gly Arg Val His Phe Thr Ser Asn
                85                  90                  95

Asp Leu Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
        115                 120                 125

Ala Asn Lys Lys Ile His Leu Val Val Leu Val Lys Pro Ser Gly Ala
    130                 135                 140

Arg Cys Tyr Val Asp Gly Ser Glu Glu Ile Gly Ser Asp Phe Lys Ile
145                 150                 155                 160

Lys Cys Glu Pro Lys Glu Gly Ser Leu Pro Leu Gln Tyr Glu Trp Gln
                165                 170                 175

Lys Leu Ser Asp Ser Gln Lys Met Pro Thr Ser Trp Leu Ala Glu Met
            180                 185                 190

Thr Ser Ser Val Ile Ser Val Lys Asn Ala Ser Ser Glu Tyr Ser Gly
        195                 200                 205

Thr Tyr Ser Cys Thr Val Arg Asn Arg Val Gly Ser Asp Gln Cys Leu
    210                 215                 220

Leu Arg Leu Asn Val Val Pro Pro Ser Asn Lys Ala Gly Leu Ile Ala
225                 230                 235                 240

Gly Ala Ile Ile Gly Thr Leu Leu Ala Leu Ala Leu Ile Gly Leu Ile
                245                 250                 255

Ile Phe Cys Cys Arg Lys Lys Arg Arg Glu Glu Lys Tyr Glu Lys Glu
            260                 265                 270

Val His His Asp Ile Arg Glu Asp Val Pro Pro Lys Ser Arg Thr
        275                 280                 285

Ser Thr Ala Arg Ser Tyr Ile Gly Ser Asn His Ser Ser Leu Gly Ser
    290                 295                 300

Met Ser Pro Ser Asn Met Glu Gly Tyr Ser Lys Thr Gln Tyr Asn Gln
305                 310                 315                 320

Val Pro Ser Glu Asp Phe Glu Arg Thr Pro Gln Ser Pro Thr Leu Pro
                325                 330                 335

Pro Ala Lys Val Ala Ala Pro Asn Leu Ser Arg Met Gly Ala Ile Pro
            340                 345                 350
```

Val Met Ile Pro Ala Gln Ser Lys Asp Gly Ser Ile Val
            355                 360                 365

<210> SEQ ID NO 79
<211> LENGTH: 1588
<212> TYPE: DNA
<213> ORGANISM: Homo sapiens

<400> SEQUENCE: 79

| | | | | | |
|---|---|---|---|---|---|
| gtcgacccac | gcgtccggca | gcagcagcca | ggtgtggcag | tgacagggag | gtgtgaatga | 60 |
| ggcaggatga | actggacagg | tttgtacacc | ttgctcagtg | gcgtgaaccg | gcattctact | 120 |
| gccattggcc | gagtatggct | ctcggtcatc | ttcatcttca | gaatcatggt | gctggtggtg | 180 |
| gctgcagaga | gtgtgtgggg | tgatgagaaa | tcttccttca | tctgcaacac | actccagcct | 240 |
| ggctgcaaca | gcgtttgcta | tgaccaattc | ttccccatct | cccatgtgcg | gctgtggtcc | 300 |
| ctgcagctca | tcctagtttc | caccccagct | ctcctcgtgg | ccatgcacgt | ggctcaccag | 360 |
| caacacatag | agaagaaaat | gctacggctt | gagggccatg | ggaccccct | acacctggag | 420 |
| gaggtgaaga | ggcacaaggt | ccacatctca | gggacactgt | ggtggaccta | tgtcatcagc | 480 |
| gtggtgttcc | ggctgttgtt | tgaggccgtc | ttcatgtatg | tcttttatct | gctctaccct | 540 |
| ggctatgcca | tggtgcggct | ggtcaagtgc | gacgtctacc | cctgccccaa | cacagtggac | 600 |
| tgcttcgtgt | cccgccccac | cgagaaaacc | gtcttcaccg | tcttcatgct | agctgccttct | 660 |
| ggcatctgca | tcatcctcaa | tgtggccgag | gtggtgtacc | tcatcatccg | ggcctgtgcc | 720 |
| cgccgagccc | agcgccgctc | caatccacct | tcccgcaagg | gctcgggctt | cggccaccgc | 780 |
| ctctcacctg | aatacaagca | gaatgagatc | aacaagctgc | tgagtgagca | ggatggctcc | 840 |
| ctgaaagaca | tactgcgccg | cagccctggc | accggggctg | ggctggctga | aaagagcgac | 900 |
| cgctgctcgg | cctgctgatg | ccacatacca | ggcaacctcc | catcccaccc | ccgaccctgc | 960 |
| cctgggcgag | cccctccttc | tcccctgccg | gtgcacaggc | ctctgcctgc | tggggattac | 1020 |
| tcgatcaaaa | ccttccttcc | ctggctactt | cccttcctcc | cggggccttc | cttttgagga | 1080 |
| gctgaggggg | tggggagcta | gaggccacct | atgccagtgc | tcaaggttac | tgggagtgtg | 1140 |
| ggctgccctt | gttgcctgca | cccttccctc | ttccctctcc | ctctctctgg | gaccactggg | 1200 |
| tacaagagat | gggatgctcc | gacagcgtct | ccaattatga | aactaatctt | aaccctgtgc | 1260 |
| tgtcagatac | cctgtttctg | gagtcacatc | agtgaggagg | gatgtgggta | agaggagcag | 1320 |
| agggcagggg | tgctgtggac | atgtgggtgg | agaagggagg | gtggccagca | ctagtaaagg | 1380 |
| aggaatagtg | cttgctggcc | acaaggaaaa | ggaggaggtg | tctggggtga | gggagttagg | 1440 |
| gagagagaag | caggcagata | agttggagca | ggggttggtc | aaggccacct | ctgcctctag | 1500 |
| tccccaaggc | ctctctctgc | ctgaaatgtt | acacattaaa | caggattta | cagtaaatga | 1560 |
| aaaaaaaaaa | aaaaaaaagg | gcggccgc | | | | 1588 |

<210> SEQ ID NO 80
<211> LENGTH: 283
<212> TYPE: PRT
<213> ORGANISM: Homo sapiens

<400> SEQUENCE: 80

Met Asn Trp Thr Gly Leu Tyr Thr Leu Leu Ser Gly Val Asn Arg His
1               5                   10                  15

Ser Thr Ala Ile Gly Arg Val Trp Leu Ser Val Ile Phe Ile Phe Arg
            20                  25                  30

```
Ile Met Val Leu Val Ala Ala Glu Ser Val Trp Gly Asp Glu Lys
         35                  40                  45

Ser Ser Phe Ile Cys Asn Thr Leu Gln Pro Gly Cys Asn Ser Val Cys
 50                  55                  60

Tyr Asp Gln Phe Phe Pro Ile Ser His Val Arg Leu Trp Ser Leu Gln
 65                  70                  75                  80

Leu Ile Leu Val Ser Thr Pro Ala Leu Leu Val Ala Met His Val Ala
                 85                  90                  95

His Gln Gln His Ile Glu Lys Lys Met Leu Arg Leu Glu Gly His Gly
                100                 105                 110

Asp Pro Leu His Leu Glu Glu Val Lys Arg His Lys Val His Ile Ser
            115                 120                 125

Gly Thr Leu Trp Trp Thr Tyr Val Ile Ser Val Phe Arg Leu Leu
            130                 135                 140

Phe Glu Ala Val Phe Met Tyr Val Phe Tyr Leu Leu Tyr Pro Gly Tyr
145                 150                 155                 160

Ala Met Val Arg Leu Val Lys Cys Asp Val Tyr Pro Cys Pro Asn Thr
                165                 170                 175

Val Asp Cys Phe Val Ser Arg Pro Thr Glu Lys Thr Val Phe Thr Val
            180                 185                 190

Phe Met Leu Ala Ala Ser Gly Ile Cys Ile Ile Leu Asn Val Ala Glu
        195                 200                 205

Val Val Tyr Leu Ile Ile Arg Ala Cys Ala Arg Ala Gln Arg Arg
    210                 215                 220

Ser Asn Pro Pro Ser Arg Lys Gly Ser Gly Phe Gly His Arg Leu Ser
225                 230                 235                 240

Pro Glu Tyr Lys Gln Asn Glu Ile Asn Lys Leu Leu Ser Glu Gln Asp
                245                 250                 255

Gly Ser Leu Lys Asp Ile Leu Arg Arg Ser Pro Gly Thr Gly Ala Gly
            260                 265                 270

Leu Ala Glu Lys Ser Asp Arg Cys Ser Ala Cys
            275                 280

<210> SEQ ID NO 81
<211> LENGTH: 3337
<212> TYPE: DNA
<213> ORGANISM: Homo sapiens

<400> SEQUENCE: 81
gtcgacccac gcgtccggag ccagctctcc cgagcccgta accttcgcat cccaagagct        60
gcagtttcag ccgcgacagc aagaacggca gagccggcga ccgcggcggc ggcggcggcg       120
gaggcaggag cagcctgggc gggtcgcagg gtctccgcgg gcgcaggaag gcagcagag        180 atatcctctg agagccaagc aaagaacatt aaggaaggaa ggaggaatga ggctggatac       240
ggtgcagtga aaaaggcact tccaagagtg gggcactcac tacgcacaga ctcgacggtg       300
ccatcagcat gagaacttac cgctacttct tgctgctctt ttgggtgggc cagccctacc       360
caactctctc aactccacta tcaaagagga ctagtggttt cccagcaaag aaaagggccc       420
tggagctctc tggaaacagc aaaaatgagc tgaaccgttc aaaaaggagc tggatgtgga       480
atcagttctt tctcctggag gaatacacag gatccgatta tcagtatgtg ggcaagttac       540
attcagacca ggatagagga gatggatcac ttaaatatat cctttcagga gatggagcag       600
gagatctctt cattattaat gaaaacacag gcgacataca ggccaccaag aggctggaca       660
gggaagaaaa acccgtttac atccttcgag ctcaagctat aaacagaagg acagggagac       720
```

```
ccgtggagcc cgagtctgaa ttcatcatca agatccatga catcaatgac aatgaaccaa    780
tattcaccaa ggaggtttac acagccactg tccctgaaat gtctgatgtc ggtacatttg    840
ttgtccaagt cactgcgacg gatgcagatg atccaacata tgggaacagt gctaaagttg    900
tctacagtat tctacaggga cagccctatt tttcagttga atcagaaaca ggtattatca    960
agacagcttt gctcaacatg gatcgagaaa acagggagca gtaccaagtg gtgattcaag   1020
ccaaggatat gggcggccag atgggaggat tatctgggac caccaccgtg aacatcacac   1080
tgactgatgt caacgacaac cctccccgat tcccccagag tacataccag tttaaaactc   1140
ctgaatcttc tccaccgggg acaccaattg gcagaatcaa agccagcgac gctgatgtgg   1200
gagaaaatgc tgaaattgag tacagcatca cagacggtga ggggctggat atgtttgatg   1260
tcatcaccga ccaggaaacc caggaaggga ttataactgt caaaaagctc ttggactttg   1320
aaaagaagaa agtgtatacc cttaaagtgg aagcctccaa tccttatgtt gagccacgat   1380
ttctctactt ggggccttc aaagattcag ccacggttag aattgtggtg gaggatgtag   1440
atgagccacc tgtcttcagc aaactggcct acatcttaca aataagagaa gatgctcaga   1500
taaacaccac aataggctcc gtcacagccc aagatccaga tgctgccagg aatcctgtca   1560
agtactctgt agatcgacac acagatatgg acagaatatt caacattgat tctggaaatg   1620
gttcgatttt tacatcgaaa cttcttgacc gagaaacact gctatggcac aacattacag   1680
tgatagcaac agagatcaat aatccaaagc aaagtagtcg agtacctcta tatattaaag   1740
ttctagatgt caatgacaac gccccagaat ttgctgagtt ctatgaaact tttgtctgtg   1800
aaaaagcaaa ggcagatcag ttgattcaga ccctgcatgc tgttgacaag gatgacccett   1860 atagtggaca ccaattttcg ttttccttgg cccctgaagc agccagtggc tcaaacttta   1920
ccattcaaga caacaaagac aacacggcgg gaatcttaac tcggaaaaat ggctataata   1980
gacacgagat gagcacctat ctcttgcctg tggtcatttc agacaacgac tacccagttc   2040
aaagcagcac tgggacagtg actgtccggg tctgtgcatg tgaccaccac gggaacatgc   2100
aatcctgcca tgcggaggcg ctcatccacc ccacgggact gagcacgggg gctctggttg   2160
ccatccttct gtgcatcgtg atcctactag tgacagtggg gctgtttgca gctctgaggc   2220
ggcagcgaaa aaaagagcct ttgatcattt ccaaagagga catcagagat aacattgtca   2280
gttacaacga cgaaggtggt ggagaggagg acacccaggc ttttgatatc ggcacccctga   2340 ggaatcctga agccatagag gacaacaaat tacgaaggga cattgtgccc gaagccctt   2400 tcctaccccg acggactcca acagctcgcg acaacaccga tgtcagagat ttcattaacc   2460
aaaggttaaa ggaaaatgac acggacccca ctgccccgcc atacgactcc ttggccactt   2520
acgcctatga aggcactggc tccgtggcgg attccctgag ctcgctggag tcagtgacca   2580
cggatgcaga tcaagactat gattaccta gtgactgggg acctcgattc aaaaagcttg   2640
cagatatgta tggaggagtg gacagtgaca aagactccta atctgttgcc ttttcattt   2700 tccaatacga cactgaaata tgtgaagtgg ctatttcttt atatttatcc actactccgt   2760
gaaggcttct ctgttctacc cgttccaaaa gccaatggct gcagtccgtg tggatccaat   2820
gttagagact tttttctagt acacttttat gagcttccaa ggggcaaatt tttatttttt   2880
agtgcatcca gttaaccaag tcagcccaac aggcaggtgc cggaggggag gacagggaac   2940
agtatttcca cttgttctca gggcagcgtg cccgcttccg ctgtcctggt gttttactac   3000
actccatgtc aggtcagcca actgccctaa ctgtacattt cacaggctaa tgggataaag   3060
```

```
gactgtgctt taaagataaa aatatcatca tagtaaaaga aatgagggca tatcggctca    3120
caaagagata aactacatag gggtgtttat ttgtgtcaca aagaatttaa aataacactt    3180
gcccatgcta tttgttcttc aagaactttc tctgccatca actactattc aaaacctcaa    3240
atccacccat atgttaaaat tctcattact cttaaggaat agaagcaaat taaacggtaa    3300
catccaaaag caaaaaaaaa aaaaaagggg cggccgc                             3337
```

<210> SEQ ID NO 82
<211> LENGTH: 790
<212> TYPE: PRT
<213> ORGANISM: Homo sapiens

<400> SEQUENCE: 82

| Met | Arg | Thr | Tyr | Arg | Tyr | Phe | Leu | Leu | Leu | Phe | Trp | Val | Gly | Gln | Pro |
|---|---|---|---|---|---|---|---|---|---|---|---|---|---|---|---|
| 1 | | | | 5 | | | | | 10 | | | | | 15 | |

| Tyr | Pro | Thr | Leu | Ser | Thr | Pro | Leu | Ser | Lys | Arg | Thr | Ser | Gly | Phe | Pro |
| | | | 20 | | | | | 25 | | | | | 30 | | |

| Ala | Lys | Lys | Arg | Ala | Leu | Glu | Leu | Ser | Gly | Asn | Ser | Lys | Asn | Glu | Leu |
| | | 35 | | | | | 40 | | | | | 45 | | | |

| Asn | Arg | Ser | Lys | Arg | Ser | Trp | Met | Trp | Asn | Gln | Phe | Phe | Leu | Leu | Glu |
| | 50 | | | | | 55 | | | | | 60 | | | | |

| Glu | Tyr | Thr | Gly | Ser | Asp | Tyr | Gln | Tyr | Val | Gly | Lys | Leu | His | Ser | Asp |
| 65 | | | | | 70 | | | | | 75 | | | | | 80 |

| Gln | Asp | Arg | Gly | Asp | Gly | Ser | Leu | Lys | Tyr | Ile | Leu | Ser | Gly | Asp | Gly |
| | | | | 85 | | | | | 90 | | | | | 95 | |

| Ala | Gly | Asp | Leu | Phe | Ile | Ile | Asn | Glu | Asn | Thr | Gly | Asp | Ile | Gln | Ala |
| | | | 100 | | | | | 105 | | | | | 110 | | |

| Thr | Lys | Arg | Leu | Asp | Arg | Glu | Glu | Lys | Pro | Val | Tyr | Ile | Leu | Arg | Ala |
| | | 115 | | | | | 120 | | | | | 125 | | | |

| Gln | Ala | Ile | Asn | Arg | Arg | Thr | Gly | Arg | Pro | Val | Glu | Pro | Glu | Ser | Glu |
| | 130 | | | | | 135 | | | | | 140 | | | | |

| Phe | Ile | Ile | Lys | Ile | His | Asp | Ile | Asn | Asp | Asn | Glu | Pro | Ile | Phe | Thr |
| 145 | | | | | 150 | | | | | 155 | | | | | 160 |

| Lys | Glu | Val | Tyr | Thr | Ala | Thr | Val | Pro | Glu | Met | Ser | Asp | Val | Gly | Thr |
| | | | | 165 | | | | | 170 | | | | | 175 | |

| Phe | Val | Val | Gln | Val | Thr | Ala | Thr | Asp | Ala | Asp | Asp | Pro | Thr | Tyr | Gly |
| | | | 180 | | | | | 185 | | | | | 190 | | |

| Asn | Ser | Ala | Lys | Val | Val | Tyr | Ser | Ile | Leu | Gln | Gly | Gln | Pro | Tyr | Phe |
| | | 195 | | | | | 200 | | | | | 205 | | | |

| Ser | Val | Glu | Ser | Glu | Thr | Gly | Ile | Ile | Lys | Thr | Ala | Leu | Leu | Asn | Met |
| | 210 | | | | | 215 | | | | | 220 | | | | |

| Asp | Arg | Glu | Asn | Arg | Glu | Gln | Tyr | Gln | Val | Val | Ile | Gln | Ala | Lys | Asp |
| 225 | | | | | 230 | | | | | 235 | | | | | 240 |

| Met | Gly | Gly | Gln | Met | Gly | Gly | Leu | Ser | Gly | Thr | Thr | Val | Asn | Ile |
| | | | | 245 | | | | | 250 | | | | | 255 |

| Thr | Leu | Thr | Asp | Val | Asn | Asp | Asn | Pro | Pro | Arg | Phe | Pro | Gln | Ser | Thr |
| | | | 260 | | | | | 265 | | | | | 270 | | |

| Tyr | Gln | Phe | Lys | Thr | Pro | Glu | Ser | Ser | Pro | Gly | Thr | Pro | Ile | Gly |
| | | 275 | | | | | 280 | | | | | 285 | | | |

| Arg | Ile | Lys | Ala | Ser | Asp | Ala | Asp | Val | Gly | Glu | Asn | Ala | Glu | Ile | Glu |
| | 290 | | | | | 295 | | | | | 300 | | | | |

| Tyr | Ser | Ile | Thr | Asp | Gly | Glu | Gly | Leu | Asp | Met | Phe | Asp | Val | Ile | Thr |
| 305 | | | | | 310 | | | | | 315 | | | | | 320 |

| Asp | Gln | Glu | Thr | Gln | Glu | Gly | Ile | Ile | Thr | Val | Lys | Lys | Leu | Leu | Asp |

```
                      325                 330                 335
            Phe Glu Lys Lys Lys Val Tyr Thr Leu Lys Val Glu Ala Ser Asn Pro
                              340                 345                 350
            Tyr Val Glu Pro Arg Phe Leu Tyr Leu Gly Pro Phe Lys Asp Ser Ala
                              355                 360                 365
            Thr Val Arg Ile Val Val Glu Asp Val Asp Glu Pro Pro Val Phe Ser
                    370                 375                 380
            Lys Leu Ala Tyr Ile Leu Gln Ile Arg Glu Asp Ala Gln Ile Asn Thr
            385                 390                 395                 400
            Thr Ile Gly Ser Val Thr Ala Gln Asp Pro Asp Ala Ala Arg Asn Pro
                              405                 410                 415
            Val Lys Tyr Ser Val Asp Arg His Thr Asp Met Asp Arg Ile Phe Asn
                              420                 425                 430
            Ile Asp Ser Gly Asn Gly Ser Ile Phe Thr Ser Lys Leu Leu Asp Arg
                        435                 440                 445
            Glu Thr Leu Leu Trp His Asn Ile Thr Val Ile Ala Thr Glu Ile Asn
                    450                 455                 460
            Asn Pro Lys Gln Ser Ser Arg Val Pro Leu Tyr Ile Lys Val Leu Asp
            465                 470                 475                 480
            Val Asn Asp Asn Ala Pro Glu Phe Ala Glu Phe Tyr Glu Thr Phe Val
                              485                 490                 495
            Cys Glu Lys Ala Lys Ala Asp Gln Leu Ile Gln Thr Leu His Ala Val
                        500                 505                 510
            Asp Lys Asp Asp Pro Tyr Ser Gly His Gln Phe Ser Phe Ser Leu Ala
                        515                 520                 525
            Pro Glu Ala Ala Ser Gly Ser Asn Phe Thr Ile Gln Asp Asn Lys Asp
                    530                 535                 540
            Asn Thr Ala Gly Ile Leu Thr Arg Lys Asn Gly Tyr Asn Arg His Glu
            545                 550                 555                 560
            Met Ser Thr Tyr Leu Leu Pro Val Val Ile Ser Asp Asn Asp Tyr Pro
                              565                 570                 575
            Val Gln Ser Ser Thr Gly Thr Val Thr Val Arg Val Cys Ala Cys Asp
                        580                 585                 590
            His His Gly Asn Met Gln Ser Cys His Ala Glu Ala Leu Ile His Pro
                        595                 600                 605
            Thr Gly Leu Ser Thr Gly Ala Leu Val Ala Ile Leu Leu Cys Ile Val
                    610                 615                 620
            Ile Leu Leu Val Thr Val Val Leu Phe Ala Ala Leu Arg Arg Gln Arg
            625                 630                 635                 640
            Lys Lys Glu Pro Leu Ile Ile Ser Lys Glu Asp Ile Arg Asp Asn Ile
                              645                 650                 655
            Val Ser Tyr Asn Asp Glu Gly Gly Gly Glu Glu Asp Thr Gln Ala Phe
                              660                 665                 670
            Asp Ile Gly Thr Leu Arg Asn Pro Glu Ala Ile Glu Asp Asn Lys Leu
                        675                 680                 685
            Arg Arg Asp Ile Val Pro Glu Ala Leu Phe Leu Pro Arg Arg Thr Pro
                        690                 695                 700
            Thr Ala Arg Asp Asn Thr Asp Val Arg Asp Phe Ile Asn Gln Arg Leu
            705                 710                 715                 720
            Lys Glu Asn Asp Thr Asp Pro Thr Ala Pro Pro Tyr Asp Ser Leu Ala
                              725                 730                 735
            Thr Tyr Ala Tyr Glu Gly Thr Gly Ser Val Ala Asp Ser Leu Ser Ser
                              740                 745                 750
```

```
Leu Glu Ser Val Thr Thr Asp Ala Asp Gln Asp Tyr Asp Tyr Leu Ser
            755                 760                 765
Asp Trp Gly Pro Arg Phe Lys Lys Leu Ala Asp Met Tyr Gly Gly Val
        770                 775                 780
Asp Ser Asp Lys Asp Ser
785                 790

<210> SEQ ID NO 83
<211> LENGTH: 1070
<212> TYPE: DNA
<213> ORGANISM: Homo sapiens

<400> SEQUENCE: 83
gtcgacccac gcgtccgctt tgggtgaccg gaaaactcca cctcaagttt tcttttgtgg      60
ggctgccccc caagtgtcgt tgttttact gtagggtctc ccgcccggcg cccccagtgt     120
tttctgaggg cggaaatggc caattcgggc ctgcagttgc tgggcttctc catggccctg     180
ctgggctggg tgggtctggt ggcctgcacc gccatcccgc agtggcagat gagctcctat     240
gcgggtgaca acatcatcac ggcccaggcc atgtacaagg gctgtggat ggactgcgtc     300
acgcagagca cggggatgat gagctgcaaa atgtacgact cggtgctcgc cctgtccgcg     360
gccttgcagg ccactcgagc cctaatggtg gtctccctgg tgctgggctt cctggccatg     420
tttgtggcca cgatgggcat gaagtgcacg cgctgtgggg agacgacaa agtgaagaag     480
gcccgtatag ccatgggtgg aggcataatt ttcatcgtgg caggtcttgc cgccttggta     540
gcttgctcct ggtatggcca tcagattgtc acagactttt ataaccctt gatccctacc     600
aacattaagt atgagtttgg ccctgccatc tttattggct gggcagggtc tgccctagtc     660
atcctgggag gtgcactgct ctcctgttcc tgtcctggga atgagagcaa ggctgggtac     720
cgtgcaccc gctcttaccc taagtccaac tcttccaagg agtatgtgtg acctgggatc      780
tccttgcccc agcctgacag gctatgggag tgtctagatg cctgaaaggg cctggggctg     840
agctcagcct gtgggcaggg tgccggacaa aggcctcctg gtcactctgt ccctgcactc     900
catgtatagt cctcttgggt tgggggtggg gggtgccgt tggtgggaga gacaaaaaga     960
gggagagtgt gcttttttgta cagtaataaa aaataagtat tgggaagcag gcaaaaaaaa    1020
aaaaaaaaaa aaaaaaaaaa aaaaaaaaaa aaaaaaaaaa gggcggccgc               1070

<210> SEQ ID NO 84
<211> LENGTH: 211
<212> TYPE: PRT
<213> ORGANISM: Homo sapiens

<400> SEQUENCE: 84

Met Ala Asn Ser Gly Leu Gln Leu Leu Gly Phe Ser Met Ala Leu Leu
1               5                  10                  15
Gly Trp Val Gly Leu Val Ala Cys Thr Ala Ile Pro Gln Trp Gln Met
            20                  25                  30
Ser Ser Tyr Ala Gly Asp Asn Ile Ile Thr Ala Gln Ala Met Tyr Lys
        35                  40                  45
Gly Leu Trp Met Asp Cys Val Thr Gln Ser Thr Gly Met Met Ser Cys
    50                  55                  60
Lys Met Tyr Asp Ser Val Leu Ala Leu Ser Ala Ala Leu Gln Ala Thr
65                  70                  75                  80
Arg Ala Leu Met Val Val Ser Leu Val Leu Gly Phe Leu Ala Met Phe
                85                  90                  95
```

```
Val Ala Thr Met Gly Met Lys Cys Thr Arg Cys Gly Gly Asp Asp Lys
            100                 105                 110
Val Lys Lys Ala Arg Ile Ala Met Gly Gly Ile Ile Phe Ile Val
        115                 120                 125
Ala Gly Leu Ala Ala Leu Val Ala Cys Ser Trp Tyr Gly His Gln Ile
    130                 135                 140
Val Thr Asp Phe Tyr Asn Pro Leu Ile Pro Thr Asn Ile Lys Tyr Glu
145                 150                 155                 160
Phe Gly Pro Ala Ile Phe Ile Gly Trp Ala Gly Ser Ala Leu Val Ile
                165                 170                 175
Leu Gly Gly Ala Leu Leu Ser Cys Ser Cys Pro Gly Asn Glu Ser Lys
            180                 185                 190
Ala Gly Tyr Arg Ala Pro Arg Ser Tyr Pro Lys Ser Asn Ser Ser Lys
        195                 200                 205
Glu Tyr Val
    210

<210> SEQ ID NO 85
<211> LENGTH: 1733
<212> TYPE: DNA
<213> ORGANISM: Homo sapiens

<400> SEQUENCE: 85
gtcgacccac gcgtccgctg gtcctgcct  tcgacaccac cccaaggctt cctaccttgc      60
gtgcctggag tctgccccag gggcccttgt cctgggccat ggcccagaag ggggtcctgg     120
ggcctgggca gctgggggct gtggccattc tgctctatct tggattactc cggtcaggga     180
caggagcgga aggggcagaa gctccctgcg tgtggccccc caagcacgc atcacaggtg      240 gcagcagtgc agtcgccggt cagtggccct ggcaggtcag catcacctat gaaggcgtcc     300
atgtgtgtgg tggctctctc gtgtctgagc agtgggtgct gtcagctgct cactgcttcc     360
ccagcgagca ccacaaggaa gcctatgagg tcaagctggg ggcccaccag ctagactcct     420
actccgagga cgccaaggtc agcaccctga aggacatcat ccccaccccc agctacctcc     480
aggagggctc ccagggcgac attgcactcc tccaactcag cagacccatc accttctccc     540
gctacatccg gccatctgc ctccctgcag ccaacgcctc cttccccaac ggcctccact      600
gcactgtcac tggctgggt catgtggccc cctcagtgag cctcctgacg cccaagccac      660
tgcagcaact cgaggtgcct ctgatcagtc gtgagacgtg taactgcctg tacaacatcg      720
acgccaagcc tgaggagccg cactttgtcc aagaggacat ggtgtgtgct ggctatgtgg     780 agggggggcaa ggacgcctgc agggtgact ctggggcccc actctcctgc cctgtggagg     840
gtctctggta cctgacgggc attgtgagct ggggagatgc ctgtggggcc cgcaacaggc     900
ctggtgtgta cactctggcc tccagctatg cctcctggat ccaaagcaag gtgacagaac     960
tccagcctcg tgtggtgccc caaacccagg agtcccagcc cgacagcaac ctctgtggca    1020
gccacctggc cttcagctct gccccagccc agggcttgct gaggcccatc cttttcctgc    1080
ctctgggcct ggctctgggc ctcctctccc catggctcag cgagcactga gctggcccta    1140
cttccaggat ggatgcatca cactcaagga caggagcctg gtccttccct gatgcctttt    1200
ggacccaggg cctgacttga gccactcctt ccttcaggac tctgcgggag ctggggccc     1260 catcttgatc tttgagcccca ttcttctggg tgtgcttttt ggaccatca ctgagagtca    1320 ggagttttac tgcctgtagc aatggccaga gcctctggcc cctcacccac catggaccag    1380
```

```
cccattggcc gagctcctgg ggagctcctg ggacccttgg ctatgaaaat gagccctggc    1440
tcccacctgt ttctggaaga ctgctcccgg cccgcctgcc cagactgatg agcacatctc    1500
tctgccctct ccctgtgttc tgggctgggg ccacctttgt gcagcttcga ggacaggaaa    1560
ggccccaatc ttgcccactg gccgctgagc gccccgagc cctgactcct ggactccgga     1620
ggactgagcc cccaccggaa ctgggctggc gcttggatct ggggtgggag taacagggca    1680
gaaatgatta aaatgtttga gcacaaaaaa aaaaaaaaa aaagggcggc cgc            1733
```

<210> SEQ ID NO 86
<211> LENGTH: 343
<212> TYPE: PRT
<213> ORGANISM: Homo sapiens

<400> SEQUENCE: 86

```
Met Ala Gln Lys Gly Val Leu Gly Pro Gly Gln Leu Gly Ala Val Ala
1               5                   10                  15

Ile Leu Leu Tyr Leu Gly Leu Leu Arg Ser Gly Thr Gly Ala Glu Gly
                20                  25                  30

Ala Glu Ala Pro Cys Gly Val Ala Pro Gln Ala Arg Ile Thr Gly Gly
            35                  40                  45

Ser Ser Ala Val Ala Gly Gln Trp Pro Trp Gln Val Ser Ile Thr Tyr
        50                  55                  60

Glu Gly Val His Val Cys Gly Gly Ser Leu Val Ser Glu Gln Trp Val
65                  70                  75                  80

Leu Ser Ala Ala His Cys Phe Pro Ser Glu His His Lys Glu Ala Tyr
                85                  90                  95

Glu Val Lys Leu Gly Ala His Gln Leu Asp Ser Tyr Ser Glu Asp Ala
            100                 105                 110

Lys Val Ser Thr Leu Lys Asp Ile Ile Pro His Pro Ser Tyr Leu Gln
        115                 120                 125

Glu Gly Ser Gln Gly Asp Ile Ala Leu Leu Gln Leu Ser Arg Pro Ile
    130                 135                 140

Thr Phe Ser Arg Tyr Ile Arg Pro Ile Cys Leu Pro Ala Ala Asn Ala
145                 150                 155                 160

Ser Phe Pro Asn Gly Leu His Cys Thr Val Thr Gly Trp Gly His Val
                165                 170                 175

Ala Pro Ser Val Ser Leu Leu Thr Pro Lys Pro Leu Gln Gln Leu Glu
            180                 185                 190

Val Pro Leu Ile Ser Arg Glu Thr Cys Asn Cys Leu Tyr Asn Ile Asp
        195                 200                 205

Ala Lys Pro Glu Glu Pro His Phe Val Gln Glu Asp Met Val Cys Ala
    210                 215                 220

Gly Tyr Val Glu Gly Gly Lys Asp Ala Cys Gln Gly Asp Ser Gly Gly
225                 230                 235                 240

Pro Leu Ser Cys Pro Val Glu Gly Leu Trp Tyr Leu Thr Gly Ile Val
                245                 250                 255

Ser Trp Gly Asp Ala Cys Gly Ala Arg Asn Arg Pro Gly Val Tyr Thr
            260                 265                 270

Leu Ala Ser Ser Tyr Ala Ser Trp Ile Gln Ser Lys Val Thr Glu Leu
        275                 280                 285

Gln Pro Arg Val Val Pro Gln Thr Gln Glu Ser Gln Pro Asp Ser Asn
    290                 295                 300

Leu Cys Gly Ser His Leu Ala Phe Ser Ser Ala Pro Ala Gln Gly Leu
305                 310                 315                 320
```

Leu Arg Pro Ile Leu Phe Leu Pro Leu Gly Leu Ala Leu Gly Leu Leu
            325                 330                 335

Ser Pro Trp Leu Ser Glu His
            340

<210> SEQ ID NO 87
<211> LENGTH: 4188
<212> TYPE: DNA
<213> ORGANISM: Homo sapiens
<220> FEATURE:
<221> NAME/KEY: modified_base
<222> LOCATION: (3457)..(3457)
<223> OTHER INFORMATION: a, c, t or g
<220> FEATURE:
<221> NAME/KEY: modified_base
<222> LOCATION: (3481)..(3481)
<223> OTHER INFORMATION: a, c, t or g
<220> FEATURE:
<221> NAME/KEY: modified_base
<222> LOCATION: (3707)..(3707)
<223> OTHER INFORMATION: a, c, t or g
<220> FEATURE:
<221> NAME/KEY: modified_base
<222> LOCATION: (3716)..(3716)
<223> OTHER INFORMATION: a, c, t or g
<220> FEATURE:
<221> NAME/KEY: modified_base
<222> LOCATION: (3723)..(3723)
<223> OTHER INFORMATION: a, c, t or g
<220> FEATURE:
<221> NAME/KEY: modified_base
<222> LOCATION: (3733)..(3733)
<223> OTHER INFORMATION: a, c, t or g
<220> FEATURE:
<221> NAME/KEY: modified_base
<222> LOCATION: (3736)..(3736)
<223> OTHER INFORMATION: a, c, t or g
<220> FEATURE:
<221> NAME/KEY: modified_base
<222> LOCATION: (3746)..(3746)
<223> OTHER INFORMATION: a, c, t or g
<220> FEATURE:
<221> NAME/KEY: modified_base
<222> LOCATION: (3751)..(3751)
<223> OTHER INFORMATION: a, c, t or g
<220> FEATURE:
<221> NAME/KEY: modified_base
<222> LOCATION: (3828)..(3828)
<223> OTHER INFORMATION: a, c, t or g
<220> FEATURE:
<221> NAME/KEY: modified_base
<222> LOCATION: (3853)..(3853)
<223> OTHER INFORMATION: a, c, t or g
<220> FEATURE:
<221> NAME/KEY: modified_base
<222> LOCATION: (3857)..(3857)
<223> OTHER INFORMATION: a, c, t or g
<220> FEATURE:
<221> NAME/KEY: modified_base
<222> LOCATION: (3863)..(3863)
<223> OTHER INFORMATION: a, c, t or g
<220> FEATURE:
<221> NAME/KEY: modified_base
<222> LOCATION: (3883)..(3883)
<223> OTHER INFORMATION: a, c, t or g
<220> FEATURE:
<221> NAME/KEY: modified_base
<222> LOCATION: (3890)..(3890)
<223> OTHER INFORMATION: a, c, t or g
<220> FEATURE:
<221> NAME/KEY: modified_base
<222> LOCATION: (4126)..(4126)
<223> OTHER INFORMATION: a, c, t or g

<400> SEQUENCE: 87

-continued

```
ggctccttac ccacccggag acttttttt gaaaggaaac tagggaggga gggagaggga      60
gagagggaga aaacgaaggg gagctcgtcc atccattgaa gcacagttca ctatgatctt    120
actcacattc agcactggaa gacggttgga tttcgtgcat cattcggggg tgttttcctt    180
gcaaaccttg cttggatttt tatgtgctac agtctgcgga acggagcagt atttcaatgt   240
ggaggtttgg ttacaaaagt acggctacct tccaccgact gaccccagaa tgtcagtgct   300
gcgctctgca gagaccatgc agtctgccct agctgccatg cagcagttct atggcattaa   360
catgacagga aaagtggaca gaaacacaat tgactggatg aagaagcccc gatgcggtgt   420
acctgaccag acaagaggta gctccaaatt tcatattcgt cgaaagcgat atgcattgac   480
aggacagaaa tggcagcaca agcacatcac ttacagtata aagaacgtaa ctccaaaagt   540
aggagaccct gagactcgta aagctattcg ccgtgccttt gatgtgtggc agaatgtaac   600
tcctctgaca tttgaagaag ttccctacag tgaattagaa aatggcaaac gtgatgtgga   660
tataaccatt atttttgcat ctggtttcca tggggacagc tctcccttg atggagaggg    720
aggattttg gcacatgcct acttccctgg accaggaatt ggaggagata cccattttga    780
ctcagatgag ccatggacac taggaaatcc taatcatgat ggaaatgact tatttcttgt   840
agcagtccat gaactgggac atgctctggg attggagcat tccaatgacc ccactgccat   900
catggctcca ttttaccagt acatggaaac agacaacttc aaactaccta atgatgattt   960
acagggcatc cagaagatat atggtccacc tgacaagatt cctccaccta caagacctct  1020
accgacagtg ccccccacacc gctctattcc tccggctgac ccaaggaaaa atgacaggcc  1080
aaaacctcct cggcctccaa ccggcagacc ctcctatccc ggagccaaac ccaacatctg  1140
tgatgggaac tttaacactc tagctattct tcgtcgtgag atgtttgttt tcaaggacca  1200
gtggttttgg cgagtgagaa caacagggt gatggatgga tacccaatgc aaattactta   1260
cttctggcgg ggcttgcctc ctagtatcga tgcagtttat gaaaatagcg acgggaattt  1320
tgtgttcttt aaaggtaaca aatattggt gttcaaggat acaactcttc aacctggtta   1380
ccctcatgac ttgataaccc ttggaagtgg aattcccct catggtattg attcagccat   1440
ttggtgggag gacgtcggga aaacctattt cttcaaggga gacagatatt ggagatatag  1500
tgaagaaatg aaaacaatgg accctggcta tcccaagcca atcacagtct ggaaagggat  1560
ccctgaatct cctcagggag catttgtaca caaagaaaat ggcttacgt atttctacaa    1620
aggaaaggag tattggaaat caacaaccaa gatactcaag gtagaacctg gatatccaag  1680
atccatcctc aaggattttta tgggctgtga tggaccaaca gacagagtta agaaggaca   1740
cagcccacca gatgatgtag acattgtcat caaactggac aacacagcca gcactgtgaa  1800
agccatagct attgtcattc cctgcatctt ggccttatgc ctccttgtat tggtttacac  1860
tgtgttccag ttcaagagga aggaacacc ccgccacata ctgtactgta aacgctctat   1920
gcaagagtgg gtgtgatgta gggttttttc ttctttctt ctttgcagg agtttgtggt    1980
aacttgagat tcaagacaag agctgttatg ctgtttccta gctaggagca ggcttgtggc  2040
agcctgattc ggggctgacc ttcaaccca gagggttgct ggtcctgcac atgagtggaa   2100
atacactcat ggggaagctt ccatgatgca cagtatctgc tgttcttcag tcctttgtct  2160
ttcttgtca ttcagttcta ggcctttcct ctgcacgctc aatgcccagt aaatttcag    2220
gattaactaa agaagaggag aaaagaagaa aaagattctt tcttaaaagt ttctaatgtt  2280
attttccttc tgaagtctga gcccatttct gggggagaa aaaaaaagca aatcagaaaa    2340
cccacggttt ttctttttt cttttttct tttttctttt tttggcttta aacaaaggg    2400
```

```
aaaaaagagt ttaaacaaaa aacccacaat tgaacttcca ggaaagtgtg aagacccaaa    2460
acagctttgt ctccaaagaa gatagctctc tgactgcttt ggatagtctc ctacgcacca    2520
ttttgtcagg tgggagattt ggaatacaca tgcaggacgt tagactgttg ggacagccat    2580
tttccaacaa ccaaggggcc aaaatatctg caatatagta acagccttaa taatacatcc    2640 attttcgtt ttatacagct gttctcagct atgtcctcag tgtttcatcg catttatatt    2700
catagctatt ttcaaacacg acctttaat tgttttgaa gtatttctaa acccttctt     2760 tccaccttac tcctccatca ttgtgataat cttcccaagt tgtattaggc cattgcccca    2820
ggccttccat gggtctgtca ggaatattcg ttacaaagca gagcaagaag gcagtatgtc    2880
tctgaagtgg attacagtgg cagttatttt acaaggattt gtgacactag ttacataccc    2940
gtgttaccct ttgagaacta tcagaccagc tytcagagtc ttaggattgt cgstcttgcg    3000
atctgataaa ttatagaact gggcaatggt aaaaacagtc acaagttcaa gaagttcagg    3060
tttttaaaac agatatccta taatgtcata taattttta atgatttaca agactacata    3120
aatgtgttta taacaaacag aaatgatgtt acttgccaaa attttctgg caaataaaaa    3180 aggtatttta ttaagattct cataaatctg aaatttttatt tgaaaaaact gataatagcc    3240
taagtcttct tttctttttt ttaggcatac tgaatttctg ttttaaaatc cattgcatga    3300
aaattcaatt tgccttggta tatgcagtta gcattgccat tttaaaaatg aattaaaacg    3360
gtgactctga agttgcatga atatcctcca gtgcattacc tattgcatgt ccaccatagt    3420
tctcaaaggg ttagtgtggc ttctggcatt tagccgncca tttgatcact gacagagcca    3480
ngagaccacc aaagcatttc attgttgagt gtaatttgtc ctaacagcag tattgtcatt    3540
ttcatgtgac ctgcagagca ggtttgtatc aatattttt tcctagagaa aagtcagcaa    3600
ctgacagacc tctttattga ttttttaggag ctgcttcttg cagtgaaagg ctttacagcc    3660
actgggctgt gaacttatta gagatggtca gaatgaatgc accccantga gtcagnamca    3720
ttnggctttg tgntgnaaag cccagnctttt ngaggggatt agccttttgg aaaacaaatg    3780
aaccagcctt gcccttgaaa cttgaattaa ttgatcctat tgactgtnca ttaacaacaa    3840
cttaaacatt gtncttnctg tgnaaaattt tccttgaaga gtncctgttn ctatgtcttt    3900 gcccttgac ctttaacttg caaactggca caaactgaag gaaatctggt gttgcttctc    3960
cattggatta gttgttctct aaaacctagt aagcatgagc tgtttcctta gagtggagag    4020
agtggtgatg gcagatctgc agatggacac tttgctcttt acatgcacac tctgaaaatg    4080
ccctataggt agaagtgaat tttaatttca ttttaatata atttcnaagt ctaaattcat    4140
cattttagta caaattacaa aaactatagg aaaaaaaaaa aaaaaaaa                  4188
```

<210> SEQ ID NO 88
<211> LENGTH: 607
<212> TYPE: PRT
<213> ORGANISM: Homo sapiens

<400> SEQUENCE: 88

```
Met Ile Leu Leu Thr Phe Ser Thr Gly Arg Arg Leu Asp Phe Val His
1               5                   10                  15

His Ser Gly Val Phe Phe Leu Gln Thr Leu Leu Trp Ile Leu Cys Ala
            20                  25                  30

Thr Val Cys Gly Thr Glu Gln Tyr Phe Asn Val Glu Val Trp Leu Gln
        35                  40                  45

Lys Tyr Gly Tyr Leu Pro Pro Thr Asp Pro Arg Met Ser Val Leu Arg
```

-continued

```
                50                  55                  60
Ser Ala Glu Thr Met Gln Ser Leu Ala Ala Met Gln Gln Phe Tyr
65                  70                  75                  80

Gly Ile Asn Met Thr Gly Lys Val Asp Arg Asn Thr Ile Asp Trp Met
                    85                  90                  95

Lys Lys Pro Arg Cys Gly Val Pro Asp Gln Thr Arg Gly Ser Ser Lys
                100                 105                 110

Phe His Ile Arg Arg Lys Arg Tyr Ala Leu Thr Gly Gln Lys Trp Gln
                115                 120                 125

His Lys His Ile Thr Tyr Ser Ile Lys Asn Val Thr Pro Lys Val Gly
                130                 135                 140

Asp Pro Glu Thr Arg Lys Ala Ile Arg Arg Ala Phe Asp Val Trp Gln
145                 150                 155                 160

Asn Val Thr Pro Leu Thr Phe Glu Glu Val Pro Tyr Ser Glu Leu Glu
                165                 170                 175

Asn Gly Lys Arg Asp Val Asp Ile Thr Ile Phe Ala Ser Gly Phe
                180                 185                 190

His Gly Asp Ser Ser Pro Phe Asp Gly Glu Gly Gly Phe Leu Ala His
                195                 200                 205

Ala Tyr Phe Pro Gly Pro Gly Ile Gly Gly Asp Thr His Phe Asp Ser
                210                 215                 220

Asp Glu Pro Trp Thr Leu Gly Asn Pro Asn His Asp Gly Asn Asp Leu
225                 230                 235                 240

Phe Leu Val Ala Val His Glu Leu Gly His Ala Leu Gly Leu Glu His
                245                 250                 255

Ser Asn Asp Pro Thr Ala Ile Met Ala Pro Phe Tyr Gln Tyr Met Glu
                260                 265                 270

Thr Asp Asn Phe Lys Leu Pro Asn Asp Asp Leu Gln Gly Ile Gln Lys
                275                 280                 285

Ile Tyr Gly Pro Pro Asp Lys Ile Pro Pro Pro Thr Arg Pro Leu Pro
                290                 295                 300

Thr Val Pro Pro His Arg Ser Ile Pro Pro Ala Asp Pro Arg Lys Asn
305                 310                 315                 320

Asp Arg Pro Lys Pro Pro Arg Pro Pro Thr Gly Arg Pro Ser Tyr Pro
                325                 330                 335

Gly Ala Lys Pro Asn Ile Cys Asp Gly Asn Phe Asn Thr Leu Ala Ile
                340                 345                 350

Leu Arg Arg Glu Met Phe Val Phe Lys Asp Gln Trp Phe Trp Arg Val
                355                 360                 365

Arg Asn Asn Arg Val Met Asp Gly Tyr Pro Met Gln Ile Thr Tyr Phe
370                 375                 380

Trp Arg Gly Leu Pro Pro Ser Ile Asp Ala Val Tyr Glu Asn Ser Asp
385                 390                 395                 400

Gly Asn Phe Val Phe Phe Lys Gly Asn Lys Tyr Trp Val Phe Lys Asp
                405                 410                 415

Thr Thr Leu Gln Pro Gly Tyr Pro His Asp Leu Ile Thr Leu Gly Ser
                420                 425                 430

Gly Ile Pro Pro His Gly Ile Asp Ser Ala Ile Trp Trp Glu Asp Val
                435                 440                 445

Gly Lys Thr Tyr Phe Phe Lys Gly Asp Arg Tyr Trp Arg Tyr Ser Glu
                450                 455                 460

Glu Met Lys Thr Met Asp Pro Gly Tyr Pro Lys Pro Ile Thr Val Trp
465                 470                 475                 480
```

```
Lys Gly Ile Pro Glu Ser Pro Gln Gly Ala Phe Val His Lys Glu Asn
            485                 490                 495
Gly Phe Thr Tyr Phe Tyr Lys Gly Lys Glu Tyr Trp Lys Phe Asn Asn
        500                 505                 510
Gln Ile Leu Lys Val Glu Pro Gly Tyr Pro Arg Ser Ile Leu Lys Asp
            515                 520                 525
Phe Met Gly Cys Asp Gly Pro Thr Asp Arg Val Lys Glu Gly His Ser
        530                 535                 540
Pro Pro Asp Asp Val Asp Ile Val Ile Lys Leu Asp Asn Thr Ala Ser
545                 550                 555                 560
Thr Val Lys Ala Ile Ala Ile Val Ile Pro Cys Ile Leu Ala Leu Cys
            565                 570                 575
Leu Leu Val Leu Val Tyr Thr Val Phe Gln Phe Lys Arg Lys Gly Thr
            580                 585                 590
Pro Arg His Ile Leu Tyr Cys Lys Arg Ser Met Gln Glu Trp Val
            595                 600                 605

<210> SEQ ID NO 89
<211> LENGTH: 3438
<212> TYPE: DNA
<213> ORGANISM: Homo sapiens

<400> SEQUENCE: 89
atccccgggc cgagctcga attccaggtg ccccagtagc ccgaccgccg agatgcccag      60
cccgccgggg ctccgggcgc tatggctttg cgccgcgctg tgcgcttccc ggagggccgg     120
cggcgccccc cagcccggcc cggggcccac cgcctgcccg gcccctgcc actgccagga     180 ggacggcatc atgctgtctg ccgactgctc tgagctcggg ctgtccgccg ttccggggga    240
cctggacccc ctgacggctt acctggacct cagcatgaac aacctcacag agcttcagcc    300
tggcctcttc caccacctgc gcttcttgga ggagctgcgt ctctctggga ccatctctc    360 acacatccca ggacaagcat tctctggtct ctacagcctg aaaatcctga tgctgcagaa    420
caatcagctg ggaggaatcc ccgcagaggc gctgtgggag ctgccgagcc tgcagtcgct    480
gcgcctagat gccaacctca tctccctggt cccggagagg agctttgagg ggctgtcctc    540
cctccgccac ctctggctgg acgacaatgc actcacggag atccctgtca gggccctcaa    600
caacctccct gccctgcagg ccatgaccct ggccctcaac cgcatcagcc acatccccga    660
ctacgcgttc cagaatctca ccagccttgt ggtgctgcat ttgcataaca accgcatcca    720
gcatctgggg acccacagct cgaggggct gcacaatctg gagacactag acctgaatta    780
taacaagctg caggagttcc ctgtggccat ccggaccctg ggcagactgc aggaactggg    840
gttccataac aacaacatca aggccatccc agaaaaggcc ttcatgggga ccctctgct    900 acagacgata cacttttatg ataacccaat ccagtttgtg ggaagatcgg cattccagta    960
cctgcctaaa ctccacacac tatctctgaa tggtgccatg gacatccagg agtttccaga   1020
tctcaaaggc accaccagcc tggagatcct gaccctgacc cgcgcaggca tccggctgct   1080
cccatcgggg atgtgccaac agctgcccag gctccgagtc ctggaactgt ctcacaatca   1140
aattgaggag ctgccagcc tgcacaggtg tcagaaattg gaggaaatcg gcctccaaca   1200
caaccgcatc tgggaaattg agctgacac cttcagccag ctgagctccc tgcaagccct   1260
ggatcttagc tggaacgcca tccggtccat ccaccctgag gccttctcca ccctgcactc   1320
cctggtcaag ctgaccctga cagacaacca gctgaccaca ctgccctgg ctggacttgg   1380
```

```
gggcttgatg catctgaagc tcaaagggaa ccttgctctc tcccaggcct tctccaagga    1440
cagtttccca aaactgagga tcctggaggt gccttatgcc taccagtgct gtccctatgg    1500
gatgtgtgcc agcttcttca aggcctctgg gcagtgggag gctgaagacc ttcaccttga    1560
tgatgaggag tcttcaaaaa ggcccctggg cctccttgcc agacaagcag agaaccacta    1620
tgaccaggac ctggatgagc tccagctgga gatggaggac tcaaagccac ccccagtgt    1680
ccagtgtagc cctactccag gccccttcaa gccctgtgag tacctctttg aaagctgggg    1740
catccgcctg gccgtgtggg ccatcgtgtt gctctccgtg ctctgcaatg gactggtgct    1800
gctgaccgtg ttcgctggcg ggcctgcccc cctgccccg gtcaagtttg tggtaggtgc     1860
gattgcaggc gccaacacct tgactggcat ttcctgtggc cttctagcct cagtcgatgc    1920
cctgaccttt ggtcagttct ctgagtacga agcccgctgg gagacggggc taggctgccg    1980
ggccactggc ttcctggcag tacttgggtc ggaggcatcg gtgctgctgc tcactctggc    2040
cgcagtgcag tgcagcgtct ccgtctcctg tgtccgggcc tatgggaagt cccctcct    2100
gggcagcgtt cgagcagggg tcctaggctg cctggcactg gcaggctggg ccgccgcact    2160
gcccctggcc tcagtgggag aatacggggc ctccccactc tgcctgccct acgcgccacc    2220
tgagggtcag ccagcagccc tgggcttcac cgtggcctg gtgatgatga actccttctg    2280
tttcctggtc gtggccggtg cctacatcaa actgtactgt gacctgccgc ggggcgactt    2340
tgaggccgtg tgggactgcg ccatggtgag gcacgtggcc tggctcatct cgcagacgg    2400
gctcctctac tgtcccgtgg ccttcctcag cttcgcctcc atgctgggcc tcttccctgt    2460
cacgcccgag gccgtcaagt ctgtcctgct ggtggtgctg ccctgcctg cctgcctcaa    2520
cccactgctg tacctgctct tcaaccccca cttccgggat gaccttcggc ggcttcggcc    2580
ccgcgcaggg gactcagggc ccctagccta tgctgcggcc ggggagctgg agaagagctc    2640
ctgtgattct acccaggccc tggtagcctt ctctgatgtg gatctcattc tggaagcttc    2700
tgaagctggg cggccccctg ggctggagac ctatggcttc ccctcagtga ccctcatctc    2760
ctgtcagcag ccaggggccc ccaggctgga gggcagccat tgtgtagagc cagaggggaa    2820
ccactttggg aaccccaac cctccatgga tggagaactg ctgctgaggg cagagggatc    2880
tacgccagca ggtggaggct tgtcaggggg tggcggcttt cagccctctg gcttggcctt    2940
tgcttcacac gtgctcgagc aaaagttgat ttctgaagaa gatttgaacg gtgaacaaaa    3000
gctaatctcc gaggaagact tgaacggtga acaaaaatta atctcagaag aagacttgaa    3060
cggatcatag atctctaatt ccggttattt tccaccatat tgccgtcttt tggcaatgtg    3120
agggcccgga aacctggccc tgtcttcttg acgagcattc ctaggggtct ttcccctctc    3180
gccaaaggaa tgcaaggtct gttgaatgtc gtgaaggaag cagttcctct ggaagcttct    3240
tgaagacaaa caacgtctgt agcgaccctt tgcaggcagc ggaacccccc acctggcgac    3300
aggtgcctct gcggccaaaa gccacgtgta taagatacac ctgcaaaggc ggcacaaccc    3360
cagtgccacg ttgtgagttg gatagttgtg gaaagagtca aatggctctc ctcaagcgta    3420
ttcaacaagg ggctgaag                                                 3438
```

<210> SEQ ID NO 90
<211> LENGTH: 1005
<212> TYPE: PRT
<213> ORGANISM: Homo sapiens

<400> SEQUENCE: 90

Met Pro Ser Pro Pro Gly Leu Arg Ala Leu Trp Leu Cys Ala Ala Leu

-continued

```
1               5                   10                  15
Cys Ala Ser Arg Arg Ala Gly Gly Ala Pro Gln Pro Gly Pro Gly Pro
            20                  25                  30
Thr Ala Cys Pro Ala Pro Cys His Cys Gln Glu Asp Gly Ile Met Leu
            35                  40                  45
Ser Ala Asp Cys Ser Glu Leu Gly Leu Ser Ala Val Pro Gly Asp Leu
50                  55                  60
Asp Pro Leu Thr Ala Tyr Leu Asp Leu Ser Met Asn Asn Leu Thr Glu
65                  70                  75                  80
Leu Gln Pro Gly Leu Phe His His Leu Arg Phe Leu Glu Glu Leu Arg
            85                  90                  95
Leu Ser Gly Asn His Leu Ser His Ile Pro Gly Gln Ala Phe Ser Gly
            100                 105                 110
Leu Tyr Ser Leu Lys Ile Leu Met Leu Gln Asn Asn Gln Leu Gly Gly
            115                 120                 125
Ile Pro Ala Glu Ala Leu Trp Glu Leu Pro Ser Leu Gln Ser Leu Arg
130                 135                 140
Leu Asp Ala Asn Leu Ile Ser Leu Val Pro Glu Arg Ser Phe Glu Gly
145                 150                 155                 160
Leu Ser Ser Leu Arg His Leu Trp Leu Asp Asp Asn Ala Leu Thr Glu
            165                 170                 175
Ile Pro Val Arg Ala Leu Asn Asn Leu Pro Ala Leu Gln Ala Met Thr
            180                 185                 190
Leu Ala Leu Asn Arg Ile Ser His Ile Pro Asp Tyr Ala Phe Gln Asn
            195                 200                 205
Leu Thr Ser Leu Val Val Leu His Leu His Asn Asn Arg Ile Gln His
            210                 215                 220
Leu Gly Thr His Ser Phe Glu Gly Leu His Asn Leu Glu Thr Leu Asp
225                 230                 235                 240
Leu Asn Tyr Asn Lys Leu Gln Glu Phe Pro Val Ala Ile Arg Thr Leu
            245                 250                 255
Gly Arg Leu Gln Glu Leu Gly Phe His Asn Asn Ile Lys Ala Ile
            260                 265                 270
Pro Glu Lys Ala Phe Met Gly Asn Pro Leu Leu Gln Thr Ile His Phe
            275                 280                 285
Tyr Asp Asn Pro Ile Gln Phe Val Gly Arg Ser Ala Phe Gln Tyr Leu
            290                 295                 300
Pro Lys Leu His Thr Leu Ser Leu Asn Gly Ala Met Asp Ile Gln Glu
305                 310                 315                 320
Phe Pro Asp Leu Lys Gly Thr Thr Ser Leu Glu Ile Leu Thr Leu Thr
            325                 330                 335
Arg Ala Gly Ile Arg Leu Leu Pro Ser Gly Met Cys Gln Gln Leu Pro
            340                 345                 350
Arg Leu Arg Val Leu Glu Leu Ser His Asn Gln Ile Glu Glu Leu Pro
            355                 360                 365
Ser Leu His Arg Cys Gln Lys Leu Glu Glu Ile Gly Leu Gln His Asn
            370                 375                 380
Arg Ile Trp Glu Ile Gly Ala Asp Thr Phe Ser Gln Leu Ser Ser Leu
385                 390                 395                 400
Gln Ala Leu Asp Leu Ser Trp Asn Ala Ile Arg Ser Ile His Pro Glu
            405                 410                 415
Ala Phe Ser Thr Leu His Ser Leu Val Lys Leu Asp Leu Thr Asp Asn
            420                 425                 430
```

```
Gln Leu Thr Thr Leu Pro Leu Ala Gly Leu Gly Gly Leu Met His Leu
            435                 440                 445

Lys Leu Lys Gly Asn Leu Ala Leu Ser Gln Ala Phe Ser Lys Asp Ser
    450                 455                 460

Phe Pro Lys Leu Arg Ile Leu Glu Val Pro Tyr Ala Tyr Gln Cys Cys
465                 470                 475                 480

Pro Tyr Gly Met Cys Ala Ser Phe Phe Lys Ala Ser Gly Gln Trp Glu
                485                 490                 495

Ala Glu Asp Leu His Leu Asp Asp Glu Ser Ser Lys Arg Pro Leu
            500                 505                 510

Gly Leu Leu Ala Arg Gln Ala Glu Asn His Tyr Asp Gln Asp Leu Asp
            515                 520                 525

Glu Leu Gln Leu Glu Met Glu Asp Ser Lys Pro His Pro Ser Val Gln
530                 535                 540

Cys Ser Pro Thr Pro Gly Pro Phe Lys Pro Cys Glu Tyr Leu Phe Glu
545                 550                 555                 560

Ser Trp Gly Ile Arg Leu Ala Val Trp Ala Ile Val Leu Leu Ser Val
                565                 570                 575

Leu Cys Asn Gly Leu Val Leu Leu Thr Val Phe Ala Gly Gly Pro Ala
            580                 585                 590

Pro Leu Pro Pro Val Lys Phe Val Val Gly Ala Ile Ala Gly Ala Asn
            595                 600                 605

Thr Leu Thr Gly Ile Ser Cys Gly Leu Leu Ala Ser Val Asp Ala Leu
610                 615                 620

Thr Phe Gly Gln Phe Ser Glu Tyr Gly Ala Arg Trp Glu Thr Gly Leu
625                 630                 635                 640

Gly Cys Arg Ala Thr Gly Phe Leu Ala Val Leu Gly Ser Glu Ala Ser
                645                 650                 655

Val Leu Leu Leu Thr Leu Ala Ala Val Gln Cys Ser Val Ser Val Ser
            660                 665                 670

Cys Val Arg Ala Tyr Gly Lys Ser Pro Ser Leu Gly Ser Val Arg Ala
            675                 680                 685

Gly Val Leu Gly Cys Leu Ala Leu Ala Gly Leu Ala Ala Ala Leu Pro
            690                 695                 700

Leu Ala Ser Val Gly Glu Tyr Gly Ala Ser Pro Leu Cys Leu Pro Tyr
705                 710                 715                 720

Ala Pro Pro Glu Gly Gln Pro Ala Ala Leu Gly Phe Thr Val Ala Leu
                725                 730                 735

Val Met Met Asn Ser Phe Cys Phe Leu Val Val Ala Gly Ala Tyr Ile
            740                 745                 750

Lys Leu Tyr Cys Asp Leu Pro Arg Gly Asp Phe Glu Ala Val Trp Asp
            755                 760                 765

Cys Ala Met Val Arg His Val Ala Trp Leu Ile Phe Ala Asp Gly Leu
770                 775                 780

Leu Tyr Cys Pro Val Ala Phe Leu Ser Phe Ala Ser Met Leu Gly Leu
785                 790                 795                 800

Phe Pro Val Thr Pro Glu Ala Val Lys Ser Val Leu Val Val Leu
                805                 810                 815

Pro Leu Pro Ala Cys Leu Asn Pro Leu Leu Tyr Leu Leu Phe Asn Pro
            820                 825                 830

His Phe Arg Asp Asp Leu Arg Arg Leu Arg Pro Arg Ala Gly Asp Ser
            835                 840                 845
```

```
Gly Pro Leu Ala Tyr Ala Ala Ala Gly Glu Leu Glu Lys Ser Ser Cys
    850                 855                 860

Asp Ser Thr Gln Ala Leu Val Ala Phe Ser Asp Val Asp Leu Ile Leu
865                 870                 875                 880

Glu Ala Ser Glu Ala Gly Arg Pro Pro Gly Leu Glu Thr Tyr Gly Phe
                885                 890                 895

Pro Ser Val Thr Leu Ile Ser Cys Gln Gln Pro Gly Ala Pro Arg Leu
            900                 905                 910

Glu Gly Ser His Cys Val Glu Pro Gly Asn His Phe Gly Asn Pro
        915                 920                 925

Gln Pro Ser Met Asp Gly Glu Leu Leu Arg Ala Glu Gly Ser Thr
    930                 935                 940

Pro Ala Gly Gly Gly Leu Ser Gly Gly Gly Phe Gln Pro Ser Gly
945                 950                 955                 960

Leu Ala Phe Ala Ser His Val Leu Glu Gln Lys Leu Ile Ser Glu Glu
                965                 970                 975

Asp Leu Asn Gly Glu Gln Lys Leu Ile Ser Glu Glu Asp Leu Asn Gly
            980                 985                 990

Glu Gln Lys Leu Ile Ser Glu Glu  Asp Leu Asn Gly Ser
    995                 1000                1005

<210> SEQ ID NO 91
<211> LENGTH: 2196
<212> TYPE: DNA
<213> ORGANISM: Homo sapiens
<220> FEATURE:
<221> NAME/KEY: modified_base
<222> LOCATION: (1952)..(1952)
<223> OTHER INFORMATION: a, c, t or g
<220> FEATURE:
<221> NAME/KEY: modified_base
<222> LOCATION: (1960)..(1960)
<223> OTHER INFORMATION: a, c, t or g

<400> SEQUENCE: 91
aaacacactc agcccttgca ctgacctgcc ttctgattgg aggctggttg cttcggataa      60
tgacctccag gaccccactg ttggttacag cctgtttgta ttattcttac tgcaactcaa     120
gacacctgca gcagggcgtg agaaaaagta aaagaccagt attttcacat tgccaggtac     180
cagaaacaca gaagactgac acccgccact taagtgggc cagggctggt gtctgcccat      240
gttgccatcc tgatgggctg cttgccacaa tgagggatct tcttcaatac atcgcttgct    300
tctttgcctt tttctctgct gggttttga ttgtggccac ctggactgac tgttggatgg      360
tgaatgctga tgactctctg gaggtgagca caaaatgccg aggcctctgg tgggaatgcg     420
tcacaaatgc ttttgatggg attcgcacct gtgatgagta cgattccata cttgcggagc     480
atcccttgaa gctggtggta actcgagcgt tgatgattac tgcagatatt ctagctgggt     540
ttggatttct caccctgctc cttggtcttg actgcgtgaa attcctccct gatgagccgt     600
acattaaagt ccgcatctgc tttgttgctg agccacgtt actaatagca ggtacccag      660
gaatcattgg ctctgtgtgg tatgctgttg atgtgtatgt ggaacgttct actttggttt    720
tgcacaatat atttcttggt atccaatata aatttggttg gtcctgttgg ctcggaatgg    780
ctgggtctct gggttgcttt ttggctggag ctgttctgac ctgctgctta tatctttta     840
aagatgttgg acctgagaga aactatcctt attccttgag gaaagcctat tcagccgcgg    900
gtgtttccat ggccaagtca tactcagccc ctcgcacaga gacggccaaa atgtatgctg    960
tagacacaag ggtgtaaaat gcacgtttca gggtgtgttt gcatatgatt taatcaatca   1020
```

```
gtatggttac attgataaaa tagtaagtca atccaggaac agttatttag aattcatatt    1080
gaattaaatt aattgctagc ttaatcaaaa tgtttgattc tcctatactt tttctttcta    1140
ttactcttat attttcccgt cattctctct gctaaccttc caccttatgc acacactttc    1200
cctatatttt aagataagtc tgctaggatg tagaaatatt tgtttgtgat ttctatatag    1260
ctattagaga ttatgacata gtaatattaa aatgaaatga tacttaaaca gaaagcaatt    1320
tccaaagagg ccagggaccc taatctttga agagatgaag aaacttactt ttctccctgg    1380
cttttggttc acttttttgta cttttaacaa gtgggtgaat tatttgataa ttttgaggaa    1440
gattattctt ttaaattcaa actagtatgt caatgcctac cattactctg attatattaa    1500
aacagaaaaa ggaaataaca acttcgtata ccagccactg gtgagagtta aagacaagag    1560 ctgcccccccc accccaaat gtcaaaggca aatgctaaat tgatactgga gctcgtggtg    1620
actttctacc tcactaacaa cataagggat ctccatatta tttcaccact attctagctt    1680
tgctgagata ttgccaaatg attagactac acaatagttc aaccagagaa tttactcatt    1740
tattgattaa acatccaaat actattgtaa tatactatgt taaaattcat caattcaagt    1800
gcccacacac cactgaatca tcagcaccaa gcaatatatt agacatatgg caaaattcaa    1860
caaatatatt ttgatataaa taaataaacg ttcacgactt tacttaaaaa atcaatgttg    1920
cggctgggca cggtagctcg cgtctgtaat cnccgcactn tgggaggcca aggcgggtgg    1980
atcacgaggt caagagacgg agaccatcct ggctaacatg gtgaaaccct gtctctacta    2040
aaaatacaaa aattagccgg gcgtggtggc ggtgcctgta gtcccagcta ctcgggaggc    2100
tgaggcagga gaatcgtttg aacccaggag gtggaggttg cagtgagcgg agatcgcacc    2160
attgcactcc agtctggcaa cagagcgaga ctccat                              2196
```

<210> SEQ ID NO 92
<211> LENGTH: 305
<212> TYPE: PRT
<213> ORGANISM: Homo sapiens

<400> SEQUENCE: 92

```
Met Thr Ser Arg Thr Pro Leu Leu Val Thr Ala Cys Leu Tyr Tyr Ser
1               5                   10                  15

Tyr Cys Asn Ser Arg His Leu Gln Gln Gly Val Arg Lys Ser Lys Arg
            20                  25                  30

Pro Val Phe Ser His Cys Gln Val Pro Glu Thr Gln Lys Thr Asp Thr
        35                  40                  45

Arg His Leu Ser Gly Ala Arg Ala Gly Val Cys Pro Cys Cys His Pro
    50                  55                  60

Asp Gly Leu Leu Ala Thr Met Arg Asp Leu Leu Gln Tyr Ile Ala Cys
65                  70                  75                  80

Phe Phe Ala Phe Phe Ser Ala Gly Phe Leu Ile Val Ala Thr Trp Thr
                85                  90                  95

Asp Cys Trp Met Val Asn Ala Asp Asp Ser Leu Glu Val Ser Thr Lys
            100                 105                 110

Cys Arg Gly Leu Trp Trp Glu Cys Val Thr Asn Ala Phe Asp Gly Ile
        115                 120                 125

Arg Thr Cys Asp Glu Tyr Asp Ser Ile Leu Ala Glu His Pro Leu Lys
    130                 135                 140

Leu Val Val Thr Arg Ala Leu Met Ile Thr Ala Asp Ile Leu Ala Gly
145                 150                 155                 160
```

-continued

```
Phe Gly Phe Leu Thr Leu Leu Leu Gly Leu Asp Cys Val Lys Phe Leu
                165                 170                 175
Pro Asp Glu Pro Tyr Ile Lys Val Arg Ile Cys Phe Val Ala Gly Ala
            180                 185                 190
Thr Leu Leu Ile Ala Gly Thr Pro Gly Ile Ile Gly Ser Val Trp Tyr
        195                 200                 205
Ala Val Asp Val Tyr Val Glu Arg Ser Thr Leu Val Leu His Asn Ile
    210                 215                 220
Phe Leu Gly Ile Gln Tyr Lys Phe Gly Trp Ser Cys Trp Leu Gly Met
225                 230                 235                 240
Ala Gly Ser Leu Gly Cys Phe Leu Ala Gly Ala Val Leu Thr Cys Cys
                245                 250                 255
Leu Tyr Leu Phe Lys Asp Val Gly Pro Glu Arg Asn Tyr Pro Tyr Ser
                260                 265                 270
Leu Arg Lys Ala Tyr Ser Ala Ala Gly Val Ser Met Ala Lys Ser Tyr
            275                 280                 285
Ser Ala Pro Arg Thr Glu Thr Ala Lys Met Tyr Ala Val Asp Thr Arg
        290                 295                 300
Val
305

<210> SEQ ID NO 93
<211> LENGTH: 7460
<212> TYPE: DNA
<213> ORGANISM: Homo sapiens

<400> SEQUENCE: 93
cgtccgggag aacgctgcag aaattctcat cctggccgac ctccacagtg cagatcagtt      60
gaaaactcag gcagtggatt tcatcaacta tcatgcttcg gatgtcttgg agacctctgg     120
gtggaagtca atggtggtgt cacatcccca cttggtggct gaggcatacc gctctctggc     180
ttcagcacag tgccctttc tgggaccccc acgcaaacgc tgaagcaat cctaagatcc      240
tgcttgttgt aagactccgt ttaatttcca gaagcagcag ccactgttgc tgccactgac     300
caccaggtag acagcgcaat ctgtggagct tttactctgt tgtgagggga agagactgca     360
ttgtggcccc agacttttaa aacagcacta ataacttgg gggaaacggg gggagggaaa      420
atgaaatgaa aaccctgttg ctgcgtcact gtgttcctt tggcctggct gagtttgata      480
ctgtggggat tcagtttagg cgctggcccg aggatatccc agcggtggta cttcggagac     540
acctgtctgc atctgactga gccggctctc tggcctcgc gctgcacatt ctctcctggc     600
ggcggcgcca cctgcagtag cgttcgcccg aacatggcga cacggagcag caggagggag     660
tcgcgactcc cgttcctatt caccctggtc gcactgctgc cgcccggagc tctctgcgaa     720
gtctggacgc agaggctgca cggcggcagc gcgcccttgc ccaggaccg gggcttcctc     780
gtggtgcagg gcgacccgcg cgagctgcgg ctgtgggcgc gcggggatgc caggggggcg    840
agccgcgcgg acgagaagcc gctccggagg aaacggagcg ctgccctgca gcccgagccc     900
atcaaggtgt acggacaggt tagtctgaat gattcccaca atcagatggt ggtgcactgg     960
gctggagaga aaagcaacgt gatcgtggcc ttggcccgag atagcctggc attggcgagg    1020
cccaagagca gtgatgtgta cgtgtcttac gactatggaa atcattcaa gaaaattca     1080
gacaagttaa actttggctt gggaaatagg agtgaagctg ttatcgccca gttctaccac    1140
agccctgcgg acaacaagcg gtacatcttt gcagacgctt atgcccagta cctctggatc    1200
acgtttgact tctgcaacac tcttcaaggc ttttccatcc catttcgggc agctgatctc    1260
```

```
ctcctacaca gtaaggcctc caaccttctc ttgggctttg acaggtccca ccccaacaag   1320
cagctgtgga agtcagatga ctttggccag acctggatca tgattcagga acatgtcaag   1380
tccttttctt ggggaattga tccctatgac aaaccaaata ccatctacat tgaacgacac   1440
gaaccctctg gctactccac tgtcttccga agtacagatt tcttccagtc ccgggaaaac   1500
caggaagtga tccttgagga agtgagagat tttcagcttc gggacaagta catgtttgct   1560
acaaaggtgg tgcatctctt gggcagtgaa cagcagtctt ctgtccagct ctgggtctcc   1620
tttggccgga agcccatgag agcagcccag tttgtcacaa gacatcctat taatgaatat   1680
tacatcgcag atgcctccga ggaccaggtg tttgtgtgtg tcagccacag taacaaccgc   1740
accaatttat acatctcaga ggcagagggg ctgaagttct ccctgtcctt ggagaacgtg   1800
ctctattaca gcccaggagg ggccggcagt gacaccttgg tgaggtattt tgcaaatgaa   1860
ccatttgctg acttccaccg agtggaagga ttgcaaggag tctacattgc tactctgatt   1920
aatggttcta tgaatgagga gaacatgaga tcggtcatca cctttgacaa agggggaacc   1980
tgggagtttc ttcaggctcc agccttcacg ggatatggag agaaaatcaa ttgtgagctt   2040
tcccagggct gttcccttca tctggctcag cgcctcagtc agctcctcaa cctccagctc   2100
cggagaatgc ccatcctgtc caaggagtcg gctccaggcc tcatcatcgc cactggctca   2160
gtgggaaaga acttggctag caagacaaac gtgtacatct ctagcagtgc tggagccagg   2220
tggcgagagg cacttcctgg acctcactac tacacatggg gagaccacgg cggaatcatc   2280
acggccattg cccagggcat ggaaaccaac gagctaaaat acagtaccaa tgaaggggag   2340
acctggaaaa cattcatctt ctctgagaag ccagtgtttg tgtatggcct cctcacagaa   2400 cctgggggaga agagcactgt cttcaccatc tttggctcga caaagagaa tgtccacagc   2460 tggctgatcc tccaggtcaa tgccacggat gccttgggag ttccctgcac agagaatgac   2520
tacaagctgt ggtcaccatc tgatgagcgg gggaatgagt gtttgctggg acacaagact   2580
gttttcaaac ggcggacccc ccatgccaca tgcttcaatg agaggactt tgacaggccg   2640 gtggtcgtgt ccaactgctc ctgcacccgg gaggactatg agtgtgactt cggtttcaag   2700
atgagtgaag atttgtcatt agaggtttgt gttccagatc cggaattttc tggaaagtca   2760
tactcccctc ctgtgccttg ccctgtgggt tctacttaca ggagaacgag aggctaccgg   2820
aagatttctg gggacacttg tagcggagga gatgttgaag cgcgactgga aggagagctg   2880 gtccccctgtc ccctggcaga agagaacgag ttcattctgt atgctgtgag gaaatccatc   2940
taccgctatg acctggcctc gggagccacc gagcagttgc ctctcaccgg gctacgggca   3000
gcagtggccc tggactttga ctatgagcac aactgtttgt attggtccga cctggccttg   3060
gacgtcatcc agcgcctctg tttgaatgga agcacagggc aagaggtgat catcaattct   3120
ggcctggaga cagtagaagc tttggctttt gaaccctca gccagctgct ttactgggta   3180
gatgcaggct tcaaaagat tgaggtagct aatccagatg cgacttccg actcacaatc   3240 gtcaattcct ctgtgcttga tcgtcccagg gctctggtcc tcgtgcccca agaggggtg   3300 atgttctgga cagactgggg agacctgaag cctgggattt atcggagcaa tatggatggt   3360
tctgctgcct atcacctggt gtctgaggat gtgagtggcc caatggcat ctctgtggac   3420 gaccagtgga tttactggac ggatgcctac ctggagtgca tagagcggat cacgttcagt   3480
ggccagcagc gctctgtcat tctggacaac ctcccgcacc cctatgccat tgctgtcttt   3540
aagaatgaaa tctactggga tgactggtca cagctcagca tattccgagc ttccaaatac   3600
```

```
agtgggtccc agatggagat tctggcaaac cagctcacgg ggctcatgga catgaagatt   3660
ttctacaagg ggaagaacac tggaagcaat gcctgtgtgc ccaggccatg cagcctgctg   3720
tgcctgccca aggccaacaa cagtagaagc tgcaggtgtc cagaggatgt gtccagcagt   3780
gtgcttccat caggggacct gatgtgtgac tgccctcagg gctatcagct caagaacaat   3840
acctgtgtca agaagagaaa cacctgtctt cgcaaccagt atcgctgcag caacgggaac   3900
tgtatcaaca gcatttggtg gtgtgacttt gacaacgact gtggagacat gagcgatgag   3960
agaaactgcc ctaccaccat ctgtgacctg gacacccagt ttcgttgcca ggagtctggg   4020
acttgtatcc cactgtccta taaatgtgac cttgaggatg actgtggaga caacagtgat   4080
gaaagtcatt gtgaaatgca ccagtgccgg agtgacgagt acaactgcag ttccggcatg   4140
tgcatccgct cctcctgggt atgtgacggg gacaacgact gcagggactg gtctgatgaa   4200
gccaactgta ccgccatcta tcacacctgt gaggcctcca acttccagtg ccgaaacggg   4260
cactgcatcc cccagcggtg ggcgtgtgac ggggatacgg actgccagga tggttccgat   4320
gaggatccag tcaactgtga agaagtgc aatggattcc gctgcccaaa cggcacttgc   4380
atcccatcca gcaaacattg tgatggtctg cgtgattgct ctgatggctc cgatgaacag   4440
cactgcgagc ccctctgtac gcacttcatg gactttgtgt gtaagaaccg ccagcagtgc   4500
ctgttccact ccatggtctg tgacggaatc atccagtgcc gcgacgggtc cgatgaggat   4560
gcggcgtttg caggatgctc ccaagatcct gagttccaca aggtatgtga tgagttcggt   4620
ttccagtgtc agaatggagt gtgcatcagt ttgatttgga agtgcgacgg gatggatgat   4680
tgcggcgatt attctgatga agccaactgc gaaaacccca cagaagcccc aaactgctcc   4740
cgctacttcc agtttcggtg tgagaatggc cactgcatcc ccaacagatg gaaatgtgac   4800
agggagaacg actgtgggga ctggtctgat gagaaggatt gtggagattc acatattctt   4860
cccttctcga ctcctgggcc ctccacgtgt ctgcccaatt actaccgctg cagcagtggg   4920
acctgcgtga tggacacctg ggtgtgcgac gggtaccgag attgtgcaga tggctctgac   4980
gaggaagcct gccccttgct tgcaaacgtc actgctgcct ccactcccac ccaacttggg   5040
cgatgtgacc gatttgagtt cgaatgccac caaccgaaga cgtgtattcc caactggaag   5100
cgctgtgacg gccaccaaga ttgccaggat ggccgggacg aggccaattg ccccacacac   5160
agcaccttga cttgcatgag cagggagttc cagtgcgagg acgggggaggc ctgcattgtg   5220
ctctcggagc gctgcgacgg cttcctggac tgctcggacg agagcgatga aaaggcctgc   5280
agtgatgagt tgactgtgta caaagtacag aatcttcagt ggacagctga cttctctggg   5340
gatgtgactt tgacctggat gaggcccaaa aaaatgccct ctgcatcttg tgtatataat   5400
gtctactaca gggtggttgg agagagcata tggaagactc tggagaccca cagcaataag   5460
acaaacactg tattaaaagt cttgaaacca gataccacgt atcaggttaa agtacaggtt   5520
cagtgtctca gcaaggcaca caacaccaat gactttgtga ccctgaggac cccagaggga   5580
ttgccagatg cccctcgaaa tctccagctg tcactcccca gggaagcaga aggtgtgatt   5640
gtaggccact gggctcctcc catccacacc catggcctca tccgtgagta cattgtagaa   5700
tacagcagga gtggttccaa gatgtgggcc tcccagaggg ctgctagtaa ctttacagaa   5760
atcaagaact tattggtcaa cactctatac accgtcagag tggctgcggt gactagtcgt   5820
ggaataggaa actggagcga ttctaaatcc attaccacca taaaaggaaa agtgatccca   5880
ccaccagata tccacattga cagctatggt gaaaattatc taagcttcac cctgaccatg   5940
gagagtgata tcaaggtgaa tggctatgtg gtgaacctta tctgggcatt tgacacccac   6000
```

-continued

```
aagcaagaga ggagaacttt gaacttccga ggaagcatat tgtcacacaa agttggcaat    6060
ctgacagctc atacatccta tgagatttct gcctgggcca agactgactt ggggggatagc   6120
cctctggcat ttgagcatgt tatgaccaga ggggttcgcc cacctgcacc tagcctcaag    6180
gccaaagcca tcaaccagac tgcagtggaa tgtacctgga ccggcccccg gaatgtggtt    6240
tatggtatt tctatgccac gtcctttctt gacctctatc gcaacccgaa gagcttgact     6300
acttcactcc acaacaagac ggtcattgtc agtaaggatg agcagtattt gtttctggtc    6360
cgtgtagtgg taccctacca ggggccatcc tctgactacg ttgtagtgaa gatgatcccg    6420
gacagcaggc ttccaccccg tcacctgcat gtggttcata cgggcaaaac ctccgtggtc    6480
atcaagtggg aataccgta tgactctcct gaccaggact tgttgtatgc aattgcagtc    6540
aaagatctca taagaaagac tgacaggagc tacaaagtaa atcccgtaa cagcactgtg     6600
gaatacaccc ttaacaagtt ggagcctggc gggaaatacc acatcattgt ccaactgggg   6660
aacatgagca agattccag cataaaaatt accacagttt cattatcagc acctgatgcc    6720
ttaaaaatca taacagaaaa tgatcatgtt cttctgtttt ggaaaagcct ggctttaaag    6780
gaaaagcatt ttaatgaaag caggggctat gagatacaca tgtttgatag tgccatgaat   6840
atcacagctt accttgggaa tactactgac aatttcttta aaatttccaa cctgaagatg    6900
ggtcataatt acacgttcac cgtccaagca agatgccttt ttggcaacca gatctgtggg   6960
gagcctgcca tcctgctgta cgatgagctg gggtctggtg cagatgcatc tgcaacgcag    7020
gctgccagat ctacggatgt tgctgctgtg gtggtgccca tcttattcct gatactgctg    7080
agcctggggg tggggtttgc catcctgtac acgaagcacc ggaggctgca gagcagcttc    7140
accgccttcg ccaacagcca ctacagctcc aggctggggt ccgcaatctt ctcctctggg    7200
gatgacctgg gggaagatga tgaagatgcc cctatgataa ctggattttc agatgacgtc    7260
cccatggtga tagcctgaaa gagctttcct cactagaaac caaatggtgt aaatatttta   7320
tttgataaag atagttgatg gtttatttta aaagatgcac tttgagttgc aatatgttat    7380
ttttatatgg gccaaaaaca aaaacaaaa aaaaaaaaa agggcggccg cgaatgaata    7440
aactttgtag taatcaactg                                               7460
```

<210> SEQ ID NO 94
<211> LENGTH: 2214
<212> TYPE: PRT
<213> ORGANISM: Homo sapiens

<400> SEQUENCE: 94

```
Met Ala Thr Arg Ser Ser Arg Arg Glu Ser Arg Leu Pro Phe Leu Phe
1               5                   10                  15

Thr Leu Val Ala Leu Leu Pro Pro Gly Ala Leu Cys Glu Val Trp Thr
            20                  25                  30

Gln Arg Leu His Gly Gly Ser Ala Pro Leu Pro Gln Asp Arg Gly Phe
        35                  40                  45

Leu Val Val Gln Gly Asp Pro Arg Glu Leu Arg Leu Trp Ala Arg Gly
    50                  55                  60

Asp Ala Arg Gly Ala Ser Arg Ala Asp Glu Lys Pro Leu Arg Arg Lys
65                  70                  75                  80

Arg Ser Ala Ala Leu Gln Pro Glu Pro Ile Lys Val Tyr Gly Gln Val
                85                  90                  95

Ser Leu Asn Asp Ser His Asn Gln Met Val Val His Trp Ala Gly Glu
            100                 105                 110
```

-continued

```
Lys Ser Asn Val Ile Val Ala Leu Ala Arg Asp Ser Leu Ala Leu Ala
            115                 120                 125

Arg Pro Lys Ser Ser Asp Val Tyr Val Ser Tyr Asp Tyr Gly Lys Ser
130                 135                 140

Phe Lys Lys Ile Ser Asp Lys Leu Asn Phe Gly Leu Gly Asn Arg Ser
145                 150                 155                 160

Glu Ala Val Ile Ala Gln Phe Tyr His Ser Pro Ala Asp Asn Lys Arg
                165                 170                 175

Tyr Ile Phe Ala Asp Ala Tyr Ala Gln Tyr Leu Trp Ile Thr Phe Asp
                180                 185                 190

Phe Cys Asn Thr Leu Gln Gly Phe Ser Ile Pro Phe Arg Ala Ala Asp
            195                 200                 205

Leu Leu Leu His Ser Lys Ala Ser Asn Leu Leu Leu Gly Phe Asp Arg
        210                 215                 220

Ser His Pro Asn Lys Gln Leu Trp Lys Ser Asp Asp Phe Gly Gln Thr
225                 230                 235                 240

Trp Ile Met Ile Gln Glu His Val Lys Ser Phe Ser Trp Gly Ile Asp
                245                 250                 255

Pro Tyr Asp Lys Pro Asn Thr Ile Tyr Ile Glu Arg His Glu Pro Ser
            260                 265                 270

Gly Tyr Ser Thr Val Phe Arg Ser Thr Asp Phe Phe Gln Ser Arg Glu
        275                 280                 285

Asn Gln Glu Val Ile Leu Glu Glu Val Arg Asp Phe Gln Leu Arg Asp
290                 295                 300

Lys Tyr Met Phe Ala Thr Lys Val Val His Leu Leu Gly Ser Glu Gln
305                 310                 315                 320

Gln Ser Ser Val Gln Leu Trp Val Ser Phe Gly Arg Lys Pro Met Arg
                325                 330                 335

Ala Ala Gln Phe Val Thr Arg His Pro Ile Asn Glu Tyr Tyr Ile Ala
            340                 345                 350

Asp Ala Ser Glu Asp Gln Val Phe Val Cys Val Ser His Ser Asn Asn
        355                 360                 365

Arg Thr Asn Leu Tyr Ile Ser Glu Ala Glu Gly Leu Lys Phe Ser Leu
    370                 375                 380

Ser Leu Glu Asn Val Leu Tyr Tyr Ser Pro Gly Gly Ala Gly Ser Asp
385                 390                 395                 400

Thr Leu Val Arg Tyr Phe Ala Asn Glu Pro Phe Ala Asp Phe His Arg
                405                 410                 415

Val Glu Gly Leu Gln Gly Val Tyr Ile Ala Thr Leu Ile Asn Gly Ser
            420                 425                 430

Met Asn Glu Glu Asn Met Arg Ser Val Ile Thr Phe Asp Lys Gly Gly
        435                 440                 445

Thr Trp Glu Phe Leu Gln Ala Pro Ala Phe Thr Gly Tyr Gly Glu Lys
    450                 455                 460

Ile Asn Cys Glu Leu Ser Gln Gly Cys Ser Leu His Leu Ala Gln Arg
465                 470                 475                 480

Leu Ser Gln Leu Leu Asn Leu Gln Leu Arg Arg Met Pro Ile Leu Ser
                485                 490                 495

Lys Glu Ser Ala Pro Gly Leu Ile Ile Ala Thr Gly Ser Val Gly Lys
            500                 505                 510

Asn Leu Ala Ser Lys Thr Asn Val Tyr Ile Ser Ser Ser Ala Gly Ala
        515                 520                 525
```

```
Arg Trp Arg Glu Ala Leu Pro Gly Pro His Tyr Tyr Thr Trp Gly Asp
            530                 535                 540

His Gly Gly Ile Ile Thr Ala Ile Ala Gln Gly Met Glu Thr Asn Glu
545                 550                 555                 560

Leu Lys Tyr Ser Thr Asn Glu Gly Glu Thr Trp Lys Thr Phe Ile Phe
                565                 570                 575

Ser Glu Lys Pro Val Phe Val Tyr Gly Leu Leu Thr Glu Pro Gly Glu
            580                 585                 590

Lys Ser Thr Val Phe Thr Ile Phe Gly Ser Asn Lys Glu Asn Val His
        595                 600                 605

Ser Trp Leu Ile Leu Gln Val Asn Ala Thr Asp Ala Leu Gly Val Pro
    610                 615                 620

Cys Thr Glu Asn Asp Tyr Lys Leu Trp Ser Pro Ser Asp Glu Arg Gly
625                 630                 635                 640

Asn Glu Cys Leu Leu Gly His Lys Thr Val Phe Lys Arg Arg Thr Pro
                645                 650                 655

His Ala Thr Cys Phe Asn Gly Glu Asp Phe Asp Arg Pro Val Val Val
            660                 665                 670

Ser Asn Cys Ser Cys Thr Arg Glu Asp Tyr Glu Cys Asp Phe Gly Phe
        675                 680                 685

Lys Met Ser Glu Asp Leu Ser Leu Glu Val Cys Val Pro Asp Pro Glu
690                 695                 700

Phe Ser Gly Lys Ser Tyr Ser Pro Val Pro Cys Pro Val Gly Ser
705                 710                 715                 720

Thr Tyr Arg Arg Thr Arg Gly Tyr Arg Lys Ile Ser Gly Asp Thr Cys
                725                 730                 735

Ser Gly Gly Asp Val Glu Ala Arg Leu Glu Gly Glu Leu Val Pro Cys
            740                 745                 750

Pro Leu Ala Glu Glu Asn Glu Phe Ile Leu Tyr Ala Val Arg Lys Ser
        755                 760                 765

Ile Tyr Arg Tyr Asp Leu Ala Ser Gly Ala Thr Glu Gln Leu Pro Leu
    770                 775                 780

Thr Gly Leu Arg Ala Ala Val Ala Leu Asp Phe Asp Tyr Glu His Asn
785                 790                 795                 800

Cys Leu Tyr Trp Ser Asp Leu Ala Leu Asp Val Ile Gln Arg Leu Cys
                805                 810                 815

Leu Asn Gly Ser Thr Gly Gln Glu Val Ile Ile Asn Ser Gly Leu Glu
            820                 825                 830

Thr Val Glu Ala Leu Ala Phe Glu Pro Leu Ser Gln Leu Leu Tyr Trp
        835                 840                 845

Val Asp Ala Gly Phe Lys Lys Ile Glu Val Ala Asn Pro Asp Gly Asp
    850                 855                 860

Phe Arg Leu Thr Ile Val Asn Ser Ser Val Leu Asp Arg Pro Arg Ala
865                 870                 875                 880

Leu Val Leu Val Pro Gln Glu Gly Val Met Phe Trp Thr Asp Trp Gly
                885                 890                 895

Asp Leu Lys Pro Gly Ile Tyr Arg Ser Asn Met Asp Gly Ser Ala Ala
            900                 905                 910

Tyr His Leu Val Ser Glu Asp Val Lys Trp Pro Asn Gly Ile Ser Val
        915                 920                 925

Asp Asp Gln Trp Ile Tyr Trp Thr Asp Ala Tyr Leu Glu Cys Ile Glu
    930                 935                 940

Arg Ile Thr Phe Ser Gly Gln Gln Arg Ser Val Ile Leu Asp Asn Leu
```

```
            945                 950                 955                 960
         Pro His Pro Tyr Ala Ile Ala Val Phe Lys Asn Glu Ile Tyr Trp Asp
                         965                 970                 975
         Asp Trp Ser Gln Leu Ser Ile Phe Arg Ala Ser Lys Tyr Ser Gly Ser
                         980                 985                 990
         Gln Met Glu Ile Leu Ala Asn Gln Leu Thr Gly Leu Met Asp Met Lys
                         995                1000                1005
         Ile Phe Tyr Lys Gly Lys Asn Thr Gly Ser Asn Ala Cys Val Pro
             1010                1015                1020
         Arg Pro Cys Ser Leu Leu Cys Leu Pro Lys Ala Asn Asn Ser Arg
             1025                1030                1035
         Ser Cys Arg Cys Pro Glu Asp Val Ser Ser Val Leu Pro Ser
             1040                1045                1050
         Gly Asp Leu Met Cys Asp Cys Pro Gln Gly Tyr Gln Leu Lys Asn
             1055                1060                1065
         Asn Thr Cys Val Lys Glu Glu Asn Thr Cys Leu Arg Asn Gln Tyr
             1070                1075                1080
         Arg Cys Ser Asn Gly Asn Cys Ile Asn Ser Ile Trp Trp Cys Asp
             1085                1090                1095
         Phe Asp Asn Asp Cys Gly Asp Met Ser Asp Glu Arg Asn Cys Pro
             1100                1105                1110
         Thr Thr Ile Cys Asp Leu Asp Thr Gln Phe Arg Cys Gln Glu Ser
             1115                1120                1125
         Gly Thr Cys Ile Pro Leu Ser Tyr Lys Cys Asp Leu Glu Asp Asp
             1130                1135                1140
         Cys Gly Asp Asn Ser Asp Glu Ser His Cys Glu Met His Gln Cys
             1145                1150                1155
         Arg Ser Asp Glu Tyr Asn Cys Ser Ser Gly Met Cys Ile Arg Ser
             1160                1165                1170
         Ser Trp Val Cys Asp Gly Asp Asn Asp Cys Arg Asp Trp Ser Asp
             1175                1180                1185
         Glu Ala Asn Cys Thr Ala Ile Tyr His Thr Cys Glu Ala Ser Asn
             1190                1195                1200
         Phe Gln Cys Arg Asn Gly His Cys Ile Pro Gln Arg Trp Ala Cys
             1205                1210                1215
         Asp Gly Asp Thr Asp Cys Gln Asp Gly Ser Asp Glu Asp Pro Val
             1220                1225                1230
         Asn Cys Glu Lys Lys Cys Asn Gly Phe Arg Cys Pro Asn Gly Thr
             1235                1240                1245
         Cys Ile Pro Ser Ser Lys His Cys Asp Gly Leu Arg Asp Cys Ser
             1250                1255                1260
         Asp Gly Ser Asp Glu Gln His Cys Glu Pro Leu Cys Thr His Phe
             1265                1270                1275
         Met Asp Phe Val Cys Lys Asn Arg Gln Gln Cys Leu Phe His Ser
             1280                1285                1290
         Met Val Cys Asp Gly Ile Ile Gln Cys Arg Asp Gly Ser Asp Glu
             1295                1300                1305
         Asp Ala Ala Phe Ala Gly Cys Ser Gln Asp Pro Glu Phe His Lys
             1310                1315                1320
         Val Cys Asp Glu Phe Gly Phe Gln Cys Gln Asn Gly Val Cys Ile
             1325                1330                1335
         Ser Leu Ile Trp Lys Cys Asp Gly Met Asp Asp Cys Gly Asp Tyr
             1340                1345                1350
```

```
Ser Asp Glu Ala Asn Cys Glu Asn Pro Thr Glu Ala Pro Asn Cys
    1355            1360            1365

Ser Arg Tyr Phe Gln Phe Arg Cys Glu Asn Gly His Cys Ile Pro
    1370            1375            1380

Asn Arg Trp Lys Cys Asp Arg Glu Asn Asp Cys Gly Asp Trp Ser
    1385            1390            1395

Asp Glu Lys Asp Cys Gly Asp Ser His Ile Leu Pro Phe Ser Thr
    1400            1405            1410

Pro Gly Pro Ser Thr Cys Leu Pro Asn Tyr Tyr Arg Cys Ser Ser
    1415            1420            1425

Gly Thr Cys Val Met Asp Thr Trp Val Cys Asp Gly Tyr Arg Asp
    1430            1435            1440

Cys Ala Asp Gly Ser Asp Glu Glu Ala Cys Pro Leu Leu Ala Asn
    1445            1450            1455

Val Thr Ala Ala Ser Thr Pro Thr Gln Leu Gly Arg Cys Asp Arg
    1460            1465            1470

Phe Glu Phe Glu Cys His Gln Pro Lys Thr Cys Ile Pro Asn Trp
    1475            1480            1485

Lys Arg Cys Asp Gly His Gln Asp Cys Gln Asp Gly Arg Asp Glu
    1490            1495            1500

Ala Asn Cys Pro Thr His Ser Thr Leu Thr Cys Met Ser Arg Glu
    1505            1510            1515

Phe Gln Cys Glu Asp Gly Glu Ala Cys Ile Val Leu Ser Glu Arg
    1520            1525            1530

Cys Asp Gly Phe Leu Asp Cys Ser Asp Glu Ser Asp Glu Lys Ala
    1535            1540            1545

Cys Ser Asp Glu Leu Thr Val Tyr Lys Val Gln Asn Leu Gln Trp
    1550            1555            1560

Thr Ala Asp Phe Ser Gly Asp Val Thr Leu Thr Trp Met Arg Pro
    1565            1570            1575

Lys Lys Met Pro Ser Ala Ser Cys Val Tyr Asn Val Tyr Tyr Arg
    1580            1585            1590

Val Val Gly Glu Ser Ile Trp Lys Thr Leu Glu Thr His Ser Asn
    1595            1600            1605

Lys Thr Asn Thr Val Leu Lys Val Leu Lys Pro Asp Thr Thr Tyr
    1610            1615            1620

Gln Val Lys Val Gln Val Gln Cys Leu Ser Lys Ala His Asn Thr
    1625            1630            1635

Asn Asp Phe Val Thr Leu Arg Thr Pro Glu Gly Leu Pro Asp Ala
    1640            1645            1650

Pro Arg Asn Leu Gln Leu Ser Leu Pro Arg Glu Ala Glu Gly Val
    1655            1660            1665

Ile Val Gly His Trp Ala Pro Pro Ile His Thr His Gly Leu Ile
    1670            1675            1680

Arg Glu Tyr Ile Val Glu Tyr Ser Arg Ser Gly Ser Lys Met Trp
    1685            1690            1695

Ala Ser Gln Arg Ala Ala Ser Asn Phe Thr Glu Ile Lys Asn Leu
    1700            1705            1710

Leu Val Asn Thr Leu Tyr Thr Val Arg Val Ala Ala Val Thr Ser
    1715            1720            1725

Arg Gly Ile Gly Asn Trp Ser Asp Ser Lys Ser Ile Thr Thr Ile
    1730            1735            1740
```

```
Lys Gly Lys Val Ile Pro Pro Asp Ile His Ile Asp Ser Tyr
    1745            1750            1755

Gly Glu Asn Tyr Leu Ser Phe Thr Leu Thr Met Glu Ser Asp Ile
    1760            1765            1770

Lys Val Asn Gly Tyr Val Val Asn Leu Phe Trp Ala Phe Asp Thr
    1775            1780            1785

His Lys Gln Glu Arg Arg Thr Leu Asn Phe Arg Gly Ser Ile Leu
    1790            1795            1800

Ser His Lys Val Gly Asn Leu Thr Ala His Thr Ser Tyr Glu Ile
    1805            1810            1815

Ser Ala Trp Ala Lys Thr Asp Leu Gly Asp Ser Pro Leu Ala Phe
    1820            1825            1830

Glu His Val Met Thr Arg Gly Val Arg Pro Pro Ala Pro Ser Leu
    1835            1840            1845

Lys Ala Lys Ala Ile Asn Gln Thr Ala Val Glu Cys Thr Trp Thr
    1850            1855            1860

Gly Pro Arg Asn Val Val Tyr Gly Ile Phe Tyr Ala Thr Ser Phe
    1865            1870            1875

Leu Asp Leu Tyr Arg Asn Pro Lys Ser Leu Thr Thr Ser Leu His
    1880            1885            1890

Asn Lys Thr Val Ile Val Ser Lys Asp Glu Gln Tyr Leu Phe Leu
    1895            1900            1905

Val Arg Val Val Val Pro Tyr Gln Gly Pro Ser Ser Asp Tyr Val
    1910            1915            1920

Val Val Lys Met Ile Pro Asp Ser Arg Leu Pro Pro Arg His Leu
    1925            1930            1935

His Val Val His Thr Gly Lys Thr Ser Val Val Ile Lys Trp Glu
    1940            1945            1950

Ser Pro Tyr Asp Ser Pro Asp Gln Asp Leu Leu Tyr Ala Ile Ala
    1955            1960            1965

Val Lys Asp Leu Ile Arg Lys Thr Asp Arg Ser Tyr Lys Val Lys
    1970            1975            1980

Ser Arg Asn Ser Thr Val Glu Tyr Thr Leu Asn Lys Leu Glu Pro
    1985            1990            1995

Gly Gly Lys Tyr His Ile Ile Val Gln Leu Gly Asn Met Ser Lys
    2000            2005            2010

Asp Ser Ser Ile Lys Ile Thr Thr Val Ser Leu Ser Ala Pro Asp
    2015            2020            2025

Ala Leu Lys Ile Ile Thr Glu Asn Asp His Val Leu Leu Phe Trp
    2030            2035            2040

Lys Ser Leu Ala Leu Lys Glu Lys His Phe Asn Glu Ser Arg Gly
    2045            2050            2055

Tyr Glu Ile His Met Phe Asp Ser Ala Met Asn Ile Thr Ala Tyr
    2060            2065            2070

Leu Gly Asn Thr Thr Asp Asn Phe Phe Lys Ile Ser Asn Leu Lys
    2075            2080            2085

Met Gly His Asn Tyr Thr Phe Thr Val Gln Ala Arg Cys Leu Phe
    2090            2095            2100

Gly Asn Gln Ile Cys Gly Glu Pro Ala Ile Leu Leu Tyr Asp Glu
    2105            2110            2115

Leu Gly Ser Gly Ala Asp Ala Ser Ala Thr Gln Ala Ala Arg Ser
    2120            2125            2130

Thr Asp Val Ala Ala Val Val Val Pro Ile Leu Phe Leu Ile Leu
```

```
                      2135                2140                2145
Leu  Ser  Leu  Gly  Val  Gly  Phe  Ala  Ile  Leu  Tyr  Thr  Lys  His  Arg
          2150                2155                2160

Arg  Leu  Gln  Ser  Ser  Phe  Thr  Ala  Phe  Ala  Asn  Ser  His  Tyr  Ser
     2165                2170                2175

Ser  Arg  Leu  Gly  Ser  Ala  Ile  Phe  Ser  Ser  Gly  Asp  Asp  Leu  Gly
2180                2185                2190

Glu  Asp  Asp  Glu  Asp  Ala  Pro  Met  Ile  Thr  Gly  Phe  Ser  Asp  Asp
     2195                2200                2205

Val  Pro  Met  Val  Ile  Ala
     2210

<210> SEQ ID NO 95
<211> LENGTH: 5980
<212> TYPE: DNA
<213> ORGANISM: Homo sapiens

<400> SEQUENCE: 95
gccatgctgt catgagaaag tggcttcttc tcaatgaccc ggaagatacc agttcaggtt      60
ctaaaggtta tatgaaagtc agcatgtttg tcctgggaac cggagatgag cctcctcctg     120
agagacgaga tcgtgataat gacagtgatg atgtggagag taatttgtta ctccctgctg     180
gcattgccct gggaaccgga gatgagcctc ctcctgagag acgagatcgt gataatgaca     240
gtgatgatgt ggagagtaat tgttactcc ctgctggcat tgccctccgg tgggtgacct      300
tcttgctgaa atctaccga gctgaggaca tcccccagat ggatgatgcc ttctcacaga      360
cagtaaagga atatttgga ggcaatgcag ataagaaaaa tctcgtggat cctttgtag      420 aagtttcctt tgctggaaaa aaggtttgta caaacataat tgagaaaaat gcaacccag      480 agtggaatca ggtcgtcaat cttcagatca gtttccttc agtgtgtgaa aaaataaaac      540
taacaatata tgactgggac cgtcttacta aaaatgatgt agttggaaca acatatctac      600
acctctctaa aattgctgcc tctggtgggg aagtggaaga tttctcatct tcgggaactg     660
gggctgcatc atatacagta aacacaggag aaacagaggt aggctttgtt ccaacgtttg     720
gaccttgtta cctgaatctt tatggaagcc ccagagagta cacgggattc ccagaccct      780 atgatgagct gaatactgga aaggggaag gagttgccta cagaggcagg atcttggttg     840
aattagccac ttttcttgag aagacaccac cagataaaaa gcttgagccc atttcaaatg     900
atgacctgct ggttgttgag aaataccagc gaaggcggaa gtacagcctg tctgccgtgt     960
ttcattcagc caccatgttg caagatgttg gtgaggccat tcagtttgaa gtcagcattg    1020
ggaactatgg caacaagttt gacaccacct gtaagccttt ggcatcaaca actcagtaca    1080
gccgtgctgt atttgatggc aactactatt attacttgcc ttgggcccac accaagccag    1140 ttgttacccct gacttcatac tgggaggata ttagtcatcg cctggatgcg gtgaacactc    1200
tcctagctat ggcagaacgg ctgcaaacaa atatagaagc tctaaaatca gggatacaag    1260
gtaaaattcc tgcaaaccag ctggctgaat tgtggctgaa gctgatagat gaagttatag    1320 aagcacgag atacacgttg cctctcacag aaggaaaagc caacgtcaca gttctcgata    1380
ctcagatccg aaagctgcgg tccaggtctc tctcccaaat acatgaggcg ctgtgagga    1440 tgaggtcgga agccacagat gtgaagtcca cactggcaga aattgaggac tggcttgata    1500
aattaatgca gctgactgaa gagccacaga acagcatgcc tgacatcatc atctggatga    1560
tccggggaga gaagagactg gcctatgcac gaattcccgc acatcaggtc ttgtactcca    1620
```

```
ccagtggtga gaatgcatct ggaaaatact gtgggaaaac ccaaaccatc tttctgaagt    1680
atccacagga gaaaaacaac gggccaaagg tgcctgtgga gttgcgagtg aacatctggc    1740
taggcttaag tgctgtggag aagaagttta acagcttcgc agaaggaact ttcaccgtct    1800
ttgctgaaat gtatgaaaat caagctctca tgtttggaaa atgggtact tctggattag     1860 taggacgtca taagttttct gatgtcacag gaaaaataaa actcaagagg gaatttttc     1920 tgcctccaaa aggctgggaa tgggaaggag agtggatagt tgatcctgaa agaagcttgc    1980
tgactgaggc agatgcaggt cacacggagt tcactgatga agtctatcag aacgagagcc    2040
gctaccccgg gggcgactgg aagccggccg aggacaccta cacgatgcg aacggcgata     2100 aagcagcatc acccagcgag ttgacttgtc ctccaggttg ggaatgggaa gatgatgcat    2160
ggtcttatga cataaatcga gcggtggatg agaaaggctg ggaatatgga atcaccattc    2220
ctcctgatca taagcccaaa tcctgggttg cagcagagaa aatgtaccac actcatagac    2280
ggcgaaggct ggtccgaaaa cgcaagaaag atttaacaca gactgcttca agcaccgcaa    2340
gggccatgga ggaattgcaa gaccaagagg gctgggaata tgcttctcta attggctgga    2400
aatttcactg gaaacaacgt agttcagata ccttccgccg cagacgctgg aggagaaaaa    2460
tggctccttc agaaacacat ggtgcagctg ccatctttaa acttgaaggt gcccttgggg    2520
cagacactac cgaagatggg gatgagaaga gcctggagaa acagaagcac agtgccacca    2580
ctgtgttcgg agcaaacacc cccattgttt cctgcaattt tgacagagtc tacatctacc    2640
atctgcgctg ctatgtctat caagccagaa acctcttggc tttagataag gatagctttt    2700
cagatccata tgctcatatc tgtttcctcc atcggagcaa aaccactgag atcatccatt    2760
caaccctgaa tcccacgtgg gaccaaacaa ttatattcga tgaagttgaa atctatgggg    2820
aaccccaaac agttctacag aatccaccca aagttatcat ggaacttttt gacaatgacc    2880
aagtgggcaa agatgaattt ttaggacgaa gcattttctc tcctgtggtg aaactgaact    2940
cagaaatgga catcacaccc aaacttctct ggcacccagt aatgaatgga gacaaagcct    3000
gcggggatgt tcttgtaact gcagagctga ttctgagggg caaggatggc tccaaccttc    3060
ccattcttcc ccctcaaagg gcgccaaatc tatacatggt cccccagggg atcaggcctg    3120
tggtccagct cactgccatt gagattctag cttggggctt aagaaatatg aaaaacttcc    3180
agatggcttc tatcacatcc cccagtcttg ttgtggagtg tggaggagaa agggtggaat    3240
cggtggtgat caaaaacctt aagaagacac ccaactttcc aagttctgtt ctcttcatga    3300
aagtgttctt gcccaaggag gaattgtaca tgcccccact ggtgatcaag gtcatcgacc    3360
acaggcagtt tgggcggaag cctgtcgtcg gccagtgcac catcgagcgc ctggaccgct    3420
ttcgctgtga cccttatgca gggaaagagg acatcgtccc acagctcaaa gcctcccttc    3480
tgtctgcccc accatgccgg gacatcgtta tcgaaatgga agacaccaaa ccattactgg    3540
cttctaagct gacagaaaag gaggaagaaa tcgtggactg tgtggagtaa ttttatgctt    3600
cctcagggga acatgaaaaa tgcggacagt atattcagaa aggctattcc aagctcaaga    3660
tatataattg cgaactagaa aatgtagcag aatttgaggg cctgacagac ttctcagata    3720
cgttcaagtt gtaccgaggc aagtcggatg aaaatgaaga tccttctgtg gttggagagt    3780
ttaagggctc ctttcggatc taccctctgc cggatgaccc cagcgtgcca gcccctccca    3840
gacagtttcg ggaattacct gacagcgtcc cacaggaatg cacggttagg atttacattg    3900
ttcgaggctt agagctccag ccccaggaca acaatgcct gtgtgaccct tacataaaaa     3960
taacactggg caaaaaagtc attgaagacc gagatcacta cattcccaac actctcaacc    4020
```

```
cagtctttgg caggatgtac gaactgagct gctacttacc tcaagaaaaa gacctgaaaa    4080
tttctgtcta tgattatgac acctttaccc gggatgaaaa agtaggagaa acaattattg    4140
atctggaaaa ccgattcctt tcccgctttg gtcccactg cggcatacca gaggagtact    4200
gtgtttctgg agtcaatacc tggcgagatc aactgagacc aacacagctg cttcaaaatg    4260
tcgccagatt caaaggcttc cacaaccca tcctttccga agatgggagt agaatcagat    4320
atggaggacg agactacagc ttggatgaat ttgaagccaa caaatcctg caccagcacc    4380
tcggggcccc tgaagagcgg cttgctcttc acatcctcag gactcagggg ctggtccctg    4440
agcacgtgga acaaggact tgcacagca ccttccagcc aacatttcc cagggaaaac    4500
ttcagatgtg ggtggatgtt ttccccaaga gtttggggcc accaggccct cctttcaaca    4560
tcacaccccg gaaagccaag aaatactacc tgcgtgtgat catctggaac accaaggacg    4620
ttatcttgga cgagaaaagc atcacaggag aggaaatgag tgacatctac gtcaaaggct    4680
ggattcctgg caatgaagaa acaaacagaa aacagatgt ccattacaga tctttggatg    4740
gtgaagggaa ttttaactgg cgatttgttt tcccgtttga ctaccttcca gccgaacaac    4800
tctgtatcgt tgcgaaaaaa gagcatttct ggagtattga ccaaacggaa tttcgaatcc    4860
cacccaggct gatcattcag atatgggaca atgacaagtt ttctctggat gactacttgg    4920
gtttcctaga acttgacttg cgtcacacga tcattcctgc aaaatcacca gagaaatgca    4980
ggttggacat gattccggac ctcaaagcca tgaaccccct aaagccaag acagcctccc    5040
tctttgagca aagtccatg aaaggatggt ggccatgcta cgcagagaaa gatggcgccc    5100
gcgtaatggc tgggaaagtg gagatgacat tggaaatcct caacgagaag gaggccgacg    5160
agaggccagc cgggaagggg cgggacgaac ccaacatgaa ccccaagctg gacttaccaa    5220
atcgaccaga aacctccttc ctctggttca ccaacccatg caagaccatg aagttcatcg    5280
tgtggcgccg ctttaagtgg gtcatcatcg gcttgctgtt cctgcttatc ctgctgctct    5340
tcgtggccgt gctcctctac tctttgccga actatttgtc aatgaagatt gtaaagccaa    5400
atgtgtaaca aagcaaagg cttcatttca agagtcatcc agcaatgaga gaatcctgcc    5460
tctgtagacc aacatccagt gtgattttgt gtctgagacc acaccccagt agcaggttac    5520
gccatgtcac cgagccccat tgattccag aggktcttag tcctgggaaa gtcaggccaa    5580
caagcaacgt ttgcatcatg ttatctctta agtattaaaa gttttatttt ctaaagttta    5640
aatcatggtt tttymaaata ttttcaagg tggctggttc catttaaaaa tcatcttttt    5700
atatgtgtct tcggttctag acttcagctt ttggaaattg ctaaatagaa ttcaaaaatc    5760
tctgcatcct gaggtgatat acttcatatt tgtaatcaac tgaaagagct gtgcattata    5820
aaatcagtta gaatagttag aacaattctt atttatgccc acaaccattg ctatattttg    5880
tatggatgtc ataaaagtct atttaacctc tgtaatgaaa ctaaataaaa atgtttcacc    5940
tttaaagaca aaaaaaaaaa gattgagagg acggccgatc                         5980
```

<210> SEQ ID NO 96
<211> LENGTH: 1798
<212> TYPE: PRT
<213> ORGANISM: Homo sapiens

<400> SEQUENCE: 96

Met Arg Lys Trp Leu Leu Leu Asn Asp Pro Glu Asp Thr Ser Ser Gly
1               5                   10                  15

Ser Lys Gly Tyr Met Lys Val Ser Met Phe Val Leu Gly Thr Gly Asp

```
                    20                  25                  30
Glu Pro Pro Pro Glu Arg Arg Asp Arg Asp Asn Asp Ser Asp Val
                35                  40                  45
Glu Ser Asn Leu Leu Leu Pro Ala Gly Ile Ala Leu Gly Thr Gly Asp
    50                  55                  60
Glu Pro Pro Pro Glu Arg Arg Asp Arg Asp Asn Asp Ser Asp Val
65                  70                  75                  80
Glu Ser Asn Leu Leu Leu Pro Ala Gly Ile Ala Leu Arg Trp Val Thr
                85                  90                  95
Phe Leu Leu Lys Ile Tyr Arg Ala Glu Asp Ile Pro Gln Met Asp Asp
                100                 105                 110
Ala Phe Ser Gln Thr Val Lys Glu Ile Phe Gly Gly Asn Ala Asp Lys
            115                 120                 125
Lys Asn Leu Val Asp Pro Phe Val Glu Val Ser Phe Ala Gly Lys Lys
            130                 135                 140
Val Cys Thr Asn Ile Ile Glu Lys Asn Ala Asn Pro Glu Trp Asn Gln
145                 150                 155                 160
Val Val Asn Leu Gln Ile Lys Phe Pro Ser Val Cys Glu Lys Ile Lys
            165                 170                 175
Leu Thr Ile Tyr Asp Trp Asp Arg Leu Thr Lys Asn Asp Val Val Gly
            180                 185                 190
Thr Thr Tyr Leu His Leu Ser Lys Ile Ala Ala Ser Gly Gly Glu Val
            195                 200                 205
Glu Asp Phe Ser Ser Ser Gly Thr Gly Ala Ala Ser Tyr Thr Val Asn
        210                 215                 220
Thr Gly Glu Thr Glu Val Gly Phe Val Pro Thr Phe Gly Pro Cys Tyr
225                 230                 235                 240
Leu Asn Leu Tyr Gly Ser Pro Arg Glu Tyr Thr Gly Phe Pro Asp Pro
                245                 250                 255
Tyr Asp Glu Leu Asn Thr Gly Lys Gly Glu Gly Val Ala Tyr Arg Gly
                260                 265                 270
Arg Ile Leu Val Glu Leu Ala Thr Phe Leu Glu Lys Thr Pro Pro Asp
            275                 280                 285
Lys Lys Leu Glu Pro Ile Ser Asn Asp Asp Leu Leu Val Val Glu Lys
        290                 295                 300
Tyr Gln Arg Arg Arg Lys Tyr Ser Leu Ser Ala Val Phe His Ser Ala
305                 310                 315                 320
Thr Met Leu Gln Asp Val Gly Glu Ala Ile Gln Phe Glu Val Ser Ile
                325                 330                 335
Gly Asn Tyr Gly Asn Lys Phe Asp Thr Thr Cys Lys Pro Leu Ala Ser
                340                 345                 350
Thr Thr Gln Tyr Ser Arg Ala Val Phe Asp Gly Asn Tyr Tyr Tyr Tyr
            355                 360                 365
Leu Pro Trp Ala His Thr Lys Pro Val Val Thr Leu Thr Ser Tyr Trp
        370                 375                 380
Glu Asp Ile Ser His Arg Leu Asp Ala Val Asn Thr Leu Leu Ala Met
385                 390                 395                 400
Ala Glu Arg Leu Gln Thr Asn Ile Glu Ala Leu Lys Ser Gly Ile Gln
                405                 410                 415
Gly Lys Ile Pro Ala Asn Gln Leu Ala Glu Leu Trp Leu Lys Leu Ile
                420                 425                 430
Asp Glu Val Ile Glu Asp Thr Arg Tyr Thr Leu Pro Leu Thr Glu Gly
            435                 440                 445
```

```
Lys Ala Asn Val Thr Val Leu Asp Thr Gln Ile Arg Lys Leu Arg Ser
    450             455                 460

Arg Ser Leu Ser Gln Ile His Glu Ala Ala Val Arg Met Arg Ser Glu
465             470                 475                 480

Ala Thr Asp Val Lys Ser Thr Leu Ala Glu Ile Glu Asp Trp Leu Asp
                485                 490                 495

Lys Leu Met Gln Leu Thr Glu Glu Pro Gln Asn Ser Met Pro Asp Ile
            500                 505                 510

Ile Ile Trp Met Ile Arg Gly Glu Lys Arg Leu Ala Tyr Ala Arg Ile
        515                 520                 525

Pro Ala His Gln Val Leu Tyr Ser Thr Ser Gly Glu Asn Ala Ser Gly
    530                 535                 540

Lys Tyr Cys Gly Lys Thr Gln Thr Ile Phe Leu Lys Tyr Pro Gln Glu
545                 550                 555                 560

Lys Asn Asn Gly Pro Lys Val Pro Val Glu Leu Arg Val Asn Ile Trp
                565                 570                 575

Leu Gly Leu Ser Ala Val Glu Lys Lys Phe Asn Ser Phe Ala Glu Gly
            580                 585                 590

Thr Phe Thr Val Phe Ala Glu Met Tyr Glu Asn Gln Ala Leu Met Phe
        595                 600                 605

Gly Lys Trp Gly Thr Ser Gly Leu Val Gly Arg His Lys Phe Ser Asp
    610                 615                 620

Val Thr Gly Lys Ile Lys Leu Lys Arg Glu Phe Phe Leu Pro Pro Lys
625                 630                 635                 640

Gly Trp Glu Trp Glu Gly Glu Trp Ile Val Asp Pro Glu Arg Ser Leu
                645                 650                 655

Leu Thr Glu Ala Asp Ala Gly His Thr Glu Phe Thr Asp Glu Val Tyr
            660                 665                 670

Gln Asn Glu Ser Arg Tyr Pro Gly Gly Asp Trp Lys Pro Ala Glu Asp
        675                 680                 685

Thr Tyr Thr Asp Ala Asn Gly Asp Lys Ala Ala Ser Pro Ser Glu Leu
    690                 695                 700

Thr Cys Pro Pro Gly Trp Glu Trp Glu Asp Asp Ala Trp Ser Tyr Asp
705                 710                 715                 720

Ile Asn Arg Ala Val Asp Glu Lys Gly Trp Glu Tyr Gly Ile Thr Ile
                725                 730                 735

Pro Pro Asp His Lys Pro Lys Ser Trp Val Ala Ala Glu Lys Met Tyr
            740                 745                 750

His Thr His Arg Arg Arg Leu Val Arg Lys Arg Lys Asp Leu
        755                 760                 765

Thr Gln Thr Ala Ser Ser Thr Ala Arg Ala Met Glu Glu Leu Gln Asp
    770                 775                 780

Gln Glu Gly Trp Glu Tyr Ala Ser Leu Ile Gly Trp Lys Phe His Trp
785                 790                 795                 800

Lys Gln Arg Ser Ser Asp Thr Phe Arg Arg Arg Trp Arg Arg Lys
                805                 810                 815

Met Ala Pro Ser Glu Thr His Gly Ala Ala Ile Phe Lys Leu Glu
            820                 825                 830

Gly Ala Leu Gly Ala Asp Thr Thr Glu Asp Gly Asp Glu Lys Ser Leu
        835                 840                 845

Glu Lys Gln Lys His Ser Ala Thr Thr Val Phe Gly Ala Asn Thr Pro
    850                 855                 860
```

```
Ile Val Ser Cys Asn Phe Asp Arg Val Tyr Ile Tyr His Leu Arg Cys
865                 870                 875                 880

Tyr Val Tyr Gln Ala Arg Asn Leu Leu Ala Leu Asp Lys Asp Ser Phe
                885                 890                 895

Ser Asp Pro Tyr Ala His Ile Cys Phe Leu His Arg Ser Lys Thr Thr
            900                 905                 910

Glu Ile Ile His Ser Thr Leu Asn Pro Thr Trp Asp Gln Thr Ile Ile
        915                 920                 925

Phe Asp Glu Val Glu Ile Tyr Gly Glu Pro Gln Thr Val Leu Gln Asn
    930                 935                 940

Pro Pro Lys Val Ile Met Glu Leu Phe Asp Asn Asp Gln Val Gly Lys
945                 950                 955                 960

Asp Glu Phe Leu Gly Arg Ser Ile Phe Ser Pro Val Val Lys Leu Asn
                965                 970                 975

Ser Glu Met Asp Ile Thr Pro Lys Leu Leu Trp His Pro Val Met Asn
            980                 985                 990

Gly Asp Lys Ala Cys Gly Asp Val Leu Val Thr Ala Glu Leu Ile Leu
        995                 1000                1005

Arg Gly Lys Asp Gly Ser Asn Leu Pro Ile Leu Pro Pro Gln Arg
    1010                1015                1020

Ala Pro Asn Leu Tyr Met Val Pro Gln Gly Ile Arg Pro Val Val
    1025                1030                1035

Gln Leu Thr Ala Ile Glu Ile Leu Ala Trp Gly Leu Arg Asn Met
    1040                1045                1050

Lys Asn Phe Gln Met Ala Ser Ile Thr Ser Pro Ser Leu Val Val
    1055                1060                1065

Glu Cys Gly Gly Glu Arg Val Glu Ser Val Val Ile Lys Asn Leu
    1070                1075                1080

Lys Lys Thr Pro Asn Phe Pro Ser Ser Val Leu Phe Met Lys Val
    1085                1090                1095

Phe Leu Pro Lys Glu Glu Leu Tyr Met Pro Pro Leu Val Ile Lys
    1100                1105                1110

Val Ile Asp His Arg Gln Phe Gly Arg Lys Pro Val Val Gly Gln
    1115                1120                1125

Cys Thr Ile Glu Arg Leu Asp Arg Phe Arg Cys Asp Pro Tyr Ala
    1130                1135                1140

Gly Lys Glu Asp Ile Val Pro Gln Leu Lys Ala Ser Leu Leu Ser
    1145                1150                1155

Ala Pro Pro Cys Arg Asp Ile Val Ile Glu Met Glu Asp Thr Lys
    1160                1165                1170

Pro Leu Leu Ala Ser Lys Leu Thr Glu Lys Glu Glu Ile Val
    1175                1180                1185

Asp Trp Trp Ser Lys Phe Tyr Ala Ser Ser Gly Glu His Glu Lys
    1190                1195                1200

Cys Gly Gln Tyr Ile Gln Lys Gly Tyr Ser Lys Leu Lys Ile Tyr
    1205                1210                1215

Asn Cys Glu Leu Glu Asn Val Ala Glu Phe Glu Gly Leu Thr Asp
    1220                1225                1230

Phe Ser Asp Thr Phe Lys Leu Tyr Arg Gly Lys Ser Asp Glu Asn
    1235                1240                1245

Glu Asp Pro Ser Val Val Gly Glu Phe Lys Gly Ser Phe Arg Ile
    1250                1255                1260

Tyr Pro Leu Pro Asp Asp Pro Ser Val Pro Ala Pro Pro Arg Gln
```

```
              1265                1270                1275

Phe Arg Glu Leu Pro Asp Ser Val Pro Gln Cys Thr Val Arg
                 1280                1285                1290

Ile Tyr Ile Val Arg Gly Leu Glu Leu Gln Pro Gln Asp Asn Asn
                 1295                1300                1305

Gly Leu Cys Asp Pro Tyr Ile Lys Ile Thr Leu Gly Lys Lys Val
                 1310                1315                1320

Ile Glu Asp Arg Asp His Tyr Ile Pro Asn Thr Leu Asn Pro Val
                 1325                1330                1335

Phe Gly Arg Met Tyr Glu Leu Ser Cys Tyr Leu Pro Gln Glu Lys
                 1340                1345                1350

Asp Leu Lys Ile Ser Val Tyr Asp Tyr Asp Thr Phe Thr Arg Asp
                 1355                1360                1365

Glu Lys Val Gly Glu Thr Ile Ile Asp Leu Glu Asn Arg Phe Leu
                 1370                1375                1380

Ser Arg Phe Gly Ser His Cys Gly Ile Pro Glu Glu Tyr Cys Val
                 1385                1390                1395

Ser Gly Val Asn Thr Trp Arg Asp Gln Leu Arg Pro Thr Gln Leu
                 1400                1405                1410

Leu Gln Asn Val Ala Arg Phe Lys Gly Phe Pro Gln Pro Ile Leu
                 1415                1420                1425

Ser Glu Asp Gly Ser Arg Ile Arg Tyr Gly Gly Arg Asp Tyr Ser
                 1430                1435                1440

Leu Asp Glu Phe Glu Ala Asn Lys Ile Leu His Gln His Leu Gly
                 1445                1450                1455

Ala Pro Glu Glu Arg Leu Ala Leu His Ile Leu Arg Thr Gln Gly
                 1460                1465                1470

Leu Val Pro Glu His Val Glu Thr Arg Thr Leu His Ser Thr Phe
                 1475                1480                1485

Gln Pro Asn Ile Ser Gln Gly Lys Leu Gln Met Trp Val Asp Val
                 1490                1495                1500

Phe Pro Lys Ser Leu Gly Pro Pro Gly Pro Pro Phe Asn Ile Thr
                 1505                1510                1515

Pro Arg Lys Ala Lys Lys Tyr Tyr Leu Arg Val Ile Ile Trp Asn
                 1520                1525                1530

Thr Lys Asp Val Ile Leu Asp Glu Lys Ser Ile Thr Gly Glu Glu
                 1535                1540                1545

Met Ser Asp Ile Tyr Val Lys Gly Trp Ile Pro Gly Asn Glu Glu
                 1550                1555                1560

Asn Lys Gln Lys Thr Asp Val His Tyr Arg Ser Leu Asp Gly Glu
                 1565                1570                1575

Gly Asn Phe Asn Trp Arg Phe Val Phe Pro Phe Asp Tyr Leu Pro
                 1580                1585                1590

Ala Glu Gln Leu Cys Ile Val Ala Lys Lys Glu His Phe Trp Ser
                 1595                1600                1605

Ile Asp Gln Thr Glu Phe Arg Ile Pro Pro Arg Leu Ile Ile Gln
                 1610                1615                1620

Ile Trp Asp Asn Asp Lys Phe Ser Leu Asp Asp Tyr Leu Gly Phe
                 1625                1630                1635

Leu Glu Leu Asp Leu Arg His Thr Ile Ile Pro Ala Lys Ser Pro
                 1640                1645                1650

Glu Lys Cys Arg Leu Asp Met Ile Pro Asp Leu Lys Ala Met Asn
                 1655                1660                1665
```

```
Pro Leu Lys Ala Lys Thr Ala Ser Leu Phe Glu Gln Lys Ser Met
    1670                1675                1680

Lys Gly Trp Trp Pro Cys Tyr Ala Glu Lys Asp Gly Ala Arg Val
    1685                1690                1695

Met Ala Gly Lys Val Glu Met Thr Leu Glu Ile Leu Asn Glu Lys
    1700                1705                1710

Glu Ala Asp Glu Arg Pro Ala Gly Lys Gly Arg Asp Glu Pro Asn
    1715                1720                1725

Met Asn Pro Lys Leu Asp Leu Pro Asn Arg Pro Glu Thr Ser Phe
    1730                1735                1740

Leu Trp Phe Thr Asn Pro Cys Lys Thr Met Lys Phe Ile Val Trp
    1745                1750                1755

Arg Arg Phe Lys Trp Val Ile Ile Gly Leu Leu Phe Leu Leu Ile
    1760                1765                1770

Leu Leu Leu Phe Val Ala Val Leu Leu Tyr Ser Leu Pro Asn Tyr
    1775                1780                1785

Leu Ser Met Lys Ile Val Lys Pro Asn Val
    1790                1795

<210> SEQ ID NO 97
<211> LENGTH: 3724
<212> TYPE: DNA
<213> ORGANISM: Homo sapiens

<400> SEQUENCE: 97
gaattccggc cggcatccc gatggccgcc gctgggcccc ggcgctccgt gcgcggagcc      60
gtctgcctgc atctgctgct gaccctcgtg atcttcagtc gtgatggtga agcctgcaaa     120
aaggtgatac ttaatgtacc ttctaaacta gaggcagaca aataattgg cagagttaat     180
ttggaagagt gcttcaggtc tgcagacctc atccggtcaa gtgatcctga tttcagagtt     240
ctaaatgatg ggtcagtgta cacagccagg gctgttgcgc tgtctgataa gaaaagatca     300
tttaccatat ggcttttctga caaaaggaaa cagacacaga agaggttac tgtgctgcta     360
gaacatcaga agaaggtatc gaagacaaga cacactagaa aaactgttct caggcgtgcc     420
aagaggagat gggcacctat tccttgctct atgcaagaga attccttggg ccctttccca     480
ttgtttcttc aacaagttga atctgatgca gcacagaact atactgtctt ctactcaata     540
agtggacgtg gagttgataa agaaccttta aatttgtttt atatagaaag agacactgga     600
aatctatttt gcactcggcc tgtggatcgt gaagaatatg atgttttga tttgattgct     660
tatgcgtcaa ctgcagatgg atattcagca gatctgcccc tcccactacc catcagggta     720
gaggatgaaa atgacaacca ccctgttttc acagaagcaa tttataattt tgaagttttg     780
gaaagtagta gacctggtac tacagtgggg gtggtttgtg ccacagacag agatgaaccg     840
gacacaatgc atacgcgcct gaaatacagc atttttgcagc agacaccaag gtcacctggg     900
ctcttttctg tgcatcccag cacaggcgta atcaccacag tctctcatta tttggacaga     960
gaggttgtag acaagtactc attgataatg aaagtacaag acatggatgg ccagtttttt    1020
ggattgatag gcacatcaac ttgtatcata acagtaacag attcaaatga taatgcaccc    1080
actttcagac aaaatgctta tgaagcattt gtagaggaaa atgcattcaa tgtggaaatc    1140
ttacgaatac ctatagaaga taagattta attaacactg ccaattggag agtcaatttt    1200
accattttaa aggaaatga aaatggacat ttcaaaatca gcacagacaa agaaactaat    1260
gaaggtgttc tttctgttgt aaagccactg aattatgaag aaaccgtca gtgaacctg    1320
```

```
gaaattggag taaacaatga agcgccattt gctagagata ttcccagagt gacagccttg    1380
aacagagcct tggttacagt tcatgtgagg gatctggatg aggggcctga atgcactcct    1440
gcagcccaat atgtgcggat taaagaaaac ttagcagtgg ggtcaaagat caacggctat    1500
aaggcatatg accccgaaaa tagaaatggc aatggtttaa ggtacaaaaa attgcatgat    1560
cctaaaggtt ggatcaccat tgatgaaatt tcagggtcaa tcataacttc caaaatcctg    1620
gatagggagg ttgaaactcc caaaaatgag ttgtataata ttacagtcct ggcaatagac    1680
aaagatgata gatcatgtac tggaacactt gctgtgaaca ttgaagatgt aaatgataat    1740
ccaccagaaa tacttcaaga atatgtagtc atttgcaaac caaaaatggg gtataccgac    1800
attttagctg ttgatcctga tgaacctgtc catggagctc cattttattt cagtttgccc    1860
aatacttctc cagaaatcag tagactgtgg agcctcacca aagttaatga tacagctgcc    1920
cgtctttcat atcagaaaaa tgctggattt caagaatata ccattcctat tactgtaaaa    1980
gacagggccg gccaagctgc aacaaaatta ttgagagtta atctgtgtga atgtactcat    2040
ccaactcagt gtcgtgcgac ttcaaggagt acaggagtaa tacttggaaa atgggcaatc    2100
cttgcaatat tactgggtat agcactgctc ttttctgtat tgctaacttt agtatgtgga    2160
gttttggtg caactaaagg gaaacgtttt cctgaagatt tagcacagca aaacttaatt    2220
atatcaaaca cagaagcacc tggagacgat agagtgtgct ctgccaatgg atttatgacc    2280
caaactacca acaactctag ccaaggtttt tgtggtacta tgggatcagg aatgaaaaat    2340
ggagggcagg aaaccattga aatgatgaaa ggaggaaacc agaccttgga atcctgccgg    2400
ggggctgggc atcatcatac cctggactcc tgcaggggag gacacacgga ggtggacaac    2460
tgcagataca cttactcgga gtggcacagt tttactcagc cccgtctcgg tgaaaaattg    2520
catcgatgta atcagaatga agaccgcatg ccatcccaag attatgtcct cacttataac    2580
tatgagggaa gaggatctcc agctggttct gtgggctgct gcagtgaaaa gcaggaagaa    2640
gatggccttg actttttaaa taatttggaa cccaaattta ttacattagc agaagcatgc    2700
agtgctacaa ttaggtcttt gtcagacatt ctggaggttt ccaaaaataa tattgtaaag    2760
ttcaatttca acatgtatgt atatgatgat tttttctca attttgaatt atgctactca    2820
ccaattatat ttttaaagca agttgttgct tatcttttcc aaaaagtgaa aaatgttaaa    2880
acagacaact ggtaaatctc aaactccagc actggaatta aggtctctaa agcatctgct    2940
ctttttttt ttacggatat tttagtaata aatatgctgg ataaatatta gtccaacaat    3000
agctaagtta tgctaatatc acattattat gtattcactt taagtgatag tttaaaaaat    3060
aaacaagaaa tattgagtat cactatgtga agaaagtttt ggaaagaaa caatgaagac    3120
tgaattaaat taaaaatgtt gcagctcata agaattgggg actcacccct actgcactac    3180
caaattcatt tgactttgga ggcaaaatgt gttgaagtgc cctatgaagt agcaattttc    3240
tataggaata tagttggaaa taatgtgtg tgtgtatatt attattaatc aatgcaatat    3300
ttaaaatgaa atgagaacaa agaggaagat ggtaaaaact tgaaatgagg ctggggtata    3360
gtttgttcta caatgaaaaa agagagagct ttctaggcct gggctcttaa atgctgcatt    3420
ataactgagt ctatgaggaa ataagtcctg ttcaaattgt gtaatttgtt taaaatgtaa    3480
ataaataaac ttttctggtt tctgtgggaa ggaaataggg aatccaatgg aacagtagct    3540
ttgctttgca gtctgtttca agatttctgc atccacaagt tagtagcaaa ctggggaata    3600
ctcgctgcag ctggggttcc ctgcttttg gtagcaaggg tccagagatg agggtgtttt    3660
```

```
tttcgggag ctaataacaa aaacatttta aaacttacct ttactgaagt taaatcctta    3720
ttgc                                                                3724
```

<210> SEQ ID NO 98
<211> LENGTH: 896
<212> TYPE: PRT
<213> ORGANISM: Homo sapiens

<400> SEQUENCE: 98

```
Met Ala Ala Gly Pro Arg Arg Ser Val Arg Gly Ala Val Cys Leu
1               5                   10                  15

His Leu Leu Leu Thr Leu Val Ile Phe Ser Arg Asp Gly Glu Ala Cys
            20                  25                  30

Lys Lys Val Ile Leu Asn Val Pro Ser Lys Leu Glu Ala Asp Lys Ile
            35                  40                  45

Ile Gly Arg Val Asn Leu Glu Glu Cys Phe Arg Ser Ala Asp Leu Ile
        50                  55                  60

Arg Ser Ser Asp Pro Asp Phe Arg Val Leu Asn Asp Gly Ser Val Tyr
65                  70                  75                  80

Thr Ala Arg Ala Val Ala Leu Ser Asp Lys Lys Arg Ser Phe Thr Ile
                85                  90                  95

Trp Leu Ser Asp Lys Arg Lys Gln Thr Gln Lys Glu Val Thr Val Leu
            100                 105                 110

Leu Glu His Gln Lys Lys Val Ser Lys Thr Arg His Thr Arg Glu Thr
        115                 120                 125

Val Leu Arg Arg Ala Lys Arg Arg Trp Ala Pro Ile Pro Cys Ser Met
130                 135                 140

Gln Glu Asn Ser Leu Gly Pro Phe Pro Leu Phe Leu Gln Gln Val Glu
145                 150                 155                 160

Ser Asp Ala Ala Gln Asn Tyr Thr Val Phe Tyr Ser Ile Ser Gly Arg
                165                 170                 175

Gly Val Asp Lys Glu Pro Leu Asn Leu Phe Tyr Ile Glu Arg Asp Thr
            180                 185                 190

Gly Asn Leu Phe Cys Thr Arg Pro Val Asp Arg Glu Glu Tyr Asp Val
        195                 200                 205

Phe Asp Leu Ile Ala Tyr Ala Ser Thr Ala Asp Gly Tyr Ser Ala Asp
210                 215                 220

Leu Pro Leu Pro Leu Pro Ile Arg Val Glu Asp Glu Asn Asp Asn His
225                 230                 235                 240

Pro Val Phe Thr Glu Ala Ile Tyr Asn Phe Glu Val Leu Glu Ser Ser
                245                 250                 255

Arg Pro Gly Thr Thr Val Gly Val Val Cys Ala Thr Asp Arg Asp Glu
            260                 265                 270

Pro Asp Thr Met His Thr Arg Leu Lys Tyr Ser Ile Leu Gln Gln Thr
        275                 280                 285

Pro Arg Ser Pro Gly Leu Phe Ser Val His Pro Ser Thr Gly Val Ile
290                 295                 300

Thr Thr Val Ser His Tyr Leu Asp Arg Glu Val Val Asp Lys Tyr Ser
305                 310                 315                 320

Leu Ile Met Lys Val Gln Asp Met Asp Gly Gln Phe Phe Gly Leu Ile
                325                 330                 335

Gly Thr Ser Thr Cys Ile Ile Thr Val Thr Asp Ser Asn Asp Asn Ala
            340                 345                 350

Pro Thr Phe Arg Gln Asn Ala Tyr Glu Ala Phe Val Glu Glu Asn Ala
```

```
              355                 360                 365
   Phe Asn Val Glu Ile Leu Arg Ile Pro Ile Glu Asp Lys Asp Leu Ile
   370                 375                 380

Asn Thr Ala Asn Trp Arg Val Asn Phe Thr Ile Leu Lys Gly Asn Glu
   385                 390                 395                 400

Asn Gly His Phe Lys Ile Ser Thr Asp Lys Glu Thr Asn Glu Gly Val
                       405                 410                 415

Leu Ser Val Val Lys Pro Leu Asn Tyr Glu Glu Asn Arg Gln Val Asn
                       420                 425                 430

Leu Glu Ile Gly Val Asn Asn Glu Ala Pro Phe Ala Arg Asp Ile Pro
                   435                 440                 445

Arg Val Thr Ala Leu Asn Arg Ala Leu Val Thr Val His Val Arg Asp
               450                 455                 460

Leu Asp Glu Gly Pro Glu Cys Thr Pro Ala Ala Gln Tyr Val Arg Ile
   465                 470                 475                 480

Lys Glu Asn Leu Ala Val Gly Ser Lys Ile Asn Gly Tyr Lys Ala Tyr
                       485                 490                 495

Asp Pro Glu Asn Arg Asn Gly Asn Gly Leu Arg Tyr Lys Lys Leu His
                       500                 505                 510

Asp Pro Lys Gly Trp Ile Thr Ile Asp Glu Ile Ser Gly Ser Ile Ile
                   515                 520                 525

Thr Ser Lys Ile Leu Asp Arg Glu Val Glu Thr Pro Lys Asn Glu Leu
               530                 535                 540

Tyr Asn Ile Thr Val Leu Ala Ile Asp Lys Asp Asp Arg Ser Cys Thr
   545                 550                 555                 560

Gly Thr Leu Ala Val Asn Ile Glu Asp Val Asn Asp Asn Pro Pro Glu
                       565                 570                 575

Ile Leu Gln Glu Tyr Val Val Ile Cys Lys Pro Lys Met Gly Tyr Thr
                       580                 585                 590

Asp Ile Leu Ala Val Asp Pro Asp Glu Pro Val His Gly Ala Pro Phe
                   595                 600                 605

Tyr Phe Ser Leu Pro Asn Thr Ser Pro Glu Ile Ser Arg Leu Trp Ser
               610                 615                 620

Leu Thr Lys Val Asn Asp Thr Ala Ala Arg Leu Ser Tyr Gln Lys Asn
   625                 630                 635                 640

Ala Gly Phe Gln Glu Tyr Thr Ile Pro Ile Thr Val Lys Asp Arg Ala
                       645                 650                 655

Gly Gln Ala Ala Thr Lys Leu Leu Arg Val Asn Leu Cys Glu Cys Thr
                       660                 665                 670

His Pro Thr Gln Cys Arg Ala Thr Ser Arg Ser Thr Gly Val Ile Leu
                   675                 680                 685

Gly Lys Trp Ala Ile Leu Ala Ile Leu Leu Gly Ile Ala Leu Leu Phe
               690                 695                 700

Ser Val Leu Leu Thr Leu Val Cys Gly Val Phe Gly Ala Thr Lys Gly
   705                 710                 715                 720

Lys Arg Phe Pro Glu Asp Leu Ala Gln Gln Asn Leu Ile Ile Ser Asn
                       725                 730                 735

Thr Glu Ala Pro Gly Asp Asp Arg Val Cys Ser Ala Asn Gly Phe Met
                       740                 745                 750

Thr Gln Thr Thr Asn Asn Ser Ser Gln Gly Phe Cys Gly Thr Met Gly
                   755                 760                 765

Ser Gly Met Lys Asn Gly Gly Gln Glu Thr Ile Glu Met Met Lys Gly
               770                 775                 780
```

Gly Asn Gln Thr Leu Glu Ser Cys Arg Gly Ala Gly His His His Thr
785                 790                 795                 800

Leu Asp Ser Cys Arg Gly Gly His Thr Glu Val Asp Asn Cys Arg Tyr
            805                 810                 815

Thr Tyr Ser Glu Trp His Ser Phe Thr Gln Pro Arg Leu Gly Glu Lys
        820                 825                 830

Leu His Arg Cys Asn Gln Asn Glu Asp Arg Met Pro Ser Gln Asp Tyr
            835                 840                 845

Val Leu Thr Tyr Asn Tyr Glu Gly Arg Gly Ser Pro Ala Gly Ser Val
    850                 855                 860

Gly Cys Cys Ser Glu Lys Gln Glu Glu Asp Gly Leu Asp Phe Leu Asn
865                 870                 875                 880

Asn Leu Glu Pro Lys Phe Ile Thr Leu Ala Glu Ala Cys Thr Lys Arg
                885                 890                 895

<210> SEQ ID NO 99
<211> LENGTH: 2391
<212> TYPE: DNA
<213> ORGANISM: Homo sapiens

<400> SEQUENCE: 99

```
gtcgacccac gcgtccgccg ctacgaggcc ctgcgtgggg agcagccccc ggaccttgag        60
acaacagtca ttctgcctga gtctgtcttc agagagacgc ccccgtggt caggcccgca       120 ggccccggag aggcccagga gccagaggag ctggcacggc gacagcgacg gcacccggag       180
ctgagccagg gtgaggctgt ggccagcgtc atcatctacc gcaccctggc cgggctactg       240
cctcataact atgaccctga caagcgcagc ttgagagtcc ccaaacgccc gatcatcaac       300
acacccgtgg tgagcatcag cgtccatgat gatgaggagc ttctgccccg ggccctggac       360
aaacccgtca cggtgcagtt ccgcctgctg agacagagg agcggaccaa gcccatctgt       420
gtcttctgga accattcaat cctggtcagt ggcacaggtg gctggtcggc cagaggctgt       480
gaagtcgtct tccgcaatga gagccacgtc agctgccagt gcaaccacat gacgagcttc       540
gctgtgctca tggacgtttc tcggcgggag aatggggaga tcctgccact gaagacactg       600
acatacgtgg ctctaggtgt caccttggct gcccttctgc tcaccttctt cttcctcact       660
ctcttgcgta tcctgcgctc caaccaacac ggcatccgac gtaacctgac agctgccctg       720
ggcctggctc agctggtctt cctcctggga atcaaccagg ctgacctccc ttttgcctgc       780
acagtcattg ccatcctgct gcacttcctg tacctctgca cctttttcctg ggctctgctg       840 gaggccttgc acctgtaccg ggcactcact gaggtgcgcg atgtcaacac cggccccatg       900
cgcttctact acatgctggg ctggggcgtg cctgccttca tcacagggct agccgtgggc       960 ctggacccccg agggctacgg gaaccctgac ttctgctggc tctccatcta tgacacgctc      1020
atctggagtt ttgctggccc ggtggccttt gccgtctcga tgagtgtctt cctgtacatc      1080
ctggcggccc gggcctcctg tgctgcccag cggcagggct tgagaagaa aggtcctgtc      1140 tcgggcctgc agccctcctt cgccgtcctc ctgctgctga gcgccacgtg gctgctggca      1200
ctgctctctg tcaacagcga caccctcctc ttccactacc tctttgctac ctgcaattgc      1260
atccagggcc ccttcatctt cctctcctat gtggtgctta gcaaggaggt ccggaaagca      1320
ctcaagcttg cctgcagccg caagcccagc cctgaccctg ctctgaccac caagtccacc      1380
ctgacctcgt cctacaactg ccccagcccc tacgcagatg gcggctgta ccagccctac      1440 ggagactcgg ccggctctct gcacagcacc agtcgctcgg gcaagagtca gccccagctac      1500
```

-continued

```
atcccttct tgctgaggga ggagtccgca ctgaaccctg gccaagggcc cctggcctg    1560 ggggatccag gcagcctgtt cctggaaggt caagaccagc agcatgatcc tgacacggac   1620
tccgacagtg acctgtcctt agaagacgac cagagtggct cctatgcctc tacccactca   1680
tcagacagtg aggaggaaga agaggaggag aagaggagg ccgccttccc tggagagcag    1740
ggctgggata gcctgctggg gcctggagca gagagactgc ccctgcacag tactcccaag   1800 gatggggcc cagggcctgg caaggccccc tggccaggag actttgggac acagcaaaa    1860 gagagtagtg gcaacggggc ccctgaggag cggctgcggg agaatggaga tgccctgtct   1920
cgagaggggt ccctaggccc ccttccaggc tcttctgccc agcctcacaa aggcatcctt   1980
aagaagaagt gtctgcccac catcagcgag aagagcagcc tcctgcggct ccccctggag   2040
caatgcacag ggtcttcccg ggctcctcc gctagtgagg gcagccgggg cggcccccct    2100
ccccgcccac cgccccggca gagcctccag gagcagctga acggggtcat gcccatcgcc   2160
atgagcatca aggcaggcac ggtggatgag gactcgtcag gctccgacag cgacgaaacg   2220
tccatctgag gagcctgggc cttgccggga ggggtactca ccccacctaa ggccatctag   2280
tgccaactcc ccccccacca ttcccctcac tgcactttgg accctgggg ccaacatctc    2340 caagacaaag ttttcagaa aagaggaaaa aaaaaaaaa agggcggccg c              2391
```

<210> SEQ ID NO 100
<211> LENGTH: 565
<212> TYPE: PRT
<213> ORGANISM: Homo sapiens

<400> SEQUENCE: 100

```
Met Thr Ser Phe Ala Val Leu Met Asp Val Ser Arg Arg Glu Asn Gly
1               5                   10                  15

Glu Ile Leu Pro Leu Lys Thr Leu Thr Tyr Val Ala Leu Gly Val Thr
            20                  25                  30

Leu Ala Ala Leu Leu Thr Phe Phe Leu Thr Leu Leu Arg Ile
        35                  40                  45

Leu Arg Ser Asn Gln His Gly Ile Arg Arg Asn Leu Thr Ala Ala Leu
    50                  55                  60

Gly Leu Ala Gln Leu Val Phe Leu Leu Ile Asn Gln Ala Asp Leu Pro
65                  70                  75                  80

Phe Ala Cys Thr Val Ile Ala Ile Leu Leu His Phe Leu Tyr Leu Cys
                85                  90                  95

Thr Phe Ser Trp Ala Leu Leu Glu Ala Leu His Leu Tyr Arg Ala Leu
            100                 105                 110

Thr Glu Val Arg Asp Val Asn Thr Gly Pro Met Arg Phe Tyr Tyr Met
        115                 120                 125

Leu Gly Trp Gly Val Pro Ala Phe Ile Thr Gly Leu Ala Val Gly Leu
    130                 135                 140

Asp Pro Glu Gly Tyr Gly Asn Pro Asp Phe Cys Trp Leu Ser Ile Tyr
145                 150                 155                 160

Asp Thr Leu Ile Trp Ser Phe Ala Gly Pro Val Ala Phe Ala Val Ser
                165                 170                 175

Met Ser Val Phe Leu Tyr Ile Leu Ala Ala Arg Ala Ser Cys Ala Ala
            180                 185                 190

Gln Arg Gln Gly Phe Glu Lys Lys Gly Pro Val Ser Gly Leu Gln Pro
        195                 200                 205

Ser Phe Ala Val Leu Leu Leu Leu Ser Ala Thr Trp Leu Leu Ala Leu
```

Leu Ser Val Asn Ser Asp Thr Leu Leu Phe His Tyr Leu Phe Ala Thr
225                 230                 235                 240

Cys Asn Cys Ile Gln Gly Pro Phe Ile Phe Leu Ser Tyr Val Val Leu
            245                 250                 255

Ser Lys Glu Val Arg Lys Ala Leu Lys Leu Ala Cys Ser Arg Lys Pro
            260                 265                 270

Ser Pro Asp Pro Ala Leu Thr Thr Lys Ser Thr Leu Thr Ser Ser Tyr
            275                 280                 285

Asn Cys Pro Ser Pro Tyr Ala Asp Gly Arg Leu Tyr Gln Pro Tyr Gly
290                 295                 300

Asp Ser Ala Gly Ser Leu His Ser Thr Ser Arg Ser Gly Lys Ser Gln
305                 310                 315                 320

Pro Ser Tyr Ile Pro Phe Leu Leu Arg Glu Glu Ser Ala Leu Asn Pro
            325                 330                 335

Gly Gln Gly Pro Pro Gly Leu Gly Asp Pro Gly Ser Leu Phe Leu Glu
            340                 345                 350

Gly Gln Asp Gln Gln His Asp Pro Asp Thr Asp Ser Asp Ser Asp Leu
            355                 360                 365

Ser Leu Glu Asp Asp Gln Ser Gly Ser Tyr Ala Ser Thr His Ser Ser
370                 375                 380

Asp Ser Glu Glu Glu Glu Glu Glu Glu Glu Ala Ala Phe Pro
385                 390                 395                 400

Gly Glu Gln Gly Trp Asp Ser Leu Leu Gly Pro Gly Ala Glu Arg Leu
            405                 410                 415

Pro Leu His Ser Thr Pro Lys Asp Gly Gly Pro Gly Pro Gly Lys Ala
            420                 425                 430

Pro Trp Pro Gly Asp Phe Gly Thr Thr Ala Lys Glu Ser Ser Gly Asn
            435                 440                 445

Gly Ala Pro Glu Glu Arg Leu Arg Glu Asn Gly Asp Ala Leu Ser Arg
450                 455                 460

Glu Gly Ser Leu Gly Pro Leu Pro Gly Ser Ser Ala Gln Pro His Lys
465                 470                 475                 480

Gly Ile Leu Lys Lys Lys Cys Leu Pro Thr Ile Ser Glu Lys Ser Ser
            485                 490                 495

Leu Leu Arg Leu Pro Leu Glu Gln Cys Thr Gly Ser Ser Arg Gly Ser
            500                 505                 510

Ser Ala Ser Glu Gly Ser Arg Gly Gly Pro Pro Arg Pro Pro Pro
            515                 520                 525

Arg Gln Ser Leu Gln Glu Gln Leu Asn Gly Val Met Pro Ile Ala Met
530                 535                 540

Ser Ile Lys Ala Gly Thr Val Asp Glu Asp Ser Ser Gly Ser Asp Ser
545                 550                 555                 560

Asp Glu Thr Ser Ile
            565

<210> SEQ ID NO 101
<211> LENGTH: 3748
<212> TYPE: DNA
<213> ORGANISM: Homo sapiens

<400> SEQUENCE: 101
gggaacccag gcatgaatga ccatgcccct cacattctgt accctacctc aaccaactcg     60
tcagcagcct tcgagatggt gcctcgaact gcccctgctg gctacctggt caccaaagtc    120

```
atagctatgg actcagactc tgggcaaaat gcttggcttt tttaccatct agcccagact    180
tctgacctgg acctctttaa ggtagagctg cacacaggag aaattaggac taccaggaag    240
atgggagatg agagtggtag cactttcaac ctgaccgtgg tggtccgaga taatggagag    300
ccatcactat cagcctctgt ggccattaca gtagctgtgg tggataggt ttccaaaatc     360 ctccctgaca ctcagaggca tgttaagagc cctcggacat actctgaaat tacccttat     420 ctaataatag cattaagcac agtgtctttt atatttcttt tgacaatcat cattttgagc    480
atcatcaagt gctaccgcta cactgcgtat ggcactgcat gctgtggagg cttctgtgga    540
gtaagggaaa ggtcccctgc agaactgtac aaacaagcca acaacaatat tgatgccagg    600
ataccgcatg gcctcaaagt gcagcctcac ttcattgaag ttcgagggaa tggctccctc    660
accaagacct actgctacaa ggcctgtctg acagcaggct cagggagtga cactttcatg    720
ttttacaata caggggccca gacaggacca gggccttcgg gagcccaagc agcagtgact    780
gacagcagga atctcacagg ccaaagtggt cagaatgctg ggaacctgat tattctcaaa    840
aatgaggctg tttctcaaaa tgagccacga cagcccaacc ctgactggcg ttactctgcc    900
tccctgagag caggcatgca cagctctgtg cacctagagg aggctggcat tctacgggct    960
ggtccaggag ggcctgatca gcagtggcca acagtatcca gtgcaacacc agaaccagag   1020
gcaggagaag tgtcccctcc agtcggtgcg ggtgtcaaca gcaacagctg gacctttaaa   1080
tacggaccag gcaaccccaa acaatccggt cccggtgagt tgcccgacaa attcattatc   1140
ccaggatctc ctgcaatcat ctccatccgg caggagccta ctaacagcca aattgacaaa   1200
agtgacttca taaccttcgg caaaaaggag gagaccaaga aaagaagaa aaagaagaag    1260 ggtaacaaga cccaggagaa aaaagagaaa gggaacagca cgactgacaa cagtgaccag   1320
tgaggtcctc aaatggaaac aagccactta gccagttttt gtaataatgg caaatctctc   1380
ccatgtagca attccctgct cctttttcct atctacatga gccctcttag agacctcaga   1440
aatctgcaga aagttccctg tgtctgtcta gaacgcattt aacaggtttt gtcgtaaaag   1500
ctttactaag tctggtgtta actctttctc tccactctgg cttgttttca gaacctaaaa   1560
agcagaccca agtttccttt ctcctccgcc gcaaaggaga ggcttcccag ccccgccagt   1620
gagaggttgg actctctgcc ctgtgctccg gggatcctgt cttgatgaca cttgcagggc   1680
aggctgaaaa gttttgagat tgagcagctt gggagtttgt ggccactggg tatgtgtggc   1740
taccgcgggt atgcgagtgc cagatattgg ctgagacgag ccagcttaga ctaattggta   1800
caaggaaggc aagaaaacaa agacaaataa acagcggaag ttatcagtat ggaggggaag   1860
tgtaaactta aagggaccag actttctaaa tcttacaact caagaggtgg cagccaccct   1920
ctaggagaca aaactacccc cactgacaag gctttaggag accctaaagt ctgatggctg   1980
tgacgtcatt atacctaaaa tctgcatcat acctgcaagc caacagttca gtgttttaac   2040
agagaaccac cctgggaaac agaagcagat ctgatgtgtt tcctatacat gtcctgtgct   2100
cactttatta aaaattcttt tgcacacaat gtttatgaaa aggccagatc cttttccaat   2160
acttatgcaa aagcaaaaga aaaccccgac acctcacctt tcgctgtttg ttgtttcata   2220
gatttattta aaaaaagaga aagtctatag ctataaatct ttaaagagaa atatgaatac   2280
aattccccta aactctcctc aaaagagaat tcagtctaca gccatttaaa tgatcattgc   2340
tgctacagaa gtgctttaag agaattgcct gaaacatctg tattatatcg gccacctgcc   2400
aatcacagct ttactctttc aggtcactct ggggctgcct cttgcatgta ttactaaata   2460
```

```
aaatgatctc tctttctctc tctctctctc ttttctaaga aacaattatg tgcactttga    2520
tacacaacct tctctaacca actatatatc aagacccaaa aattgaagaa aatatattgtt    2580 ttctcataca gtgagcagat ttttcaatct actaattctg tgacttgtct tggtgtgcta    2640
gcctacacct tctctttggt ttagttttcc ttttctataa cactctgaat tgctaatctt    2700
actaacacct atgatgttac ctgaaatcaa tctcccatat gtatgctgta tgctatgcta    2760
agactcctga aatatactta ctctgtgctt gtgtatgtga atgttaatgc aactattacc    2820
tagagtgaac tttaagcttt attgttgaat gtaattccat tatatttcct tttgtacacc    2880
tgtgaaaaag tggagtagtg ttttttttaac cattgttaat cagcttttgt gtatgaaaga    2940
cacagtaaaa tttctttctt aaatcaagat actggtgatt caaggaattt tatttatggt    3000
ccagccaaga gccatctcgt gccaagactt ctgctggcaa gggaatggat aaagctgttt    3060
tgttctagta acaattttgg aatgaatact gacaatattc catgagggtg tgcaagcaca    3120
aattttacca atctgacctc tttgaagttg cagaatgctt tgaaattcta atggtatctg    3180
aaatatcagc tcatagaaag taacaaaatt tgctgtcacc ttaaataaga catttttaatt    3240 ttgttataat gtacaattta gaagtttgat taattatatt atctatttag gcattaaatat    3300 aaaagaggta ggagtctgtt atttaaaaaa agcattaaat ttaaaaaaaa actgtcttgt    3360
ctacttttag cttcattctc ccatattttg aagggtgtgt aacttcagct ctgcaggatt    3420
gccatggggt aaaacttgtt acccaacaca tgtgaaccat tgcctacatt gtaggttgtg    3480
atcattttgc cccactgaag cccatgtatc tgaccttacg tgccttttga actaggagaa    3540
tcgggctaat ttattaatga tgataattat aatgtatctg tacagcactt tttacatttg    3600
cgaagtgctt tccaatccat gttagttact agttattaca gctgtaagga taaaacacgt    3660
catgtggatt cattttgaat tggtgctatt ggtatttcct ctgttattgc taataaatga    3720
aaatggtggt atgaaaaaaa aaaaaaaa                                       3748
```

<210> SEQ ID NO 102
<211> LENGTH: 436
<212> TYPE: PRT
<213> ORGANISM: Homo sapiens

<400> SEQUENCE: 102

```
Met Asn Asp His Ala Pro His Ile Leu Tyr Pro Thr Ser Thr Asn Ser
1               5                   10                  15

Ser Ala Ala Phe Glu Met Val Pro Arg Thr Ala Pro Ala Gly Tyr Leu
            20                  25                  30

Val Thr Lys Val Ile Ala Met Asp Ser Asp Ser Gly Gln Asn Ala Trp
        35                  40                  45

Leu Phe Tyr His Leu Ala Gln Thr Ser Asp Leu Asp Leu Phe Lys Val
    50                  55                  60

Glu Leu His Thr Gly Glu Ile Arg Thr Thr Arg Lys Met Gly Asp Glu
65                  70                  75                  80

Ser Gly Ser Thr Phe Asn Leu Thr Val Val Arg Asp Asn Gly Glu
            85                  90                  95

Pro Ser Leu Ser Ala Ser Val Ala Ile Thr Val Ala Val Val Asp Arg
            100                 105                 110

Val Ser Lys Ile Leu Pro Asp Thr Gln Arg His Val Lys Ser Pro Arg
        115                 120                 125

Thr Tyr Ser Glu Ile Thr Leu Tyr Leu Ile Ile Ala Leu Ser Thr Val
    130                 135                 140
```

```
Ser Phe Ile Phe Leu Leu Thr Ile Ile Ile Leu Ser Ile Ile Lys Cys
145                 150                 155                 160

Tyr Arg Tyr Thr Ala Tyr Gly Thr Ala Cys Cys Gly Gly Phe Cys Gly
                165                 170                 175

Val Arg Glu Arg Ser Pro Ala Glu Leu Tyr Lys Gln Ala Asn Asn Asn
            180                 185                 190

Ile Asp Ala Arg Ile Pro His Gly Leu Lys Val Gln Pro His Phe Ile
        195                 200                 205

Glu Val Arg Gly Asn Gly Ser Leu Thr Lys Thr Tyr Cys Tyr Lys Ala
    210                 215                 220

Cys Leu Thr Ala Gly Ser Gly Ser Asp Thr Phe Met Phe Tyr Asn Thr
225                 230                 235                 240

Gly Ala Gln Thr Gly Pro Gly Pro Ser Gly Ala Gln Ala Ala Val Thr
                245                 250                 255

Asp Ser Arg Asn Leu Thr Gly Gln Ser Gly Gln Asn Ala Gly Asn Leu
            260                 265                 270

Ile Ile Leu Lys Asn Glu Ala Val Ser Gln Asn Glu Pro Arg Gln Pro
        275                 280                 285

Asn Pro Asp Trp Arg Tyr Ser Ala Ser Leu Arg Ala Gly Met His Ser
    290                 295                 300

Ser Val His Leu Glu Glu Ala Gly Ile Leu Arg Ala Gly Pro Gly Gly
305                 310                 315                 320

Pro Asp Gln Gln Trp Pro Thr Val Ser Ser Ala Thr Pro Glu Pro Glu
                325                 330                 335

Ala Gly Glu Val Ser Pro Val Gly Ala Gly Val Asn Ser Asn Ser
            340                 345                 350

Trp Thr Phe Lys Tyr Gly Pro Gly Asn Pro Lys Gln Ser Gly Pro Gly
        355                 360                 365

Glu Leu Pro Asp Lys Phe Ile Ile Pro Gly Ser Pro Ala Ile Ile Ser
    370                 375                 380

Ile Arg Gln Glu Pro Thr Asn Ser Gln Ile Asp Lys Ser Asp Phe Ile
385                 390                 395                 400

Thr Phe Gly Lys Lys Glu Glu Thr Lys Lys Lys Lys Lys Lys Lys Lys
                405                 410                 415

Gly Asn Lys Thr Gln Glu Lys Lys Glu Lys Gly Asn Ser Thr Thr Asp
            420                 425                 430

Asn Ser Asp Gln
        435

<210> SEQ ID NO 103
<211> LENGTH: 2429
<212> TYPE: DNA
<213> ORGANISM: Homo sapiens

<400> SEQUENCE: 103
gtcgacccac gcgtccgcgg acgcgtgggc ggctgagcgc tggcggtcgg tgcggcgtca      60
ggtgcgcccg ccaggtgagc gcgctccctg gcaccgttgg cccccggagg gtcgggccca     120
gttgcggcga gcggattggt ttatcttgga agctaaaggg cattgctcat cctgaagatc     180
agctgaccat tgacaatcag ccatgtcatc caggcctctt gaaagtccac ctccttacag     240
gcctgatgaa ttcaaaccga atcattatgc accaagcaat gacatatatg gtggagagat     300
gcatgttcga ccaatgctct ctcagccagc ctactctttt tacccagaag atgaaattct     360
tcacttctac aaatggacct ctcctccagg agtgattcgg atcctgtcta tgctcattat     420
```

```
tgtgatgtgc attgccatct ttgcctgtgt ggcctccacg cttgcctggg acagaggcta    480
tggaacttcc cttttaggag gtagtgtagg ctacccttat ggaggaagtg gctttggtag    540
ctacggaagt ggctatggct atggctatgg ttatggctat ggctacggag gctatacaga    600
cccaagagca gcaaagggct tcatgttggc catggctgcc ttttgtttca ttgccgcgtt    660
ggtgatcttt gttaccagtg ttataagatc tgaaatgtcc agaacaagaa gatactactt    720
aagtgtgata atagtgagtg ctatcctggg catcatggtg tttattgcca caattgtcta    780
tataatggga gtgaacccaa ctgctcagtc ttctggatct ctatatggtt cacaaatata    840
tgccctctgc aaccaatttt atacacctgc agctactgga ctctacgtgg atcagtattt    900
gtatcactac tgtgttgtgg atccccagga ggccattgcc attgtactgg ggttcatgat    960
tattgtggct tttgctttaa taattttctt tgctgtgaaa actcgaagaa agatggacag   1020
gtatgacaag tccaatattt tgtgggacaa ggaacacatt tatgatgagc agccccccaa   1080
tgtcgaggag tgggttaaaa atgtgtctgc aggcacacag gacgtgcctt cacccccatc   1140
tgactatgtg gaaagagttg acagtccat ggcatactct tccaatggca aagtgaatga   1200
caagcggttt tatccagagt cttcctataa atccacgccg gttcctgaag tggttcagga   1260
gcttccatta acttcgcctg tggatgactt caggcagcct cgttacagca gcggtggtaa   1320
ctttgagaca ccttcaaaaa gagcacctgc aaagggaaga gcaggaaggt caaagagaac   1380
agagcaagat cactatgaga cagactacac aactggcggc gagtcctgtg atgagctgga   1440
ggaggactgg atcagggaat atccacctat cacttcagat caacaaagac aactgtacaa   1500
gaggaatttt gacactggcc tacaggaata caagagctta caatcagaac ttgatgagat   1560
caataaagaa ctctcccgtt tggataaaga attggatgac tatagagaag aaagtgaaga   1620
gtacatggct gctgctgatg aatacaatag actgaagcaa gtgaagggat ctgcagatta   1680
caaaagtaag aagaatcatt gcaagcagtt aaagagcaaa ttgtcacaca tcaagaagat   1740
ggttggagac tatgatagac agaaaacata gaaggctgat gccaagttgt ttgagaaatt   1800
aagtatctga catctctgca atcttctcag aaggcaaatg actttggacc ataaccccgg   1860
aagccaaacc tctgtgagca tcacaaagtt ttggttgctt taacatcatc agtattgaag   1920
cattttataa atcgcttttg ataatcaact gggctgaaca ctccaattaa ggattttatg   1980
ctttaaacat tggttcttgt attaagaatg aaatactgtt tgaggttttt aagccttaaa   2040
ggaaggttct ggtgtgaact aaactttcac accccagacg atgtcttcat acctacatgt   2100
atttgtttgc ataggtgatc tcatttaatc ctctcaacca cctttcagat aactgttatt   2160
tataatcact tttttccaca taaggaaact gggttcctgc aatgaagtct ctgaagtgaa   2220
actgcttgtt tcctagcaca cacttttggt taagtctgtt ttatgacttc attaataata   2280
aattccctgg cctttcatat tttagctact atatatgtga tgatctacca gcctccctat   2340
tttttttctg ttatataaat ggttaaaaga ggttttcttt aaataataaa gatcatgtaa   2400
aagtaaaaaa aaaaaaaaag ggcggccgc                                     2429
```

<210> SEQ ID NO 104  
<211> LENGTH: 522  
<212> TYPE: PRT  
<213> ORGANISM: Homo sapiens

<400> SEQUENCE: 104

Met Ser Ser Arg Pro Leu Glu Ser Pro Pro Tyr Arg Pro Asp Glu  
1               5                   10                  15

```
Phe Lys Pro Asn His Tyr Ala Pro Ser Asn Asp Ile Tyr Gly Gly Glu
             20                  25                  30

Met His Val Arg Pro Met Leu Ser Gln Pro Ala Tyr Ser Phe Tyr Pro
         35                  40                  45

Glu Asp Glu Ile Leu His Phe Tyr Lys Trp Thr Ser Pro Pro Gly Val
 50                  55                  60

Ile Arg Ile Leu Ser Met Leu Ile Ile Val Met Cys Ile Ala Ile Phe
 65                  70                  75                  80

Ala Cys Val Ala Ser Thr Leu Ala Trp Asp Arg Gly Tyr Gly Thr Ser
             85                  90                  95

Leu Leu Gly Gly Ser Val Gly Tyr Pro Tyr Gly Gly Ser Gly Phe Gly
            100                 105                 110

Ser Tyr Gly Ser Gly Tyr Gly Tyr Gly Tyr Gly Tyr Gly Tyr Gly Tyr
            115                 120                 125

Gly Gly Tyr Thr Asp Pro Arg Ala Ala Lys Gly Phe Met Leu Ala Met
    130                 135                 140

Ala Ala Phe Cys Phe Ile Ala Ala Leu Val Ile Phe Val Thr Ser Val
145                 150                 155                 160

Ile Arg Ser Glu Met Ser Arg Thr Arg Arg Tyr Tyr Leu Ser Val Ile
                165                 170                 175

Ile Val Ser Ala Ile Leu Gly Ile Met Val Phe Ile Ala Thr Ile Val
            180                 185                 190

Tyr Ile Met Gly Val Asn Pro Thr Ala Gln Ser Ser Gly Ser Leu Tyr
    195                 200                 205

Gly Ser Gln Ile Tyr Ala Leu Cys Asn Gln Phe Tyr Thr Pro Ala Ala
    210                 215                 220

Thr Gly Leu Tyr Val Asp Gln Tyr Leu Tyr His Tyr Cys Val Val Asp
225                 230                 235                 240

Pro Gln Glu Ala Ile Ala Ile Val Leu Gly Phe Met Ile Ile Val Ala
                245                 250                 255

Phe Ala Leu Ile Ile Phe Phe Ala Val Lys Thr Arg Arg Lys Met Asp
                260                 265                 270

Arg Tyr Asp Lys Ser Asn Ile Leu Trp Asp Lys Glu His Ile Tyr Asp
    275                 280                 285

Glu Gln Pro Pro Asn Val Glu Glu Trp Val Lys Asn Val Ser Ala Gly
    290                 295                 300

Thr Gln Asp Val Pro Ser Pro Ser Asp Tyr Val Glu Arg Val Asp
305                 310                 315                 320

Ser Pro Met Ala Tyr Ser Ser Asn Gly Lys Val Asn Asp Lys Arg Phe
            325                 330                 335

Tyr Pro Glu Ser Ser Tyr Lys Ser Thr Pro Val Pro Glu Val Val Gln
            340                 345                 350

Glu Leu Pro Leu Thr Ser Pro Val Asp Asp Phe Arg Gln Pro Arg Tyr
    355                 360                 365

Ser Ser Gly Gly Asn Phe Glu Thr Pro Ser Lys Arg Ala Pro Ala Lys
    370                 375                 380

Gly Arg Ala Gly Arg Ser Lys Arg Thr Glu Gln Asp His Tyr Glu Thr
385                 390                 395                 400

Asp Tyr Thr Thr Gly Gly Glu Ser Cys Asp Glu Leu Glu Glu Asp Trp
                405                 410                 415

Ile Arg Glu Tyr Pro Pro Ile Thr Ser Asp Gln Gln Arg Gln Leu Tyr
                420                 425                 430

Lys Arg Asn Phe Asp Thr Gly Leu Gln Glu Tyr Lys Ser Leu Gln Ser
```

|  |  | 435 |  |  | 440 |  |  | 445 |  |  |  |
|--|--|--|--|--|--|--|--|--|--|--|--|

Glu Leu Asp Glu Ile Asn Lys Glu Leu Ser Arg Leu Asp Lys Glu Leu
            450                 455                 460

Asp Asp Tyr Arg Glu Glu Ser Glu Glu Tyr Met Ala Ala Ala Asp Glu
465                 470                 475                 480

Tyr Asn Arg Leu Lys Gln Val Lys Gly Ser Ala Asp Tyr Lys Ser Lys
                    485                 490                 495

Lys Asn His Cys Lys Gln Leu Lys Ser Lys Leu Ser His Ile Lys Lys
            500                 505                 510

Met Val Gly Asp Tyr Asp Arg Gln Lys Thr
            515                 520

<210> SEQ ID NO 105
<211> LENGTH: 2985
<212> TYPE: DNA
<213> ORGANISM: Homo sapiens
<220> FEATURE:
<221> NAME/KEY: modified_base
<222> LOCATION: (15)..(15)
<223> OTHER INFORMATION: a, c, t or g

<400> SEQUENCE: 105

| cccgcgtccg gattntttg ataagtacgg gacgttattg atggtagaga atatttttat | 60 |
|---|---|
| agactgttgg agttggaagt cttcttgctt ggcattaagg aagagactga taaaggtaat | 120 |
| gggtgtgaac cactcttaaa gatgtaggca atgaaaaaat agcctggaga gagaacaagg | 180 |
| ccaagtgaag tttgtcattc cccacctccc cccacccctcc atcttccaaa ccaaggagaa | 240 |
| ggagccagtg gagaacaaag gagcttaagg aacattcgag taaagttcct caagattcag | 300 |
| tagtagatct taaaaatgaa atgtattagg atatattaca tatggactgt ttctataata | 360 |
| tactcttcct ttctcctctc agctttgaca tctttatata atagcatgat attttactta | 420 |
| catatatctt taaaaaatca ttctatagga gtgtccctag ttgtaacaga aactgtcgat | 480 |
| gcaggtttat ttggagaagg attggggaga gttttgattc atgcatggga gcatttactt | 540 |
| ttacagccaa agaccaaagg tgaaagtgct aattgtgaaa agtatgggaa agttatacca | 600 |
| gcaagtgctg ttatatttgg gatggcagta gaatgtgcag agataagaag acatcataga | 660 |
| gtgggtatta aggacattgc tggtatccat ttgccaacaa atgtgaaatt tcagagtccg | 720 |
| gcttattctt ctgtagatac tgaagaaaca attgaacctt atacaactga aaagatgagt | 780 |
| cgagttcctg gaggatattt ggctttgaca gagtgctttg aaattatgac agtagatttc | 840 |
| aacaaccttc aggaattaaa aagtcttgca actaaaaagc ctgataagat tggtattcct | 900 |
| gttattaaag aaggcatact agatgctatt atggtttggt tgtgctcca gcttgatgat | 960 |
| gaacatagtt tatccacaag tcctagtgag gaaacatgtt gggaacaggc tgtctacccc | 1020 |
| gtacaggacc ttgcagacta ctggataaag cctggagacc atgtgatgat ggaagtatct | 1080 |
| tgtcaagact gttacttaag aatccagagt attagtgtct tgggtttgga atgtgaaatg | 1140 |
| gatgttgcaa aaagttttac ccagaataaa gacttgttat cgttaggaaa tgaggctgaa | 1200 |
| ctttgtagtg ccctcgctaa ccttcagacc agtaaaccag atgctgtaga gcagacatgt | 1260 |
| atattggaat ctacagaaat tgctttgctt aacaacatcc catatcatga aggctttaaa | 1320 |
| atggcaatga gcaaagtttt gtcttcactg actccagaga aactgtatca gaccatggat | 1380 |
| actcactgtc agaatgagat gagctctgga actggacaga gtaatactgt acagaacatc | 1440 |
| cttgaacctt tctacgtgtt agatgtgtcc gaaggcttct ctgttctgcc tgttattgct | 1500 |

```
ggcacacttg ggcaggttaa accatacagt tctgtggaga aagaccagca tcgtattgct    1560
ctggacctca tatctgaagc caatcacttt cctaaagaaa cacttgagtt ttggctgaga    1620
catgtggagg atgaatctgc tatgttacaa aggccaaaat cagacaagtt atggagcata    1680
attatattgg atgtcattga gccatctggg ctcattcagc aggaaataat ggaaaaagct    1740
gcaatatcca ggtgtttact acaatctgga ggcaagatct ttcctcagta tgtgctgatg    1800 tttggggttgc ttgtggaatc acagacactc ctagaggaga atgctgttca aggaacagaa    1860
gtactcttgg attaaatata gcaccttta  ttaaccagtt tcaggtacct atacgtgtat    1920 ttttggaccct atcctcattg ccctgtatac ctttaagcaa gccagtggaa ctcttaagac    1980
tagatttaat gactccgtat ttgaacacct ctaacagaga agtaaaggta tacgtttgta    2040
aatctggaag actgactgct attccatttt ggtatcatat gtaccttgat gaagagatta    2100
ggttggatac ttcaagtgaa gcctcccact ggaaacaagc tgcagttgtt ttagataatc    2160
ccatccaggt tgaaatggga gaggaacttg tactcagcat tcagcatcac aaaagcaatg    2220
tcagcatcac agtaaagcaa tgaagagcag ttttccaatg aaaactgtgt aaatagagca    2280
tcaacaagta caaaattctt gtcttaatta gtggggtat  ataaaaattc cttgtaatgg    2340
tcaaatattt tttaaaattg acattaataa agcatatttt aaaagattct aaaaaaaaaa    2400
aaaamgsayk mkkrkmgamw ymctgctgca gatttgcttt ctggaaaagg atacatcact    2460
agttttttaa attaggaaac ttcttttgct cgatttttaca gaatagggat tttaaaagtc    2520
ttatcgttat tgacatgtgt aagtaaagca aaacttttact tttgtaggca tcttggcctt    2580
ttttcttaaa tccaaacttg taattgggaa acactgaaag gcttccactg aagactgagg    2640
gttatggtta cctgtaaatt ccaatcttgc ttcctttaaa tactcagtgt acatctgaaa    2700
catctcaggt tttgttttga gaatgcaagc ttgaaaaaga atttaagcta taagctaaat    2760
gtaattaaaa cagtaaagga gttagggaat aaatcttcag gaggcagcat ttttcttggt    2820
ctactttggc aaaagaacat ttaaaagctg gtaacaaaac aaagttaaat tgaaggaaga    2880
cttaatccta tactattttt caaagttttg atttggatgt acaataagta cattaattga    2940 tccatttttta caaaccttttt gaataaggag atcataatat gcctc                  2985
```

<210> SEQ ID NO 106
<211> LENGTH: 519
<212> TYPE: PRT
<213> ORGANISM: Homo sapiens

<400> SEQUENCE: 106

Met Lys Cys Ile Arg Ile Tyr Tyr Ile Trp Thr Val Ser Ile Ile Tyr
1               5                   10                  15

Ser Ser Phe Leu Leu Ser Ala Leu Thr Ser Leu Tyr Asn Ser Met Ile
            20                  25                  30

Phe Tyr Leu His Ile Ser Leu Lys Asn His Ser Ile Gly Val Ser Leu
        35                  40                  45

Val Val Thr Glu Thr Val Asp Ala Gly Leu Phe Gly Glu Gly Leu Gly
    50                  55                  60

Arg Val Leu Ile His Ala Trp Glu His Leu Leu Leu Gln Pro Lys Thr
65                  70                  75                  80

Lys Gly Glu Ser Ala Asn Cys Glu Lys Tyr Gly Lys Val Ile Pro Ala
                85                  90                  95

Ser Ala Val Ile Phe Gly Met Ala Val Glu Cys Ala Glu Ile Arg Arg
            100                 105                 110

```
His His Arg Val Gly Ile Lys Asp Ile Ala Gly Ile His Leu Pro Thr
            115                 120                 125

Asn Val Lys Phe Gln Ser Pro Ala Tyr Ser Ser Val Asp Thr Glu Glu
            130                 135                 140

Thr Ile Glu Pro Tyr Thr Thr Glu Lys Met Ser Arg Val Pro Gly Gly
145                 150                 155                 160

Tyr Leu Ala Leu Thr Glu Cys Phe Glu Ile Met Thr Val Asp Phe Asn
                165                 170                 175

Asn Leu Gln Glu Leu Lys Ser Leu Ala Thr Lys Lys Pro Asp Lys Ile
            180                 185                 190

Gly Ile Pro Val Ile Lys Glu Gly Ile Leu Asp Ala Ile Met Val Trp
            195                 200                 205

Phe Val Leu Gln Leu Asp Asp Glu His Ser Leu Ser Thr Ser Pro Ser
210                 215                 220

Glu Glu Thr Cys Trp Glu Gln Ala Val Tyr Pro Val Gln Asp Leu Ala
225                 230                 235                 240

Asp Tyr Trp Ile Lys Pro Gly Asp His Val Met Met Glu Val Ser Cys
                245                 250                 255

Gln Asp Cys Tyr Leu Arg Ile Gln Ser Ile Ser Val Leu Gly Leu Glu
            260                 265                 270

Cys Glu Met Asp Val Ala Lys Ser Phe Thr Gln Asn Lys Asp Leu Leu
            275                 280                 285

Ser Leu Gly Asn Glu Ala Glu Leu Cys Ser Ala Leu Ala Asn Leu Gln
            290                 295                 300

Thr Ser Lys Pro Asp Ala Val Glu Gln Thr Cys Ile Leu Glu Ser Thr
305                 310                 315                 320

Glu Ile Ala Leu Leu Asn Asn Ile Pro Tyr His Glu Gly Phe Lys Met
                325                 330                 335

Ala Met Ser Lys Val Leu Ser Ser Leu Thr Pro Glu Lys Leu Tyr Gln
            340                 345                 350

Thr Met Asp Thr His Cys Gln Asn Glu Met Ser Ser Gly Thr Gly Gln
            355                 360                 365

Ser Asn Thr Val Gln Asn Ile Leu Glu Pro Phe Tyr Val Leu Asp Val
            370                 375                 380

Ser Glu Gly Phe Ser Val Leu Pro Val Ile Ala Gly Thr Leu Gly Gln
385                 390                 395                 400

Val Lys Pro Tyr Ser Ser Val Glu Lys Asp Gln His Arg Ile Ala Leu
                405                 410                 415

Asp Leu Ile Ser Glu Ala Asn His Phe Pro Lys Glu Thr Leu Glu Phe
            420                 425                 430

Trp Leu Arg His Val Glu Asp Glu Ser Ala Met Leu Gln Arg Pro Lys
            435                 440                 445

Ser Asp Lys Leu Trp Ser Ile Ile Ile Leu Asp Val Ile Glu Pro Ser
450                 455                 460

Gly Leu Ile Gln Gln Glu Ile Met Glu Lys Ala Ala Ile Ser Arg Cys
465                 470                 475                 480

Leu Leu Gln Ser Gly Gly Lys Ile Phe Pro Gln Tyr Val Leu Met Phe
                485                 490                 495

Gly Leu Leu Val Glu Ser Gln Thr Leu Leu Glu Glu Asn Ala Val Gln
            500                 505                 510

Gly Thr Glu Val Leu Leu Asp
            515
```

<210> SEQ ID NO 107
<211> LENGTH: 2467
<212> TYPE: DNA
<213> ORGANISM: Homo sapiens
<220> FEATURE:
<221> NAME/KEY: modified_base
<222> LOCATION: (2453)..(2467)
<223> OTHER INFORMATION: a, c, t or g

<400> SEQUENCE: 107

```
cgaccacgcg tccgcccgca gcggccgagc tgcagcccgg gctcagtctc cgccgccgcc    60
gtgaacatgg agcccccgga cgcaccggcc caggcgcgcg ggccccgcg gctgctgttg    120
ctcgcagtcc tgctggcggc gcacccagat gcccaggcgg aggtgcgctt gtctgtaccc    180
ccgctggtgg aggtgatgcg aggaaagtct gtcattctgg actgcacccc tacgggaacc    240
cacgaccatt atatgctgga atggttcctt accgaccgct cgggagctcg ccccgcta    300
gcctcggctg agatgcaggg ctctgagctc caggtcacaa tgcacgacac cggggccgc    360
agtcccccat accagctgga ctcccagggg cgcctggtgc tggctgaggc ccaggtgggc    420
gacgagcgag actacgtgtg cgtggtgagg gcagggcgg caggcactgc tgaggccact    480
gcgcggctca acgtgtttgc aaagccagag gccactgagg tctcccccaa caaagggaca    540
ctgtctgtga tggaggactc tgcccaggag atcgccacct gcaacagccg gaacgggaac    600
ccggccccca agatcacgtg gtatcgcaac gggcagcgcc tggaggtgcc cgtagagatg    660
aacccagagg gctacatgac cagccgcacg gtccgggagg cctcgggcct gctctccctc    720
accagcaccc tctacctgcg gctccgcaag gatgaccgag acgccagctt ccactgcgcc    780
gcccactaca gcctgcccga gggccgccac ggccgcctgg acagccccac cttccacctc    840
accctgcact atcccacgga gcacgtgcag ttctgggtgg gcagcccgtc caccccagca    900
ggctgggtac gcgagggtga cactgtccag ctgctctgcc gggggacgg cagccccagc    960
ccggagtata cgcttttccg ccttcaggat gagcaggagg aagtgctgaa tgtgaatctc    1020
gaggggaact tgaccctgga gggagtgacc cggggccaga gcgggaccta tggctgcaga    1080
gtggaggatt acgacgcggc agatgacgtg cagctctcca agacgctgga gctgcgcgtg    1140
gcctatctgg acccctgga gctcagcgag gggaaggtgc tttccttacc tctaaacagc    1200
agtgcagtcg tgaactgctc cgtgcacggc ctgcccaccc ctgccctacg ctggaccaag    1260
gactccactc ccctgggcga tggccccatg ctgtcgctca gttctatcac cttcgattcc    1320
aatggcaccct acgtatgtga ggcctccctg cccacagtcc cggtcctcag ccgcacccag    1380
aacttcacgc tgctggtcca aggctcgcca gagctaaaga cagcggaaat agagcccaag    1440
gcagatggca gctggagga aggagacgaa gtcacactca tctgctctgc ccgcggccat    1500
ccagacccca aactcagctg gagccaattg ggggcagcc ccgcagagcc aatccccgga    1560
cggcagggtt gggtgagcag ctctctgacc ctgaaagtga ccagcgccct gagccgcgat    1620
ggcatctcct gtgaagcctc caaccccac gggaacaagc gccatgtctt ccacttcggc    1680
gccgtgagcc cccagacctc ccaggctgga gtggccgtca tggccgtggc cgtcagcgtg    1740
ggcctcctgc tcctcgtcgt tgctgtcttc tactgcgtga acgcaaaagg gggccctgc    1800
tgccgccagc ggcgggagaa gggggctccg ccgccagggg agccagggct gagccactcg    1860
gggtcggagc aaccagagca gaccggcctt tcatgggag gtgcctccgg aggagccagg    1920
ggtggcagcg gggcttcgg agacgagtgc tgagccaaga acctcctaga ggctgtccct    1980
ggacctggag ctgcaggcat cagagaacca gccctgctca cgccatgccc gccccgcct    2040
```

```
tccctcttcc ctcttccctc tccctgccca gccctcccta ccttcctctg ccggcaaggc    2100
agggacccac agtggctgcc tgcctccggg agggaaggag agggagggtg ggtgggtggg    2160 aggggggcctt cctccaggga atgtgactct cccaggcccc agaatagctc ctggacccaa   2220
gcccaaggcc cagcctggga caaggctccg agggtcggct ggccggagct attttaccttt    2280 cccgcctccc ctgctggtcc ccccacctga cgtcttgctg cagagtctga cactggattc    2340 cccccccctca cccgcccct ggtcccactc ctgccccgc cctacctccg ccccacccca     2400
tcatctgtgg acactggagt ctggaataaa tgctgtttgt cacatcaaca ccnnnnnnnn    2460 nnnnnnn                                                              2467
```

<210> SEQ ID NO 108
<211> LENGTH: 628
<212> TYPE: PRT
<213> ORGANISM: Homo sapiens

<400> SEQUENCE: 108

```
Met Glu Pro Pro Asp Ala Pro Ala Gln Ala Arg Gly Ala Pro Arg Leu
1               5                   10                  15

Leu Leu Leu Ala Val Leu Ala Ala His Pro Asp Ala Gln Ala Glu
            20                  25                  30

Val Arg Leu Ser Val Pro Pro Leu Val Glu Val Met Arg Gly Lys Ser
        35                  40                  45

Val Ile Leu Asp Cys Thr Pro Thr Gly Thr His Asp His Tyr Met Leu
    50                  55                  60

Glu Trp Phe Leu Thr Asp Arg Ser Gly Ala Arg Pro Arg Leu Ala Ser
65                  70                  75                  80

Ala Glu Met Gln Gly Ser Glu Leu Gln Val Thr Met His Asp Thr Arg
                85                  90                  95

Gly Arg Ser Pro Pro Tyr Gln Leu Asp Ser Gln Gly Arg Leu Val Leu
            100                 105                 110

Ala Glu Ala Gln Val Gly Asp Glu Arg Asp Tyr Val Cys Val Val Arg
        115                 120                 125

Ala Gly Ala Ala Gly Thr Ala Glu Ala Thr Ala Arg Leu Asn Val Phe
    130                 135                 140

Ala Lys Pro Glu Ala Thr Glu Val Ser Pro Asn Lys Gly Thr Leu Ser
145                 150                 155                 160

Val Met Glu Asp Ser Ala Gln Glu Ile Ala Thr Cys Asn Ser Arg Asn
                165                 170                 175

Gly Asn Pro Ala Pro Lys Ile Thr Trp Tyr Arg Asn Gly Gln Arg Leu
            180                 185                 190

Glu Val Pro Val Glu Met Asn Pro Glu Gly Tyr Met Thr Ser Arg Thr
        195                 200                 205

Val Arg Glu Ala Ser Gly Leu Leu Ser Leu Thr Ser Thr Leu Tyr Leu
    210                 215                 220

Arg Leu Arg Lys Asp Asp Arg Asp Ala Ser Phe His Cys Ala Ala His
225                 230                 235                 240

Tyr Ser Leu Pro Glu Gly Arg His Gly Arg Leu Asp Ser Pro Thr Phe
                245                 250                 255

His Leu Thr Leu His Tyr Pro Thr Glu His Val Gln Phe Trp Val Gly
            260                 265                 270

Ser Pro Ser Thr Pro Ala Gly Trp Val Arg Glu Gly Asp Thr Val Gln
        275                 280                 285

Leu Leu Cys Arg Gly Asp Gly Ser Pro Ser Pro Glu Tyr Thr Leu Phe
```

```
                    290                 295                 300
Arg Leu Gln Asp Glu Gln Glu Val Leu Asn Val Asn Leu Glu Gly
305                 310                 315                 320

Asn Leu Thr Leu Glu Gly Val Thr Arg Gly Gln Ser Gly Thr Tyr Gly
                325                 330                 335

Cys Arg Val Glu Asp Tyr Asp Ala Ala Asp Val Gln Leu Ser Lys
                340                 345                 350

Thr Leu Glu Leu Arg Val Ala Tyr Leu Asp Pro Leu Glu Leu Ser Glu
                355                 360                 365

Gly Lys Val Leu Ser Leu Pro Leu Asn Ser Ser Ala Val Asn Cys
370                 375                 380

Ser Val His Gly Leu Pro Thr Pro Ala Leu Arg Trp Thr Lys Asp Ser
385                 390                 395                 400

Thr Pro Leu Gly Asp Gly Pro Met Leu Ser Leu Ser Ser Ile Thr Phe
                405                 410                 415

Asp Ser Asn Gly Thr Tyr Val Cys Glu Ala Ser Leu Pro Thr Val Pro
                420                 425                 430

Val Leu Ser Arg Thr Gln Asn Phe Thr Leu Leu Val Gln Gly Ser Pro
                435                 440                 445

Glu Leu Lys Thr Ala Glu Ile Glu Pro Lys Ala Asp Gly Ser Trp Arg
450                 455                 460

Glu Gly Asp Glu Val Thr Leu Ile Cys Ser Ala Arg Gly His Pro Asp
465                 470                 475                 480

Pro Lys Leu Ser Trp Ser Gln Leu Gly Gly Ser Pro Ala Glu Pro Ile
                485                 490                 495

Pro Gly Arg Gln Gly Trp Val Ser Ser Leu Thr Leu Lys Val Thr
                500                 505                 510

Ser Ala Leu Ser Arg Asp Gly Ile Ser Cys Glu Ala Ser Asn Pro His
                515                 520                 525

Gly Asn Lys Arg His Val Phe His Phe Gly Ala Val Ser Pro Gln Thr
530                 535                 540

Ser Gln Ala Gly Val Ala Val Met Ala Val Ala Val Ser Val Gly Leu
545                 550                 555                 560

Leu Leu Leu Val Val Ala Val Phe Tyr Cys Val Arg Arg Lys Gly Gly
                565                 570                 575

Pro Cys Cys Arg Gln Arg Arg Glu Lys Gly Ala Pro Pro Gly Glu
                580                 585                 590

Pro Gly Leu Ser His Ser Gly Ser Glu Gln Pro Glu Gln Thr Gly Leu
                595                 600                 605

Leu Met Gly Gly Ala Ser Gly Gly Ala Arg Gly Gly Ser Gly Gly Phe
610                 615                 620

Gly Asp Glu Cys
625

<210> SEQ ID NO 109
<211> LENGTH: 3825
<212> TYPE: DNA
<213> ORGANISM: Homo sapiens

<400> SEQUENCE: 109
ccaagttcta cctcatgttt ggaggatctt gctagctatg ccctcgtac tcggctccct      60 gttgctgctg gggctgtgcg ggaactcctt tcaggaggg cagccttcat ccacagatgc     120
tcctaaggct tggaattatg aattgcctgc aacaaattat gagacccaag actcccataa    180
```

-continued

```
agctggaccc attggcattc tctttgaact agtgcatatc tttctctatg tggtacagcc    240
gcgtgatttc ccagaagata ctttgagaaa attcttacag aaggcatatg aatccaaaat    300
tgattatgac aagccagaaa ctgtaatctt aggtctaaag attgtctact atgaagcagg    360
gattattcta tgctgtgtcc tggggctgct gtttattatt ctgatgcctc tggtggggta    420
tttcttttgt atgtgtcgtt gctgtaacaa atgtggtgga gaaatgcacc agcgacagaa    480
ggaaaatggg cccttcctga ggaaatgctt tgcaatctcc ctgttggtga tttgtataat    540
aataagcatt ggcatcttct atggttttgt ggcaaatcac caggtaagaa cccggatcaa    600
aaggagtcgg aaactggcag atagcaattt caaggacttg cgaactctct tgaatgaaac    660
tccagagcaa atcaaatata tattggccca gtacaacact accaaggaca aggcgttcac    720
agatctgaac agtatcaatt cagtgctagg aggcggaatt cttgaccgac tgagacccaa    780
catcatccct gttcttgatg agattaagtc catggcaaca gcgatcaagg agaccaaaga    840
ggcgttggag aacatgaaca gcaccttgaa gagcttgcac caacaaagta cacagcttag    900
cagcagtctg accagcgtga aaactagcct gcggtcatct ctcaatgacc ctctgtgctt    960
ggtgcatcca tcaagtgaaa cctgcaacag catcagattg tctctaagcc agctgaatag   1020
caaccctgaa ctgaggcagc ttccacccgt ggatgcagaa cttgacaacg ttaataacgt   1080
tcttaggaca gatttggatg gcctggtcca acagggctat caatccctta atgatatacc   1140
tgacagagta caacgccaaa ccacgactgt cgtagcaggt atcaaaaggg tcttgaattc   1200
cattggttca gatatcgaca atgtaactca gcgtcttcct attcaggata tactctcagc   1260
attctctgtt tatgttaata acactgaaag ttacatccac agaaatttac ctacattgga   1320
agagtatgat tcatactggt ggctgggtgg cctggtcatc tgctctctgc tgaccctcat   1380
cgtgattttt tactacctgg gcttactgtg tggcgtgtgc ggctatgaca ggcatgccac   1440
cccgaccacc cgaggctgtg tctccaacac cggaggcgtc ttcctcatgg ttggagttgg   1500
attaagtttc ctcttttgct ggatattgat gatcattgtg gttcttacct ttgtctttgg   1560
tgcaaatgtg gaaaaactga tctgtgaacc ttacacgagc aaggaattat ccgggttttt   1620
ggatacaccc tacttactaa atgaagactg ggaaatactat ctctctggga agctattttaa   1680 taaatcaaaa atgaagctca cttttgaaca gtttacagt gactgcaaaa aaaatagagg   1740
cacttacggc actcttcacc tgcagaacag cttcaatatc agtgaacatc tcaacattaa   1800
tgagcatact ggaagcataa gcagtgaatt ggaaagtctg aaggtaaatc ttaatatctt   1860
tctgttgggt gcagcaggaa gaaaaaacct tcaggatttt gctgcttgtg aatagacag   1920 aatgaattat gacagctact ggctcagac tggtaaatcc cccgcaggag tgaatctttt   1980
atcatttgca tatgatctag aagcaaaagc aaacagtttg cccccaggaa atttgaggaa   2040
ctccctgaaa agagatgcac aaactattaa aacaattcac cagcaacgag tccttcctat   2100
agaacaatca ctgagcactc tataccaaag cgtcaagata cttcaacgca cagggaatgg   2160
attgttggag agagtaacta ggattctagc ttctctggat tttgctcaga acttcatcac   2220
aaacaatact tcctctgtta ttattgagga aactaagaag tatgggagaa caataatagg   2280
atattttgaa cattatctgc agtggatcga gttctctatc agtgagaaag tggcatcgtg   2340
caaacctgtg gccaccgctc tagatactgc tgttgatgtc tttctgtgta gctacattat   2400
cgaccccttg aatttgtttt ggtttggcat aggaaaagct actgtatttt acttccggc    2460 tctaattttt gcggtaaaac tggctaagta ctatcgtcga atggattcgg aggacgtata   2520
cgatgatgtt gaaactatac ccatgaaaaa tatggaaaat ggtaataatg ttatcataa    2580
```

```
agatcatgta tatggtattc acaatcctgt tatgacaagc ccatcacaac attgatagct    2640
gatgttgaaa ctgcttgagc atcaggatac tcaaagtgga aaggatcaca gattttttggt   2700 agtttctggg tctacaagga cttttccaaat ccaggagcaa cgccagtggc aacgtagtga   2760
ctcaggcggg caccaaggca acggcaccat tggtctctgg gtagtgcttt aagaatgaac    2820
acaatcacgt tatagtccat ggtccatcac tattcaagga tgactccctc ccttcctgtc    2880 tattttttgtt ttttactttt ttacactgag tttctattta gacactacaa catatggggt   2940
gtttgttccc attggatgca tttctatcaa aactctatca aatgtgatgg ctagattcta    3000
acatattgcc atgtgtggag tgtgctgaac acacaccagt ttacaggaaa gatgcattt    3060 gtgtacagta acggtgtat ataccttttg ttaccacaga ttttttaaa caaatgagta     3120 ttataggact tcttctaaa tgagctaaat aagtcaccat tgacttcttg gtgctgttga    3180
aaataatcca ttttcactaa aagtgtgtga aacctacagc atattcttca cgcagagatt   3240
ttcatctatt atactttatc aaagattggc catgttccac ttggaaatgg catgcaaaag   3300
ccatcataga gaaacctgcg taactccatc tgacaaattc aaaagagaga gagagatctt   3360
gagagagaaa tgctgtycgt tccaaaagtg gagttgtttt taaaccagat gcccaattac   3420
ggtgtaccag ttttaaccaga gttttcctgt tgccattagg ataaacatta attggagtgc   3480
cagcctaaca tgagtatcca tccagaccta gtatcaagtg ttcctaaaat gaaatatgag   3540
aagatccctg tcacaattcc ttagatctgg tgtcccagca tggatgaaac ctttgagttt    3600
ggtccctaaa tttgcatgaa agcacaaggt aaatattcat ttgcttcagg agtttcatgt   3660
tggatctgtc attatcaaaa gtgatcagca atgaagaact ggtcggacaa aatttaacgt   3720
tgatgtaatg raattccaga tgtaggcatt ccccccaggt cttttcatgt gcagattgca   3780
gttctgattc atttgaataa aaaggaactt ggaaaacaaa aaaaa                   3825
```

<210> SEQ ID NO 110
<211> LENGTH: 865
<212> TYPE: PRT
<213> ORGANISM: Homo sapiens

<400> SEQUENCE: 110

```
Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
```

-continued

```
            145                 150                 155                 160
Ser Leu Leu Val Ile Cys Ile Ile Ser Ile Gly Ile Phe Tyr Gly
                165                 170                 175

Phe Val Ala Asn His Gln Val Arg Thr Arg Ile Lys Arg Ser Arg Lys
                180                 185                 190

Leu Ala Asp Ser Asn Phe Lys Asp Leu Arg Thr Leu Leu Asn Glu Thr
                195                 200                 205

Pro Glu Gln Ile Lys Tyr Ile Leu Ala Gln Tyr Asn Thr Thr Lys Asp
210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
                260                 265                 270

Met Asn Ser Thr Leu Lys Ser Leu His Gln Gln Ser Thr Gln Leu Ser
                275                 280                 285

Ser Ser Leu Thr Ser Val Lys Thr Ser Leu Arg Ser Ser Leu Asn Asp
290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
                340                 345                 350

Leu Asp Gly Leu Val Gln Gln Gly Tyr Gln Ser Leu Asn Asp Ile Pro
                355                 360                 365

Asp Arg Val Gln Arg Gln Thr Thr Thr Val Val Ala Gly Ile Lys Arg
                370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415

Glu Ser Tyr Ile His Arg Asn Leu Pro Thr Leu Glu Glu Tyr Asp Ser
                420                 425                 430

Tyr Trp Trp Leu Gly Gly Leu Val Ile Cys Ser Leu Leu Thr Leu Ile
                435                 440                 445

Val Ile Phe Tyr Tyr Leu Gly Leu Leu Cys Gly Val Cys Gly Tyr Asp
                450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
                500                 505                 510

Lys Leu Ile Cys Glu Pro Tyr Thr Ser Lys Glu Leu Phe Arg Val Leu
                515                 520                 525

Asp Thr Pro Tyr Leu Leu Asn Glu Asp Trp Glu Tyr Tyr Leu Ser Gly
                530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575
```

```
Asn Ser Phe Asn Ile Ser Glu His Leu Asn Ile Asn Glu His Thr Gly
            580                 585                 590
Ser Ile Ser Ser Glu Leu Glu Ser Leu Lys Val Asn Leu Asn Ile Phe
        595                 600                 605
Leu Leu Gly Ala Ala Gly Arg Lys Asn Leu Gln Asp Phe Ala Ala Cys
    610                 615                 620
Gly Ile Asp Arg Met Asn Tyr Asp Ser Tyr Leu Ala Gln Thr Gly Lys
625                 630                 635                 640
Ser Pro Ala Gly Val Asn Leu Leu Ser Phe Ala Tyr Asp Leu Glu Ala
                645                 650                 655
Lys Ala Asn Ser Leu Pro Pro Gly Asn Leu Arg Asn Ser Leu Lys Arg
            660                 665                 670
Asp Ala Gln Thr Ile Lys Thr Ile His Gln Gln Arg Val Leu Pro Ile
        675                 680                 685
Glu Gln Ser Leu Ser Thr Leu Tyr Gln Ser Val Lys Ile Leu Gln Arg
    690                 695                 700
Thr Gly Asn Gly Leu Leu Glu Arg Val Thr Arg Ile Leu Ala Ser Leu
705                 710                 715                 720
Asp Phe Ala Gln Asn Phe Ile Thr Asn Asn Thr Ser Val Ile Ile
                725                 730                 735
Glu Glu Thr Lys Lys Tyr Gly Arg Thr Ile Ile Gly Tyr Phe Glu His
            740                 745                 750
Tyr Leu Gln Trp Ile Glu Phe Ser Ile Ser Glu Lys Val Ala Ser Cys
        755                 760                 765
Lys Pro Val Ala Thr Ala Leu Asp Thr Ala Val Asp Val Phe Leu Cys
    770                 775                 780
Ser Tyr Ile Ile Asp Pro Leu Asn Leu Phe Trp Phe Gly Ile Gly Lys
785                 790                 795                 800
Ala Thr Val Phe Leu Leu Pro Ala Leu Ile Phe Ala Val Lys Leu Ala
                805                 810                 815
Lys Tyr Tyr Arg Arg Met Asp Ser Glu Asp Val Tyr Asp Asp Val Glu
            820                 825                 830
Thr Ile Pro Met Lys Asn Met Glu Asn Gly Asn Gly Tyr His Lys
        835                 840                 845
Asp His Val Tyr Gly Ile His Asn Pro Val Met Thr Ser Pro Ser Gln
    850                 855                 860
His
865

<210> SEQ ID NO 111
<211> LENGTH: 673
<212> TYPE: DNA
<213> ORGANISM: Homo sapiens

<400> SEQUENCE: 111
ttgaattcgc caaggctggg tttccctcat gtatggcaag agctctactc gtgcggtgct    60
tcttctcctt ggcatacagc tcacagctct ttggcctata gcagctgtgg aaatttatac   120
ctcccgggtg ctggaggctg ttaatgggac agatgctcgg ttaaaatgca ctttctccag   180
ctttgcccct gtgggtgatg ctctaacagt gacctggaat tttcgtcctc tagacggggg   240
acctgagcag tttgtattct actaccacat agatcccttc caacccatga gtgggcggtt   300
taaggaccgg gtgtcttggg atgggaatcc tgagcggtac gatgcctcca tccttctctg   360
gaaactgcag ttcgacgaca atggcacata cacctgccag gtgaagaacc cacctgatgt   420
```

```
tgatggggtg ataggggaga tccggctcag cgtcgtgcac actgtacgct tctctgagat      480
ccacttcctg gctctggcca ttggctctgc ctgtgcactg atgatcataa tagtaattgt      540
agtggtcctc ttccagcatt accggaaaaa gcgatgggcc gaaagagctc ataaagtggt      600
ggagataaaa tcaaaagaag aggaaaggct caaccaagag aaaaaggtct ctgtttattt      660
agaagacaca gac                                                         673
```

<210> SEQ ID NO 112
<211> LENGTH: 215
<212> TYPE: PRT
<213> ORGANISM: Homo sapiens

<400> SEQUENCE: 112

```
Met Tyr Gly Lys Ser Ser Thr Arg Ala Val Leu Leu Leu Gly Ile
1               5                   10                  15

Gln Leu Thr Ala Leu Trp Pro Ile Ala Ala Val Glu Ile Tyr Thr Ser
                20                  25                  30

Arg Val Leu Glu Ala Val Asn Gly Thr Asp Ala Arg Leu Lys Cys Thr
                35                  40                  45

Phe Ser Ser Phe Ala Pro Val Gly Asp Ala Leu Thr Val Thr Trp Asn
    50                  55                  60

Phe Arg Pro Leu Asp Gly Gly Pro Glu Gln Phe Val Phe Tyr Tyr His
65                  70                  75                  80

Ile Asp Pro Phe Gln Pro Met Ser Gly Arg Phe Lys Asp Arg Val Ser
                85                  90                  95

Trp Asp Gly Asn Pro Glu Arg Tyr Asp Ala Ser Ile Leu Leu Trp Lys
                100                 105                 110

Leu Gln Phe Asp Asp Asn Gly Thr Tyr Thr Cys Gln Val Lys Asn Pro
            115                 120                 125

Pro Asp Val Asp Gly Val Ile Gly Glu Ile Arg Leu Ser Val Val His
    130                 135                 140

Thr Val Arg Phe Ser Glu Ile His Phe Leu Ala Leu Ala Ile Gly Ser
145                 150                 155                 160

Ala Cys Ala Leu Met Ile Ile Ile Val Ile Val Val Leu Phe Gln
                165                 170                 175

His Tyr Arg Lys Lys Arg Trp Ala Glu Arg Ala His Lys Val Val Glu
            180                 185                 190

Ile Lys Ser Lys Glu Glu Glu Arg Leu Asn Gln Glu Lys Lys Val Ser
            195                 200                 205

Val Tyr Leu Glu Asp Thr Asp
            210             215
```

COMPOSITIONS, KITS, AND METHODS FOR IDENTIFICATION, ASSESSMENT, PREVENTION AND THERAPY OF BREAST AND OVARIAN CANCER

RELATED APPLICATIONS

The present application is a continuation of U.S. patent application Ser. No. 13/629,973, filed on Sep. 28, 2012, which is a continuation of U.S. patent application Ser. No. 12/317,003, filed on Dec. 17, 2008, issued as U.S. Pat. No. 8,323,906 on Dec. 4, 2012, which is a continuation application of U.S. patent application Ser. No. 11/080,991, filed on Mar. 11, 2005, issued as U.S. Pat. No. 7,494,775 on Feb. 24, 2009; which is a continuation application of U.S. patent application Ser. No. 10/176,847, filed on Jun. 21, 2002, abandoned; which claims priority from U.S. Provisional Application No. 60/300,159, filed on Jun. 21, 2001; and which claims priority from U.S. Provisional Application No. 60/301,351, filed on Jun. 27, 2001. The entire contents of each of the foregoing applications are expressly incorporated by reference.

SEQUENCE LISTING

The instant application contains a Sequence Listing which has been submitted in ASCII format via EFS-Web and is hereby incorporated by reference in its entirety. Said ASCII copy, created on May 25, 2016, is named SeqList.txt and is 530,436 bytes in size.

FIELD OF THE INVENTION

The field of the invention is cancer, particularly breast and ovarian cancers, including diagnosis, characterization, management, and therapy of breast and ovarian cancers.

BACKGROUND OF THE INVENTION

The increased number of cancer cases reported in the United States, and, indeed, around the world, is a major concern. Currently there are only a handful of treatments available for specific types of cancer, and these provide no absolute guarantee of success. In order to be most effective, these treatments require not only an early detection of the malignancy, but a reliable assessment of the severity of the malignancy.

The incidence of breast cancer, a leading cause of death in women, has been gradually increasing in the United States over the last thirty years. In 1997, it was estimated that 181,000 new cases were reported in the U.S., and that 44,000 people would die of breast cancer (Parker et al, 1997, *CA Cancer J. Clin.* 47:5-27; Chu et al, 1996, *J. Nat. Cancer Inst.* 88:1571-1579). While the pathogenesis of breast cancer is unclear, transformation of normal breast epithelium to a malignant phenotype may be the result of genetic factors, especially in women under 30 (Mild et al., 1994, *Science*, 266:66-71). The discovery and characterization of BRCA1 and BRCA2 has recently expanded our knowledge of genetic factors which can contribute to familial breast cancer. Germ-line mutations within these two loci are associated with a 50 to 85% lifetime risk of breast and/or ovarian cancer (Casey, 1997, *Curr. Opin. Oncol.* 9:88-93; Marcus et al, 1996, *Cancer* 77:697-709). However, it is likely that other, non-genetic factors also have a significant effect on the etiology of the disease. Regardless of its origin, breast cancer morbidity and mortality increases significantly if it is not detected early in its progression. Thus, considerable effort has focused on the early detection of cellular transformation and tumor formation in breast tissue.

Currently, the principal manner of identifying breast cancer is through detection of the presence of dense tumorous tissue. This may be accomplished to varying degrees of effectiveness by direct examination of the outside of the breast, or through mammography or other X-ray imaging methods (Jatoi, 1999, *Am. J. Surg.* 177:518-524). The latter approach is not without considerable cost, however. Every time a mammogram is taken, the patient incurs a small risk of having a breast tumor induced by the ionizing properties of the radiation used during the test. In addition, the process is expensive and the subjective interpretations of a technician can lead to imprecision, e.g., one study showed major clinical disagreements for about one-third of a set of mammograms that were interpreted individually by a surveyed group of radiologists. Moreover, many women find that undergoing a mammogram is a painful experience. Accordingly, the National Cancer Institute has not recommended mammograms for women under fifty years of age, since this group is not as likely to develop breast cancers as are older women. It is compelling to note, however, that while only about 22% of breast cancers occur in women under fifty, data suggests that breast cancer is more aggressive in pre-menopausal women.

Ovarian cancer is also responsible for significant morbidity and mortality in populations around the world. Ovarian cancer is classified, on the basis of clinical and pathological features, in three groups, namely epithelial ovarian cancer (EOC; >90% of ovarian cancer in Western countries), germ cell tumors (circa 2-3% of ovarian cancer), and stromal ovarian cancer (circa 5% of ovarian cancer; Ozols et al., 1997, *Cancer Principles and Practice of Oncology*, 5th ed., DeVita et al., Eds. pp. 1502). Relative to EOC, germ cell tumors and stromal ovarian cancers are more easily detected and treated at an early stage, translating into higher/better survival rates for patients afflicted with these two types of ovarian cancer.

There are numerous types of ovarian tumors, some of which are benign, and others of which are malignant. Treatment (including non-treatment) options and predictions of patient outcome depend on accurate classification of the ovarian cancer. Ovarian cancers are named according to the type of cells from which the cancer is derived and whether the ovarian cancer is benign or malignant. Recognized histological tumor types include, for example, serous, mucinous, endometrioid, and clear cell tumors. In addition, ovarian cancers are classified according to recognized grade and stage scales.

In grade I, the tumor tissue is well differentiated from normal ovarian tissue. In grade II, tumor tissue is moderately well differentiated. In grade III, the tumor tissue is poorly differentiated from normal tissue, and this grade correlates with a less favorable prognosis than grades I and II. Stage I is generally confined within the capsule surrounding one (stage IA) or both (stage IB) ovaries, although in some stage I (i.e. stage IC) cancers, malignant cells may be detected in ascites, in peritoneal rinse fluid, or on the surface of the ovaries. Stage II involves extension or metastasis of the tumor from one or both ovaries to other pelvic structures. In stage IIA, the tumor extends or has metastasized to the uterus, the fallopian tubes, or both. Stage IIB involves extension of the tumor to the pelvis. Stage IIC is stage IIA or IIB in which malignant cells may be detected in ascites, in peritoneal rinse fluid, or on the surface of the ovaries. In stage III, the tumor comprises at least one malignant extension to the small bowel or the omentum, has formed extrapelvic peritoneal implants of microscopic (stage IIIA) or macroscopic (<2 centimeter diameter, stage IIIB; >2 centimeter diameter, stage IIIC) size, or has metastasized to a retroperitoneal or inguinal lymph node (an alternate indicator of stage IIIC). In stage IV, distant (i.e. non-peritoneal) metastases of the tumor can be detected.

The durations of the various stages of ovarian cancer are not presently known, but are believed to be at least about a year each (Richart et al., 1969, Am. J. Obstet. Gynecol. 105:386). Prognosis declines with increasing stage designation. For example, 5-year survival rates for patients diagnosed with stage I, II, III, and IV ovarian cancer are 80%, 57%, 25%, and 8%, respectively.

Despite being the third most prevalent gynecological cancer, ovarian cancer is the leading cause of death among those afflicted with gynecological cancers. The disproportionate mortality of ovarian cancer is attributable to a substantial absence of symptoms among those afflicted with early-stage ovarian cancer and to difficulty diagnosing ovarian cancer at an early stage. Patients afflicted with ovarian cancer most often present with non-specific complaints, such as abnormal vaginal bleeding, gastrointestinal symptoms, urinary tract symptoms, lower abdominal pain, and generalized abdominal distension. These patients rarely present with paraneoplastic symptoms or with symptoms which clearly indicate their affliction. Presently, less than about 40% of patients afflicted with ovarian cancer present with stage I or stage II. Management of ovarian cancer would be significantly enhanced if the disease could be detected at an earlier stage, when treatments are much more generally efficacious.

Ovarian cancer may be diagnosed, in part, by collecting a routine medical history from a patient and by performing physical examination, x-ray examination, and chemical and hematological studies on the patient. Hematological tests which may be indicative of ovarian cancer in a patient include analyses of serum levels of proteins designated CA125 and DF3 and plasma levels of lysophosphatidic acid (LPA). Palpation of the ovaries and ultrasound techniques (particularly including endovaginal ultrasound and color Doppler flow ultrasound techniques) can aid detection of ovarian tumors and differentiation of ovarian cancer from benign ovarian cysts. However, a definitive diagnosis of ovarian cancer typically requires performing exploratory laparotomy of the patient.

Potential tests for the detection of ovarian cancer (e.g., screening, reflex or monitoring) may be characterized by a number of factors. The "sensitivity" of an assay refers to the probability that the test will yield a positive result in an individual afflicted with ovarian cancer. The "specificity" of an assay refers to the probability that the test will yield a negative result in an individual not afflicted with ovarian cancer. The "positive predictive value" (PPV) of an assay is the ratio of true positive results (i.e. positive assay results for patients afflicted with ovarian cancer) to all positive results (i.e. positive assay results for patients afflicted with ovarian cancer+positive assay results for patients not afflicted with ovarian cancer). It has been estimated that in order for an assay to be an appropriate population-wide screening tool for ovarian cancer the assay must have a PPV of at least about 10% (Rosenthal et al., 1998, Sem. Oncol. 25:315-325). It would thus be desirable for a screening assay for detecting ovarian cancer in patients to have a high sensitivity and a high PPV. Monitoring and reflex tests would also require appropriate specifications.

Owing to the cost, limited sensitivity, and limited specificity of known methods of detecting ovarian cancer, screening is not presently performed for the general population. In addition, the need to perform laparotomy in order to diagnose ovarian cancer in patients who screen positive for indications of ovarian cancer limits the desirability of population-wide screening, such that a PPV even greater than 10% would be desirable.

Prior use of serum CA125 level as a diagnostic marker for ovarian cancer indicated that this method exhibited insufficient specificity for use as a general screening method. Use of a refined algorithm for interpreting CA125 levels in serial retrospective samples obtained from patients improved the specificity of the method without shifting detection of ovarian cancer to an earlier stage (Skakes, 1995, Cancer 76:2004). Screening for LPA to detect gynecological cancers including ovarian cancer exhibited a sensitivity of about 96% and a specificity of about 89%. However, CA125-based screening methods and LPA-based screening methods are hampered by the presence of CA125 and LPA, respectively, in the serum of patients afflicted with conditions other than ovarian cancer. For example, serum CA125 levels are known to be associated with menstruation, pregnancy, gastrointestinal and hepatic conditions such as colitis and cirrhosis, pericarditis, renal disease, and various non-ovarian malignancies. Serum LPA is known, for example, to be affected by the presence of non-ovarian gynecological malignancies. A screening method having a greater specificity for ovarian cancer than the current screening methods for CA125 and LPA could provide a population-wide screening for early stage ovarian cancer.

Presently greater than about 60% of ovarian cancers diagnosed in patients are stage III or stage IV cancers. Treatment at these stages is largely limited to cytoreductive surgery (when feasible) and chemotherapy, both of which aim to slow the spread and development of metastasized tumor. Substantially all late stage ovarian cancer patients currently undergo combination chemotherapy as primary treatment, usually a combination of a platinum compound and a taxane. Median survival for responding patients is about one year. Combination chemotherapy involving agents such as doxorubicin, cyclophosphamide, cisplatin, hexamethylmelamine, paclitaxel, and methotrexate may improve survival rates in these groups, relative to single-agent therapies. Various recently-developed chemotherapeutic agents and treatment regimens have also demonstrated usefulness for treatment of advanced ovarian cancer. For example, use of the topoisomerase I inhibitor topectan, use of amifostine to minimize chemotherapeutic side effects, and use of intraperitoneal chemotherapy for patients having peritoneally implanted tumors have demonstrated at least limited utility. Presently, however, the 5-year survival rate for patients afflicted with stage III ovarian cancer is 25%, and the survival rate for patients afflicted with stage IV ovarian cancer is 8%.

It would therefore be beneficial to provide specific methods and reagents for the diagnosis, staging, prognosis, monitoring, and treatment of diseases associated with breast and/or ovarian cancer, or to indicate a predisposition to such for preventative measures. The present invention is directed towards these needs.

SUMMARY OF THE INVENTION

The invention relates to breast and/or ovarian cancer markers (hereinafter "markers" or "markers of the invention"), which are listed in Tables 1-5. The invention provides nucleic acids and proteins that are encoded by or correspond to the markers (hereinafter "marker nucleic acids" and "marker proteins," respectively). Table 1 provides the sequence identifiers of the sequences of such marker nucleic acids and proteins listed in the accompanying Sequence Listing. The invention further provides antibodies, antibody derivatives and antibody fragments which bind specifically with such proteins and/or fragments of the proteins.

The invention also relates to various methods, reagents and kits for diagnosing, staging, prognosing, monitoring and treating cancers, particularly breast and ovarian cancers. "Breast cancer" and "ovarian cancer" as used herein include carcinomas, (e.g., carcinoma in situ, invasive carcinoma, metastatic carcinoma) and pre-malignant conditions. In one embodiment, the invention provides a diagnostic method of assessing whether a patient has breast or ovarian cancer or has higher than normal risk for developing breast or ovarian cancer, comprising the steps of comparing the level of expression of a marker of the invention in a patient sample and the normal level of expression of the marker in a control, e.g., a sample from a patient without breast or ovarian cancer. A significantly higher level of expression of the marker in the patient sample as compared to the normal level is an indication that the patient is afflicted with breast or ovarian cancer or has higher than normal risk for developing breast or ovarian cancer.

According to the invention, the markers are selected such that the positive predictive value of the methods of the invention is at least about 10%, preferably about 25%, more preferably about 50% and most preferably about 90%. Also preferred for use in the methods of the invention are markers that are differentially expressed, as compared to normal breast cells, by at least two-fold in at least about 20%, more preferably about 50% and most preferably about 75% of any of the following conditions: stage 0 breast cancer patients, stage I breast cancer patients, stage IIA breast cancer patients, stage JIB breast cancer patients, stage IIIA breast cancer patients, stage IIIB breast cancer patients, stage IV breast cancer patients, grade I breast cancer patients, grade II breast cancer patients, grade III breast cancer patients, malignant breast cancer patients, ductal carcinoma breast cancer patients, and lobular carcinoma breast cancer patients. Further preferred for use in the methods of the invention are markers that are differentially expressed, as compared to normal ovarian cells, by at least two-fold in at least about 20%, more preferably about 50%, and most preferably about 75% of any of the following conditions: stage I ovarian cancer patients, stage II ovarian cancer patients, stage III ovarian cancer patients, stage IV ovarian cancer patients, grade I ovarian cancer patients, grade II ovarian cancer patients, grade III ovarian cancer patients, epithelial ovarian cancer patients, stromal ovarian cancer patients, germ cell ovarian cancer patients, malignant ovarian cancer patients, benign ovarian cancer patients, serous neoplasm ovarian cancer patients, mucinous neoplasm ovarian cancer patients, endometrioid neoplasm ovarian cancer patients and/or clear cell neoplasm ovarian cancer patients.

In a preferred diagnostic method of assessing whether a patient is afflicted with breast or ovarian cancer (e.g., new detection ("screening"), detection of recurrence, reflex testing), the method comprises comparing:
  a) the level of expression of a marker of the invention in a patient sample, and
  b) the normal level of expression of the marker in a control non-cancerous breast or non-cancerous ovarian cancer sample.

A significantly higher level of expression of the marker in the patient sample as compared to the normal level is an indication that the patient is afflicted with breast or ovarian cancer. In a preferred diagnostic method for breast cancer, the marker is selected from the markers in Table 2. In a preferred diagnostic method for ovarian cancer, the marker is selected from the markers in Table 3.

The invention also provides methods for assessing the efficacy of a therapy for inhibiting breast or ovarian cancer in a patient. Such methods comprise comparing:
  a) expression of a marker of the invention in a first sample obtained from the patient prior to providing at least a portion of the therapy to the patient, and
  b) expression of the marker in a second sample obtained from the patient following provision of the portion of the therapy.

A significantly lower level of expression of the marker in the second sample relative to that in the first sample is an indication that the therapy is efficacious for inhibiting breast or ovarian cancer in the patient. In a preferred method for breast cancer, the marker is selected from the markers in Table 2. In a preferred method for ovarian cancer, the marker is selected from the markers in Table 3.

It will be appreciated that in these methods the "therapy" may be any therapy for treating breast or ovarian cancer including, but not limited to, chemotherapy, radiation therapy, surgical removal of tumor tissue, gene therapy and biologic therapy such as the administering of antibodies and chemokines. Thus, the methods of the invention may be used to evaluate a patient before, during and after therapy, for example, to evaluate the reduction in tumor burden.

In a preferred embodiment, the methods are directed to therapy using a chemical or biologic agent. These methods comprise comparing:
  a) expression of a marker of the invention in a first sample obtained from the patient and maintained in the presence of the chemical or biologic agent, and
  b) expression of the marker in a second sample obtained from the patient and maintained in the absence of the agent.

A significantly lower level of expression of the marker in the second sample relative to that in the first sample is an indication that the agent is efficacious for inhibiting breast or ovarian cancer, in the patient. In one embodiment, the first and second samples can be portions of a single sample obtained from the patient or portions of pooled samples obtained from the patient. In a preferred embodiment, the methods are directed to therapy for treating breast cancer and the marker is selected from the markers in Table 2. In another preferred embodiment, the methods are directed to therapy for treating ovarian cancer and the marker is selected from the markers in Table 3.

The invention additionally provides a monitoring method for assessing the progression of breast or ovarian cancer in a patient, the method comprising:
  a) detecting in a patient sample at a first time point, the expression of a marker of the invention;
  b) repeating step a) at a subsequent time point in time; and
  c) comparing the level of expression detected in steps a) and b), and therefrom monitoring the progression of breast or ovarian cancer in the patient.

A significantly higher level of expression of the marker in the sample at the subsequent time point from that of the sample at the first time point is an indication that the breast or ovarian cancer has progressed, whereas a significantly lower level of expression is an indication that the breast or ovarian cancer has regressed. In a preferred embodiment for breast cancer, the marker is selected from the markers in Table 2. In a preferred embodiment for ovarian cancer, the marker is selected from the markers in Table 3.

The invention further provides a diagnostic method for determining whether breast or ovarian cancer has metastasized or is likely to metastasize, the method comprising comparing:
 a) the level of expression of a marker of the invention in a patient sample, and
 b) the normal level (or non-metastatic level) of expression of the marker in a control sample.

A significantly higher level of expression in the patient sample as compared to the normal level (or non-metastatic level) is an indication that the breast or ovarian cancer has metastasized or is likely to metastasize. In a preferred diagnostic method for breast cancer, the marker is selected from the markers in Table 2. In a preferred diagnostic method for ovarian cancer, the marker is selected from the markers in Table 3.

The invention moreover provides a test method for selecting a composition for inhibiting breast or ovarian cancer in a patient. This method comprises the steps of:
 a) obtaining a sample comprising cancer cells from the patient;
 b) separately maintaining aliquots of the sample in the presence of a plurality of test compositions;
 c) comparing expression of a marker of the invention in each of the aliquots; and
 d) selecting one of the test compositions which significantly reduces the level of expression of the marker in the aliquot containing that test composition, relative to the levels of expression of the marker in the presence of the other test compositions.

In a preferred method for selecting a composition for inhibiting breast cancer, the marker is selected from the markers in Table 2. In a preferred method for selecting a composition for inhibiting ovarian cancer, the marker is selected from the markers in Table 3.

The invention additionally provides a test method of assessing the breast or ovarian carcinogenic potential of a compound. This method comprises the steps of:
 a) maintaining separate aliquots of breast or ovarian cells in the presence and absence of the compound; and
 b) comparing expression of a marker of the invention in each of the aliquots.

A significantly higher level of expression of the marker in the aliquot maintained in the presence of the compound, relative to that of the aliquot maintained in the absence of the compound, is an indication that the compound possesses breast or ovarian carcinogenic potential. In a preferred method for assessing breast carcinogenic potential, the marker is selected from the markers in Table 2. In a preferred method for assessing ovarian carcinogenic potential, the marker is selected from the markers in Table 3.

In addition, the invention further provides a method of inhibiting breast or ovarian cancer in a patient. This method comprises the steps of:
 a) obtaining a sample comprising cancer cells from the patient;
 b) separately maintaining aliquots of the sample in the presence of a plurality of compositions;
 c) comparing expression of a marker of the invention in each of the aliquots; and
 d) administering to the patient at least one of the compositions which significantly lowers the level of expression of the marker in the aliquot containing that composition, relative to the levels of expression of the marker in the presence of the other compositions.

In a preferred method for breast cancer, the marker is selected from the markers in Table 2. In a preferred method for ovarian cancer, the marker is selected from the markers in Table 3.

In the aforementioned methods, the samples or patient samples can comprise a breast- or ovary-associated body fluid. Breast-associated fluids include, for example, blood fluids, lymph and cystic fluids, as well as nipple aspirates. Ovary-associated body fluids include, for example, blood fluids, lymph, ascites fluids, gynecological fluids, cystic fluids, urine, and fluids collected by peritoneal rinsing. The cells may be found in an ovarian or breast tissue sample collected, for example, by an ovarian or breast tissue biopsy or histology section. In another embodiment, the sample comprises cells obtained from the patient. In another embodiment, the patient sample is in vivo.

According to the invention, the level of expression of a marker of the invention in a sample can be assessed, for example, by detecting the presence in the sample of:
 the corresponding marker protein (e.g., a protein having one of the sequences of the even numbered SEQ ID NOs. such as SEQ ID NOs: 2, 4, 6, 8, etc.) or a fragment of the protein (e.g. by using a reagent, such as an antibody, an antibody derivative, an antibody fragment or single-chain antibody, which binds specifically with the protein or protein fragment)
 the corresponding marker nucleic acid (e.g. a nucleotide transcript having one of the sequences of the odd numbered SEQ ID NOs. such as SEQ ID NOs: 1, 3, 5, 7, etc., or a complement thereof), or a fragment of the nucleic acid (e.g. by contacting transcribed polynucleotides obtained from the sample with a substrate having affixed thereto one or more nucleic acids having the entire or a segment of the sequence of any of the odd numbered SEQ ID NOs., or a complement thereof)
 a metabolite which is produced directly (i.e., catalyzed) or indirectly by the corresponding marker protein.

According to the invention, any of the aforementioned methods may be performed using a plurality (e.g. 2, 3, 5, or 10 or more) of breast or ovarian cancer markers, including breast or ovarian cancer markers known in the art. In such methods, the level of expression in the sample of each of a plurality of markers, at least one of which is a marker of the invention, is compared with the normal level of expression of each of the plurality of markers in samples of the same type obtained from control humans not afflicted with breast or ovarian cancer. A significantly altered (i.e., increased or decreased as specified in the above-described methods using a single marker) level of expression in the sample of one or more markers of the invention, or some combination thereof, relative to that marker's corresponding normal levels, is an indication that the patient is afflicted with breast or ovarian cancer. For all of the aforementioned methods, the marker(s) are preferably selected such that the positive predictive value of the method is at least about 10%.

In a further aspect, the invention provides an antibody, an antibody derivative, or an antibody fragment, which binds specifically with a marker protein (e.g., a protein having the sequence of any of the even numbered SEQ ID NOs.) or a fragment of the protein. The invention also provides methods for making such antibody, antibody derivative, and antibody fragment. Such methods may comprise immunizing a mammal with a protein or peptide comprising the entirety, or a segment of 10 or more amino acids, of a marker protein (e.g., a protein having the sequence of any of the even numbered SEQ ID NOs.), wherein the protein or peptide may be obtained from a cell or by chemical synthesis. The methods of the invention also encompass producing monoclonal and single-chain antibodies, which would further comprise isolating splenocytes from the immunized mammal, fusing the isolated splenocytes with an immortalized cell line to form hybridomas, and screening individual hybridomas for those that produce an antibody that binds specifically with a marker protein or a fragment of the protein.

The markers of the invention are predicted to code for secreted or extracellular proteins, as well as for other types of transmembrane proteins (e.g., integral membrane proteins, type I and type II transmembrane proteins, multitransmembrane proteins), and are therefore attractive targets for anticancer therapy and detection techniques, e.g., using antibodies and derivatives. Thus, markers of Table 2 are useful targets for detecting and treating breast cancer cancers and markers of Table 3 are useful targets for detecting and treating ovarian cancer. Further, certain markers of the invention (listed in Table 4) are selectively expressed in multiple types of cancers and thus are useful targets for detecting and treating several types of cancers. Table 4 indicates the usefulness of a marker as a target for a specific type of cancer with a plus sign in that cancer's column. In one embodiment, Markers 1, 2, 3, 26 and 32 each can be used as a target for diagnosis and treatment of breast and lung cancers. In another embodiment, Markers 6, 23, 43 and 47 each can be used as a target for diagnosis and treatment of ovarian, breast, lung and colon cancers. In a further embodiment, Markers 5 and 7 each can be used as a target for diagnosis and treatment of ovarian, breast, lung, colon and prostate cancers. In a further embodiment, Markers 5 and 7 each can be used as a target for diagnosis and treatment of ovarian, breast, lung, colon and prostate cancers. In yet another embodiment, Marker 22 can be used as a target for diagnosis and treatment of breast, lung and colon cancers. In another embodiment, Marker 36 can be used as a target for diagnosis and treatment of ovarian, breast and lung, cancers. In a further additional embodiment, Marker 39 can be used as a target for diagnosis and treatment of ovarian and lung cancers. In yet a further embodiment, Marker 45 can be used as a target for diagnosis and treatment of ovarian and colon cancers. In another additional embodiment, Marker 56 can be used as a target for diagnosis and treatment of ovarian lung and colon cancers. In a preferred embodiment of the invention, Marker 7 and Marker 32 can be used as targets for inhibiting angiogenesis associated with tumor growth. Antibodies, antibody derivatives, and antibody fragments which bind specifically with a marker protein of the invention (i.e., a protein comprising the sequence of any of the even numbered) or a fragment of the protein, may thus be used to treat a cancer of which the corresponding marker is a target.

In another aspect, the invention relates to various diagnostic and test kits. In one embodiment, the invention provides a kit for assessing whether a patient is afflicted with breast or ovarian cancer. The kit comprises a reagent for assessing expression of a marker of the invention. In another embodiment, the invention provides a kit for assessing the suitability of a chemical or biologic agent for inhibiting an breast or ovarian cancer in a patient. Such kit comprises a reagent for assessing expression of a marker of the invention, and may also comprise one or more of such agents. In a further embodiment, the invention provides kits for assessing the presence of breast or ovarian cancer cells or treating breast or ovarian cancers. Such kits comprise an antibody, an antibody derivative, or an antibody fragment, which binds specifically with a marker protein, or a fragment of the protein. Such kits may also comprise a plurality of antibodies, antibody derivatives, or antibody fragments wherein the plurality of such antibody agents binds specifically with a marker protein, or a fragment of the protein.

In an additional embodiment, the invention also provides a kit for assessing the presence of breast or ovarian cancer cells, wherein the kit comprises a nucleic acid probe that binds specifically with a marker nucleic acid or a fragment of the nucleic acid. The kit may also comprise a plurality of probes, wherein each of the probes binds specifically with a marker nucleic acid, or a fragment of the nucleic acid.

In a further aspect, the invention relates to methods for treating a patient afflicted with cancer, particularly breast or ovarian cancer or at risk of developing such a cancer. The methods may comprise reducing the expression and/or interfering with the biological function of a marker of the invention so as to treat a cancer of which the marker has been identified herein as a useful diagnosis and therapeutic target. In one embodiment, the method comprises providing to the patient an antisense oligonucleotide or polynucleotide complementary to a marker nucleic acid, or a segment thereof. For example, an antisense polynucleotide may be provided to the patient through the delivery of a vector that expresses an anti-sense polynucleotide of a marker nucleic acid or a fragment thereof. In another embodiment, the method comprises providing to the patient an antibody, an antibody derivative, or antibody fragment, which binds specifically with a marker protein or a fragment of the protein. In a preferred embodiment, the antibody, antibody derivative or antibody fragment binds specifically with a protein having the sequence of an even numbered SEQ ID NO., or a fragment of the protein.

It will be appreciated that the methods and kits of the present invention may also include known cancer markers including known breast or ovarian cancer markers. It will further be appreciated that the methods and kits may be used to identify cancers other than breast or ovarian cancer.

DETAILED DESCRIPTION OF THE INVENTION

The invention relates to newly discovered Markers 1-56 (Table 1) associated with cancer and more particularly the cancerous state of breast and/or ovarian cells. Table 1 lists the markers of the invention, which are over-expressed in breast and/or ovarian cancer cells compared to normal (i.e., non-cancerous) cells and provides the sequence listing identifiers of the cDNA sequence of a nucleotide transcript and the amino acid sequence of a protein encoded by or corresponding to each marker. It has been discovered that higher than normal level of expression of any of Markers 1-33 (Table 2) or a combination of these markers correlates with the presence of cancer, particularly breast cancer in a patient. Likewise, it has been discovered that higher than normal level of expression of any of Markers 34-56 (Table 3) or a combination of these markers correlates with the presence of cancer, particularly ovarian cancer in a patient. Methods are provided for detecting the presence of cancer, particularly breast or ovarian cancer in a sample, the absence of breast or ovarian cancer in a sample, the stage of a breast or ovarian cancer, and with other characteristics of breast or ovarian cancer that are relevant to prevention, diagnosis, characterization, and therapy of breast or ovarian cancer in a patient. Methods of treating cancer, particularly breast or ovarian cancer are also provided.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "marker" is a gene whose altered level of expression in a tissue or cell from its expression level in normal or healthy tissue or cell is associated with a disease state, such as cancer. A "marker nucleic acid" is a nucleic acid (e.g., mRNA, cDNA) encoded by or corresponding to a marker of the invention. Such marker nucleic acids include DNA (e.g., cDNA) comprising the entire or a partial sequence of any of the odd number SEQ ID NOs. or the complement of such a sequence. The marker nucleic acids also include RNA comprising the entire or a partial sequence of any odd number SEQ ID NO. or the complement of such a sequence, wherein all thymidine residues are replaced with uridine residues. A "marker protein" is a protein encoded by or corresponding to a marker of the invention. A marker protein comprises the entire or a partial sequence of any of the even numbered SEQ ID NOs. The terms "protein" and "polypeptide" are used interchangeably.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

A "breast-associated" body fluid is a fluid which, when in the body of a patient, contacts or passes through breast cells or into which cells or proteins shed from breast cells are capable of passing. Exemplary breast-associated body fluids include, for example, blood fluids, lymph and cystic fluids, as well as nipple aspirates.

An "ovarian-associated" body fluid is a fluid which, when in the body of a patient contacts or passes through ovarian cells or into which cells or proteins shed from ovarian cells are capable of passing. Ovary-associated body fluids include, for example, fluids include blood fluids (e.g. whole blood, blood serum, blood having platelets removed therefrom, etc.), lymph, ascitic fluids, gynecological fluids (e.g. ovarian, fallopian, and uterine secretions, menses, vaginal douching fluids, fluids used to rinse ovarian cell samples, etc.), cystic fluid, urine, fluids collected by peritoneal rinsing (e.g. fluids applied and collected during laparoscopy or fluids instilled into and withdrawn from the peritoneal cavity of a human patient), a fluid collected by uterine rinsing, a uterine fluid, a uterine exudate or menses, a pleural fluid, or an ovarian exudate.

The "normal" level of expression of a marker is the level of expression of the marker in breast or ovarian cells of a human subject or patient not afflicted with breast or ovarian cancer An "over-expression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subjects not having the marker associated disease) and preferably, the average expression level of the marker in several control samples.

A "significantly lower level of expression" of a marker refers to an expression level in a test sample that is at least twice, and more preferably three, four, five or ten times lower than the expression level of the marker in a control sample (e.g., sample from a healthy subjects not having the marker associated disease) and preferably, the average expression level of the marker in several control samples.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue-specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATT-GCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

As used herein, a "naturally-occurring" nucleic acid molecule refers to an RNA or DNA molecule having a nucleotide sequence that occurs in an organism found in nature.

A cancer is "inhibited" if at least one symptom of the cancer is alleviated, terminated, slowed, or prevented. As used herein, breast or ovarian cancer is also "inhibited" if recurrence or metastasis of the cancer is reduced, slowed, delayed, or prevented.

A kit is any manufacture (e.g. a package or container) comprising at least one reagent, e.g. a probe, for specifically detecting the expression of a marker of the invention. The kit may be promoted, distributed, or sold as a unit for performing the methods of the present invention.

"Proteins of the invention" encompass marker proteins and their fragments; variant marker proteins and their fragments; peptides and polypeptides comprising an at least 15 amino acid segment of a marker or variant marker protein; and fusion proteins comprising a marker or variant marker protein, or an at least 15 amino acid segment of a marker or variant marker protein.

Unless otherwise specified herewithin, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody moiety.

Description

The present invention is based, in part, on newly identified markers which are over-expressed in breast or ovarian cancer cells as compared to their expression in normal (i.e. non-cancerous) breast or ovarian cells. The enhanced expression of one or more of these markers in breast or ovarian cells is herein correlated with the cancerous state of the tissue. The invention provides compositions, kits, and methods for assessing the cancerous state of breast or ovarian cells (e.g. cells obtained from a human, cultured human cells, archived or preserved human cells and in vivo cells) as well as treating patients afflicted with breast or ovarian cancer.

The compositions, kits, and methods of the invention have the following uses, among others:
1) assessing whether a patient is afflicted with breast or ovarian cancer;
2) assessing the stage of breast or ovarian cancer in a human patient;
3) assessing the grade of breast or ovarian cancer in a patient;
4) assessing the benign or malignant nature of breast or ovarian cancer in a patient;
5) assessing the metastatic potential of breast or ovarian cancer in a patient;
6) assessing the histological type of neoplasm associated with breast or ovarian cancer in a patient;
7) making antibodies, antibody fragments or antibody derivatives that are useful for treating breast or ovarian cancer and/or assessing whether a patient is afflicted with breast or ovarian cancer;
8) assessing the presence of breast or ovarian cancer cells;
9) assessing the efficacy of one or more test compounds for inhibiting breast or ovarian cancer in a patient;
10) assessing the efficacy of a therapy for inhibiting breast or ovarian cancer in a patient;
11) monitoring the progression of breast or ovarian cancer in a patient;
12) selecting a composition or therapy for inhibiting breast or ovarian cancer in a patient;
13) treating a patient afflicted with breast or ovarian cancer;
14) inhibiting breast or ovarian cancer in a patient;
15) assessing the breast or ovarian carcinogenic potential of a test compound; and
16) preventing the onset of breast or ovarian cancer in a patient at risk for developing breast or ovarian cancer.

The invention thus includes a method of assessing whether a patient is afflicted with breast or ovarian cancer which includes assessing whether the patient has pre-metastasized breast or ovarian cancer. This method comprises comparing the level of expression of a marker of the invention in a patient sample and the normal level of expression of the marker in a control, e.g., a non-cancerous breast or ovarian sample. A significantly higher level of expression of the marker in the patient sample as compared to the normal level is an indication that the patient is afflicted with breast or ovarian cancer.

Gene delivery vehicles, host cells and compositions (all described herein) containing nucleic acids comprising the entirety, or a segment of 15 or more nucleotides, of any of the sequences of the odd numbered SEQ ID NOs. or the complement of such sequences, and polypeptides comprising the entirety, or a segment of 10 or more amino acids, of any of the sequences of the even numbered SEQ ID NOs. are also provided by this invention.

As described herein, breast or ovarian cancer in patients is associated with an increased level of expression of one or more markers of the invention. While, as discussed above, some of these changes in expression level result from occurrence of the breast or ovarian cancer, others of these changes induce, maintain, and promote the cancerous state of breast or ovarian cancer cells. Thus, breast or ovarian cancer characterized by an increase in the level of expression of one or more markers of the invention can be inhibited by reducing and/or interfering with the expression of the markers and/or function of the proteins encoded by those markers.

Expression of a marker of the invention can be inhibited in a number of ways generally known in the art. For example, an antisense oligonucleotide can be provided to the breast or ovarian cancer cells in order to inhibit transcription, translation, or both, of the marker(s). Alternately, a polynucleotide encoding an antibody, an antibody derivative, or an antibody fragment which specifically binds a marker protein, and operably linked with an appropriate promoter/regulator region, can be provided to the cell in order to generate intracellular antibodies which will inhibit the function or activity of the protein. The expression and/or function of a marker may also be inhibited by treating the breast or ovarian cancer cell with an antibody, antibody derivative or antibody fragment that specifically binds a marker protein. Using the methods described herein, a variety of molecules, particularly including molecules sufficiently small that they are able to cross the cell membrane, can be screened in order to identify molecules which inhibit expression of a marker or inhibit the function of a marker protein. The compound so identified can be provided to the patient in order to inhibit breast or ovarian cancer cells of the patient.

Any marker or combination of markers of the invention, as well as any known markers in combination with the markers of the invention, may be used in the compositions, kits, and methods of the present invention. In general, it is preferable to use markers for which the difference between the level of expression of the marker in breast or ovarian cancer cells and the level of expression of the same marker in normal breast or ovarian cells is as great as possible. Although this difference can be as small as the limit of detection of the method for assessing expression of the marker, it is preferred that the difference be at least greater than the standard error of the assessment method, and preferably a difference of at least 2-, 3-, 4-, 5-, 6-, 7-, 8-, 9-, 10-, 15-, 20-, 25-, 100-, 500-, 1000-fold or greater than the level of expression of the same marker in normal breast or ovarian tissue.

The marker proteins of the present invention are transmembrane proteins and are therefore extremely useful in the compositions, kits, and methods of the invention, owing to the fact that the such marker proteins can be detected in a breast or ovary-associated body fluid sample, which may be more easily collected from a human patient than a tissue biopsy sample. In addition, preferred in vivo techniques for detection of a marker protein include introducing into a subject a labeled antibody directed against the protein. For example, the antibody can be labeled with a radioactive marker whose presence and location in a subject can be detected by standard imaging techniques. Anti-cancer therapy utilizing antibodies directed against the marker proteins of the present invention is also provided. In particular, it has been found that Markers 7 and 32 are attractive targets for inhibiting breast, ovary, lung and colon tumors, as well as for inhibiting angiogenesis associated with tumor growth.

It will be appreciated that patient samples containing breast or ovarian cells may be used in the methods of the present invention. In these embodiments, the level of expression of the marker can be assessed by assessing the amount (e.g. absolute amount or concentration) of the marker in a breast or ovarian cell sample, e.g., breast or ovarian tissue biopsy obtained from a patient. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample.

Expression of a marker of the invention may be assessed by any of a wide variety of well known methods for detecting expression of a transcribed nucleic acid or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In a preferred embodiment, expression of a marker is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a marker protein or fragment thereof, including a marker protein which has undergone all or a portion of its normal post-translational modification.

In another preferred embodiment, expression of a marker is assessed by preparing mRNA/cDNA (i.e. a transcribed polynucleotide) from cells in a patient sample, and by hybridizing the mRNA/cDNA with a reference polynucleotide which is a complement of a marker nucleic acid, or a fragment thereof. cDNA can, optionally, be amplified using any of a variety of polymerase chain reaction methods prior to hybridization with the reference polynucleotide; preferably, it is not amplified. Expression of one or more markers can likewise be detected using quantitative PCR to assess the level of expression of the marker(s). Alternatively, any of the many known methods of detecting mutations or variants (e.g. single nucleotide polymorphisms, deletions, etc.) of a marker of the invention may be used to detect occurrence of a marker in a patient.

In a related embodiment, a mixture of transcribed polynucleotides obtained from the sample is contacted with a substrate having fixed thereto a polynucleotide complementary to or homologous with at least a portion (e.g. at least 7, 10, 15, 20, 25, 30, 40, 50, 100, 500, or more nucleotide residues) of a marker nucleic acid. If polynucleotides complementary to or homologous with are differentially detectable on the substrate (e.g. detectable using different chromophores or fluorophores, or fixed to different selected positions), then the levels of expression of a plurality of markers can be assessed simultaneously using a single substrate (e.g. a "gene chip" microarray of polynucleotides fixed at selected positions). When a method of assessing marker expression is used which involves hybridization of one nucleic acid with another, it is preferred that the hybridization be performed under stringent hybridization conditions.

Because the compositions, kits, and methods of the invention rely on detection of a difference in expression levels of one or more markers of the invention, it is preferable that the level of expression of the marker is significantly greater than the minimum detection limit of the method used to assess expression in at least one of normal breast or ovarian cells and cancerous breast or ovarian cells.

It is understood that by routine screening of additional patient samples using one or more of the markers of the invention, it will be realized that certain of the markers are over-expressed in cancers of various types, including specific breast or ovarian cancers, as well as other cancers such as lung cancer, colon cancer, etc. For example, it will be confirmed that some of the markers of the invention are over-expressed in most (i.e. 50% or more) or substantially all (i.e. 80% or more) of breast or ovarian cancers. Furthermore, it will be confirmed that certain of the markers of the invention are associated with breast cancer of various stages (i.e. stage 0, I, II, III, and IV breast cancers, as well as subclassifications IIA, IIB, IIIA, and IIIB, using the FIGO Stage Grouping system for primary carcinoma of the breast; (see Breast, In: *American Joint Committee on Cancer: AJCC Cancer Staging Manual*. Lippincott-Raven Publishers, 5th ed., 1997, pp. 171-180), or stage I, II, III, and IV ovarian cancers, as well as subclassifications IA, IB, IC, IIA, IIB, IIC, IIIA, IIIB, and IIIC, using the FIGO Stage Grouping system for primary carcinoma of the ovary; 1987, *Am. J. Obstet. Gynecol.* 156:236, of various histologic subtypes (e.g. serous, mucinous, endometroid, and clear cell subtypes, as well as subclassifications and alternate classifications adenocarcinoma, papillary adenocarcinoma, papillary cystadenocarcinoma, surface papillary carcinoma, malignant adenofibroma, cystadenofibroma, adenocarcinoma, cystadenocarcinoma, adenoacanthoma, endometrioid stromal sarcoma, mesodermal (Müllerian) mixed tumor, mesonephroid tumor, malignant carcinoma, Brenner tumor, mixed epithelial tumor, and undifferentiated carcinoma, using the WHO/FIGO system for classification of malignant breast and ovarian tumors; Scully, *Atlas of Tumor Pathology*, 3d series, Washington D.C.), and various grades (i.e. grade I {well differentiated}, grade II {moderately well differentiated}, and grade III {poorly differentiated from surrounding normal tissue})). In addition, as a greater number of patient samples are assessed for expression of the markers of the invention and the outcomes of the individual patients from whom the samples were obtained are correlated, it will also be confirmed that altered expression of certain of the markers of the invention are strongly correlated with malignant cancers and that altered expression of other markers of the invention are strongly correlated with benign tumors. The compositions, kits, and methods of the invention are thus useful for characterizing one or more of the stage, grade, histological type, and benign/malignant nature of breast or ovarian cancer in patients.

When the compositions, kits, and methods of the invention are used for characterizing one or more of the stage, grade, histological type, and benign/malignant nature of breast or ovarian cancer in a patient, it is preferred that the marker or panel of markers of the invention is selected such that a positive result is obtained in at least about 20%, and preferably at least about 40%, 60%, or 80%, and more preferably in substantially all patients afflicted with a breast or ovarian cancer of the corresponding stage, grade, histological type, or benign/malignant nature. Preferably, the marker or panel of markers of the invention is selected such that a positive predictive value (PPV) of greater than about 10% is obtained for the general population (more preferably coupled with an assay specificity greater than 80%).

When a plurality of markers of the invention are used in the compositions, kits, and methods of the invention, the level of expression of each marker in a patient sample can be compared with the normal level of expression of each of the plurality of markers in non-cancerous samples of the same type, either in a single reaction mixture (i.e. using reagents, such as different fluorescent probes, for each marker) or in individual reaction mixtures corresponding to one or more of the markers. In one embodiment, a significantly increased level of expression of more than one of the plurality of markers in the sample, relative to the corresponding normal levels, is an indication that the patient is afflicted with breast or ovarian cancer. When a plurality of markers is used, it is preferred that 2, 3, 4, 5, 8, 10, 12, 15, 20, 30, or 50 or more individual markers be used, wherein fewer markers are preferred.

In order to maximize the sensitivity of the compositions, kits, and methods of the invention (i.e. by interference attributable to cells of non-breast or ovarian origin in a patient sample), it is preferable that the marker of the invention used therein be a marker which has a restricted tissue distribution, e.g., normally not expressed in a non-breast or ovarian tissue.

Only a small number of markers are known to be associated with breast or ovarian cancers (e.g., for breast: BRCA1 and BRCA2; and, for ovarian: AKT2, Ki-RAS, ERBB2, c-MYC, RB1, and TP53). These markers are not, of course, included among the markers of the invention, although they may be used together with one or more markers of the invention in a panel of markers, for example. It is well known that certain types of genes, such as oncogenes, tumor suppressor genes, growth factor-like genes, protease-like genes, and protein kinase-like genes are often involved with development of cancers of various types. Thus, among the markers of the invention, use of those which correspond to proteins which resemble known proteins encoded by known oncogenes and tumor suppressor genes, and those which correspond to proteins which resemble growth factors, proteases, and protein kinases are preferred.

It is recognized that the compositions, kits, and methods of the invention will be of particular utility to patients having an enhanced risk of developing breast or ovarian cancer and their medical advisors. Patients recognized as having an enhanced risk of developing breast or ovarian cancer include, for example, patients having a familial history of breast or ovarian cancer, patients identified as having a mutant oncogene (i.e. at least one allele), and patients of advancing age (i.e. women older than about 50 or 60 years).

The level of expression of a marker in normal (i.e. non-cancerous) human breast or ovarian tissue can be assessed in a variety of ways. In one embodiment, this normal level of expression is assessed by assessing the level of expression of the marker in a portion of breast or ovarian cells which appears to be non-cancerous and by comparing this normal level of expression with the level of expression in a portion of the breast or ovarian cells which is suspected of being cancerous. Alternately, and particularly as further information becomes available as a result of routine performance of the methods described herein, population-average values for normal expression of the markers of the invention may be used. In other embodiments, the 'normal' level of expression of a marker may be determined by assessing expression of the marker in a patient sample obtained from a non-cancer-afflicted patient, from a patient sample obtained from a patient before the suspected onset of breast or ovarian cancer in the patient, from archived patient samples, and the like.

The invention includes compositions, kits, and methods for assessing the presence of breast or ovarian cancer cells in a sample (e.g. an archived tissue sample or a sample obtained from a patient). These compositions, kits, and methods are substantially the same as those described above, except that, where necessary, the compositions, kits, and methods are adapted for use with samples other than patient samples. For example, when the sample to be used is a parafinized, archived human tissue sample, it can be necessary to adjust the ratio of compounds in the compositions of the invention, in the kits of the invention, or the methods used to assess levels of marker expression in the sample. Such methods are well known in the art and within the skill of the ordinary artisan.

The invention includes a kit for assessing the presence of breast or ovarian cancer cells (e.g. in a sample such as a patient sample). The kit comprises a plurality of reagents, each of which is capable of binding specifically with a marker nucleic acid or protein. Suitable reagents for binding with a marker protein include antibodies, antibody derivatives, antibody fragments, and the like. Suitable reagents for binding with a marker nucleic acid (e.g. a genomic DNA, an mRNA, a spliced mRNA, a cDNA, or the like) include complementary nucleic acids. For example, the nucleic acid reagents may include oligonucleotides (labeled or non-labeled) fixed to a substrate, labeled oligonucleotides not bound with a substrate, pairs of PCR primers, molecular beacon probes, and the like.

The kit of the invention may optionally comprise additional components useful for performing the methods of the invention. By way of example, the kit may comprise fluids (e.g. SSC buffer) suitable for annealing complementary nucleic acids or for binding an antibody with a protein with which it specifically binds, one or more sample compartments, an instructional material which describes performance of a method of the invention, a sample of normal breast or ovarian cells, a sample of breast or ovarian cancer cells, and the like.

The invention also includes a method of making an isolated hybridoma which produces an antibody useful for assessing whether patient is afflicted with an breast or ovarian cancer. In this method, a protein or peptide comprising the entirety or a segment of a marker protein is synthesized or isolated (e.g. by purification from a cell in which it is expressed or by transcription and translation of a nucleic acid encoding the protein or peptide in vivo or in vitro using known methods). A vertebrate, preferably a mammal such as a mouse, rat, rabbit, or sheep, is immunized using the protein or peptide. The vertebrate may optionally (and preferably) be immunized at least one additional time with the protein or peptide, so that the vertebrate exhibits a robust immune response to the protein or peptide. Splenocytes are isolated from the immunized vertebrate and fused with an immortalized cell line to form hybridomas, using any of a variety of methods well known in the art. Hybridomas formed in this manner are then screened using standard methods to identify one or more hybridomas which produce an antibody which specifically binds with the marker protein or a fragment thereof. The invention also includes hybridomas made by this method and antibodies made using such hybridomas.

The invention also includes a method of assessing the efficacy of a test compound for inhibiting breast or ovarian cancer cells. As described above, differences in the level of expression of the markers of the invention correlate with the cancerous state of breast or ovarian cells. Although it is recognized that changes in the levels of expression of certain of the markers of the invention likely result from the cancerous state of breast or ovarian cells, it is likewise recognized that changes in the levels of expression of other of the markers of the invention induce, maintain, and promote the cancerous state of those cells. Thus, compounds which inhibit an breast or ovarian cancer in a patient will cause the level of expression of one or more of the markers of the invention to change to a level nearer the normal level of expression for that marker (i.e. the level of expression for the marker in non-cancerous breast or ovarian cells).

This method thus comprises comparing expression of a marker in a first breast or ovarian cell sample and maintained in the presence of the test compound and expression of the marker in a second breast or ovarian cell sample and maintained in the absence of the test compound. A significantly reduced expression of a marker of the invention in the presence of the test compound is an indication that the test compound inhibits breast or ovarian cancer. The breast or ovarian cell samples may, for example, be aliquots of a single sample of normal breast or ovarian cells obtained from a patient, pooled samples of normal breast or ovarian cells obtained from a patient, cells of a normal breast or ovarian cell line, aliquots of a single sample of breast or ovarian cancer cells obtained from a patient, pooled samples of breast or ovarian cancer cells obtained from a patient, cells of an breast or ovarian cancer cell line, or the like. In one embodiment, the samples are breast or ovarian cancer cells obtained from a patient and a plurality of compounds known to be effective for inhibiting various breast or ovarian cancers are tested in order to identify the compound which is likely to best inhibit the breast or ovarian cancer in the patient.

This method may likewise be used to assess the efficacy of a therapy for inhibiting breast or ovarian cancer in a patient. In this method, the level of expression of one or more markers of the invention in a pair of samples (one subjected to the therapy, the other not subjected to the therapy) is assessed. As with the method of assessing the efficacy of test compounds, if the therapy induces a significantly lower level of expression of a marker of the invention then the therapy is efficacious for inhibiting breast or ovarian cancer. As above, if samples from a selected patient are used in this method, then alternative therapies can be assessed in vitro in order to select a therapy most likely to be efficacious for inhibiting breast or ovarian cancer in the patient.

As described above, the cancerous state of human breast or ovarian cells is correlated with changes in the levels of expression of the markers of the invention. The invention includes a method for assessing the human breast or ovarian cell carcinogenic potential of a test compound. This method comprises maintaining separate aliquots of human breast or ovarian cells in the presence and absence of the test compound. Expression of a marker of the invention in each of the aliquots is compared. A significantly higher level of expression of a marker of the invention in the aliquot maintained in the presence of the test compound (relative to the aliquot maintained in the absence of the test compound) is an indication that the test compound possesses human breast or ovarian cell carcinogenic potential. The relative carcinogenic potentials of various test compounds can be assessed by comparing the degree of enhancement or inhibition of the level of expression of the relevant markers, by comparing the number of markers for which the level of expression is enhanced or inhibited, or by comparing both.

Various aspects of the invention are described in further detail in the following subsections.

I. Isolated Nucleic Acid Molecules

One aspect of the invention pertains to isolated nucleic acid molecules, including nucleic acids which encode a marker protein or a portion thereof. Isolated nucleic acids of the invention also include nucleic acid molecules sufficient for use as hybridization probes to identify marker nucleic acid molecules, and fragments of marker nucleic acid molecules, e.g., those suitable for use as PCR primers for the amplification or mutation of marker nucleic acid molecules.

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, nucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a marker nucleic acid or to the nucleotide sequence of a nucleic acid encoding a marker protein. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker nucleic acid or which encodes a marker protein. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more markers of the invention. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

The invention further encompasses nucleic acid molecules that differ, due to degeneracy of the genetic code, from the nucleotide sequence of nucleic acids encoding a marker protein (e.g., protein having the sequence of the even numbered SEQ ID NOs.), and thus encode the same protein.

It will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 7, 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a marker nucleic acid or to a nucleic acid encoding a marker protein. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a variant marker protein that contain changes in amino acid residues that are not essential for activity. Such variant marker proteins differ in amino acid sequence from the naturally-occurring marker proteins, yet retain biological activity. In one embodiment, such a variant marker protein has an amino acid sequence that is at least about 40% identical, 50%, 60%, 70%, 80%, 90%, 95%, or 98% identical to the amino acid sequence of a marker protein.

An isolated nucleic acid molecule encoding a variant marker protein can be created by introducing one or more nucleotide substitutions, additions or deletions into the nucleotide sequence of marker nucleic acids, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

The present invention encompasses antisense nucleic acid molecules, i.e., molecules which are complementary to a sense nucleic acid of the invention, e.g., complementary to the coding strand of a double-stranded marker cDNA molecule or complementary to a marker mRNA sequence. Accordingly, an antisense nucleic acid of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a marker protein. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a marker protein to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into a breast- or ovary-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a marker protein can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartel and Szostak, 1993, *Science* 261:1411-1418).

The invention also encompasses nucleic acid molecules which form triple helical structures. For example, expression of a marker of the invention can be inhibited by targeting nucleotide sequences complementary to the regulatory region of the gene encoding the marker nucleic acid or protein (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660: 27-36; and Maher (1992) *Bioassays* 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

II. Isolated Proteins and Antibodies

One aspect of the invention pertains to isolated marker proteins and biologically active portions thereof, as well as polypeptide fragments suitable for use as immunogens to raise antibodies directed against a marker protein or a fragment thereof. In one embodiment, the native marker protein can be isolated from cells or tissue sources by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein of the invention can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the marker protein.

Preferred marker proteins are encoded by nucleotide sequences comprising the sequence of any of the even numbered SEQ ID NOs. Other useful proteins are substantially identical (e.g., at least about 40%, preferably 50%, 60%, 70%, 80%, 90%, 95%, or 99%) to one of these sequences and retain the functional activity of the corresponding naturally-occurring marker protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the BLASTN and BLASTX programs of Altschul, et al. (1990) *J. Mol. Biol.* 215:403-410. BLAST nucleotide searches can be performed with the BLASTN program, score=100, wordlength=12 to obtain nucleotide sequences homologous to a nucleic acid molecules of the invention. BLAST protein searches can be performed with the BLASTP program, score=50, wordlength=3 to obtain amino acid sequences homologous to a protein molecules of the invention. To obtain gapped alignments for comparison purposes, a newer version of the BLAST algorithm called Gapped BLAST can be utilized as described in Altschul et al. (1997) *Nucleic Acids Res.* 25:3389-3402, which is able to perform gapped local alignments for the programs BLASTN, BLASTP and BLASTX. Alternatively, PSI-Blast can be used to perform an iterated search which detects distant relationships between molecules. When utilizing BLAST, Gapped BLAST, and PSI-Blast programs, the default parameters of the respective programs (e.g., BLASTX and BLASTN) can be used. See http://www.ncbi.nlm.nih.gov. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins comprising a marker protein or a segment thereof. As used herein, a "chimeric protein" or "fusion protein" comprises all or part (preferably a biologically active part) of a marker protein operably linked to a heterologous polypeptide (i.e., a polypeptide other than the marker protein). Within the fusion protein, the term "operably linked" is intended to indicate that the marker protein or segment thereof and the heterologous polypeptide are fused in-frame to each other. The heterologous polypeptide can be fused to the amino-terminus or the carboxyl-terminus of the marker protein or segment.

One useful fusion protein is a GST fusion protein in which a marker protein or segment is fused to the carboxyl terminus of GST sequences. Such fusion proteins can facilitate the purification of a recombinant polypeptide of the invention.

In another embodiment, the fusion protein contains a heterologous signal sequence at its amino terminus. For example, the native signal sequence of a marker protein can be removed and replaced with a signal sequence from another protein. For example, the gp67 secretory sequence of the baculovirus envelope protein can be used as a heterologous signal sequence (Ausubel et al., ed., *Current Protocols in Molecular Biology*, John Wiley & Sons, NY, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.

In yet another embodiment, the fusion protein is an immunoglobulin fusion protein in which all or part of a marker protein is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a marker protein Inhibition of ligand/receptor interaction can be useful therapeutically, both for treating proliferative and differentiative disorders and for modulating (e.g. promoting or inhibiting) cell survival. Moreover, the immunoglobulin fusion proteins of the invention can be used as immunogens to produce antibodies directed against a marker protein in a subject, to purify ligands and in screening assays to identify molecules which inhibit the interaction of the marker protein with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of marker proteins. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to marker proteins, fusion proteins or segments thereof having a signal sequence, as well as to such proteins from which the signal sequence has been proteolytically cleaved (i.e., the cleavage products). In one embodiment, a nucleic acid sequence encoding a signal sequence can be operably linked in an expression vector to a protein of interest, such as a marker protein or a segment thereof. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the marker proteins. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a marker protein which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the marker proteins from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of segments of a marker protein can be used to generate a variegated population of polypeptides for screening and subsequent selection of variant marker proteins or segments thereof. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811-7815; Delgrave et al., 1993, *Protein Engineering* 6(3):327-331).

Another aspect of the invention pertains to antibodies directed against a protein of the invention. In preferred embodiments, the antibodies specifically bind a marker protein or a fragment thereof. The terms "antibody" and "antibodies" as used interchangeably herein refer to immunoglobulin molecules as well as fragments and derivatives thereof that comprise an immunologically active portion of an immunoglobulin molecule, (i.e., such a portion contains an antigen binding site which specifically binds an antigen, such as a marker protein, e.g., an epitope of a marker protein). An antibody which specifically binds to a protein of the invention is an antibody which binds the protein, but does not substantially bind other molecules in a sample, e.g., a biological sample, which naturally contains the protein. Examples of an immunologically active portion of an immunoglobulin molecule include, but are not limited to, single-chain antibodies (scAb), F(ab) and F(ab')$_2$ fragments.

An isolated protein of the invention or a fragment thereof can be used as an immunogen to generate antibodies. The full-length protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the proteins of the invention, and encompasses at least one epitope of the protein such that an antibody raised against the peptide forms a specific immune complex with the protein. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions. In preferred embodiments, an isolated marker protein or fragment thereof is used as an immunogen.

An immunogen typically is used to prepare antibodies by immunizing a suitable (i.e. immunocompetent) subject such as a rabbit, goat, mouse, or other mammal or vertebrate. An appropriate immunogenic preparation can contain, for example, recombinantly-expressed or chemically-synthesized protein or peptide. The preparation can further include an adjuvant, such as Freund's complete or incomplete adjuvant, or a similar immunostimulatory agent. Preferred immunogen compositions are those that contain no other human proteins such as, for example, immunogen compositions made using a non-human host cell for recombinant expression of a protein of the invention. In such a manner, the resulting antibody compositions have reduced or no binding of human proteins other than a protein of the invention.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Preferred polyclonal and monoclonal antibody compositions are ones that have been selected for antibodies directed against a protein of the invention. Particularly preferred polyclonal and monoclonal antibody preparations are ones that contain only antibodies directed against a marker protein or fragment thereof.

Polyclonal antibodies can be prepared by immunizing a suitable subject with a protein of the invention as an immunogen The antibody titer in the immunized subject can be monitored over time by standard techniques, such as with an enzyme linked immunosorbent assay (ELISA) using immobilized polypeptide. At an appropriate time after immunization, e.g., when the specific antibody titers are highest, antibody-producing cells can be obtained from the subject and used to prepare monoclonal antibodies (mAb) by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a protein of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

The invention also provides recombinant antibodies that specifically bind a protein of the invention. In preferred embodiments, the recombinant antibodies specifically binds a marker protein or fragment thereof. Recombinant antibodies include, but are not limited to, chimeric and humanized monoclonal antibodies, comprising both human and non-human portions, single-chain antibodies and multi-specific antibodies. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Single-chain antibodies have an antigen binding site and consist of single polypeptides. They can be produced by techniques known in the art, for example using methods described in Ladner et. al U.S. Pat. No. 4,946,778 (which is incorporated herein by reference in its entirety); Bird et al., (1988) *Science* 242:423-426; Whitlow et al., (1991) *Methods in Enzymology* 2:1-9; Whitlow et al., (1991) *Methods in Enzymology* 2:97-105; and Huston et al., (1991) *Methods in Enzymology Molecular Design and Modeling: Concepts and Applications* 203:46-88. Multi-specific antibodies are antibody molecules having at least two antigen-binding sites that specifically bind different antigens. Such molecules can be produced by techniques known in the art, for example using methods described in Segal, U.S. Pat. No. 4,676,980 (the disclosure of which is incorporated herein by reference in its entirety); Holliger et al., (1993) *Proc. Natl. Acad. Sci. USA* 90:6444-6448; Whitlow et al., (1994) *Protein Eng.* 7:1017-1026 and U.S. Pat. No. 6,121,424.

Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

More particularly, humanized antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a marker of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, *Bio/technology* 12:899-903).

The antibodies of the invention can be isolated after production (e.g., from the blood or serum of the subject) or synthesis and further purified by well-known techniques. For example, IgG antibodies can be purified using protein A chromatography. Antibodies specific for a protein of the invention can be selected or (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those of the desired protein of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein of the invention.

In a preferred embodiment, the substantially purified antibodies of the invention may specifically bind to a signal peptide, a secreted sequence, an extracellular domain, a transmembrane or a cytoplasmic domain or cytoplasmic membrane of a protein of the invention. In a particularly preferred embodiment, the substantially purified antibodies of the invention specifically bind to a secreted sequence or an extracellular domain of the amino acid sequences of a protein of the invention. In a more preferred embodiment, the substantially purified antibodies of the invention specifically bind to a secreted sequence or an extracellular domain of the amino acid sequences of a marker protein.

An antibody directed against a protein of the invention can be used to isolate the protein by standard techniques, such as affinity chromatography or immunoprecipitation. Moreover, such an antibody can be used to detect the marker protein or fragment thereof (e.g., in a cellular lysate or cell supernatant) in order to evaluate the level and pattern of expression of the marker. The antibodies can also be used diagnostically to monitor protein levels in tissues or body fluids (e.g. in a breast- or ovary-associated body fluid) as part of a clinical testing procedure, e.g., to, for example, determine the efficacy of a given treatment regimen. Detection can be facilitated by the use of an antibody derivative, which comprises an antibody of the invention coupled to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibodies of the invention may also be used as therapeutic agents in treating cancers. In a preferred embodiment, completely human antibodies of the invention are used for therapeutic treatment of human cancer patients, particularly those having breast or ovarian cancer. In another preferred embodiment, antibodies that bind specifically to a marker protein or fragment thereof are used for therapeutic treatment. Further, such therapeutic antibody may be an antibody derivative or immunotoxin comprising an antibody conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugated antibodies of the invention can be used for modifying a given biological response, for the drug moiety is not to be construed as limited to classical chemical therapeutic agents. For example, the drug moiety may be a protein or polypeptide possessing a desired biological activity. Such proteins may include, for example, a toxin such as ribosome-inhibiting protein (see Better et al., U.S. Pat. No. 6,146,631, the disclosure of which is incorporated herein in its entirety), abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Accordingly, in one aspect, the invention provides substantially purified antibodies, antibody fragments and derivatives, all of which specifically bind to a protein of the invention and preferably, a marker protein. In various embodiments, the substantially purified antibodies of the invention, or fragments or derivatives thereof, can be human, non-human, chimeric and/or humanized antibodies. In another aspect, the invention provides non-human antibodies, antibody fragments and derivatives, all of which specifically bind to a protein of the invention and preferably, a marker protein. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies. In still a further aspect, the invention provides monoclonal antibodies, antibody fragments and derivatives, all of which specifically bind to a protein of the invention and preferably, a marker protein. The monoclonal antibodies can be human, humanized, chimeric and/or non-human antibodies.

The invention also provides a kit containing an antibody of the invention conjugated to a detectable substance, and instructions for use. Still another aspect of the invention is a pharmaceutical composition comprising an antibody of the invention. In one embodiment, the pharmaceutical composition comprises an antibody of the invention, a therapeutic moiety, and a pharmaceutically acceptable carrier.

III. Recombinant Expression Vectors and Host Cells

Another aspect of the invention pertains to vectors, preferably expression vectors, containing a nucleic acid encoding a marker protein (or a portion of such a protein). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of a marker protein or a segment thereof in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol. 185, Academic Press, San Diego, Calif., 1991). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., 1986, *Trends in Genetics*, Vol. 1(1).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker will survive, while the other cells die).

A host cell of the invention, such as a prokaryotic or eukaryotic host cell in culture, can be used to produce a marker protein or a segment thereof. Accordingly, the invention further provides methods for producing a marker protein or a segment thereof using the host cells of the invention. In one embodiment, the method comprises culturing the host cell of the invention (into which a recombinant expression vector encoding a marker protein or a segment thereof has been introduced) in a suitable medium such that the is produced. In another embodiment, the method further comprises isolating the a marker protein or a segment thereof from the medium or the host cell.

The host cells of the invention can also be used to produce nonhuman transgenic animals. For example, in one embodiment, a host cell of the invention is a fertilized oocyte or an embryonic stem cell into which a sequences encoding a marker protein or a segment thereof have been introduced. Such host cells can then be used to create non-human transgenic animals in which exogenous sequences encoding a marker protein of the invention have been introduced into their genome or homologous recombinant animals in which endogenous gene(s) encoding a marker protein have been altered. Such animals are useful for studying the function and/or activity of the marker protein and for identifying and/or evaluating modulators of marker protein. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid encoding a marker protein into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, 4,873,191 and in Hogan, *Manipulating the Mouse Embryo*, Cold Spring Harbor Laboratory Press, Cold Spring Harbor, N.Y., 1986. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a marker protein into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi, 1987, *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al., 1992, *Cell* 69:915). The selected cells are then injected into a blastocyst of an animal (e.g., a mouse) to form aggregation chimeras (see, e.g., Bradley, *Teratocarcinomas and Embryonic Stem Cells: A Practical Approach*, Robertson, Ed., IRL, Oxford, 1987, pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication NOS. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al., 1991, *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication NOS. WO 97/07668 and WO 97/07669.

IV. Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a marker nucleic acid or protein. Such methods comprise formulating a pharmaceutically acceptable carrier with an agent which modulates expression or activity of a marker nucleic acid or protein. Such compositions can further include additional active agents. Thus, the invention further includes methods for preparing a pharmaceutical composition by formulating a pharmaceutically acceptable carrier with an agent which modulates expression or activity of a marker nucleic acid or protein and one or more additional active compounds.

The invention also provides methods (also referred to herein as "screening assays") for identifying modulators, i.e., candidate or test compounds or agents (e.g., peptides, peptidomimetics, peptoids, small molecules or other drugs) which (a) bind to the marker, or (b) have a modulatory (e.g., stimulatory or inhibitory) effect on the activity of the marker or, more specifically, (c) have a modulatory effect on the interactions of the marker with one or more of its natural substrates (e.g., peptide, protein, hormone, co-factor, or nucleic acid), or (d) have a modulatory effect on the expression of the marker. Such assays typically comprise a reaction between the marker and one or more assay components. The other components may be either the test compound itself, or a combination of test compound and a natural binding partner of the marker.

The test compounds of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

In one embodiment, the invention provides assays for screening candidate or test compounds which are substrates of a protein encoded by or corresponding to a marker or biologically active portion thereof. In another embodiment, the invention provides assays for screening candidate or test compounds which bind to a protein encoded by or corresponding to a marker or biologically active portion thereof. Determining the ability of the test compound to directly bind to a protein can be accomplished, for example, by coupling the compound with a radioisotope or enzymatic label such that binding of the compound to the marker can be determined by detecting the labeled marker compound in a complex. For example, compounds (e.g., marker substrates) can be labeled with $^{125}$I, $^{35}$S, $^{14}$C, or $^{3}$H, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product.

In another embodiment, the invention provides assays for screening candidate or test compounds which modulate the expression of a marker or the activity of a protein encoded by or corresponding to a marker, or a biologically active portion thereof. In all likelihood, the protein encoded by or corresponding to the marker can, in vivo, interact with one or more molecules, such as but not limited to, peptides, proteins, hormones, cofactors and nucleic acids. For the purposes of this discussion, such cellular and extracellular molecules are referred to herein as "binding partners" or marker "substrate".

One necessary embodiment of the invention in order to facilitate such screening is the use of a protein encoded by or corresponding to marker to identify the protein's natural in vivo binding partners. There are many ways to accomplish this which are known to one skilled in the art. One example is the use of the marker protein as "bait protein" in a two-hybrid assay or three-hybrid assay (see, e.g., U.S. Pat. No. 5,283,317; Zervos et al, 1993, *Cell* 72:223-232; Madura et al, 1993, *J. Biol. Chem.* 268:12046-12054; Bartel et al, 1993, *Biotechniques* 14:920-924; Iwabuchi et al, 1993 *Oncogene* 8:1693-1696; Brent WO94/10300) in order to identify other proteins which bind to or interact with the marker (binding partners) and, therefore, are possibly involved in the natural function of the marker. Such marker binding partners are also likely to be involved in the propagation of signals by the marker protein or downstream elements of a marker protein-mediated signaling pathway. Alternatively, such marker protein binding partners may also be found to be inhibitors of the marker protein.

The two-hybrid system is based on the modular nature of most transcription factors, which consist of separable DNA-binding and activation domains. Briefly, the assay utilizes two different DNA constructs. In one construct, the gene that encodes a marker protein fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a marker-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be readily detected and cell colonies containing the functional transcription factor can be isolated and used to obtain the cloned gene which encodes the protein which interacts with the marker protein.

In a further embodiment, assays may be devised through the use of the invention for the purpose of identifying compounds which modulate (e.g., affect either positively or negatively) interactions between a marker protein and its substrates and/or binding partners. Such compounds can include, but are not limited to, molecules such as antibodies, peptides, hormones, oligonucleotides, nucleic acids, and analogs thereof. Such compounds may also be obtained from any available source, including systematic libraries of natural and/or synthetic compounds. The preferred assay components for use in this embodiment is a breast or ovarian cancer marker protein identified herein, the known binding partner and/or substrate of same, and the test compound. Test compounds can be supplied from any source.

The basic principle of the assay systems used to identify compounds that interfere with the interaction between the marker protein and its binding partner involves preparing a reaction mixture containing the marker protein and its binding partner under conditions and for a time sufficient to allow the two products to interact and bind, thus forming a complex. In order to test an agent for inhibitory activity, the reaction mixture is prepared in the presence and absence of the test compound. The test compound can be initially included in the reaction mixture, or can be added at a time subsequent to the addition of the marker protein and its binding partner. Control reaction mixtures are incubated without the test compound or with a placebo. The formation of any complexes between the marker protein and its binding partner is then detected. The formation of a complex in the control reaction, but less or no such formation in the reaction mixture containing the test compound, indicates that the compound interferes with the interaction of the marker protein and its binding partner. Conversely, the formation of more complex in the presence of compound than in the control reaction indicates that the compound may enhance interaction of the marker protein and its binding partner.

The assay for compounds that interfere with the interaction of the marker protein with its binding partner may be conducted in a heterogeneous or homogeneous format. Heterogeneous assays involve anchoring either the marker protein or its binding partner onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the marker proteins and the binding partners (e.g., by competition) can be identified by conducting the reaction in the presence of the test substance, i.e., by adding the test substance to the reaction mixture prior to or simultaneously with the marker and its interactive binding partner. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the marker protein or its binding partner is anchored onto a solid surface or matrix, while the other corresponding non-anchored component may be labeled, either directly or indirectly. In practice, microtitre plates are often utilized for this approach. The anchored species can be immobilized by a number of methods, either non-covalent or covalent, that are typically well known to one who practices the art. Non-covalent attachment can often be accomplished simply by coating the solid surface with a solution of the marker protein or its binding partner and drying. Alternatively, an immobilized antibody specific for the assay component to be anchored can be used for this purpose. Such surfaces can often be prepared in advance and stored.

In related embodiments, a fusion protein can be provided which adds a domain that allows one or both of the assay components to be anchored to a matrix. For example, glutathione-S-transferase/marker fusion proteins or glutathione-S-transferase/binding partner can be adsorbed onto glutathione sepharose beads (Sigma Chemical, St. Louis, Mo.) or glutathione derivatized microtiter plates, which are then combined with the test compound or the test compound and either the non-adsorbed marker or its binding partner, and the mixture incubated under conditions conducive to complex formation (e.g., physiological conditions). Following incubation, the beads or microtiter plate wells are washed to remove any unbound assay components, the immobilized complex assessed either directly or indirectly, for example, as described above. Alternatively, the complexes can be dissociated from the matrix, and the level of marker binding or activity determined using standard techniques.

Other techniques for immobilizing proteins on matrices can also be used in the screening assays of the invention. For example, either a marker protein or a marker protein binding partner can be immobilized utilizing conjugation of biotin and streptavidin. Biotinylated marker protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the protein-immobilized surfaces can be prepared in advance and stored.

In order to conduct the assay, the corresponding partner of the immobilized assay component is exposed to the coated surface with or without the test compound. After the reaction is complete, unreacted assay components are removed (e.g., by washing) and any complexes formed will remain immobilized on the solid surface. The detection of complexes anchored on the solid surface can be accomplished in a number of ways. Where the non-immobilized component is pre-labeled, the detection of label immobilized on the surface indicates that complexes were formed. Where the non-immobilized component is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds which modulate (inhibit or enhance) complex formation or which disrupt pre-formed complexes can be detected.

In an alternate embodiment of the invention, a homogeneous assay may be used. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton, A. P., Trends Biochem Sci 1993 August; 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the complex as compared to the uncomplexed molecules may be exploited to differentially separate the complex from the remaining individual reactants, for example through the use of ion-exchange chromatography resins. Such resins and chromatographic techniques are well known to one skilled in the art (see, e.g., Heegaard, 1998, J Mol. Recognit. 11:141-148; Hage and Tweed, 1997, J. Chromatogr. B. Biomed. Sci. Appl., 699:499-525). Gel electrophoresis may also be employed to separate complexed molecules from unbound species (see, e.g., Ausubel et al (eds.), In: Current Protocols in Molecular Biology, J. Wiley & Sons, New York. 1999). In this technique, protein or nucleic acid complexes are separated based on size or charge, for example. In order to maintain the binding interaction during the electrophoretic process, nondenaturing gels in the absence of reducing agent are typically preferred, but conditions appropriate to the particular interactants will be well known to one skilled in the art Immunoprecipitation is another common technique utilized for the isolation of a protein-protein complex from solution (see, e.g., Ausubel et al (eds.), In: Current Protocols in Molecular Biology, J. Wiley & Sons, New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between the marker protein and its binding partner.

Also within the scope of the present invention are methods for direct detection of interactions between the marker protein and its natural binding partner and/or a test compound in a homogeneous or heterogeneous assay system without further sample manipulation. For example, the technique of fluorescence energy transfer may be utilized (see, e.g., Lakowicz et al, U.S. Pat. No. 5,631,169; Stavrianopoulos et al, U.S. Pat. No. 4,868,103). Generally, this technique involves the addition of a fluorophore label on a first 'donor' molecule (e.g., marker or test compound) such that its emitted fluorescent energy will be absorbed by a fluorescent label on a second, 'acceptor' molecule (e.g., marker or test compound), which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter). A test substance which either enhances or hinders participation of one of the species in the preformed complex will result in the generation of a signal variant to that of background. In this way, test substances that modulate interactions between a marker and its binding partner can be identified in controlled assays.

In another embodiment, modulators of marker expression are identified in a method wherein a cell is contacted with a candidate compound and the expression of marker mRNA or protein in the cell, is determined. The level of expression of marker mRNA or protein in the presence of the candidate compound is compared to the level of expression of marker mRNA or protein in the absence of the candidate compound. The candidate compound can then be identified as a modulator of marker expression based on this comparison. For example, when expression of marker mRNA or protein is greater (statistically significantly greater) in the presence of the candidate compound than in its absence, the candidate compound is identified as a stimulator of marker mRNA or protein expression. Conversely, when expression of marker mRNA or protein is less (statistically significantly less) in the presence of the candidate compound than in its absence, the candidate compound is identified as an inhibitor of marker mRNA or protein expression. The level of marker mRNA or protein expression in the cells can be determined by methods described herein for detecting marker mRNA or protein.

In another aspect, the invention pertains to a combination of two or more of the assays described herein. For example, a modulating agent can be identified using a cell-based or a cell free assay, and the ability of the agent to modulate the activity of a marker protein can be further confirmed in vivo, e.g., in a whole animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., an marker modulating agent, an antisense marker nucleic acid molecule, an marker-specific antibody, or an marker-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

It is understood that appropriate doses of small molecule agents and protein or polypeptide agents depends upon a number of factors within the knowledge of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the nucleic acid or polypeptide of the invention. Exemplary doses of a small molecule include milligram or microgram amounts per kilogram of subject or sample weight (e.g. about 1 microgram per kilogram to about 500 milligrams per kilogram, about 100 micrograms per kilogram to about 5 milligrams per kilogram, or about 1 microgram per kilogram to about 50 micrograms per kilogram). Exemplary doses of a protein or polypeptide include gram, milligram or microgram amounts per kilogram of subject or sample weight (e.g. about 1 microgram per kilogram to about 5 grams per kilogram, about 100 micrograms per kilogram to about 500 milligrams per kilogram, or about 1 milligram per kilogram to about 50 milligrams per kilogram). It is furthermore understood that appropriate doses of one of these agents depend upon the potency of the agent with respect to the expression or activity to be modulated. Such appropriate doses can be determined using the assays described herein. When one or more of these agents is to be administered to an animal (e.g. a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine-tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes having monoclonal antibodies incorporated therein or thereon) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration. A method for lipidation of antibodies is described by Cruikshank et al. (1997) *J. Acquired Immune Deficiency Syndromes and Human Retrovirology* 14:193.

The marker nucleic acid molecules can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al., 1994, *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Predictive Medicine

The present invention pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining the level of expression of one or more marker proteins or nucleic acids, in order to determine whether an individual is at risk of developing breast or ovarian cancer. Such assays can be used for prognostic or predictive purposes to thereby prophylactically treat an individual prior to the onset of the cancer.

Yet another aspect of the invention pertains to monitoring the influence of agents (e.g., drugs or other compounds administered either to inhibit breast or ovarian cancer or to treat or prevent any other disorder {i.e. in order to understand any breast or ovarian carcinogenic effects that such treatment may have}) on the expression or activity of a marker of the invention in clinical trials. These and other agents are described in further detail in the following sections.

A. Diagnostic Assays

An exemplary method for detecting the presence or absence of a marker protein or nucleic acid in a biological sample involves obtaining a biological sample (e.g. a breast- or ovary-associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a marker protein include enzyme linked immunosorbent assays (ELISAs), Western blots, immunoprecipitations and immunofluorescence. In vitro techniques for detection of genomic DNA include Southern hybridizations. Furthermore, in vivo techniques for detection of a marker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol. Recognit.* Winter 11(1-6):141-8; Hage, D. S., and Tweed, S. A. *J Chromatogr B Biomed Sci Appl* 1997 Oct. 10; 699(1-2):499-525). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of marker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from breast or ovarian cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA marker in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the breast or ovarian cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-breast or non-ovarian cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

Preferably, the samples used in the baseline determination will be from breast or ovarian cancer or from non-breast or non-ovarian cancer cells of breast or ovarian tissue. The choice of the cell source is dependent on the use of the relative expression level. Using expression found in normal tissues as a mean expression score aids in validating whether the marker assayed is breast or ovarian specific (versus normal cells). In addition, as more data is accumulated, the mean expression value can be revised, providing improved relative expression values based on accumulated data. Expression data from breast or ovarian cells provides a means for grading the severity of the breast or ovarian cancer state.

In another embodiment of the present invention, a marker protein is detected. A preferred agent for detecting marker protein of the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from breast or ovarian cells can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbent assay (ELISA). A skilled artisan can readily adapt known protein/antibody detection methods for use in determining whether breast or ovarian cells express a marker of the present invention.

In one format, antibodies, or antibody fragments or derivatives, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from breast or ovarian cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

The invention also encompasses kits for detecting the presence of a marker protein or nucleic acid in a biological sample (e.g. a breast- or ovary-associated body fluid such as a urine sample). Such kits can be used to determine if a subject is suffering from or is at increased risk of developing breast or ovarian cancer. For example, the kit can comprise a labeled compound or agent capable of detecting a marker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for interpreting the results obtained using the kit.

For antibody-based kits, the kit can comprise, for example: (1) a first antibody (e.g., attached to a solid support) which binds to a marker protein; and, optionally, (2) a second, different antibody which binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

B. Pharmacogenomics

The marker of the invention are also useful as pharmacogenomic markers. As used herein, a "pharmacogenomic marker" is an objective biochemical marker whose expression level correlates with a specific clinical drug response or susceptibility in a patient (see, e.g., McLeod et al. (1999) *Eur. J. Cancer* 35(12): 1650-1652). The presence or quantity of the pharmacogenomic marker expression is related to the predicted responsive of the patient and more particularly the patient's tumor to therapy with a specific drug or class of drugs. By assessing the presence or quantity of the expression of one or more pharmacogenomic markers in a patient, a drug therapy which is most appropriate for the patient, or which is predicted to have a greater degree of success, may be selected. For example, based on the presence or quantity of RNA or protein encoded by specific tumor markers in a patient, a drug or course of treatment may be selected that is optimized for the treatment of the specific tumor likely to be present in the patient. The use of pharmacogenomic markers therefore permits selecting or designing the most appropriate treatment for each cancer patient without trying different drugs or regimes.

Another aspect of pharmacogenomics deals with genetic conditions that alters the way the body acts on drugs. These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the level of expression of a marker of the invention in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of expression of a marker of the invention.

C. Monitoring Clinical Trials

Monitoring the influence of agents (e.g., drug compounds) on the level of expression of a marker of the invention can be applied not only in basic drug screening, but also in clinical trials. For example, the effectiveness of an agent to affect marker expression can be monitored in clinical trials of subjects receiving treatment for breast or ovarian cancer. In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of one or more selected markers of the invention in the pre-administration sample; (iii) obtaining one or more post-administration samples from the subject; (iv) detecting the level of expression of the marker(s) in the post-administration samples; (v) comparing the level of expression of the marker(s) in the pre-administration sample with the level of expression of the marker(s) in the post-administration sample or samples; and (vi) altering the administration of the agent to the subject accordingly. For example, increased expression of the marker gene(s) during the course of treatment may indicate ineffective dosage and the desirability of increasing the dosage. Conversely, decreased expression of the marker gene(s) may indicate efficacious treatment and no need to change dosage.

D. Electronic Apparatus Readable Media and Arrays

Electronic apparatus readable media comprising a marker of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the markers of the present invention.

A variety of software programs and formats can be used to store the marker information of the present invention on the electronic apparatus readable medium. For example, the marker nucleic acid sequence can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon the markers of the present invention.

By providing the markers of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has breast or ovarian cancer or a pre-disposition to breast or ovarian cancer, wherein the method comprises the steps of determining the presence or absence of a marker and based on the presence or absence of the marker, determining whether the subject has breast or ovarian cancer or a pre-disposition to breast or ovarian cancer and/or recommending a particular treatment for breast or ovarian cancer or pre-breast or pre-ovarian cancer condition.

The present invention further provides in an electronic system and/or in a network, a method for determining whether a subject has breast or ovarian cancer or a pre-disposition to breast or ovarian cancer associated with a marker wherein the method comprises the steps of determining the presence or absence of the marker, and based on the presence or absence of the marker, determining whether the subject has breast or ovarian cancer or a pre-disposition to breast or ovarian cancer, and/or recommending a particular treatment for the breast or ovarian cancer or pre-breast or pre-ovarian cancer condition. The method may further comprise the step of receiving phenotypic information associated with the subject and/or acquiring from a network phenotypic information associated with the subject.

The present invention also provides in a network, a method for determining whether a subject has breast or ovarian cancer or a pre-disposition to breast or ovarian cancer associated with a marker, said method comprising the steps of receiving information associated with the marker receiving phenotypic information associated with the subject, acquiring information from the network corresponding to the marker and/or breast or pre-ovarian cancer, and based on one or more of the phenotypic information, the marker, and the acquired information, determining whether the subject has a breast or ovarian cancer or a pre-disposition to breast or ovarian cancer. The method may further comprise the step of recommending a particular treatment for the breast or ovarian cancer or pre-breast or pre-ovarian cancer condition.

The present invention also provides a business method for determining whether a subject has breast or ovarian cancer or a pre-disposition to breast or ovarian cancer, said method comprising the steps of receiving information associated with the marker, receiving phenotypic information associated with the subject, acquiring information from the network corresponding to the marker and/or breast or ovarian cancer, and based on one or more of the phenotypic information, the marker, and the acquired information, determining whether the subject has breast or ovarian cancer or a pre-disposition to breast or ovarian cancer. The method may further comprise the step of recommending a particular treatment for the breast or ovarian cancer or pre-breast or pre-ovarian cancer condition.

The invention also includes an array comprising a marker of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of breast or ovarian cancer, progression of breast or ovarian cancer, and processes, such a cellular transformation associated with breast or ovarian cancer.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

E. Surrogate Markers

The markers of the invention may serve as surrogate markers for one or more disorders or disease states or for conditions leading up to disease states, and in particular, breast or ovarian cancer. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The markers of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker transcription or expression, the amplified marker may be in a quantity which is more readily detectable than the drug itself. Also, the marker may be more easily detected due to the nature of the marker itself; for example, using the methods described herein, antibodies may be employed in an immune-based detection system for a protein marker, or marker-specific radiolabeled probes may be used to detect a mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

Experimental Protocol

A. Identification of Markers and Assembly of their Sequences

RNA from tumor and normal breast and ovarian tissue samples were extracted and amplified by poly-dT primed RT-PCR into cDNA using the SMART PCR kit from Clonetech. Amplified cDNA was then labeled using random priming PRIME-IT from Stratagene with a radioactive nucleotide. Labeled cDNA was hybridized to nylon filters spotted with purified PCR product from EST sequences representing known and unknown genes. Several thousand clones were spotted on each nylon filter. Duplicate independent hybridization experiments were performed to generate transcriptional profiling data (see Nature Genetics, 1999, 21). After repeated washings the nylon filters were scanned and the intensity of each spotted gene was converted electronically to indicate expression level in the sample from which the cDNA was derived. Tables were generated for each sample showing the expression level for each of the spotted ESTs. These tables were transferred to Microsoft Excel spreadsheets and the expression levels for each spotted EST was compared between samples. A total of 41 tumor samples representing both early and late stage breast cancer and 7 normal breast tissue samples were profiled on these EST arrays. Additionally, a total of 70 late stage ovarian tumor samples and 5 normal ovarian tissue samples were also profiled on the EST arrays. ESTs that displayed a 5-fold increase in the expression level over the average expression level in the normal samples in at least 30% of the tumor samples were exported to a separate data table.

The corresponding nucleotide sequences for each of these spots were imported and blasted against both public and proprietary sequence databases in order to identify other EST sequences with significant overlap. Thus, contiguous EST sequences were assembled into tentative full-length genes. Reblasting of the assembled sequences against databases of genes coding for known proteins was done to assess whether the assembled gene was a known or unknown protein. Genes in which the potential open reading frame was still open in the 5' end were experimentally extended by either 5'RACE PCR or extracted out from full length cDNA libraries by a simple PCR reaction between the vector and 5' end of the assembled electronic sequence. To predict whether an assembled gene encodes a potential integral membrane protein, hydropathy predictions of the predicted open reading frame was performed (Jones et al., 1994, *Biochemistry.* 33:3038-3049). If the open reading frame contained a predicted signal peptide in the N-terminal portion and a single membrane spanning domain, it was labeled as being a potential type I transmembrane protein. If the predicted amino acid sequence contained a transmembrane domain in the N-terminal portion of the protein, it was labeled as being a potential type II transmembrane protein. If the predicted amino acid sequence was a short hydrophobic protein (<50 amino acids) it was labeled as a potential integral membrane protein. If the predicted amino acid sequence contained multiple membrane spanning regions it was labeled as a multi-transmembrane (multi-TM) region protein B. Identification of Marker 7 and Marker 23 as Targets for Anti-Cancer Therapy Expression levels of Marker 7, a putative transmembrane protein was >5-fold higher in 25/56 breast, 17/20 colon and 26/58 ovarian cancer samples compared to normal tissues. The full-length gene was cloned and expressed and the protein found to be localized to the cell surface of transfected cells. Marker 7 does not belong to any known protein family and does not show significant homology to any protein in the public databases. Northern blots of various carcinoma cells lines reveal the presence of a single mRNA species at approximately 1.4 kb.

Expression of Marker 7 in normal and malignant human tissues was further evaluated by quantitative PCR analysis. Expression levels in breast, ovary, lung and colon tumor samples were 10-300 fold higher than corresponding normal tissues. In addition there was high expression of Marker 7 in in vitro cultured endothelial cells and Wilms tumors and hemangiomas, which are highly vascularized tumors. In situ hybridization (ISH) on tumor samples showed that Marker 7 is predominantly expressed within the tumor stroma and possibly localized to tumor vasculature. Analysis of normal human tissues, including aorta, by ISH suggested that Marker 7 is not expressed on cells within mature vessels. When human tumor cells are transplanted subcutaneously in immunodeficient mice, there is an induction of Marker 7 expression in the mouse stroma associated with tumor vasculature. Marker 7 is hence found expressed in many human cancers, (e.g. breast, ovary, colon, lung and prostate) and not in normal adult tissue.

A similar analysis of Marker 23 showed that this marker is stroma specific, and is upregulated in ovary, breast, lung and colon cancers. Marker 7 and Marker 23 are therefore attractive targets for inhibition of cancers as well as angiogenesis in general. Antibodies, antibody derivatives, and antibody fragments which bind, specifically with Marker 7 or Marker 32 protein (i.e., SEQ ID NOs: 14 and 64, respectively), or a fragment of the protein, may be used to treat cancer of the breast, ovary, lung, colon and prostate as well as generally inhibiting angiogenesis.

VII. Summary of the Data in the Tables:

Table 1 lists all of the markers of the invention.

Table 2 lists Markers 1-33 which were found to be upregulated (i.e., over-expressed) by transcription profiling (TP) in breast cancer. The markers were upregulated at least 5-fold in >30% of the tumors arrayed.

Table 3 lists Markers 34-56 which were found to be upregulated by TP in ovarian cancer. The markers were upregulated at least 5-fold in >30% of the tumors arrayed.

Table 4 lists markers in which additional expression analyses were done by either in situ hybridization (ISH), quantitative mRNA analysis (Taqman) or both. Table 5 lists markers whose encoded protein were heretofore unknown.

In Tables 1-3 and 5 the following definitions apply:

"Marker" corresponds to the arbitrary identifier used within this application to designate the marker of the invention.

"Gene Name" corresponds to the commonly used terminology for the marker gene, if it exists.

"Image Clone ID" corresponds to the cDNA clone number from the IMAGE Consortium (see, for example Lennon, G., et al., 1996, *Genomics* 33:151-152; and http://www-bio.llnl.gov/bbrp/image/image.html). All referenced IMAGE clone sequences are expressly incorporated herein by reference.

"SEQ ID NO (nts)" designates the entry number in the Sequence Listing that corresponds to the nucleotide sequence of the particular marker. "SEQ ID NO (AAs)" designates the entry number in the Sequence Listing that corresponds to the amino acid sequence of the particular marker. Each known sequence submitted to GenBank has a unique identifier number, also called the GenBank GI Accession Number, for a complete sequence record in the relevant database (see, e.g. "http://www.ncbi.nlm.nih.gov/genbank/query_form.html" and "www.derwent.com" for further information). "Acc # (NTS)" corresponds to the GenBank Accession Number for a nucleotide sequence, while "Acc # (AA)" corresponds to the GenBank Accession Number for a protein sequence. "GI # (NTS)" is the GI identification number assigned to the nucleotide sequence of the marker gene in the GenBank database (see supra). "GI # (AA)" corresponds to the GI sequence identification number assigned to that particular protein translation within a nucleotide sequence record in the GenBank database.

The following data is presented in Table 4:

"Gene" corresponds to the arbitrary identifier used within this application to designate the marker of the invention.

The "TaqMan" and "ISH" columns of Table 4, designate whether expression of this marker was analyzed using TaqMan technology or in situ hybridization, respectively. "Yes" indicates that such analysis was done, while "No" similarly indicates that such analysis was not done. "TaqMan" corresponds to the results of quantitative PCR analysis using the TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of taq polymerase digests the labeled primer, producing a free nucleotide labeled with 6-FAM, which is detected as a fluorescent signal. The PCR cycle where fluorescence is first released and detected is directly proportional to the starting amount of the gene of interest in the test sample, thus providing a way of quantitating the initial template concentration.

"Ovary", "Breast", "Lung", "Colon", and "Prostate" correspond to expression as detected by TaqMan analysis in ovarian, breast, lung, colon and prostate cancer respectively. Markers scored with a "+" were found to be upregulated by at least 3-fold in at least 20% of the tumors analyzed (n=>5) in the designated tumor type by Taqman analysis. Markers scored with a "−" were not found to be upregulated in the designated tumor type by Taqman analysis. Expression for markers scored with "ND" was not determined in the designated tumor type. In addition, ISH analysis confirmed that the genes were expressed by the carcinoma cells, except for Marker 23, which is stroma specific and Marker 7 which is expressed mostly in the stroma but can also be found on tumor cells. Evidence to support this includes Taqman RNA analysis from cancer cell lines (breast, ovary, lung, colon and prostate) and ISH.

The contents of all references, patents, published patent applications, and database records including GenBank, IMAGE consortium and Derwent cited throughout this application, are hereby incorporated by reference.

Other Embodiments

Those skilled in the art will recognize, or be able to ascertain using no more than routine experimentation, many equivalents to the specific embodiments of the invention described herein. Such equivalents are intended to be encompassed by the following claims:

TABLE 1

| Marker | Gene Name | Image Clone ID | Acc # (NTS) | GI # (NTS) | SEQ ID NO (nts) | Acc # (AA) | GI # (AA) | SEQ ID NO (AAs) |
| --- | --- | --- | --- | --- | --- | --- | --- | --- |
| Marker 1 | KIAA0018 | 840878 | D13643 | 285996 | 1 | BAA02806 | 6630632 | 2 |
| Marker 2 | Nonspecific cross reacting antigen (NCA) | 509823 | M18728 | 189084 | 3 | AAA51739 | 178691 | 4 |
| Marker 3 | Unnamed protein product | 461336 | AK001105 | 7022160 | 5 | BAA91505 | 7022161 | 6 |
| Marker 4 | Net-6 | 416374 | AF120265 | 4325179 | 7 | AAD17294 | 4325180 | 8 |
| Marker 5 | DKFZp727C191 | 785703 | AL117474 | 5911946 | 9 | | | 10 |
| Marker 6 | Interferon-induced protein 6-16 | 782513 | Q28808 | N/A | 11 | BAA01980 | 218574 | 12 |
| Marker 7 | UNNAMED | 753428 | | | 13 | | | 14 |
| Marker 8 | Alphe 2,6-sialyltransferase | 823590 | AJ251053 | 6453383 | 15 | CAB61434 | 6453384 | 16 |
| Marker 9 | Programmed cell death 9 (PCD9) | 270558 | AL355715 | 7799103 | 17 | CAB90810 | 7799104 | 18 |
| Marker 10 | DKFZp564BI264 | 813730 | AL117612 | 5912188 | 19 | | | 20 |
| Marker 11 | receptor protein tyrosine phosphatase | 41647 | AF043644 | 5468530 | 21 | AAD09421 | 6554165 | 22 |
| Marker 12 | MAT-8 | 511428 | Q14802 | N/A | 23 | CAA63604 | 1085026 | 24 |
| Marker 13 | Neuropeptide Y receptor, type 1 | 33045 | P25929 | N/A | 25 | CAA01819 | 1247453 | 26 |
| Marker 14 | Interferon-inducible protein 9-27 | 755599 | P13164 | N/A | 27 | CAA59337 | 1177476 | 28 |
| Marker 15 | UNNAMED | From substracted library | | | 29 | | | 30 |
| Marker 16 | Vascular cell adhesion molecule (VCAM) | 44477 | M30257 | 179885 | 31 | AAA51917 | 179886 | 32 |
| Marker 17 | 8D6 antigen | 770879 | AF161254 | 7406951 | 33 | AAF61850 | 7406952 | 34 |
| Marker 18 | DKFZp564E1363 | 841067 | AL110137 | 5817032 | 35 | | | 36 |
| Marker 19 | clone 25242 mRNA | 795821 | AF131854 | 4406700 | 37 | | | 38 |
| Marker 20 | multiple mambrane spanning receptor (TRC8) | 812050 | AF06480I | 3395786 | 39 | AAC39930 | 3395787 | 40 |

TABLE 1-continued

| Marker | Gene Name | Image Clone ID | Acc # (NTS) | GI # (NTS) | SEQ ID NO (nts) | Acc # (AA) | GI # (AA) | SEQ ID NO (AAs) |
|---|---|---|---|---|---|---|---|---|
| Marker 21 | hypothetical protein | From substracted library | AL080097 | 5262519 | 41 | CAB45709 | 5262520 | 42 |
| Marker 22 | hypothetical protein | 34442 | AL121740 | 6012998 | 43 | CAB57330 | 6012999 | 44 |
| Marker 23 | OSF-2 | 897910 | D13665 | 393318 | 45 | BAA02836 | 393319 | 46 |
| Marker 24 | CTL1 protein | 838689 | AJ245620 | 6996441 | 47 | CAB75541 | 6996442 | 48 |
| Marker 25 | CEGP1 protein | 346321 | AJ400877 | 8052236 | 49 | CAB92285 | 8052237 | 50 |
| Marker 26 | LIV-1 | 52933 | U41060 | 1256000 | 51 | AAA96258 | 12711793 | 52 |
| Marker 27 | Adlican | 810224 | AF245505 | 9280404 | 53 | AAF86402 | 9280405 | 54 |
| Marker 28 | UNNAMED | 754126 | | | 55 | | | 56 |
| Marker 29 | p24B protein | 260628 | AJ132270 | 4583676 | 57 | CAB40416 | 4583677 | 58 |
| Marker 30 | Unnamed protein product | From substracted library | AK001761 | 7023229 | 59 | BAA91890 | 7023230 | 60 |
| Marker 31 | Unnamed protein product | 266500 | AX084239 | 13185742 | 61 | CAC33425 | 13185743 | 62 |
| Marker 32 | ALCAM | 26617 | L38608 | 886257 | 63 | AAB59499 | 886258 | 64 |
| Marker 33 | sperm membrane protein | 290091 | S83157 | 1836034 | 65 | AAB46833 | 1836035 | 66 |
| Marker 34 | N-methyl-D-aspartate receptor | 179163 | U77783 | 2444025 | 67 | AAC15910 | 2444026 | 68 |
| Marker 35 | Claudin-4 | 770388 | AB000712 | 2570124 | 69 | BAA22984 | 2570125 | 70 |
| Marker 36 | Hypothetical Protein KIAA0247 | 292894 | D87434 | 1665762 | 71 | BAA13378 | 1665763 | 72 |
| Marker 37 | bumetanide-sensitive Na—K—Cl cotransporter | 685801 | U30246 | 903681 | 73 | AAC50561 | 903682 | 74 |
| Marker 38 | Glucose transporter, type I | 207358 | K03195 | 183302 | 75 | AAA52571 | 183303 | 76 |
| Marker 39 | coxsackie and adenovirus receptor protein | 265680 | Y07593 | 1881446 | 77 | CAA68868 | 1881447 | 78 |
| Marker 40 | connexin 26 | 288663 | BC002805 | 12803916 | 79 | AAH02805 | 12803917 | 80 |
| Marker 41 | Cadherin-6 | 739155 | D31784 | 974184 | 81 | BAA06562 | 974185 | 82 |
| Marker 42 | claudin-7 | 841645 | AJ011497 | 4128014 | 83 | CAA09626 | 4128015 | 84 |
| Marker 43 | Prostasin | 132636 | U33446 | 1143193 | 85 | AAB19071 | 1143194 | 86 |
| Marker 44 | MT3-MMP | 46916 | D85511 | 2424978 | 87 | BAA22226 | 2424979 | 88 |
| Marker 45 | UNNAMED | 771301 | | | 89 | | | 90 |
| Marker 46 | Cluadin-16 | 449034 | AF152101 | 5410526 | 91 | AAD43096 | 5410527 | 92 |
| Marker 47 | LR11, sortillin-related receptor | 279388 | U60975 | 1589775 | 93 | AAC50891 | 5030424 | 94 |
| Marker 48 | Myoferlin | 161992 | AF182316 | 6731234 | 95 | AAF27176 | 6731235 | 96 |
| Marker 49 | desmocollin type 3 | 544639 | X83929 | 1122882 | 97 | CAA58781 | 1122883 | 98 |
| Marker 50 | similar to *D. melanogaster* cadherin related tumor suppressor | 175103 | D87469 | 1665820 | 99 | BAA13407 | 1665821 | 100 |
| Marker 51 | protocadherin | 50114 | AF152304 | 5456893 | 101 | AAD43698 | 5456894 | 102 |
| Marker 52 | occludin | 243159 | U53823 | 1322281 | 103 | AAB00195 | 1322282 | 104 |
| Marker 53 | Unnamed protein | 12577 | BC004337 | 13279268 | 105 | AAH04337 | 13279269 | 106 |
| Marker 54 | Lutheran blood group protein | 160656 | X83425 | 603559 | 107 | CAA58449 | 603560 | 108 |
| Marker 55 | AC133 | 27544 | AF027208 | 2688948 | 109 | AAB92514 | 2688949 | 110 |
| Marker 56 | epithelial V-like antigen | 853998 | AF030455 | 3169829 | 111 | AAC39762 | 3169830 | 112 |

TABLE 2

| Marker | Gene Name | Image Clone ID | Acc # (NTS) | GI # (NTS) | SEQ ID NO (nts) | Acc # (AA) | GI # (AA) | SEQ ID NO (AAs) |
|---|---|---|---|---|---|---|---|---|
| Marker 1 | KIAA0018 | 840878 | D13643 | 285996 | 1 | BAA02806 | 6630632 | 2 |
| Marker 2 | Nonspecific cross reacting antigen (NCA) | 509823 | M18728 | 189084 | 3 | AAA51739 | 178691 | 4 |
| Marker 3 | Unnamed protein product | 461336 | AK001105 | 7022160 | 5 | BAA91505 | 7022161 | 6 |
| Marker 4 | Net-6 | 416374 | AF120265 | 4325179 | 7 | AAD17294 | 4325180 | 8 |
| Marker 5 | DKFZp727C191 | 785703 | AL117474 | 5911946 | 9 | | | 10 |
| Marker 6 | Interferon-induced protein 6-16 | 782513 | Q28808 | N/A | 11 | BAA01980 | 218574 | 12 |
| Marker 7 | UNNAMED | 753428 | | | 13 | | | 14 |
| Marker 8 | Alphe 2,6-sialyltransferase | 823590 | AJ251053 | 6453383 | 15 | CAB61434 | 6453384 | 16 |
| Marker 9 | Programmed cell death 9 (PCD9) | 270558 | AL355715 | 7799103 | 17 | CAB90810 | 7799104 | 18 |
| Marker 10 | DKFZp564BI264 | 813730 | AL117612 | 5912188 | 19 | AAD09421 | 6554165 | 20 |
| Marker 11 | receptor protein tyrosine phosptatase | 41647 | AF043644 | 5468530 | 21 | | | 22 |
| Marker 12 | MAT-8 | 511428 | Q14802 | N/A | 23 | CAA63604 | 1085026 | 24 |
| Marker 13 | Neuropeptide V receptor, type 1 | 33045 | P25929 | N/A | 25 | CAA01819 | 1247453 | 26 |
| Marker 14 | Interferon-inducible protein 9-27 | 755599 | P13164 | N/A | 27 | CAA59337 | 1177476 | 28 |
| Marker 15 | UNNAMED | From subtracted library | | | 29 | | | 30 |
| Marker 16 | Vascular cell adhesion molecule (VCAM) | 44477 | M30257 | 179885 | 31 | AAA51917 | 179886 | 32 |
| Marker 17 | 8D6 antigen | 770879 | AF161254 | 7406951 | 33 | AAF61850 | 7406952 | 34 |
| Marker 18 | DKFZp564E1363 | 841067 | AL110137 | 5817032 | 35 | | | 36 |
| Marker 19 | clone 25242 mRNA | 795821 | AF131854 | 4406700 | 37 | | | 38 |

TABLE 2-continued

| Marker | Gene Name | Image Clone ID | Acc # (NTS) | GI # (NTS) | SEQ ID NO (nts) | Acc # (AA) | GI # (AA) | SEQ ID NO (AAs) |
|---|---|---|---|---|---|---|---|---|
| Marker 20 | multiple mambrane spanning receptor (TRC8) | 812050 | AF064801 | 3395786 | 39 | AAC39930 | 3395787 | 40 |
| Marker 21 | hypothetical protein | From subtracted library | AL080097 | 5262519 | 41 | CAB45709 | 5262520 | 42 |
| Marker 22 | hypothetical protein | 34442 | AL121740 | 6012998 | 43 | CAB57330 | 6012999 | 44 |
| Marker 23 | OSF-2 | 897910 | D13665 | 393318 | 45 | BAA02836 | 393319 | 46 |
| Marker 24 | CTL1 protein | 838689 | AJ245620 | 6996441 | 47 | CAB75541 | 6996442 | 48 |
| Marker 25 | CEGP1 protein | 346321 | AJ400877 | 8052236 | 49 | CAB92285 | 8052237 | 50 |
| Marker 26 | LIV-1 | 52933 | U41060 | 1256000 | 51 | AAA96258 | 12711793 | 52 |
| Marker 27 | Adlican | 810224 | AF245505 | 9280404 | 53 | AAF86402 | 9280405 | 54 |
| Marker 28 | UNNAMED | 754126 | | | 55 | | | 56 |
| Marker 29 | p24B protein | 260628 | A J132270 | 4583676 | 57 | CAB40416 | 4583677 | 58 |
| Marker 30 | Unnamed protein product | From subtracted library | AK001761 | 7023229 | 59 | BAA91890 | 7023230 | 60 |
| Marker 31 | Unnamed protein product | 266500 | AX084239 | 13185742 | 61 | CAC33425 | 13185743 | 62 |
| Marker 32 | ALCAM | 26617 | L38608 | 886257 | 63 | AAB59499 | 886258 | 64 |
| Marker 33 | sperm membrane protein | 290091 | S83157 | 1836034 | 65 | AAB46833 | 1836035 | 66 |

TABLE 3

| Marker | Gene Name | Image Clone ID | Acc # (NTS) | GI # (NTS) | SEQ ID NO (nts) | Acc # (AA) | GI # (AA) | SEQ ID NO (AAs) |
|---|---|---|---|---|---|---|---|---|
| Marker 34 | N-methyl-D-aspartate receptor | 179163 | U77783 | 2444025 | 67 | AAC15910 | 2444026 | 68 |
| Marker 35 | Claudin-4 | 770388 | AB000712 | 2570124 | 69 | BAA22984 | 2570125 | 70 |
| Marker 36 | Hypothetical Protein KIAA0247 | 292894 | D87434 | 1665762 | 71 | BAA13378 | 1665763 | 72 |
| Marker 37 | bumetanide-sensitive Na—K—Cl cotransporter | 685801 | U30246 | 903681 | 73 | AAC5056I | 903682 | 74 |
| Marker 38 | Glucose transporter, type I | 207358 | K03195 | 183302 | 75 | AAA52571 | 183303 | 76 |
| Marker 39 | coxsackie and adenovirus receptor protein | 265680 | Y07593 | 1881446 | 77 | CAA68868 | 1881447 | 78 |
| Marker 40 | connexin 26 | 288663 | BC002805 | 12803916 | 79 | AAH02805 | 12803917 | 80 |
| Marker 41 | Cadherin-6 | 739155 | D31784 | 974184 | 81 | BAA06562 | 974185 | 82 |
| Marker 42 | claudin-7 | 841645 | AJ011497 | 4128014 | 83 | CAA09626 | 41280151 | 84 |
| Marker 43 | Prostasin | 132636 | U33446 | 1143193 | 85 | AAB19071 | 1143194 | 86 |
| Marker 44 | MT3-MMP | 46916 | D85511 | 2424978 | 87 | BAA22226 | 2424979 | 88 |
| Marker 45 | UNNAMED | 771301 | | | 89 | | | 90 |
| Marker 46 | Cluadin-16 | 449034 | AF152101 | 5410526 | 91 | AAD43096 | 5410527 | 92 |
| Marker 47 | LR11, sortillin-related receptor | 279388 | U60975 | 1589775 | 93 | AAC50891 | 5030424 | 94 |
| Marker 48 | Myoferlin | 161992 | AF182316 | 6731234 | 95 | AAF27176 | 6731235 | 96 |
| Marker 49 | desmocollin type 3 | 544639 | X83929 | 1122882 | 97 | CAA58781 | 1122883 | 98 |
| Marker 50 | similar to *D. melanogaster* cadherin related tumor suppressor | 175103 | D87469 | 1665820 | 99 | BAA13407 | 1665821 | 100 |
| Marker 51 | protocadherin | 50114 | AF152304 | 5456893 | 101 | AAD43698 | 5456894 | 102 |
| Marker 52 | occludin | 243159 | U53823 | 1322281 | 103 | AAB00195 | 1322282 | 104 |
| Marker 53 | Unnamed protein | 12577 | BC004337 | 13279268 | 105 | AAH04337 | 13279269 | 106 |
| Marker 54 | Lutheran blood group protein | 160656 | X83425 | 603559 | 107 | CAA58449 | 603560 | 108 |
| Marker 55 | AC133 | 27544 | AF027208 | 2688948 | 109 | AAB92514 | 2688949 | 110 |
| Marker 56 | epithelial V-like antigen | 853998 | AF030455 | 3169829 | 111 | AAC39762 | 3169830 | 112 |

TABLE 4

| Gene | TaqMan | ISH | Ovary | Breast | Lung | Colon | Prostate |
|---|---|---|---|---|---|---|---|
| Marker 1 | Yes | Yes | − | + | + | − | ND |
| Marker 2 | Yes | Yes | − | + | − | − | − |
| Marker 3 | Yes | Yes | − | + | + | − | − |
| Marker 4 | Yes | Yes | + | + | + | + | + |
| Marker 6 | Yes | Yes | + | + | + | + | − |
| Marker 7 | Yes | Yes | + | + | − | + | + |
| Marker 22 | Yes | Yes | − | + | + | + | − |
| Marker 23 | Yes | Yes | + | + | + | + | ND |
| Marker 26 | Yes | Yes | − | + | − | − | + |
| Marker 32 | Yes | Yes | − | + | + | − | + |
| Marker 36 | Yes | No | + | + | + | − | ND |
| Marker 39 | Yes | No | + | − | + | − | ND |
| Marker 43 | Yes | No | + | + | − | + | ND |
| Marker 45 | Yes | Yes | + | − | − | + | |
| Marker 47 | Yes | No | + | + | + | + | |
| Marker 56 | Yes | No | + | − | + | + | − |

TABLE 5

| Marker | Gene Name | Image Clone ID | Acc # (NTS) | GI # (NTS) | SEQ ID NO (nts) | Acc # (AA) | GI # (AA) | SEQ ID NO (AAs) |
|---|---|---|---|---|---|---|---|---|
| Marker 5 | DKFZp727C191 | 785703 | AL117474 | 5911946 | 9 | | | 10 |
| Marker 7 | UNNAMED | 753428 | | | 13 | | | 14 |
| Marker 10 | DKFZp564B1264 | 813730 | AL117612 | 5912188 | 19 | | | 20 |
| Marker 15 | UNNAMED | | | | 29 | | | 30 |
| Marker 18 | DKFZp564EI363 | 841067 | AL110137 | 5817032 | 35 | | | 36 |
| Marker 19 | clone 25242 mRN A | 795821 | AF131854 | 4406700 | 37 | | | 38 |
| Marker 28 | UNNAMED | 754126 | | | 55 | | | 56 |
| Marker 45 | UNNAMED | 771301 | | | 89 | | | 90 |

What is claimed:

1. A method of diagnosing and-treating breast cancer in a human patient, the method comprising:
   a) obtaining a sample from a human patient, wherein the patient sample is a breast tissue sample;
   b) detecting whether Marker 7 is present in tumor stroma and/or on tumor cells within the sample by contacting the patient sample with a nucleic acid molecule or an antibody that specifically binds to the Marker 7, wherein the Marker 7 is at least 95% identical to the entire sequence of SEQ ID NO:13, or an entire complement thereof, or the Marker 7 consists of SEQ ID NO:14;
   c) diagnosing the patient with breast cancer when the presence of the Marker 7 in tumor stroma and/or on tumor cells within the sample is detected to be higher than the level of Marker 7 in a control sample; and
   d) administering an effective amount of an antibody, or antigen binding portion thereof, that specifically binds Marker 7 conjugated to a therapeutic moiety, to the diagnosed patient, wherein administering an effective amount of the antibody, or antigen binding portion thereof, conjugated to a therapeutic moiety inhibits angiogenesis in the breast cancer,
   thereby diagnosing and treating breast cancer in the human patient.

2. The method of claim 1, wherein the step of detecting whether the Marker 7 is present in tumor stroma and/or on tumor cells within the patient sample comprises detecting the presence of a Marker 7 protein in the sample.

3. The method of claim 2, wherein the antibody that specifically binds to the marker is selected from the group consisting of an antibody, an antibody derivative, and an antigen-binding antibody fragment.

4. The method of claim 3, wherein the antibody is labelled.

5. The method of claim 1, wherein the step of detecting whether the Marker 7 is present in tumor stroma and/or on tumor cells within the patient sample comprises detecting a transcribed polynucleotide or portion thereof.

6. The method of claim 5, wherein the transcribed polynucleotide or portion thereof is a mRNA or a cDNA.

7. The method of claim 5, wherein the step of detecting a transcribed polynucleotide further comprises amplifying the transcribed polynucleotide.

8. The method of claim 1, wherein the level of expression of the Marker 7 present in tumor stroma and/or on tumor cells within the patient sample differs from the level of expression of the Marker 7 in a control sample by a factor selected from the group consisting of: a factor of at least about 2, a factor of at least about 3, a factor of at least about 4, and a factor of at least about 5.

9. The method of claim 1, wherein the step of detecting whether the Marker 7 is present in tumor stroma and/or on tumor cells within the patient sample comprises using a technique selected from the group consisting of Northern hybridization, polymerase chain reaction analysis, RT-PCR, probe array and in situ hybridization.

10. The method of claim 1, wherein the step of detecting whether the Marker 7 is present in tumor stroma and/or on tumor cells within the patient sample comprises assessing the level of expression of the marker in the patient sample using a technique selected from the group consisting of enzyme immunoassay, radioimmunoassay, Western blot analysis, enzyme linked immuoabsorbant assay (ELISA), immunoprecipitation and immunofluorescence.

11. The method of claim 1, wherein the Marker 7 comprises SEQ ID NO:13, or an entire complement thereof.

12. The method of claim 1, wherein the Marker 7 consists of SEQ ID NO: 14.

13. The method of claim 1, wherein the therapeutic moiety is a cytotoxin.

14. The method of claim 13, wherein the cytotoxin is selected from the group consisting of taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, a glucocorticoid, procaine, tetracaine, lidocaine, propranolol, and puromycin, and analogs or homologs thereof.

15. The method of claim 1, wherein the therapeutic moiety is an antimetabolite.

16. The method of claim 15, wherein the antimetabolite is selected from the group consisting of methotrexate, 6-mercaptopurine, 6-thioguanine, cytarabine, 5-fluorouracil and decarbazine.

17. The method of claim 1, wherein the therapeutic moiety is an alkylating agent.

18. The method of claim 17, wherein the alkylating agent is selected from the group consisting of mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin.

19. The method of claim 1, wherein the therapeutic moiety is an anthracycline.

20. The method of claim 19, wherein the anthracycline is selected from the group consisting of aunorubicin and doxorubicin.

21. The method of claim 1, wherein the therapeutic moiety is an antibiotic.

22. The method of claim 21, wherein the antibiotic is selected from the group consisting of dactinomycin, bleomycin, mithramycin, and anthramycin (AMC).

23. The method of claim 1, wherein the therapeutic moiety is an antimitotic agent.

24. The method of claim 23, wherein the antimitotic agent is selected from the group consisting of vincristine and vinblastine.

* * * * *